(12) United States Patent
Baumhof et al.

(10) Patent No.: US 10,568,958 B2
(45) Date of Patent: *Feb. 25, 2020

(54) VACCINE COMPOSITION COMPRISING COMPLEXED IMMUNOSTIMULATORY NUCLEIC ACIDS AND ANTIGENS PACKAGED WITH DISULFIDE-LINKED POLYETHYLENEGLYCOL/PEPTIDE CONJUGATES

(71) Applicant: CureVac AG, Tübingen (DE)

(72) Inventors: Patrick Baumhof, Dusslingen (DE);
Karl-Josef Kallen, Tübingen (DE);
Mariola Fotin-Mleczek, Sindelfingen (DE)

(73) Assignee: CureVac AG, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,036

(22) Filed: Jul. 8, 2016

(65) Prior Publication Data

US 2017/0028059 A1 Feb. 2, 2017

Related U.S. Application Data

(63) Continuation of application No. 13/824,449, filed as application No. PCT/EP2012/000614 on Feb. 10, 2012, now Pat. No. 9,421,255.

(30) Foreign Application Priority Data

Feb. 21, 2011 (WO) .................. PCT/EP2011/000827

(51) Int. Cl.
| | | |
|---|---|---|
| A61K 39/39 | (2006.01) | |
| A61K 39/00 | (2006.01) | |
| A61K 47/60 | (2017.01) | |
| A61K 47/54 | (2017.01) | |
| A61K 47/64 | (2017.01) | |
| A61K 47/55 | (2017.01) | |

(52) U.S. Cl.
CPC .......... *A61K 39/39* (2013.01); *A61K 39/0011* (2013.01); *A61K 47/549* (2017.08); *A61K 47/55* (2017.08); *A61K 47/60* (2017.08); *A61K 47/6455* (2017.08); *A61K 2039/53* (2013.01); *A61K 2039/55561* (2013.01); *A61K 2039/57* (2013.01); *A61K 2039/575* (2013.01)

(58) Field of Classification Search
None
See application file for complete search history.

(56) References Cited

U.S. PATENT DOCUMENTS

| | | | | |
|---|---|---|---|---|
| 8,206,990 B2* | 6/2012 | Ritt | ..................... | C12N 15/1006 436/161 |
| 8,460,941 B2* | 6/2013 | Ritt | ..................... | C12N 15/1006 436/161 |
| 8,703,906 B2* | 4/2014 | Baumhof | ........... | A61K 48/0041 530/300 |
| 8,771,728 B2 | 7/2014 | Huang et al. | | |
| 8,852,472 B2* | 10/2014 | Keil | ................. | A61K 47/48815 264/4 |
| 8,968,746 B2* | 3/2015 | Baumhof | ............... | C12N 15/87 424/193.1 |
| 8,969,543 B2* | 3/2015 | Jeong | .................... | C12N 15/111 536/23.1 |
| 9,314,535 B2* | 4/2016 | Baumhof | ......... | A61K 47/48215 |
| 9,421,255 B2* | 8/2016 | Baumhof | ......... | A61K 47/48092 |
| 9,629,812 B2* | 4/2017 | Medarova | ................ | A61K 9/51 |
| 9,687,262 B2* | 6/2017 | Rousseau | ............... | A61B 17/22 |
| 2005/0032730 A1 | 2/2005 | Von Der Mulbe et al. | | |
| 2005/0059624 A1 | 3/2005 | Hoerr et al. | | |
| 2005/0250723 A1 | 11/2005 | Hoerr et al. | | |
| 2006/0142227 A1* | 6/2006 | Lamensdorf | ........... | A61K 48/00 514/44 A |
| 2006/0188990 A1 | 8/2006 | Kretschmer et al. | | |
| 2007/0280929 A1 | 12/2007 | Hoerr et al. | | |

(Continued)

FOREIGN PATENT DOCUMENTS

| | | |
|---|---|---|
| DE | 102004035227 | 2/2006 |
| DE | 102006007433 | 8/2007 |

(Continued)

OTHER PUBLICATIONS

Dohmen et al, Nanoparticle-based programmed drug and nucleic acid delivery—an option for nanomedicine. J. Vascular Research, Oct. 2011, 48/s1:67. Abstract IS45 (Year: 2011).*
Cancer.Net, What are Cancer Vaccines? Jun. 2018, 4 pages (Year: 2018).*
Melief et al, Nature Reviews/Cancer, May 2008, vol. 8:351-360. published online:Apr. 17, 2008 (Year: 2008).*
Zhang et al, Vaccine. 2017, 35:1094-1100. available online: Jul. 20, 2016 (Year: 2017).*
Mocellin et al, The Lancet/Oncology. Nov. 2004, vol. 5:681-689 (Year: 2004).*
National Cancer Institute. Fact Sheet, Cancer Vaccines, Jun. 21, 2011, 9 pages (Year: 2011).*

(Continued)

*Primary Examiner* — Nita M. Minnifield
(74) *Attorney, Agent, or Firm* — Parker Highlander PLLC

(57) ABSTRACT

The present invention is directed to a composition or vaccine composition comprising a) an adjuvant component comprising or consisting of at least one immunostimulatory nucleic acid sequence, complexed with a complexing agent; b) an antigen, preferably a protein or peptide antigen and/or a nucleic acid sequence encoding said antigen; and c) a carrier molecule for combined packaging the adjuvant component and the antigen. The present invention is also directed to the first medical use of such a composition or vaccine composition and to the second medical use of such a composition or vaccine composition or components thereof for the treatment of diseases, such as infectious or cancer or tumour diseases as defined herein. The present invention furthermore discloses kits comprising such a composition or vaccine composition.

12 Claims, 13 Drawing Sheets

Figure 1:
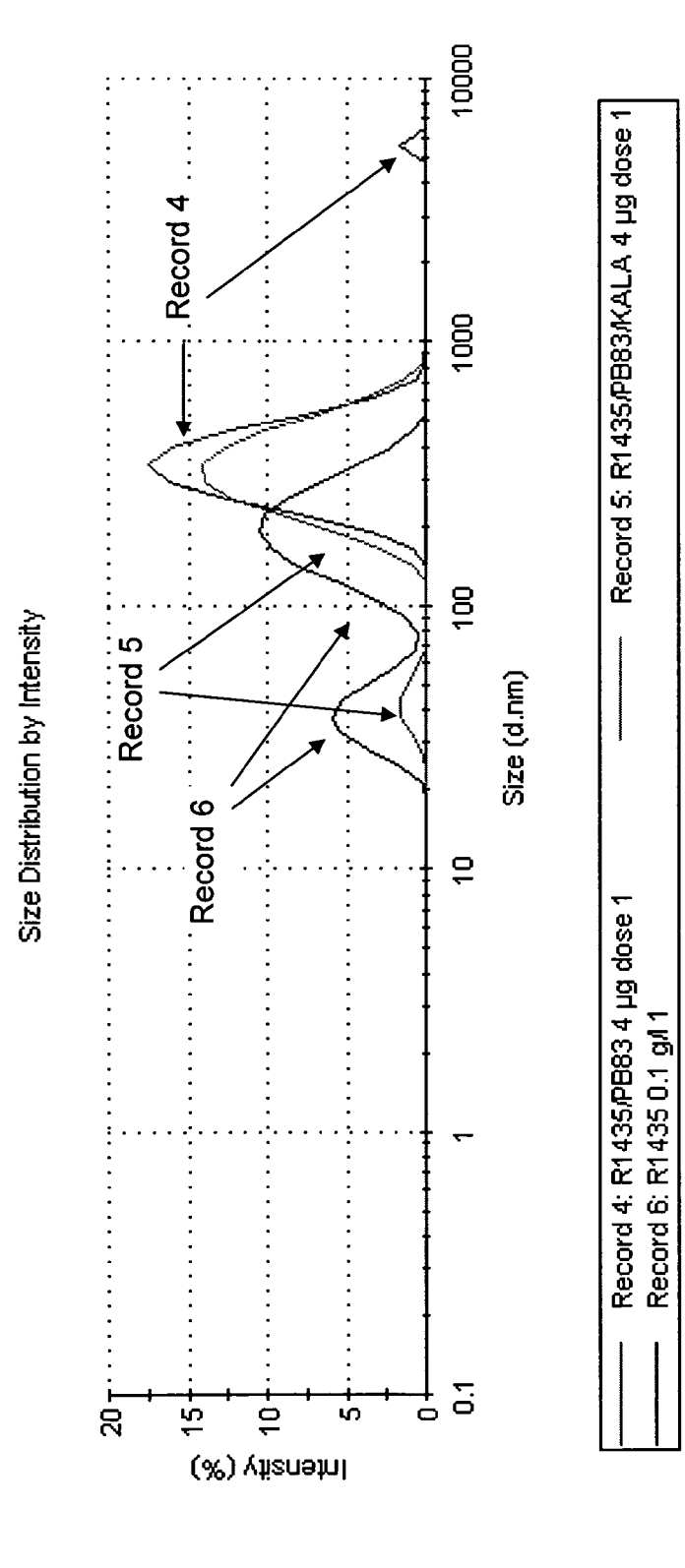

Specification includes a Sequence Listing.

(56) References Cited

U.S. PATENT DOCUMENTS

| | | | |
|---|---|---|---|
| 2008/0025944 A1 | 1/2008 | Hoerr et al. | |
| 2008/0145375 A1 | 6/2008 | Bembridge et al. | |
| 2008/0153166 A1 | 6/2008 | Huang et al. | |
| 2008/0171711 A1 | 7/2008 | Hoerr et al. | |
| 2008/0267873 A1 | 10/2008 | Hoerr et al. | |
| 2009/0324584 A1 | 12/2009 | Hoerr et al. | |
| 2010/0048883 A1 | 2/2010 | Ketterer et al. | |
| 2010/0062967 A1* | 3/2010 | Keil | A61K 47/48815 514/19.3 |
| 2010/0184953 A1 | 7/2010 | Huang et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |
| 2011/0053829 A1* | 3/2011 | Baumhof | A61K 48/0041 514/1.2 |
| 2011/0243897 A1* | 10/2011 | Seymour | A61K 47/48092 424/93.6 |
| 2012/0219573 A1 | 8/2012 | Baumhof et al. | |
| 2012/0258046 A1 | 10/2012 | Mutzke | |
| 2012/0258104 A1* | 10/2012 | Echeverri | A61K 47/48092 424/134.1 |
| 2013/0121988 A1* | 5/2013 | Hoerr | A61K 39/39 424/130.1 |
| 2013/0142818 A1* | 6/2013 | Baumhof | C12N 15/87 424/193.1 |
| 2013/0259879 A1* | 10/2013 | Baumhof | A61K 47/48092 424/178.1 |
| 2013/0281382 A1 | 10/2013 | Huang et al. | |
| 2014/0037660 A1 | 2/2014 | Fotin-Mleczek | |
| 2014/0241996 A1* | 8/2014 | Medarova | A61K 9/51 424/9.322 |
| 2014/0294877 A1* | 10/2014 | Baumhof | A61K 48/0041 424/185.1 |
| 2015/0037326 A1* | 2/2015 | Butler-Ransohoff | A61K 47/48284 424/133.1 |
| 2015/0118183 A1 | 4/2015 | Baumhof | |
| 2015/0118264 A1* | 4/2015 | Baumhof | A61K 39/0011 424/209.1 |
| 2015/0258214 A1* | 9/2015 | Baumhof | C12N 15/87 424/193.1 |
| 2016/0317679 A1* | 11/2016 | Baumhof | A61K 48/0041 |
| 2016/0331844 A1* | 11/2016 | Fotin-Mleczek | A61K 39/3955 |
| 2017/0028059 A1* | 2/2017 | Baumhof | A61K 47/48092 |

FOREIGN PATENT DOCUMENTS

| | | | |
|---|---|---|---|
| EP | 1083232 | 3/2001 | |
| EP | 1905844 | 12/2002 | |
| WO | WO 1998/019710 | 5/1998 | |
| WO | WO 1998/047913 | 10/1998 | |
| WO | WO 2003/059381 | 7/2003 | |
| WO | WO 2003/068942 | 8/2003 | |
| WO | WO-2005035549 A2 * | 4/2005 | A61K 48/00 |
| WO | WO 2006/046978 | 5/2006 | |
| WO | WO-2006069782 A2 * | 7/2006 | A61K 47/48815 |
| WO | WO 2007/031319 | 3/2007 | |
| WO | WO 2007/014979 | 2/2008 | |
| WO | WO 2008/022046 | 2/2008 | |
| WO | WO 2009/030254 | 3/2009 | |
| WO | WO 2009/095226 | 8/2009 | |
| WO | WO 2009/144230 | 12/2009 | |
| WO | WO 2010/027827 | 3/2010 | |
| WO | WO 2010/037539 | 4/2010 | |
| WO | WO 2010/088927 | 8/2010 | |
| WO | WO-2011011631 A2 * | 1/2011 | C12N 15/87 |
| WO | WO 2011/026641 | 3/2011 | |
| WO | WO 2012/019780 | 2/2012 | |
| WO | WO-2012013326 A1 * | 2/2012 | A61K 47/48315 |
| WO | WO 2012/113413 | 8/2012 | |
| WO | WO 2012/113513 | 8/2012 | |
| WO | WO-2012113513 A1 * | 8/2012 | A61K 47/48092 |
| WO | WO-2012116811 A1 * | 9/2012 | A61K 39/00 |
| WO | WO 2012/013326 | 2/2013 | |
| WO | WO 2013/113201 | 8/2013 | |
| WO | WO 2013/113325 | 8/2013 | |
| WO | WO 2013/113326 | 8/2013 | |
| WO | WO 2013/113501 | 8/2013 | |
| WO | WO 2013/113502 | 8/2013 | |
| WO | WO 2013/174409 | 11/2013 | |
| WO | WO-2016170176 A1 * | 10/2016 | A61K 39/3955 |

OTHER PUBLICATIONS

Bettinger et al., "Peptide-mediated RNA delivery: a novel approach for enhanced transfection of primary and post-mitotic cells," *Nucleic Acids Research*, 29(18):3882-3891, 2001.

Bolhassani et al., "Improvement of different vaccine delivery systems for cancer therapy," *Molecular Cancer*, 10(1):3, 2011.

Bot et al., "Induction of hum oral and cellular immunity against influenza virus by immunization of newborn mice with a plasmid bearing a hemagglutinin gene," *International Immunology*, 9(11):1641-1650, 1997.

Bot et al., "Enhanced protection against influenza virus of mice immunized as newborns with a mixture of plasmids expressing hemagglutinin and nucleoprotein," *Vaccine*, 16(17):1675-1682, 1998.

Bot et al., "Genetic immunization of neonates," *Microbes and Infection*, 4(4):511-520, 2002.

Brito et al, "Non-viral eNOS gene delivery and transfection with stents for the treatment of restenosis," *Biomed Eng*, 9:56, 2010.

Burke et al., "Extracellular barriers to in Vivo PEI and PEGylated PEI Polyplex-Mediated Gene Delivery to the Liver," *Bioconjugate Chem.*, 19(3):693-704, 2008.

Carralot et al., "Polarization of immunity induced by direct injection of naked sequence-stabilized mRNA vaccines," *CMLS Cellular and Molecular Life Sciences*, 61(18):2418-2424, 2004.

Casciato et al., "Manual of Clinical Oncology," 6th edition, Lippincott Williams & Wilkins: Philadelphia, p. xi, 2009.

Danhier et al., "PLGA-based nanoparticles: An overview of biomedical applications," *Journal of Controlled Release*, 161:505-522, 2012.

Deshayes et al., "Cell-penetrating peptides: tools for intracellular delivery of therapeutics," *Cell Mol Life Sci.*, 62(16): 1839-49, 2005.

Fajac et al., "Histidylated polylysine as a synthetic vector for gene transfer into immortalized cystic fibrosis airway surface and airway gland serous cells," *J Gene Med.*, 2(5):368-78, 2000.

Foerg et al., "On the biomedical promise of cell penetrating peptides: limits versus prospects," *J Pharm Sci.*, 97(1):144-62. Review, 2008.

Fotin-Mleczek et al., "Highly potent mRNA based cancer vaccines represent an attractive platform for combination therapies supporting an improved therapeutic effect," *The Journal of Gene Medicine*, 14:428-439, 2012.

Fotin-Mleczek et al., "Messenger RNA-based vaccines with dual activity induce balanced TLR-7 dependent adaptive immune responses and provide antitumor activity," *Journal of Immunotherapy*, 34(1):1-15, 2011.

Fujita et al., "Calcium enhanced delivery of tetraarginine-PEG-lipid-coated DNA/protamine complexes," *International Journal of Pharmaceutics*, 368(1-2):186-192, 2009.

Gao et al., "Nonviral gene delivery: what we know and what is next," *AAPS J.*, 9(1):E92-104, 2007.

Garinot et al., "PEGylated PLGA-based nanoparticles targeting M cells for oral vaccination," *Journal of Controlled Release*, 120(3):195-204, 2007.

Giel-Peitraszuk et al., "Interaction of HIV Tat model peptides with tRNA and 5S rRNA," Database Biosis, DB Acc. No. Prev199800116011, Abstract, 1997.

Gravekamp et al., "Cancer vaccines in old age," *Experimental Gerontology*, 42(5):441-450, 2007.

Hamidi et al., "Pharmacokinetic consequences of pegylation," *Drug Deliv.*, 13(6):399-409, 2006.

Heidenreich et al., "RNAdjuvant, a novel highly potent RNA-based induction of balanced immune response (TH1 and TH2) and anti-

(56) References Cited

OTHER PUBLICATIONS tumor activity," *J. Immunotherapy*, Meeting Info: 26th Annual Scientific Meeting of Society of Immunotherapy of Cancer, Abstract only, 34(9):663-664, 2011.
Heil et al., "Species-specific recognition of single-stranded RNA via Toll-like receptor 7 and 8," *Science*, 303:1526-1529, 2004.
Kallen et al., "A novel, disruptive vaccination technology," *Human Vaccines & Immunotherapeutics*, 9(10):2263-2276, 2013.
Knop et al., "Poly(ethylene glycol) in drug delivery: pros and cons as well as potential alternatives," *Angew. Chem. Int. Ed.*, 49:6288-6308, 2010.
Kovarik et al., "Optimization of vaccine responses in early life: The role of delivery systems and immunomodulators," *Immunology and Cell Biology*, 76(3):222-236, 1998.
Kwok et al., "Formulation of highly soluble poly( ethylene glycol)-peptide DNA condensates," *J Pharm Sci.*, 88(10):996-1003, 1999.
Lochmann et al., "Drug delivery of oligonucleotides by peptides," *European Journal of Pharmaceutics and Biopharmaceutics*, 58(2):237-251, 2004.
Martin et al., "Peptide-guided gene delivery," *AAPSJ.*, 9(1):E18-29, 2007.
Mattner et al., "Vaccination with Poly-I-Arginine as Immunostimulant for Peptide Vaccines: Induction of Potent and Long-Lasting T-cell Response against Cancer Antigens," *Cancer Research*, 62:1477-1480, 2002.
Nakamura et al., "Octaarginine-modified multifunctional envelope-type nano device for siRNA," *J Control Release*, 119(3):360-7, 2007.
Neu et al., "Recent advances in rational gene transfer vector design based on poly( ethylene imine) and its derivatives," *J Gene Med.*, 7(8):992-1009, 2005.
Office Action issued in U.S. Appl. No. 13/824,449, dated Jan. 29, 2016.
Office Action issued in U.S. Appl. No. 13/824,449, dated May 8, 2015.
Office Action issued in U.S. Appl. No. 13/824,449, dated Sep. 17, 2014.
Oupicky et al., "Importance of lateral and steric stabilization of polyelectrolyte gene delivery vectors for extended systemic circulation," *Mol Ther.*, 5(4):463-72, 2002.
Oupicky et al., "Laterally stabilized complexes of DNA with linear reducible polycations: strategy for triggered intracellular activation of DNA delivery vectors," *J Am Chem Soc.*, 124(1):8-9, 2002.
Parker et al., "Enhanced gene transfer activity of peptide-targeted gene-delivery vectors," *J Drug Target*, 13(1):39-51, 2005.
Pichon et al., "Poly [Lys-(AEDTP)]: A cationic polymer that allows dissociation of pDNA/cationic polymer complexes in a reductive medium and enhances polyfection," *Bioconjug Chem.*, 13(1):76-82, 2002.
Pomroy et al., Solubilization of hydrophobic peptides by reversible cysteine PEGylation, Biochem Biophys Res Commun. Apr. 17, 1998;245(2):618-21, 1998.
Radu et al., "Plasmid expressing the influenza HA gene protects old mice from lethal challenge with influenza virus," *Viral Immunology*, 12(3):217-226, 1999.
Read et al., "A versatile reducible polycation-based system for efficient delivery of a broad range of nucleic acids," *Nucleic Acids Res.*, 33(9):e86, 2005.
Read et al., "RNA-based therapeutic strategies for cancer," *Expert Opinion on Therapeutic Patents*, 13(5):627-638, 2003.
Read et al., "Vectors based on reducible polycations facilitate intracellular release of nucleic acids," *J Gene Med.*, 5(3):232-45, 2003.
Sakae et al., "Highly efficient in vivo gene transfection by plasmid/ PEI complexes coated by anionic PEG derivatives bearing carboxyl groups and RGD peptide," *Biomedicine and Pharmacotherapy*, 62(7):448-453, 2008.
Scheel et al., "Therapeutic anti-tumor immunity triggered by injections of immunostimulating single-stranded RNA," *Eur J Immunol*, 36(10):2807-2816, 2006.
Scheel et al., "Toll-like receptor-dependent activation of several human blood cell types by protamine-condensed mRNA," *Eur J Immunol*, 35(5): 1557-1566, 2005.
Shiffman et al., "Protein dissociation from DNA in model systems and chromatin," *Nucleic Acids Res.*, 5(9):3409-26, 1978.
Takae et al., "PEG-detachable polyplex micelles based on disulfide-linked block catiomers as bioresponsive nonviral gene vectors," *J Am Chem Soc.*, 130(18):6001-9, 2008.
Tonges et al., "Stearylated octaarginine and artificial virus-like particles for transfection of siRNA into primary rat neurons," *RNA*, 12(7):1431-8, 2006.
Unnamalai et al., "Cationic oligopeptide-mediated delivery of dsRNA for post-transcriptional gene silencing in plant cells," *FEBS Lett.*, 566(1-3):307-10, 2004.
Vives et al., "A truncated HIV-1 Tat protein basic domain rapidly translocates through the plasma membrane and accumulates in the cell nucleus," *J Biol Chem.*, 272(25):16010-16017, 1997.
Wang et al., "An intracellular delivery method for siRNA by an arginine-rich peptide," *J Biochem Biophys Methods*, 70(4):579-86, 2007.
Yoshitomi et al., "Design of core-shell-type nanoparticles carrying stable radicals in the core," *Biomacromolecules*, 10:596-601, 2009.
Zhang et al., "Delivery of Telomerase Reverse Transcriptase Small Interfering RNA in Complex with Positively Charged Single-Walled Carbon Nanotubese Suppresses Tumor Growth," *Clinical Cancer Research*, 12: 4933-4939, 2006.
Zohra et al, "Effective delivery with enhanced translational activity synergistically accelerates mRNA-based transfection," *Biochem Biophys Res Commun.*, 358(1):373-378, 2007.

\* cited by examiner

Pp Luc R1265:

GGGAGAAAGCUUGAGGAUGGAGGACGCCAAGAACAUCAAGAAGGGCCCGGCGCCCU
UCUACCCGCUGGAGGACGGGACCGCCGGCGAGCAGCUCCACAAGGCCAUGAAGCGG
UACGCCCUGGUGCCGGGCACGAUCGCCUUCACCGACGCCCACAUCGAGGUCGACAU
CACCUACGCGGAGUACUUCGAGAUGAGCGUGCGCCUGGCCGAGGCCAUGAAGCGGU
ACGGCCUGAACACCAACCACCGGAUCGUGGUGUGCUCGGAGAACAGCCUGCAGUUC
UUCAUGCCGGUGCUGGGCGCCCUCUUCAUCGGCGUGGCCGUCGCCCCGGCGAACGA
CAUCUACAACGAGCGGGAGCUGCUGAACAGCAUGGGGAUCAGCCAGCCGACCGUGG
UGUUCGUGAGCAAGAAGGGCCUGCAGAAGAUCCUGAACGUGCAGAAGAAGCUGCCC
AUCAUCCAGAAGAUCAUCAUCAUGGACAGCAAGACCGACUACCAGGGCUUCCAGUCG
AUGUACACGUUCGUGACCAGCCACCUCCCGCCGGGCUUCAACGAGUACGACUUCGU
CCCGGAGAGCUUCGACCGGGACAAGACCAUCGCCCUGAUCAUGAACAGCAGCGGCA
GCACCGGCCUGCCGAAGGGGGUGGCCCUGCCGCACCGGACCGCCUGCGUGCGCUU
CUCGCACGCCCGGGACCCCAUCUUCGGCAACCAGAUCAUCCCGGACACCGCCAUCCU
GAGCGUGGUGCCGUUCCACCACGGCUUCGGCAUGUUCACGACCCUGGGCUACCUCA
UCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCU
UCUUCGCCAAGAGCACCCUGAUCGACAAGUACGACCUGUCGAACCUGCACGAGAUCG
CCAGCGGGGGCGCCCCGCUGAGCAAGGAGGUGGGCGAGGCCGUGGCCAAGCGGUU
CCACCUCCCGGGCAUCCGCCAGGGCUACGGCCUGACCGAGACCACGAGCGCGAUCC
UGAUCACCCCCGAGGGGGACGACAAGCCGGGCGCCGUGGGCAAGGUGGUCCCGUUC
UUCGAGGCCAAGGUGGUGGACCUGGACACCGGCAAGACCCUGGGCGUGAACCAGCG
GGGCGAGCUGUGCGUGCGGGGCCGAUGAUCAUGAGCGGCUACGUGAACAACCCGG
AGGCCACCAACGCCCUCAUCGACAAGGACGGCUGGCUGCACAGCGGCGACAUCGCC
UACUGGGACGAGGACGAGCACUUCUUCAUCGUCGACCGGCUGAAGUCGCUGAUCAA
GUACAAGGGCUACCAGGUGGCGCCGGCCGAGCUGGAGAGCAUCCUGCUCCAGCACC
CCAACAUCUUCGACGCCGGCGUGGCCGGGCUGCCGGACGACGACGCCGGCGAGCUG
CCGGCCGCGGUGGUGGUGCUGGAGCACGGCAAGACCAUGACGGAGAAGGAGAUCGU
CGACUACGUGGCCAGCCAGGUGACCACCGCCAAGAAGCUGCGGGGCGGCGUGGUGU
UCGUGGACGAGGUCCCGAAGGGCCUGACCGGGAAGCUCGACGCCCGGAAGAUCCGC
GAGAUCCUGAUCAAGGCCAAGAAGGGCGGCAAGAUCGCCGUGUAAGACUAGUUAUAA
GACUGACUAGCCCGAUGGGCCUCCCAACGGGCCCUCCUCCCCUCCUUGCACCGAGA
UUAAUAAAAAAAAAAAAAAAAAAAAAAAAAAAAAAAAAAAAAAAAAAAAAAAAAAAAA
AAAAAAAUGCAUCCCCCCCCCCCCCCCCCCCCCCCCCCCCCCCAAAGGCUCUUUUC
AGAGCCACCAGAAUU

Figure 8

Gp Luc R1283:

GGGAGAAAGCGATCCAGCCACCATGGGAGTCAAAGTTCTGTTTGCCCTG
ATCTGCATCGCTGTGGCCGAGGCCAAGCCCACCGAGAACAACGAAGACT
TCAACATCGTGGCCGTGGCCAGCAACTTCGCGACCACGGATCTCGATGC
TGACCGCGGGAAGTTGCCCGGCAAGAAGCTGCCGCTGGAGGTGCTCAA
AGAGATGGAAGCCAATGCCCGGAAAGCTGGCTGCACCAGGGGCTGTCT
GATCTGCCTGTCCCACATCAAGTGCACGCCCAAGATGAAGAAGTTCATCC
CAGGACGCTGCCACACCTACGAAGGCGACAAAGAGTCCGCACAGGGCG
GCATAGGCGAGGCGATCGTCGACATTCTGAGATTCCTGGGTTCAAGGA
CTTGGAGCCCATGGAGCAGTTCATCGCACAGGTCGATCTGTGTGTGGAC
TGCACAACTGGCTGCCTCAAGGGCTTGCCAACGTGCAGTGTTCTGACC
TGCTCAAGAAGTGGCTGCCGCAACGCTGTGCGACCTTTGCCAGCAAGAT
CCAGGGCCAGGTGGACAAGATCAAGGGGGCCGGTGGTGACTAAGCGGC
CGCTCGAGCATGCATCTAGTTATAAGACTGACTAGCCCGATGGGCCTCC
CAACGGGCCCTCCTCCCTCCTTGCACCGAGATTAATAAAAAAAAAAAAA
AAAAAAAAAAAAAAAAAAAAAAAAAAAAAAAAAAAAAAAAAAAAAAAT
ATTCCCCCCCCCCCCCCCCCCCCCCCCCCCCCCTCTAG

Figure 9

Ova R1435:

GGGAGAAAGCUUACCAUGGGCAGCAUCGGGGCCGCGUCGAUGGAGUU
CUGCUUCGACGUGUUCAAGGAGCUGAAGGUCCACCACGCCAACGAGAA
CAUCUUCUACUGCCCGAUCGCCAUCAUGAGCGCGCUCGCCAUGGUGUA
CCUGGGCGCCAAGGACAGCACCCGGACGCAGAUCAACAAGGUGGUCC
GCUUCGACAAGCUGCCCGGCUUCGGGGACUCGAUCGAGGCGCAGUGC
GGCACCAGCGUGAACGUGCACAGCUCGCUCCGGGACAUCCUGAACCAG
AUCACCAAGCCGAACGACGUCUACAGCUUCAGCCUGGCCUCGCGGCUC
UACGCCGAGGAGCGCUACCCGAUCCUGCCCGAGUACCUGCAGUGCGU
GAAGGAGCUCUACCGGGGCGGGCUGGAGCCGAUCAACUUCCAGACGG
CGGCCGACCAGGCCCGGGAGCUGAUCAACAGCUGGGUGGAGAGCCAG
ACCAACGGCAUCAUCCGCAACGUCCUCCAGCCGUCGAGCGUGGACAGC
CAGACCGCGAUGGUGCUGGUCAACGCCAUCGUGUUCAAGGGCCUGUG
GGAGAAGACGUUCAAGGACGAGGACACCCAGGCCAUGCCCUUCCGGG
UGACCGAGCAGGAGUCGAAGCCGGUCCAGAUGAUGUACCAGAUCGGG
CUCUUCCGGGUGGCGAGCAUGGCCAGCGAGAAGAUGAAGAUCCUGGA
GCUGCCGUUCGCCUCGGGCACGAUGAGCAUGCUCGUGCUGCUGCCCG
ACGAGGUCAGCGGCCUCGAGCAGCUGGAGUCGAUCAUCAACUUCGAGA
AGCUGACCGAGUGGACCAGCAGCAACGUGAUGGAGGAGCGCAAGAUCA
AGGUGUACCUCCCGCGGAUGAAGAUGGAGGAGAAGUACAACCUGACGU
CGGUCCUGAUGGCGAUGGGGAUCACCGACGUGUUCAGCAGCUCGGCC
AACCUCAGCGGCAUCAGCUCGGCCGAGAGCCUGAAGAUCAGCCAGGCG
GUGCACGCCGCCCACGCGGAGAUCAACGAGGCCGGCCGGGAGGUCGU
GGGGUCGGCCGAGGCGGGCGUGGACGCCGCCAGCGUCAGCGAGGAG
UUCCGCGCGGACCACCCGUUCCUGUUCUGCAUCAAGCACAUCGCCACC
AACGCCGUGCUCUUCUUCGGCCGGUGCGUGUCGCCCGACCACUAGU
UAUAAGACUGACUAGCCCGAUGGGCCUCCCAACGGGCCCUCCUCCCCU
CCUUGCACCGAGAUUAAUAAAAAAAAAAAAAAAAAAAAAAAAAAAAA
AAAAAAAAAAAAAAAAAAAAAAAAAAAAAUAUUCCCCCCCCCCCCC
CCCCCCCCCCCCCCCCUCUAG

Figure 10

VACCINE COMPOSITION COMPRISING COMPLEXED IMMUNOSTIMULATORY NUCLEIC ACIDS AND ANTIGENS PACKAGED WITH DISULFIDE-LINKED POLYETHYLENEGLYCOL/PEPTIDE CONJUGATES

This application is a continuation of U.S. application Ser. No. 13/824,449, filed Jun. 17, 2013, filed as a national phase application under 35 U.S.C. § 371 of International Application No. PCT/EP2012/000614, filed Feb. 10, 2012, which claims priority to International Application No. PCT/EP2011/000827, filed Feb. 21, 2011, each of which is hereby incorporated herein by reference.

The present invention is directed to an inventive composition or vaccine composition comprising a) an adjuvant component comprising or consisting of at least one immunostimulatory nucleic acid sequence, complexed with a complexing agent; b) an antigen, preferably a protein or peptide antigen and/or a nucleic acid sequence encoding said antigen; and c) a carrier molecule for combined packaging the adjuvant component and the antigen. The present invention is also directed to the first medical use of such an inventive composition or vaccine composition and to the second medical use of such an inventive composition or vaccine composition or components thereof for the treatment of diseases, such as infectious or cancer or tumour diseases as defined herein. The present invention furthermore discloses kits comprising such a composition or vaccine composition.

Induction and/or enhancement of immune responses of the innate and/or the adaptive immune system plays an important role in the treatment and prevention of numerous diseases. For such a purpose, the immune system is typically modulated by, e.g., via administration of an immunostimulatory agent, an adjuvant and/or a vaccine. However, the immune system of vertebrates such as humans is very complex and finely regulated. It consists of many types of proteins, cells, organs, and tissues, which interact in an elaborate and dynamic network. The immune system typically protects these organisms from infections with layered defences of increasing specificity. One layer of defence comprises physical or chemical barriers and allows an a priorielimination of at least some pathogens and antigens. A further layer of defence includes the innate and the adaptive immune system.

The innate immune system as part of the immune system is the dominant system of host defense in most organisms and comprises barriers such as humoral and chemical barriers including, e.g., inflammation, the complement system and cellular barriers. The innate immune system is typically based on a small number of receptors, called pattern recognition receptors. They recognize conserved molecular patterns that distinguish foreign organisms, like viruses, bacteria, fungi and parasites from cells of their hosts. Such pathogen-associated molecular patterns include viral nucleic acid sequences, components of bacterial and fungal walls, flagellar proteins, and more.

As part of the more complex immune response of vertebrates, the immune system adapts over time to recognize particular pathogens or antigens more efficiently (adaptive immune system). This adaptation process creates immunological memories and allows even more effective protection during future encounters with these pathogens. This process of adaptive or acquired immunity forms the basis for vaccination strategies. In contrast to the innate immune system as described above, the adaptive immune system is antigen-specific and requires the recognition of specific "self" or "non-self" antigens during a process called antigen presentation. Furthermore, unlike cells of the innate immune system, which recognize and respond to pathogens in a generic way, the adaptive immune system confers long-lasting or protective immunity to the host and thus allows a more tailored response to specific pathogens, pathogen-infected cells or antigens. The ability to mount these tailored responses is maintained in the body by so called "memory cells". Should an antigen or a pathogen enter/infect the body more than once, these specific memory cells are used to quickly eliminate it. The adaptive immune system thus allows for a stronger immune response as well as an immunological memory, wherein different immune responses are possible in favour of specific diseases. E.g., in case of infections, each pathogen is "remembered" by a signature antigen, whereas in case of cancer diseases tumour antigens or self-antigens may be recognized and neutralized by the adaptive immune system.

Both basic mechanisms of the immune system, i.e. the innate immune system as well as the adaptive immune system, may thus form targets for curative treatments and prevention of numerous diseases. Appropriate methods, which are presently known in the art, either utilize adjuvants to elicit an innate immune response or utilize antigens, pathogens or immunogens in order to evoke an adaptive immune response, or, in some rare cases, both.

An adaptive immune response may be elicited by administering to the cells or the host organism a specific foreign antigen as described above. Such an antigen may be either in the form of the peptide or protein antigens or the antigen may be encoded by a nucleic acid sequence, e.g. a cDNA or a messenger RNA. In order to elicit an efficient adaptive immune response, an additional unspecific stimulation of the innate immune system is advantageous, e.g. when providing an unspecific stimulus parallel to the antigen specific signal. The parallel unspecific stimulus turns the immune system into an activated state, which improves an adaptive immune response. Compounds capable of providing such an unspecific immune response are typically termed "adjuvants". A number of compounds and compositions have been proposed as adjuvants in the prior art, for example Freund's adjuvant, metal oxides, e.g. alum (aluminium hydroxide), inorganic chelates or salts thereof, various paraffin-like oils, synthetic resins, alginates, mucoids, polysaccharide compounds, caseinates, as well as compounds isolated from blood and/or blood clots, such as, for example, fibrin derivatives, etc. These adjuvants typically may be used in combination with other compounds, such as e.g. proteins, peptides, DNA or RNA molecules or other therapeutically active compounds, dependent on the result to be achieved.

However, free messenger RNA (mRNA) molecules, cDNAs or nucleic acid sequences in general, which may encode a specific antigen or any other therapeutically active protein, suitable for a specific therapy, typically do not show a significant or even no immunostimulatory property. Nevertheless, such immunostimulatory properties may be conferred to the mRNA molecule, the cDNA or the nucleic acid sequence, when complexed with a peptide or protein, such as protamin or a nucleic acid sequence binding protein. In this context, the mRNA molecule or the nucleic acid sequence may be formulated such, that a complex is formed between the mRNA molecule or the nucleic acid sequence and the peptide or protein, wherein different complexes may be formed between the mRNA molecule or the nucleic acid sequence and the peptide or protein. Particularly strong (adjuvant) complexes can occur, when the nucleic acid sequence, which is usually negatively charged at neutral pH, is bound by a cationic or polycationic peptide or protein.

When using mRNA or coding nucleic acid sequences in vaccination methods, translation of the mRNA or coding nucleic acid sequence in vivo remains the most important and essential factor for inducing an adaptive immune response or for expressing the encoded protein in general, e.g. in case of a therapeutically active protein or peptide. Accordingly, the complexed mRNA or coding nucleic acid sequence will have to be released from the complex with the (cationic) peptide or protein subsequent to transfection of the complex into the cells to allow efficient translation of the mRNA. Unfortunately, this does not occur in most cases. More typically, complexing the mRNA molecule or the nucleic acid sequence with a cationic or polycationic compound may even prevent the nucleic acid sequence from translation or at least significantly reduce the translation rate in vivo due to the strong binding of the polycationic compound to the mRNA molecule, cDNA or nucleic acid sequence in general. Accordingly, it is difficult to obtain a good immunostimulatory property of the composition with regard to the innate immune system taking these compounds and to ensure in parallel an efficient translation of the mRNA molecule, cDNA or nucleic acid sequence in general when using such a formulation.

One possibility to circumvent the above problem may be the administration of an adjuvant and mRNA in separated formulations. This, however, renders administration much more complicated. It is also preferred that the adjuvant and the antigen-encoding mRNA enter the same cell to achieve an optimal immune response. Furthermore, an adjuvant beneficially supports the induction of an adaptive immune response, if it induces an innate immune response in the same cell, in which the antigen is expressed by the encoding mRNA.

Another possibility to circumvent the above problem may be the exclusive administration of naked mRNA, cDNA or nucleic acid sequence. Such an approach, though advantageous for the purpose of efficient translation of the mRNA, cDNA or nucleic acid sequence in vivo, dispenses the advantageous activation of the innate immune system elicited by an adjuvant as described above. Furthermore, the naked mRNA, cDNA or nucleic acid sequence is typically degraded in vivo within an extremely short time limit, which does not allow providing efficient adaptive immune responses, when the antigen is encoded by the naked mRNA, cDNA or nucleic acid sequence.

A further approach may be the administration of an antigen in its protein or peptide form and additionally administering an adjuvant. However, this approach most likely leads to an extremely short exposition of the antigen to the immune system and thus to a poor (adaptive) immune response. It may even lead to a degradation of the antigen prior to recognition by the immune system and thus to a complete silencing of the desired immune response. Furthermore, similar problems may occur with regard to such an administration as already outlined before, since it cannot be ensured, that the adjuvant and the antigen enter the same cell to achieve an optimal immune response.

Thus, none of these approaches is in fact convincing and leads to an efficient innate and/or adaptive immune response. Moreover, if the antigen is administered in form of an mRNA, cDNA or nucleic acid sequence, the vaccination approach typically fails to provide a good translation of the administered mRNA, cDNA or nucleic acid sequence.

One obstacle in this context appears the necessity to both prevent degradation of an mRNA, cDNA or nucleic acid sequence to be administered in vivo while thereby allowing for a good transfection rate and subsequently an efficient translation. Additionally, it is necessary to enhance the immune response most efficiently and preferably to ensure that the adjuvant and the antigen enter the same cell to achieve an optimal immune response. In this context, many approaches have been carried out to enhance transfection rate and subsequently translation of a nucleic acid sequence to be administered. Such approaches, however, still do not lead to a good result in vivo.

As known to a skilled person, the full therapeutic potential of peptide-, protein-, and nucleic acid sequence-based drugs is frequently compromised by their limited ability to cross the plasma membrane of mammalian cells, resulting in poor cellular access and inadequate therapeutic efficacy. Today this hurdle represents a major challenge for the biomedical development and commercial success of many biopharmaceuticals (see e.g. Foerg and Merkle, Journal of Pharmaceutical Sciences, published online at www.interscience.wiley-.com, 2008, 97(1): 144-62). This hurdle also represents a major challenge, when developing new vaccines based on the transfection of an mRNA, cDNA or nucleic acid sequence encoding an antigen or a therapeutically active protein.

To achieve successful transfer of e.g. nucleic acid sequences into an individual's cells, a number of different hurdles have to be passed, which likewise amount for the additional administration of further components. As an example, the transport of nucleic acid sequences typically occurs via association of the nucleic acid sequence with the cell membrane and subsequent uptake by the endosomes. In the endosomes, the introduced nucleic acid sequences are separated from the cytosol. As expression occurs in the cytosol, these nucleic acid sequences have to depart the cytosol. If the nucleic acid sequences do not manage departing the cytosol, either the endosome fuses with the lysosome leading to a degradation of its content, or the endosome fuses with the cell membrane leading to a return of its content into the extracellular medium. For efficient transfer of nucleic acid sequences, the endosomal escape thus appears to be one of the most important steps additional to the efficiency of transfection itself. Until now, there are different approaches addressing these issues. However, no approach was at least successful in all aspects. Furthermore, when administering a vaccine, comprising an antigen and additionally further compounds such as an adjuvant, it is necessary to ensure that the antigen and the further compounds reach the same cell to provide an efficient immune response.

One approach to achieve such objects may be the use of cationic polymers for formulating and transfecting such compounds. Cationic polymers turned out to be efficient in transfection of nucleic acid sequences, as they can tightly complex and condense a negatively charged nucleic acid sequence. Thus, a number of cationic polymers have been explored as carriers for in vitro and in vivo gene delivery. These include e.g. polyethylenimine (PEI), polyamidoamine and polypropylamine dendrimers, polyallylamine, cationic dextran, chitosan, cationic proteins and cationic peptides. However, although most cationic polymers share the function of condensing DNA into small particles and facilitating cellular uptake via endocytosis through charge-charge interaction with anionic sites on cell surfaces, their transfection activity and toxicity differ dramatically. Interestingly, cationic polymers exhibit better transfection efficiency with rising molecular weight due to stronger complexation of the negatively charged nucleic acid sequence cargo. However, a rising molecular weight also leads to a rising toxicity of the cationic polymer. PEI is perhaps the most active and most studied polymer for gene delivery, but its main drawback as a transfection reagent relates to its non-biodegradable nature and toxicity. Furthermore, even though polyplexes formed by high molecular weight polymers exhibit improved stability under physiological conditions, data have indicated that such polymers can hinder nucleic acid sequence unpacking. For example, poly (L-lysine) (PLL) of 19 and 36 residues was shown to dissociate from DNA more rapidly than PLL of 180 residues resulting in significantly enhanced short-term gene expression. A minimum length of six to eight cationic amino acids is required to compact DNA into structures active in receptor-mediated gene delivery. However, polyplexes formed with short polycations are unstable under physiological conditions and typically aggregate rapidly in physiological salt solutions. To overcome this negative impact, Read et al. (see Read, M. L., K. H. Bremner, et al. (2003). "Vectors based on reducible polycations facilitate intracellular release of nucleic acid sequences." J Gene Med 5(3): 232-45; and Read, M. L., S. Singh, et al. (2005). "A versatile reducible polycation-based system for efficient delivery of a broad range of nucleic acid sequences." Nucleic acid sequences Res 33(9): e86) developed a new type of synthetic vector based on a linear reducible polycation (RPC) prepared by oxidative polycondensation of the peptide Cys-Lys$_{10}$-Cys that can be cleaved by the intracellular environment to facilitate release of nucleic acid sequences. They could show that polyplexes formed by RPC are destabilised by reducing conditions enabling efficient release of DNA and mRNA. Cleavage of the RPC also reduced toxicity of the polycation to levels comparable with low molecular weight peptides. The disadvantage of this approach of Read et al. (2003, supra) was that the endosomolytic agent chloroquine or the cationic lipid DOTAP was additionally necessary to enhance transfection efficiency to adequate levels. As a consequence Read et al. (2005, supra) included histidine residues in the RPCs which have a known endosomal buffering capacity. They could show that histidine-rich RPCs can be cleaved by the intracellular reducing environment enabling efficient cytoplasmic delivery of a broad range of nucleic acid sequences, including plasmid DNA, mRNA and siRNA molecules without the requirement for the endosomolytic agent chloroquine.

Unfortunately; Read et al. (2005, supra) did not assess whether histidine-rich RPCs can be directly used for in vivo applications. In their study, transfections were performed in the absence of serum to avoid masking the ability of histidine residues to enhance gene transfer that may have arisen from binding of serum proteins to polyplexes restricting cellular uptake. Preliminary experiments indicate that the transfection properties of histidine-rich RPC polyplexes can be affected by the presence of serum proteins with a 50% decrease in GFP-positive cells observed in 10% FCS (fetal calf serum). For in vivo application they propose modifications with the hydrophilic polymer poly-[N-(2hydroxy-propyl)methacrylamide]. Unfortunately, Read et al. (2005, supra) did not prevent aggregation of polyplexes and binding of polycationic proteins to serum proteins. Furthermore, due to the large excess of polymer, which is characterized by the high N/P ratio, strong cationic complexes are formed when complexing the nucleic acid sequence, which are only of limited use in vivo due to their strong tendency of salt induced agglomeration and interactions with serum contents (opsonization). Additionally, these complexes may excite an acute immune response, when used for purposes of gene therapy. Read et al. (2003, supra) did also not provide in vivo data for the RPC based complexes shown in the publication. It has also turned out that these strong cationic RPC based complexes are completely inactive subsequent to local administration into the dermis. Furthermore Read et al. (2005, supra) used stringent oxidation conditions (30% DMSO) to induce the generation of high molecular polymers with as long as possible chain lengths ("step-growth polymerization") to ensure complete complexation of the nucleic acid sequence cargo.

In an approach similar to Read et al. (2005, supra) McKenzie et al. (McKenzie, D. L., K. Y. Kwok, et al. (2000), J Biol Chem 275(14): 9970-7, McKenzie, D. L., E. Smiley, et al. (2000), Bioconjug Chem 11(6): 901-9, and U.S. Pat. No. 6,770,740 B1) developed self-crosslinking peptides as gene delivery agents by inserting multiple cysteines into short synthetic peptides for the purpose of decreasing toxicity as observed with high-molecular polycations. For complexation of DNA they mixed the self-crosslinking peptides with DNA to induce interpeptide disulfide bonds concurrently to complexation of the DNA cargo. For in vivo gene delivery approaches they propose the derivatization of the self-crosslinking peptides with a stealthing (e.g. polyethylene glycol) or targeting agent operatively attached to the peptide at a site distal from each terminus. In a further approach the same authors developed for the purpose of masking DNA peptide condensates and thereby reducing interaction with blood components, the derivatization of the non crosslinking cationic peptide CWK$_{18}$ with polyethylene glycol by reducible or non-reducible linkages (Kwok, K. Y., D. L. McKenzie, et al. (1999). "Formulation of highly soluble poly(ethylene glycol)-peptide DNA condensates." J Pharm Sci 88(10): 996-1003).

Summarizing the above, the present prior art utilizing cationic polymers suffers from various disadvantages. One particular disadvantage of the self-crosslinking peptides as described by Read et al. (2003, supra) or McKenzie et al. (2000 I and II, supra and U.S. Pat. No. 6,770,740 B1) concerns the high positive charge on the surface of the particles formed. Due to the high positive charge the particles exhibit a high instability towards agglomeration when subjecting these particles in vivo to raised salt concentrations. Such salt concentrations, however, typically occur in vivo in cells or extracellular media. Furthermore, high positively charged complexes show a strong tendency of opsonization. This leads to an enhanced uptake by macrophages and furthermore to a fast inactivation of the complex due to degradation. Additionally, in biological systems positively charged complexes can easily be bound or immobilized by negatively charged components of the extracellular matrix or the serum. Also, the nucleic acid sequences in the complex may be released too early, leading to reduced efficiency of the transfer and half life of the complexes in vivo. Furthermore, a reversible derivatization of carriers with a stealthing agent being advantageous for in vivo gene delivery, such as polyethylene glycol (PEG), was only possible for peptide monomers but not for self-crosslinking peptides or rather for a polymeric carrier with a defined polymer chain length. In particular, such a reversible derivatization was not possible at the terminal ends of the cross-linked cationic peptide carrier. Additionally, in the prior art only high-molecular polymers with long polymer chains or with an undefined polymer chain length consisting of self-crosslinking peptides were described, which unfortunately compact their cargo to such an extent that cargo release in the cell is limited. The extremely undefined polymer chain length is further problematic regarding approvement of a medicament based on RPC. One precondition for an approvement of a medicament is that every preparation of the medicament has always the same composition, the same structure and the same properties. This cannot be ensured for complexes based on RPC's from the prior art. Furthermore the RPC-based polymers or complexes provided in the prior art are difficult to characterize due to their undefined structure or polymer chain length. But characterization of the resulting complex or of the polymeric carrier is absolutely necessary for the approvement of a medicament.

Accordingly, there is still the need in the art for providing an efficient method for vaccination, which allows eliciting an adaptive immune response, wherein the administration is not severely impaired by early degradation of the antigen or by an inefficient translation of the mRNA due to inefficient release of the mRNA in the cell. Most importantly, there is an intensive need in the art to allow for provision of additional components, such as e.g. an adjuvant compound, and to provide same to the same cell together with the antigen before the antigen or the further component is metabolically cleaved.

This object is solved by the subject matter of the present invention, preferably by the subject matter of the attached claims. Particularly, the present invention solves the above object according to a first embodiment by a composition, preferably a vaccine composition, comprising or consisting of:

a) an adjuvant component comprising or consisting of at least one immunostimulatory nucleic acid sequence, complexed with a complexing agent;
b) an antigen, preferably a protein or peptide antigen and/or a nucleic acid sequence encoding said antigen; and
c) a carrier molecule for combined packaging the adjuvant component and the antigen.

The inventive composition or vaccine composition is preferably capable to elicit an innate and an adaptive immune response due to both the adjuvant component and the antigen contained in the inventive composition or vaccine composition, wherein the administration of the inventive composition or vaccine composition is preferably not impaired by early degradation of the antigen or by inefficient translation of a nucleic acid sequence encoding such an antigen. The inventive composition or vaccine composition; due to the use of one carrier molecule for both the adjuvant component and the antigen, furthermore ensures that the adjuvant component and the antigen are transported to the same cell before they can be metabolically cleaved or cleared from the tissue or cells. Furthermore, the carrier molecule of the inventive composition or vaccine composition as such can be cleared from the tissue subsequent to the release of its cargo before it can accumulate and reach toxic levels. The carrier also prevents agglomeration of the adjuvant component comprising or consisting of at least one immunostimulatory nucleic acid sequence, complexed with a complexing agent. The carrier furthermore efficiently prevents degradation of the antigen by RNAses, when provided as a nucleic acid sequence. Finally, the inventive composition or vaccine composition allows for incorporation of endosomolytic peptides into the vaccine, preferably into the carrier of the inventive composition or vaccine composition and/or into the complex of the adjuvant component with a complexing agent, via simplified administration of such an endosomolytic peptide to the specific component during preparation of said component.

According to the first embodiment, the inventive composition or vaccine composition comprises an adjuvant component comprising or consisting of at least one immunostimulatory nucleic acid sequence, complexed with a complexing agent. In this context, the at least one immunostimulatory nucleic acid sequence may be selected from any nucleic acid sequence, known to a skilled person to be immunostimulatory, including, without being limited thereto, immunostimulatory CpG nucleic acid sequences, immunostimulatory RNA (is)RNA, ribosomal RNA (rRNA), transfer RNA (tRNA), messenger RNA (mRNA), viral RNA (vRNA), etc. Such an immunostimulatory nucleic acid may comprise a length of about 1000 to 5000, of 500 to 5000, of 5 to 5000, or of 5 to 1000, 5 to 500, 5 to 250, of 5 to 100, of 5 to 50 or of 5 to 30 nucleotides but also a length of about 10 to 1000, 10 to 500, 20 to 500, 30 to 500, 40 to 500 or 50 to 500 nucleotides.

According to one aspect, the at least one immunostimulatory nucleic acid sequence of the adjuvant component as defined herein may be selected from an immunostimulatory CpG nucleic acid sequence, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid sequence used according to the invention is preferably in the form of CpG-RNA or CpG-DNA, more preferably in the form of single-stranded CpG-RNA (ss CpG-RNA) or CpG-DNA. Also preferably, such CpG nucleic acid sequences have a length as described above. Preferably the CpG motifs are unmethylated.

Likewise, according to a further aspect, the at least one immunostimulatory nucleic acid sequence may be selected from an immunostimulatory RNA (isRNA), which preferably elicits an innate immune response. Such an immunostimulatory RNA may be any (double-stranded or single-stranded) RNA, e.g. a coding RNA, as defined herein. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) single-stranded) non-coding RNA. In this context it is particular preferred that the isRNA carries a triphosphate at its 5'-end which is the case for in vitro transcribed RNA.

An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system, which may support an adaptive immune response, may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1 TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc NatlAcadSci USA 98, 9237-42). Furthermore, it has been reported that ligands for certain TLRs include certain nucleic acid sequences and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The immunostimulatory RNA (isRNA) used as the at least one immunostimulatory nucleic acid sequence of the adjuvant component as defined herein may thus comprise any RNA sequence known to be immunostimulatory, including, without being limited thereto, RNA sequences representing and/or encoding ligands of TLRs, preferably selected from human family members TLR1 TLR10 or murine family members TLR1 TLR13, more preferably selected from (human) family members TLR1 TLR10, even more preferably from TLR7 and TLR8, ligands for intracellular receptors for RNA (such as RIG-I or MDA-5, etc) (see e.g. Meylan, E., Tschopp, J. (2006), Mol. Cell 22, 561-569), or any other immunostimulatory RNA sequence. Furthermore, (classes of) immunostimulatory RNA molecules, used as the at least one immunostimulatory nucleic acid sequence of the adjuvant component as defined herein may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides or a length as defined above.

According to a particularly preferred aspect, such immunostimulatory nucleic acid sequences, particularly isRNA, used as the at least one immunostimulatory nucleic acid sequence of the adjuvant component as defined herein, may preferably consist of or comprise a nucleic acid sequence of formula (I) or (II):

$$G_l X_m G_n \quad \text{(formula (I))}$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
  wherein
  when l=1 G is guanosine or an analogue thereof,
  when l>1 at least 50% of the nucleotides are guanosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 G is guanosine or an analogue thereof,
  when n>1 at least 50% of the nucleotides are guanosine or an analogue thereof.

$$C_l X_m C_n \quad \text{(formula (II))}$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
  wherein
  when l=1 C is cytosine or an analogue thereof,
  when l>1 at least 50% of the nucleotides are cytosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 C is cytosine or an analogue thereof,
  when n>1 at least 50% of the nucleotides are cytosine or an analogue thereof.

The nucleic acid sequences of formula (I) or (II), which may be used as the at least one immunostimulatory nucleic acid sequence of the adjuvant component as defined herein, may be relatively short nucleic acid sequences with a typical length of approximately from 5 to 100 (but may also be longer than 100 nucleotides for specific aspects, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the at least one immunostimulatory nucleic acid sequence of the adjuvant component as defined herein has a maximum length of e.g. 100 nucleotides, m will typically be <=98. The number of nucleotides G in the nucleic acid sequence of formula (I) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_l$ or $G_n$ can be, for example, a GUGU, GGUU, UGUG, UUGG, GUUG, GGGU, GGUG, GUGG, UGGG or GGGG, etc.; when l or n=5 $G_l$ or $G_n$ can be, for example, a GGGUU, GGUGU, GUGGU, UGGGU, UGGUG, UGUGG, UUGGG, GUGUG, GGGUG, GGGGU, GGUGG, GUGGG, GUGGG, UGGGG, or GGGGG, etc.; etc. A nucleotide adjacent to $X_m$ in the nucleic acid sequence of formula (I)

according to the invention is preferably not a uracil. Similarly, the number of nucleotides C in the nucleic acid sequence of formula (II) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_l$ or $C_n$ can be, for example, a CUCU, CCUU, UCUC, UUCC, CUUC, CCCU, CCUC, CUCC, UCCC or CCCC, etc.; when l or n=5 $C_l$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid sequence of formula (I) according to the invention is preferably not a uracil. Preferably, for formula (I), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (II).

According to a particularly preferred aspect, a nucleic acid sequence according to any of formulas (I) or (II) above, which may be used as the at least one immunostimulatory nucleic acid sequence of the adjuvant component as defined herein, may be selected from a sequence preferably consisting of or comprising any of the following sequences:

```
                                            (SEQ ID NO: 1)
GGUUUUUUUUUUUUUUUGGG;

(SEQ ID NO: 2)
GGGGGUUUUUUUUUUGGGGG;

(SEQ ID NO: 3)
GGGGGUUUUUUUUUUUUUUUUUUUUUUUUUUGGGGG;

(SEQ ID NO: 4)
GUGUGUGUGUGUUUUUUUUUUUUUUUGUGUGUGUGU;

(SEQ ID NO: 5)
GGUUGGUUGGUUUUUUUUUUUUUUUGGUUGGUUGGUU;

(SEQ ID NO: 6)
GGGGGGGGGUUUGGGGGGGG;

(SEQ ID NO: 7)
GGGGGGGGUUUUGGGGGGGG;

(SEQ ID NO: 8)
GGGGGGGUUUUUGGGGGGG;

(SEQ ID NO: 9)
GGGGGGGUUUUUUGGGGGG;

(SEQ ID NO: 10)
GGGGGGUUUUUUUGGGGGG;

(SEQ ID NO: 11)
GGGGGGUUUUUUUUGGGGG;

(SEQ ID NO: 12)
GGGGGGUUUUUUUUUGGGG;

(SEQ ID NO: 13)
GGGGGUUUUUUUUUUUGGGG;

(SEQ ID NO: 14)
GGGGGUUUUUUUUUUUUGGG;

(SEQ ID NO: 15)
GGGGUUUUUUUUUUUUUGGG;

(SEQ ID NO: 16)
GGGGUUUUUUUUUUUUUUGG;

(SEQ ID NO: 17)
GGUUUUUUUUUUUUUUUUGG;

(SEQ ID NO: 18)
GUUUUUUUUUUUUUUUUUUG;

(SEQ ID NO: 19)
GGGGGGGGGGUUUGGGGGGGGG;

(SEQ ID NO: 20)
GGGGGGGGGUUUUGGGGGGGGG;

(SEQ ID NO: 21)
GGGGGGGGUUUUUGGGGGGGG;

(SEQ ID NO: 22)
GGGGGGGGUUUUUUGGGGGGG;

(SEQ ID NO: 23)
GGGGGGGUUUUUUUGGGGGGG;

(SEQ ID NO: 24)
GGGGGGGUUUUUUUUGGGGGG;

(SEQ ID NO: 25)
GGGGGGGUUUUUUUUUGGGGG;

(SEQ ID NO: 26)
GGGGGGUUUUUUUUUUGGGGG;

(SEQ ID NO: 27)
GGGGGGUUUUUUUUUUUGGGG;

(SEQ ID NO: 28)
GGGGGUUUUUUUUUUUUGGGG;

(SEQ ID NO: 29)
GGGGGUUUUUUUUUUUUUGGG;

(SEQ ID NO: 30)
GGGUUUUUUUUUUUUUUUGGG;

(SEQ ID NO: 31)
GGUUUUUUUUUUUUUUUUUGG;

(SEQ ID NO: 32)
GGGGGGGGGGUUUGGGGGGGGGG;

(SEQ ID NO: 33)
GGGGGGGGGGUUUUGGGGGGGGGG;

(SEQ ID NO: 34)
GGGGGGGGGUUUUUGGGGGGGGG;

(SEQ ID NO: 35)
GGGGGGGGGUUUUUUGGGGGGGGG;

(SEQ ID NO: 36)
GGGGGGGGUUUUUUUGGGGGGGG;

(SEQ ID NO: 37)
GGGGGGGGUUUUUUUUGGGGGGG;

(SEQ ID NO: 38)
GGGGGGGGUUUUUUUUUGGGGGG;

(SEQ ID NO: 39)
GGGGGGGUUUUUUUUUUGGGGGG;
```

-continued

GGGGGGGUUUUUUUUUUUGGGGG; (SEQ ID NO: 40)

GGGGGGUUUUUUUUUUUGGGGG; (SEQ ID NO: 41)

GGGGGGUUUUUUUUUUUGGGG; (SEQ ID NO: 42)

GGGGUUUUUUUUUUUUUGGGG; (SEQ ID NO: 43)

GGGUUUUUUUUUUUUUUGGG; (SEQ ID NO: 44)

GUUUUUUUUUUUUUUUUUUUUG; (SEQ ID NO: 45)

GGUUUUUUUUUUUUUUUUUUUGG; (SEQ ID NO: 46)

GGGUUUUUUUUUUUUUUUUUUUUGGG; (SEQ ID NO: 47)

GGGGUUUUUUUUUUUUUUUUUUUUGGG; (SEQ ID NO: 48)

GGGGGUUUUUUUUUUUUUUUUUUUUUGGGG; (SEQ ID NO: 49)

GGGGGGUUUUUUUUUUUUUUUUUUUUUUGGGGG; (SEQ ID NO: 50)

GGGGGGGUUUUUUUUUUUUUUUUUUUUUUUGGGGGG; (SEQ ID NO: 51)

GGGGGGGGUUUUUUUUUUUUUUUUUUUUUUUUGGGGGGG; (SEQ ID NO: 52)

GGGGGGGGGUUUUUUUUUUUUUUUUUUUUUUUUUGGGGGGGG; (SEQ ID NO: 53)

GGUUUGG; (SEQ ID NO: 54)

GGUUUUGG; (SEQ ID NO: 55)

GGUUUUUGG; (SEQ ID NO: 56)

GGUUUUUUGG; (SEQ ID NO: 57)

GGUUUUUUUGG; (SEQ ID NO: 58)

GGUUUUUUUUGG; (SEQ ID NO: 59)

GGUUUUUUUUUGG; (SEQ ID NO: 60)

GGUUUUUUUUUUGG; (SEQ ID NO: 61)

GGUUUUUUUUUUUGG; (SEQ ID NO: 62)

GGUUUUUUUUUUUUGG; (SEQ ID NO: 63)

GGUUUUUUUUUUUUUGG; (SEQ ID NO: 64)

GGUUUUUUUUUUUUUUGG; (SEQ ID NO: 65)

GGUUUUUUUUUUUUUUUGG; (SEQ ID NO: 66)

GGGUUUGGG; (SEQ ID NO: 67)

GGGUUUUGGG; (SEQ ID NO: 68)

GGGUUUUUGGG; (SEQ ID NO: 69)

GGGUUUUUUGGG; (SEQ ID NO: 70)

GGGUUUUUUUGGG; (SEQ ID NO: 71)

GGGUUUUUUUUGGG; (SEQ ID NO: 72)

GGGUUUUUUUUUGGG; (SEQ ID NO: 73)

GGGUUUUUUUUUUGGG; (SEQ ID NO: 74)

GGGUUUUUUUUUUUGGG; (SEQ ID NO: 75)

GGGUUUUUUUUUUUUGGG; (SEQ ID NO: 76)

GGGUUUUUUUUUUUUUGGG; (SEQ ID NO: 77)

GGGUUUUUUUUUUUUUGGGUUUUUUUUUUUUUGGGUUUUUUUUUUUUUUGGG; (SEQ ID NO: 78)

GGGUUUUUUUUUUUUUGGGGGUUUUUUUUUUUUUUGGG; (SEQ ID NO: 79)

GGGUUUGGGUUUGGGUUUGGGUUUGGGUUUGGGUUUGGGUUUGGG; (SEQ ID NO: 80)

GGUUUUUUUUUUUUUUUGGG (short GU-rich, SEQ ID NO: 81)

or

CCCUUUUUUUUUUUUUCCCUUUUUUUUUUUUUUCCCUUUUUUUUUUUUUUCCC (SEQ ID NO: 82)

CCCUUUCCCUUUCCCUUUCCCUUUCCCUUUCCCUUUCCCUUUCCCUUUCC C (SEQ ID NO: 83)

CCCUUUUUUUUUUUUUCCCCCUUUUUUUUUUUUUUCCC (SEQ ID NO: 84)

or from a sequence having at least 60%, 70%, 80%, 90%, or even 95% sequence identity with any of these sequences According to a further particularly preferred aspect, an immunostimulatory nucleic acid sequence, particularly an isRNA, used as the at least one immunostimulatory nucleic acid sequence of the adjuvant component as defined herein, preferably consists of or comprises a nucleic acid sequence of formula (III) or (IV):

$$(N_uG_lX_mG_nN_v)_a,$$ (formula (III))

wherein:

G is guanosine (guanine), uridine (uracil) or an analogue of guanosine (guanine) or uridine (uracil), preferably guanosine (guanine) or an analogue thereof;

X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleotides (nucleosides), each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
 wherein when l=1, G is guanosine (guanine) or an analogue thereof,
  when l>1, at least 50% of these nucleotides (nucleosides) are guanosine (guanine) or an analogue thereof;
m is an integer and is at least 3;
 wherein when m=3, X is uridine (uracil) or an analogue thereof, and when m>3, at least 3 successive uridines (uracils) or analogues of uridine (uracil) occur;
n is an integer from 1 to 40,
 wherein when n=1, G is guanosine (guanine) or an analogue thereof,
  when n>1, at least 50% of these nucleotides (nucleosides) are guanosine (guanine) or an analogue thereof;
u, v may be independently from each other an integer from 0 to 50,
 preferably wherein when u=0, v≥1, or when v=0, u≥1;
wherein the immunostimulatory nucleic acid sequence of formula (III) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a \quad \text{(formula (IV))}$$

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleotides (nucleosides), each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
 wherein when l=1, C is cytidine (cytosine) or an analogue thereof,
  when l>1, at least 50% of these nucleotides (nucleosides) are cytidine (cytosine) or an analogue thereof;
m is an integer and is at least 3;
 wherein when m=3, X is uridine (uracil) or an analogue thereof,
  when m>3, at least 3 successive uridines (uracils) or analogues of uridine (uracil) occur;
n is an integer from 1 to 40,
 wherein when n=1, C is cytidine (cytosine) or an analogue thereof,
  when n>1, at least 50% of these nucleotides (nucleosides) are cytidine (cytosine) or an analogue thereof.
u, v may be independently from each other an integer from 0 to 50,
 preferably wherein when u=0, v≥1, or when v=0, u≥1;
wherein the immunostimulatory nucleic acid sequence of formula (IV) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (IV), any of the definitions given above for elements N (i.e. $N_u$ and $N_v$) and X ($X_m$), particularly the core structure as defined above, as well as for integers a, l, m, n, u and v, similarly apply to elements of formula (IV) correspondingly, wherein in formula (IV) the core structure is defined by $C_l X_m C_u$. The definition of bordering elements $N_u$ and $N_v$ is identical to the definitions given above for $N_u$ and N.

According to a very particularly preferred aspect, the nucleic acid sequence according to formula (III), used as the at least one immunostimulatory nucleic acid sequence of the adjuvant component as defined herein, may be selected from e.g. any of the following sequences:

(SEQ ID NO: 85)
UAGCGAAGCUCUUGGACCUAGGUUUUUUUUUUUUUUGGGUGCGUUCCUA

GAAGUACACG (SEQ ID NO: 86)
UAGCGAAGCUCUUGGACCUAGGUUUUUUUUUUUUUUGGGUGCGUUCCUA

GAAGUACACGAUCGCUUCGAGAACCUGGAUCCAAAAAAAAAAAAAACCC

ACGCAAGGAUCUUCAUGUGC (SEQ ID NO: 87)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUC (SEQ ID NO: 88)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUUAACGAACGGCUCCUCCUCUUAGACUGCAGCGUAAGUGCGGAAU

CUGGGGAUCAAAUUACUGACUGCCUGGAUUACCCUCGGACAUAUAACCUU

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAG (SEQ ID NO: 89)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUAACGAACGGCUCCUCCUCUUAGACUGCAGCGUAAGUGCGGAAU

CUGGGGAUCAAAUUACUGACUGCCUGGAUUACCCUCGGACAUAUAACCUU

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAGAGC

UACGCAGGUUCGCAAUAAAAGCGUUGAUUAGUGUGCAUAGAACAGACCUC

UUAUUCGGUGAAACGCCAGAAUGCUAAAUUCCAAUAACUCUUCCCAAAAC

GCGUACGGCCGAAGACGCGCGCUUAUCUUGUGUACGUUCUCGCACAUGGA

AGAAUCAGCGGGCAUGGUGGUAGGGCAAUAGGGGAGCUGGGUAGCAGCGA

AAAAGGGCCCCUGCGCACGUAGCUUCGCUGUUCGUCUGAAACAACCCGGC

AUCCGUUGUAGCGAUCCCGUUAUCAGUGUUAUUCUUGUGCGCACUAAGAU

UCAUGGUGUAGUCGACAAUAACAGCGUCUUGGCAGAUUCUGGUCACGUGC

CCUAUGCCCGGGCUUGUGCCUCUCAGGUGCACAGCGAUACUUAAAGCCUU

CAAGGUACUCGACGUGGGUACCGAUUCGUGACACUUCCUAAGAUUAUUCC

ACUGUGUUAGCCCCGCACCGCCGACCUAAACUGGUCCAAUGUAUACGCAU

UCGCUGAGCGGAUCGAUAAUAAAAGCUUGAAUU (SEQ ID NO: 90)
GGGAGAAAGCUCAAGCUUAUCCAAGUAGGCUGGUCACCUGUACAACGUAG

CCGGUAUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUAGUAAAUGCGUCUAC

UGAAUCCAGCGAUGAUGCUGGCCCAGAUC (R 722 SEQ ID NO: 91)
GGGAGAAAGCUCAAGCUUAUCCAAGUAGGCUGGUCACCUGUACAACGUAG

CCGGUAUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUA (SEQ ID NO: 92)
GGGAGAAAGCUCAAGCUUAUCCAAGUAGGCUGGUCACCUGUACAACGUAG

CCGGUAUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUAGAAC

GAACUGACCUGACGCCUGAACUUAUGAGCGUGCGUAUUUUUUUUUUUUU

UUUUUUUUUCCUCCCAACAAAUGUCGAUCAAUAGCUGGGCUGUUGGAGAC

GCGUCAGCAAAUGCCGUGGCUCCAUAGGACGUGUAGACUUCUAUUUUUUU

UUUUUUUUUUUUUCCCGGGACCACAAAUAAUAUUCUUGCUUGGUUGGGC

GCAAGGGCCCCGUAUCAGGUCAUAAACGGGUACAUGUUGCACAGGCUCCU

UUUUUUUUUUUUUUUUUUUUUCGCUGAGUUAUUCCGGUCUCAAAAGACG

GCAGACGUCAGUCGACAACACGGUCUAAAGCAGUGCUACAAUCUGCCGUG

UUCGUGUUUUUUUUUUUUUUUUUUUUGUGAACCUACACGGCGUGCACUGU

AGUUCGCAAUUCAUAGGGUACCGGCUCAGAGUUAUGCCUUGGUUGAAAAC

UGCCCAGCAUACUUUUUUUUUUUUUUUUUUUCAUAUUCCCAUGCUAAGC

AAGGGAUGCCGCGAGUCAUGUUAAGCUUGAAUU

According to another very particularly preferred aspect, the nucleic acid sequence according to formula (IV), used as the at least one immunostimulatory nucleic acid sequence of the adjuvant component as defined herein, may be selected from e.g. any of the following sequences:

(SEQ ID NO: 93)
UAGCGAAGCUCUUGGACCUACCUUUUUUUUUUUUUUCCCUGCGUUCCUAG

AAGUACACG
or (SEQ ID NO: 94)
UAGCGAAGCUCUUGGACCUACCUUUUUUUUUUUUUUUCCCUGCGUUCCUA

GAAGUACACGAUCGCUUCGAGAACCUGGAUGGAAAAAAAAAAAAAAGGG

ACGCAAGGAUCUUCAUGUGC

According to a last particularly preferred aspect, an immunostimulatory nucleic acid sequence, particularly an isRNA, used as the at least one immunostimulatory nucleic acid sequence, may be a nucleic acid encoding an antigen as defined below, preferably an RNA or mRNA encoding an antigen as defined below.

As defined according to the first embodiment of the present invention, the inventive composition or vaccine composition comprises an adjuvant component comprising or consisting of at least one immunostimulatory nucleic acid sequence, complexed with a complexing agent. Such a complexing agent is preferably any compound, which may be capable of complexing and preferably thereby condensing the immunostimulatory nucleic acid sequence contained in the adjuvant component. Such a complexing agent may be selected from e.g. peptides, proteins, polymers or any further compound capable of complexing and condensing a nucleic acid sequence.

In the context of the present invention, a complexed nucleic acid sequence is usually to be understood as a nucleic acid sequence as defined herein, preferably the at least one immunostimulatory nucleic acid sequence of the adjuvant component, which interacts with one or more complexing agent(s) as defined herein by forming a non-covalent complex between the (immunostimulatory) nucleic acid sequence and the complexing agent. Herein, "non-covalent" means that a reversible association of the (immunostimulatory) nucleic acid sequence and the complexing agent is formed by non-covalent interactions of these molecules, wherein the molecules are associated together by any type of interaction of electrons, other than a covalent bond, particularly electrostatic interactions, preferably electrostatic interactions due to charged residues contained in the molecule, but also via hydrogen bonds, salt bridges and van der Waals interactions, which provide attractive forces between molecules. Association of a nucleic acid sequence, e.g. the at least one immunostimulatory nucleic acid sequence of the adjuvant component, and at least one complexing agent may be in equilibrium with dissociation of that complex, however, when using cationic or polycationic compounds as defined herein for complexing, usually no dissociation of the formed complex occurs and thus the equilibrium is preferably fully shifted towards the complex.

According to a first aspect the complexing agent may be a cationic or polycationic compound. The so called "adjuvant component" of the inventive composition or vaccine composition is then preferably prepared by complexing the at least one immunostimulatory nucleic acid sequence of the adjuvant component with a cationic or polycationic compound, preferably in a specific ratio, to form a stable complex. In this context, it is preferably important, that no free cationic or polycationic compound or only a negligible small amount of free cationic or polycationic compound remains in the adjuvant component after complexing the at least one immunostimulatory nucleic acid sequence of the adjuvant component.

The term "cationic or polycationic compound" typically refers to a positively charged molecule, which is preferably positively charged (cation) at a pH value of about 1 to 9, more preferably of a pH value of or below 9, of or below 8, of or below 7, most preferably at physiological pH values, e.g. about 7.3 to 7.4. Accordingly, a cationic or polycationic compound, e.g. cationic peptide, protein or polymer as defined according to the present invention, is preferably positively charged under physiological conditions, particularly under physiological salt conditions of the cell in viva The definition "cationic" may also refer to "polycationic" components and vice versa.

The ratio of the at least one immunostimulatory nucleic acid sequence and the cationic or polycationic compound in the adjuvant component is typically selected from a range which allows for entirely complexing the at least one immunostimulatory nucleic acid sequence in such a way that no free cationic or polycationic compound or only a negligible small amount thereof remains in the mixture. Preferably the ratio of the at least one immunostimulatory nucleic acid sequence of the adjuvant component to the cationic or polycationic compound is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). The ratio of the at least one immunostimulatory nucleic acid sequence of the adjuvant component to the cationic or polycationic compound in the adjuvant component, if present as a protein or peptide, may also be calculated on the basis of the nitrogen/phosphate ratio (N/P-ratio) of the entire adjuvant component, which resembles the ratio of nucleic acid sequences to peptides used and present in the complex.

In the context of the present invention, an N/P-ratio is preferably in the range of about 0.01-4, preferably in a range of about 0.01-3, 0.01-2 or even 0.1-2, and more preferably in a range of about 0.1-1.5, 0.1-1.0, 0.3-2, 0.3-1.0 or 0.4-2 regarding the ratio of immunostimulatory nucleic acid sequence: cationic or polycationic peptide in the complex. Likewise preferably, this ratio is in the range of about 0.4-1.5. Such an N/P ratio preferably ensures a net negative or at least a neutral charge of the entire adjuvant component, which allows a further effective packaging of the adjuvant component, preferably in complex with the antigen as defined herein, with the carrier molecule as defined herein. Even more preferably, the adjuvant component, preferably in complex with the antigen as defined herein, comprises a negative net charge to allow more efficient binding of the adjuvant component, preferably in complex with the antigen as defined herein, and the carrier molecule as defined according to the inventive composition or vaccine composition. This avoids the risk of repelling charges and thus the risk of an early degradation of the inventive composition or vaccine composition prior to targeting a cell or tissue as a whole. Accordingly, the N/P ratios of immunostimulatory nucleic acid sequence: cationic or polycationic peptide in the adjuvant component may be most preferably in the range of about 0.01-2 or 0.1-1.5 regarding the ratio of nucleic acids: cationic or polycationic peptide in the complex, and likewise most preferably in the range of about 0.1-1.

In the context of the present invention, a cationic or polycationic compound is preferably selected from any cationic or polycationic compound suitable for complexing and thereby stabilizing (and condensing) a nucleic acid sequence, particularly the at least one immunostimulatory nucleic acid sequence of the adjuvant component, e.g. by associating the at least one immunostimulatory nucleic acid sequence of the adjuvant component with the cationic or polycationic compound. Such a cationic or polycationic compound per se does not need to exhibit any adjuvant properties, since an adjuvant property, particularly the capability of inducing an innate immune response, is preferably created upon complexing the at least one immunostimulatory nucleic acid sequence of the adjuvant component with the cationic or polycationic compound. Particularly preferred, cationic or polycationic peptides or proteins may be selected from protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, L-oligomers, Arginine-rich peptides, Calcitonin-peptides, FGF, Lactoferrin, poly-L-Lysine, poly-Arginine, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, Calcitonin peptide(s), etc.

Further preferred cationic or polycationic compounds, which can be used for complexing the at least one immunostimulatory nucleic acid sequence of the adjuvant component above may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-($\alpha$-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-di hexadecyloxypropyl-oxymethyloxy)ethyl]trimethylammonium, CLIP9: rac-[2(2,3-di hexadecyloxypropyl-oxysuccinyloxy)ethyl]-trimethylammonium, oligofectamine, or cationic or polycationic polymers, e.g. modified polyaminoacids, such as P-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Blockpolymers consisting of a combination of one or more cationic blocks (e.g. selected og a cationic polymer as mentioned above) and of one or more hydrophilic- or hydrophobic blocks (e.g polyethyleneglycole); etc. Association or complexing the at least one immunostimulatory nucleic acid sequence of the adjuvant component with cationic or polycationic compounds preferably provides adjuvant properties to the at least one nucleic acid sequence and confers a stabilizing effect to the at least one immunostimulatory nucleic acid sequence of the adjuvant component by complexation. The procedure for stabilizing the at least one immunostimulatory nucleic acid is in general as described in EP-A-1083232, the disclosure of which is incorporated by reference into the present invention in its entirety.

Further preferred cationic or polycationic compounds, which can be used for complexing the at least one immunostimulatory nucleic acid sequence of the adjuvant component above, may include oligopeptides having the following sum formula (V):

$\{(Arg)_l;(Lys)_m;(His)_n;(Orn)_o;(Xaa)_x\}$;

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10%, more preferably at least 20%, at least 30%, at least 40%, at least 50% (e.g. at least 50, 51, 52, 53, 54, 55, 56, 57, 58, or 59%) at least 60% (e.g. at least 60, 61, 62, 63, 64, 65, 66, 67, 68, or 69%), at least 70% (e.g. at least 70, 71, 72, 73, 74, 75, 76, 77, 78, or 79%), at least 80% (at least 80, 81, 82, 83, 84, 85, 86, 87, 88, or 89%) at least 90% (e.g. at least 90, 91, 92, 93, 94, 95, 96, 97, 98, or 99%), or even 100% of all amino acids of the oligopeptide of formula (V); and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide of formula (V), or at least 80%, at least 70%, at least 60%, at least 50% (e.g. at least 50, 51, 52, 53, 54, 55, 56, 57, 58, or 59%), at least 40% (e.g. at least 40, 41, 42, 43, 44, 45, 46, 47, 48, or 49%), at least 30% (e.g. at least 30, 31, 32, 33, 33, 35, 36, 37, 38, or 39%), at least 20% (e.g. at least 20, 21, 22, 23, 22, 25, 26, 27, 28, or 29%), at least 10% (e.g. at least 10, 11, 12, 13, 11, 15, 16, 17, 18, or 19%), or at least 9, 8, 7, 6, 5, 4, 3, 2, 1 or even 0%. Any of amino acids Arg, Lys, His, Orn and Xaa may be positioned at any place of the oligopeptide of formula (V). In this context cationic peptides or proteins (preferably of formula (V)) in the range of 7-30 amino acids are particular preferred.

According to a particular preferred aspect, oligopeptides of formula (V) as shown above, may, without being restricted thereto, comprise at least one of the following subgroup of formulae:

(SEQ ID NOs: 95-118)
$Arg_7, Arg_8, Arg_9, Arg_{10}, Arg_{11}, Arg_{12}, Arg_{13},$ $Arg_{14}, Arg_{15}, Arg_{16}, Arg_{17}, Arg_{18}, Arg_{19}, Arg_{20},$ $Arg_{21}, Arg_{22}, Arg_{23}, Arg_{24}, Arg_{25}, Arg_{26}, Arg_{27},$ $Arg_{28}, Arg_{29}, Arg_{30},$;

(SEQ ID NOs: 119-142)
$Lys_7, Lys_8, Lys_9, Lys_{10}, Lys_{11}, Lys_{12}, Lys_{13},$ $Lys_{14}, Lys_{15}, Lys_{16}, Lys_{17}, Lys_{18}, Lys_{19}, Lys_{20},$ $Lys_{21}, Lys_{22}, Lys_{23}, Lys_{24}, Lys_{25}, Lys_{26}, Lys_{27},$ $Lys_{28}, Lys_{29}, Lys_{30},$;

(SEQ ID NOs: 143-166)
$His_7. His_8, His_9, His_{10}, His_{11}, His_{12}, His_{13},$ $His_{14}, His_{15}, His_{16}, His_{17}, His_{18}, His_{19}, His_{20},$ $His_{21}, His_{22}, His_{23}, His_{24}, His_{25}, His_{26}, His_{27},$ $His_{28}, His_{29}, His_{30},$;

(SEQ ID NOs: 167-190)
$Orn_7, Orn_8, Orn_9, Orn_{10}, Orn_{11}, Orn_{12}, Orn_{13},$ $Orn_{14}, Orn_{15}, Orn_{16}, Orn_{17}, Orn_{18}, Orn_{19}, Orn_{20},$ $Orn_{21}, Orn_{22}, Orn_{23}, Orn_{24}, Orn_{25}, Orn_{26}, Orn_{27},$ $Orn_{28}, Orn_{29}, Orn_{30},$;

According to a further particularly preferred aspect, oligopeptides of formula (V) as shown above may be preferably selected from, without being restricted thereto, at least one of the following subgroup of formulae. The following formulae (as with formula (V)) do not specify any amino acid order, but are intended to reflect sum formulae by exclusively specifying the (number of) amino acids as components of the respective peptide. Accordingly, as an example, formula $Arg_{(7-29)}Lys_1$ is intended to mean that peptides falling under this formula contain 7 to 19 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

$Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn_2$, $Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$, $Arg_{(1-26)}Lys_4$, $Arg_{(1-26)}His_4$, $Arg_{(1-26)}Orn_4$, $Lys_{(1-26)}His_4$, $Lys_{(1-26)}Orn_1$, $His_{(1-26)}Orn_4$, $Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;

$Arg_{(2-27)}Lys_2His_1$, $Arg_{(2-27)}Lys_1His_2$, $Arg_{(2-27)}Lys_1Orn_1$, $Arg_{(2-27)}Lys_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_2Lys_{(2-27)}Orn_1$, $Arg_1Lys_{(2-27)}Orn_2$, $Lys_{(2-27)}His_2Orn_1$, $Lys_{(2-27)}His_1Orn_2$, $Arg_2Lys_1His_{(2-27)}$, $Arg_1Lys_2His_{(2-27)}$, $Arg_2His_{(2-27)}Orn_1$, $ArgHis_{(2-27)}Orn_2$, $Lys_2His_{(2-27)}Orn_1$, $Lys_1His_{(2-27)}Orn_2$;

$Arg_{(1-26)}Lys_3His_1$, $Arg_{(1-26)}Lys_2His_2$, $Arg_{(1-26)}Lys_1His_3$, $Arg_{(1-26)}Lys_3Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_2Lys_{(1-26)}Orn_2$, $Arg_1Lys_{(1-26)}Orn_3$, $Lys_{(1-26)}His_3Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_3His_{(1-26)}$, $Arg_3His_{(1-26)}Orn_1$, $Arg_2His_{(1-26)}Orn_2$, $Arg_1His_{(1-26)}Orn_3$, $Lys_3His_{(1-26)}Orn_1$, $Lys_2His_{(1-26)}Orn_2$, $Lys_1His_{(1-26)}Orn_3$;

$Arg_{(2-27)}Lys_1His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;

$Arg_{(1-26)}Lys_2His_1Orn_1$, $Arg_{(1-26)}Lys_1His_2Orn_1$, $Arg_{(1-26)}Lys_1His_1Orn_2$, $Arg_2Lys_{(1-26)}His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}Orn_1$, $Arg_1Lys_2His_{(1-26)}Orn_2$, $Arg_2Lys_1His_1Orn_{(1-26)}$, $Arg_1Lys_2His_1Orn_{(1-26)}$, $Arg_1Lys_1His_2Orn_{(1-26)}$;

$Arg_{(7-14)}Lys_1$, $Arg_{(7-14)}His_1$, $Arg_{(7-14)}Orn_1$, $Lys_{(7-14)}His_1$, $Lys_{(7-14)}Orn_1$, $His_{(7-14)}Orn_1$,;

$Arg_{(6-13)}Lys_2$, $Arg_{(6-13)}His_2$, $Arg_{(6-13)}Orn_2$, $Lys_{(6-13)}His_2$, $Lys_{(6-13)}Orn_2$, $His_{(6-13)}Orn_2$,;

$Arg_{(5-12)}Lys_3$, $Arg_{(5-12)}His_3$, $Arg_{(5-12)}Orn_3$, $Lys_{(5-12)}His_3$, $Lys_{(5-12)}Orn_3$, $His_{(5-12)}Orn_3$,;

$Arg_{(4-11)}Lys_4$, $Arg_{(4-11)}His_4$, $Arg_{(4-11)}Orn_4$, $Lys_{(4-11)}His_4$, $Lys_{(4-11)}Orn_4$, $His_{(4-11)}Orn_4$,;

$Arg_{(3-10)}Lys_5$, $Arg_{(3-10)}His_5$, $Arg_{(3-10)}Orn_5$, $Lys_{(3-10)}His_5$, $Lys_{(3-10)}Orn_5$, $His_{(3-10)}Orn_5$,;

$Arg_{(2-9)}Lys_6$, $Arg_{(2-9)}His_6$, $Arg_{(2-9)}Orn_6$, $Lys_{(2-9)}His_6$, $Lys_{(2-9)}Orn_6$, $His_{(2-9)}Orn_6$,;

$Arg_{(1-8)}Lys_7$, $Arg_{(1-8)}His_7$, $Arg_{(1-8)}Orn_7$, $Lys_{(1-8)}His_7$, $Lys_{(1-8)}Orn_7$, $His_{(1-8)}Orn_7$,;

or $Arg_{(6-13)}Lys_1His_1$, $Arg_{(6-13)}Lys_1Orn_1$, $Arg_{(6-13)}His_1Orn_1$, $Arg_1Lys_{(6-13)}His_1$, $Arg_1Lys_{(6-13)}Orn_1$, $Lys_{(6-13)}His_1Orn_1$, $Arg_1Lys_1His_{(6-13)}$, $Arg_1His_{(6-13)}Orn_1$, $Lys_1His_{(6-13)}Orn_1$;

$Arg_{(5-12)}Lys_2His_1$, $Arg_{(5-12)}Lys_1His_2$, $Arg_{(5-12)}Lys_2Orn_1$, $Arg_{(5-12)}Lys_1Orn_2$, $Arg_{(5-12)}His_2Orn_1$, $Arg_{(5-12)}His_1Orn_2$, $Arg_2Lys_{(5-12)}His_1$, $Arg_1Lys_{(5-12)}His_2$, $Arg_2Lys_{(5-12)}Orn_1$, $Arg_1Lys_{(5-12)}Orn_2$, $Lys_{(5-12)}His_2Orn_1$, $Lys_{(5-12)}His_1Orn_2$, $Arg_2Lys_1His_{(5-12)}$, $Arg_1Lys_2His_{(5-12)}$, $Arg_2His_{(5-12)}Orn_1$, $Arg_1His_{(5-12)}Orn_2$, $Lys_2His_{(5-12)}Orn_1$, $Lys_1His_{(5-12)}Orn_2$;

$Arg_{(4-11)}Lys_3His_1$, $Arg_{(4-11)}Lys_2His_2$,

-continued $Arg_{(4-11)}Lys_1His_3$, $Arg_{(4-11)}Lys_3Orn_1$, $Arg_{(4-11)}Lys_2Orn_2$, $Arg_{(4-11)}Lys_1Orn_3$, $Arg_{(4-11)}His_3Orn_1$, $Arg_{(4-11)}His_2Orn_2$, $Arg_{(4-11)}His_1Orn_3$, $Arg_3Lys_{(4-11)}His_1$, $Arg_2Lys_{(4-11)}His_2$, $Arg_1Lys_{(4-11)}His_3$, $Arg_3Lys_{(4-11)}Orn_1$, $Arg_2Lys_{(4-11)}Orn_2$, $Arg_1Lys_{(4-11)}Orn_3$, $Lys_{(4-11)}His_3Orn_1$, $Lys_{(4-11)}His_2Orn_2$, $Lys_{(4-11)}His_1Orn_3$, $Arg_3Lys_1His_{(4-11)}$, $Arg_2Lys_2His_{(4-11)}$, $Arg_1Lys_3His_{(4-11)}$, $Arg_3His_{(4-11)}Orn_1$, $Arg_2His_{(4-11)}Orn_2$, $Arg_1His_{(4-11)}Orn_3$, $Lys_3His_{(4-11)}Orn_1$, $Lys_2His_{(4-11)}Orn_2$, $Lys_1His_{(4-11)}Orn_3$;

$Arg_{(3-10)}Lys_4His_1$, $Arg_{(3-10)}Lys_3His_2$, $Arg_{(3-10)}Lys_2His_3$, $Arg_{(3-10)}Lys_1His_4$, $Arg_{(3-10)}Lys_4Orn_1$, $Arg_{(3-10)}Lys_3Orn_2$, $Arg_{(3-10)}Lys_2Orn_3$, $Arg_{(3-10)}Lys_1Orn_4$, $Arg_{(3-10)}His_4Orn_1$, $Arg_{(3-10)}His_3Orn_2$, $Arg_{(3-10)}His_2Orn_3$, $Arg_{(3-10)}His_1Orn_4$, $Arg_4Lys_{(3-10)}His_1$, $Arg_3Lys_{(3-10)}His_2$, $Arg_2Lys_{(3-10)}His_3$, $Arg_1Lys_{(3-10)}His_4$, $Arg_4Lys_{(3-10)}Orn_1$, $Arg_3Lys_{(3-10)}Orn_2$, $Arg_2Lys_{(3-10)}Orn_3$, $Arg_1Lys_{(3-10)}Orn_4$, $Lys_{(3-10)}His_4Orn_1$, $Lys_{(3-10)}His_3Orn_2$, $Lys_{(3-10)}His_2Orn_3$, $Lys_{(3-10)}His_1Orn_4$, $Arg_4Lys_1His_{(3-10)}$, $Arg_3Lys_2His_{(3-10)}$, $Arg_2Lys_3His_{(3-10)}$, $Arg_1Lys_4His_{(3-10)}$, $Arg_4His_{(3-10)}Orn_1$, $Arg_3His_{(3-10)}Orn_2$, $Arg_2His_{(3-10)}Orn_3$, $Arg_1His_{(3-10)}Orn_4$, $Lys_4His_{(3-10)}Orn_1$, $Lys_3His_{(3-10)}Orn_2$, $Lys_2His_{(3-10)}Orn_3$, $Lys_1His_{(3-10)}Orn_4$;

$Arg_{(2-9)}Lys_5His_1$, $Arg_{(2-9)}Lys_4His_2$, $Arg_{(2-9)}Lys_3His_3$, $Arg_{(2-9)}Lys_2His_4$, $Arg_{(2-9)}Lys_1His_5$, $Arg_{(2-9)}Lys_5Orn_1$, $Arg_{(2-9)}Lys_4Orn_2$, $Arg_{(2-9)}Lys_3Orn_3$, $Arg_{(2-9)}Lys_2Orn_4$, $Arg_{(2-9)}Lys_1Orn_5$, $Arg_{(2-9)}His_5Orn_1$, $Arg_{(2-9)}His_4Orn_2$, $Arg_{(2-9)}His_3Orn_3$, $Arg_{(2-9)}His_2Orn_4$, $Arg_{(2-9)}His_1Orn_5$, $Arg_5Lys_{(2-9)}His_1$, $Arg_4Lys_{(2-9)}His_2$, $Arg_3Lys_{(2-9)}His_3$, $Arg_2Lys_{(2-9)}His_4$, $Arg_1Lys_{(2-9)}His_5$, $Arg_5Lys_{(2-9)}Orn_1$, $Arg_4Lys_{(2-9)}Orn_2$, $Arg_3Lys_{(2-9)}Orn_3$, $Arg_2Lys_{(2-9)}Orn_4$, $Arg_1Lys_{(2-9)}Orn_5$, $Lys_{(2-9)}His_5Orn_1$, $Lys_{(2-9)}His_4Orn_2$, $Lys_{(2-9)}His_3Orn_3$, $Lys_{(2-9)}His_2Orn_4$, $Lys_{(2-9)}His_1Orn_5$, $Arg_5Lys_1His_{(2-9)}$, $Arg_4Lys_2His_{(2-9)}$, $Arg_3Lys_3His_{(2-9)}$, $Arg_2Lys_4His_{(2-9)}$, $Arg,Lys_5His_{(2-9)}$, $Arg_5His_{(2-9)}Orn_1$, $Arg_4His_{(2-9)}Orn_2$, $Arg_3His_{(2-9)}Orn_3$, $Arg_2His_{(2-9)}Orn_4$, $Arg_1His_{(2-9)}Orn_5$, $Lys_5His_{(2-9)}Orn_1$, $Lys_4His_{(2-9)}Orn_2$, $Lys_3His_{(2-9)}Orn_3$, $Lys_2His_{(2-9)}Orn_4$, $Lys_1His_{(2-9)}Orn_5$;

$Arg_{(1-8)}Lys_6His_1$, $Arg_{(1-8)}Lys_5His_2$, $Arg_{(1-8)}Lys_4His_3$, $Arg_{(1-8)}Lys_3His_4$, $Arg_{(1-8)}Lys_2His_5$, $Arg_{(1-8)}Lys_1His_6$, $Arg_{(1-8)}Lys_6Orn_1$, $Arg_{(1-8)}Lys_5Orn_2$, $Arg_{(1-8)}Lys_4Orn_3$, $Arg_{(1-8)}Lys_3Orn_4$, $Arg_{(1-8)}Lys_2Orn_5$, $Arg_{(1-8)}Lys_1Orn_6$, $Arg_{(1-8)}His_6Orn_1$, $Arg_{(1-8)}His_5Orn_2$, $Arg_{(1-8)}His_4Orn_3$, $Arg_{(1-8)}His_3Orn_4$, $Arg_{(1-8)}His_2Orn_5$, $Arg_{(1-8)}His_1Orn_6$, $Arg_5Lys_{(1-8)}His_1$, $Arg_5Lys_{(1-8)}His_2$, $Arg_4Lys_{(1-8)}His_3$, $Arg_3Lys_{(1-8)}His_4$, $Arg_2Lys_{(1-8)}His_5$, $Arg_1Lys_{(1-8)}His_6$, $Arg_5Lys_{(1-8)}Orn_1$, $Arg_5Lys_{(1-8)}Orn_2$, $Arg_4Lys_{(1-8)}Orn_3$, $Arg_3Lys_{(1-8)}Orn_4$, $Arg_2Lys_{(1-8)}Orn_5$, $Arg_1Lys_{(1-8)}Orn_6$, $Lys_{(1-8)}His_6Orn_1$, $Lys_{(1-8)}His_5Orn_2$, $Lys_{(1-8)}His_4Orn_3$, $Lys_{(1-8)}His_3Orn_4$, $Lys_{(1-8)}His_2Orn_5$, $Lys_{(1-8)}His_1Orn_6$, $Arg_5Lys_1His_{(1-8)}$, $Arg_5Lys_2His_{(1-8)}$, $Arg_4Lys_3His_{(1-8)}$, $Arg_3Lys_4His_{(1-8)}$, $Arg_2Lys_5His_{(1-8)}$, $Arg_1Lys_6His_{(1-8)}$, $Arg_5His_{(1-8)}Orn_1$, $Arg_5His_{(1-8)}Orn_2$, $Arg_4His_{(1-8)}Orn_3$, $Arg_3His_{(1-8)}Orn_4$, $Arg_2His_{(1-8)}Orn_5$, $Arg_1His_{(1-8)}Orn_6$, $Lys_6His_{(1-8)}Orn_1$, $Lys_5His_{(1-8)}Orn_2$, $Lys_4His_{(1-8)}Orn_3$, $Lys_3His_{(1-8)}Orn_4$, $Lys_2His_{(1-8)}Orn_5$, $Lys_1His_{(1-8)}Orn_6$;

-continued

Arg$_{(5-12)}$Lys$_1$His$_1$Orn$_1$, Arg$_1$Lys$_{(5-12)}$His$_1$Orn$_1$,

Arg$_1$Lys$_1$His$_{(5-12)}$Orn$_1$, Arg$_1$Lys$_1$His$_1$Orn$_{(5-12)}$;

Arg$_{(4-11)}$Lys$_2$His$_1$Orn$_1$, Arg$_{(4-11)}$Lys$_1$His$_2$Orn$_1$,

Arg$_{(4-11)}$Lys$_1$His$_1$Orn$_2$, Arg$_2$Lys$_{(4-11)}$His$_1$Orn$_1$,

Arg$_1$Lys$_{(4-11)}$His$_2$Orn$_1$, Arg$_1$Lys$_{(4-11)}$His$_1$Orn$_2$,

Arg$_2$Lys$_1$His$_{(4-11)}$Orn$_1$, Arg$_1$Lys$_2$His$_{(4-11)}$Orn$_1$,

Arg$_1$Lys$_1$His$_{(4-11)}$Orn$_2$, Arg$_2$Lys$_1$His$_1$Orn$_{(4-11)}$,

Arg$_1$Lys$_2$His$_1$Orn$_{(4-11)}$, Arg$_1$Lys$_1$His$_2$Orn$_{(4-11)}$;

Arg$_{(3-10)}$Lys$_3$His$_1$Orn$_1$, Arg$_{(3-10)}$Lys$_2$His$_2$Orn$_1$,

Arg$_{(3-10)}$Lys$_2$His$_1$Orn$_2$, Arg$_{(3-10)}$Lys$_1$His$_2$Orn$_2$,

Arg$_{(3-10)}$Lys$_1$His$_1$Orn$_3$, Arg$_3$Lys$_{(3-10)}$His$_1$Orn$_1$,

Arg$_2$Lys$_{(3-10)}$His$_2$Orn$_1$, Arg$_2$Lys$_{(3-10)}$His$_1$Orn$_2$,

Arg$_1$Lys$_{(3-10)}$His$_2$Orn$_2$, Arg$_1$Lys$_{(3-10)}$His$_1$Orn$_3$,

Arg$_3$Lys$_1$His$_{(3-10)}$Orn$_1$, Arg$_2$Lys$_2$His$_{(3-10)}$Orn$_1$,

Arg$_2$Lys$_1$His$_{(3-10)}$Orn$_2$, Arg$_1$Lys$_2$His$_{(3-10)}$Orn$_2$,

Arg$_1$Lys$_1$His$_{(3-10)}$Orn$_3$, Arg$_3$Lys$_1$His$_1$Orn$_{(3-10)}$,

Arg$_2$Lys$_2$His$_1$Orn$_{(3-10)}$, Arg$_2$Lys$_1$His$_2$Orn$_{(3-10)}$,

Arg$_1$Lys$_2$His$_2$Orn$_{(3-10)}$, Arg$_1$Lys$_1$His$_3$Orn$_{(3-10)}$;

Arg$_{(2-9)}$Lys$_4$His$_1$Orn$_1$, Arg$_{(2-9)}$Lys$_1$His$_4$Orn$_1$,

Arg$_{(2-9)}$Lys$_1$His$_1$Orn$_4$, Arg$_{(2-9)}$Lys$_3$His$_2$Orn$_1$,

Arg$_{(2-9)}$Lys$_3$His$_1$Orn$_2$, Arg$_{(2-9)}$Lys$_2$His$_3$Orn$_1$,

Arg$_{(2-9)}$Lys$_2$His$_1$Orn$_3$, Arg$_{(2-9)}$Lys$_1$His$_2$Orn$_3$,

Arg$_{(2-9)}$Lys$_1$His$_3$Orn$_2$, Arg$_{(2-9)}$Lys$_2$His$_2$Orn$_2$,

Arg$_4$Lys$_{(2-9)}$His$_1$Orn$_1$, Arg$_1$Lys$_{(2-9)}$His$_4$Orn$_1$,

Arg$_1$Lys$_{(2-9)}$His$_1$Orn$_4$, Arg$_3$Lys$_{(2-9)}$His$_2$Orn$_1$,

Arg$_3$Lys$_{(2-9)}$His$_1$Orn$_2$, Arg$_2$Lys$_{(2-9)}$His$_3$Orn$_1$,

Arg$_2$Lys$_{(2-9)}$His$_1$Orn$_3$, Arg$_1$Lys$_{(2-9)}$His$_2$Orn$_3$,

Arg$_1$Lys$_{(2-9)}$His$_3$Orn$_2$, Arg$_2$Lys$_{(2-9)}$His$_2$Orn$_2$,

Arg$_4$Lys$_1$His$_{(2-9)}$Orn$_1$, Arg$_1$Lys$_4$His$_{(2-9)}$Orn$_1$,

Arg$_1$Lys$_1$His$_{(2-9)}$Orn$_4$, Arg$_3$Lys$_2$His$_{(2-9)}$Orn$_1$,

Arg$_3$Lys$_1$His$_{(2-9)}$Orn$_2$, Arg$_2$Lys$_3$His$_{(2-9)}$Orn$_1$,

Arg$_2$Lys$_1$His$_{(2-9)}$Orn$_3$, Arg$_1$Lys$_2$His$_{(2-9)}$Orn$_3$,

Arg$_1$Lys$_3$His$_{(2-9)}$Orn$_2$, Arg$_2$Lys$_2$His$_{(2-9)}$Orn$_2$,

Arg$_4$Lys$_1$His$_1$Orn$_{(2-9)}$, Arg$_1$Lys$_4$His$_1$Orn$_{(2-9)}$,

Arg$_1$Lys$_1$His$_4$Orn$_{(2-9)}$, Arg$_3$Lys$_2$His$_1$Orn$_{(2-9)}$,

Arg$_3$Lys$_1$His$_2$Orn$_{(2-9)}$, Arg$_2$Lys$_3$His$_1$Orn$_{(2-9)}$,

Arg$_2$Lys$_1$His$_3$Orn$_{(2-9)}$, Arg$_1$Lys$_2$His$_3$Orn$_{(2-9)}$,

Arg$_1$Lys$_3$His$_2$Orn$_{(2-9)}$, Arg$_2$Lys$_2$His$_2$Orn$_{(2-9)}$;

Arg$_{(1-8)}$Lys$_5$His$_1$Orn$_1$, Arg$_{(1-8)}$Lys$_1$His$_5$Orn$_1$,

Arg$_{(1-8)}$Lys$_1$His$_1$Orn$_5$, Arg$_{(1-8)}$Lys$_4$His$_2$Orn$_1$,

Arg$_{(1-8)}$Lys$_2$His$_4$Orn$_1$, Arg$_{(1-8)}$Lys$_2$His$_1$Orn$_4$,

Arg$_{(1-8)}$Lys$_1$His$_2$Orn$_4$, Arg$_{(1-8)}$Lys$_1$His$_4$Orn$_2$,

Arg$_{(1-8)}$Lys$_4$His$_1$Orn$_2$, Arg$_{(1-8)}$Lys$_3$His$_3$Orn$_1$,

Arg$_{(1-8)}$Lys$_3$His$_1$Orn$_3$, Arg$_{(1-8)}$Lys$_1$His$_3$Orn$_3$,

Arg$_5$Lys$_{(1-8)}$His$_1$Orn$_1$, Arg$_1$Lys$_{(1-8)}$His$_5$Orn$_1$,

Arg$_1$Lys$_{(1-8)}$His$_1$Orn$_5$, Arg$_4$Lys$_{(1-8)}$His$_2$Orn$_1$,

Arg$_2$Lys$_{(1-8)}$His$_4$Orn$_1$, Arg$_2$Lys$_{(1-8)}$His$_1$Orn$_4$,

Arg$_1$Lys$_{(1-8)}$His$_2$Orn$_4$, Arg$_1$Lys$_{(1-8)}$His$_4$Orn$_2$,

Arg$_4$Lys$_{(1-8)}$His$_1$Orn$_2$, Arg$_3$Lys$_{(1-8)}$His$_3$Orn$_1$,

Arg$_3$Lys$_{(1-8)}$His$_1$Orn$_3$, Arg$_1$Lys$_{(1-8)}$His$_3$Orn$_3$,

Arg$_5$Lys$_1$His$_{(1-8)}$Orn$_1$, Arg$_1$Lys$_5$His$_{(1-8)}$Orn$_1$,

Arg$_1$Lys$_1$His$_{(1-8)}$Orn$_5$, Arg$_4$Lys$_2$His$_{(1-8)}$Orn$_1$,

Arg$_2$Lys$_4$His$_{(1-8)}$Orn$_1$, Arg$_2$Lys$_1$His$_{(1-8)}$Orn$_4$,

Arg$_1$Lys$_2$His$_{(1-8)}$Orn$_4$, Arg$_1$Lys$_4$His$_{(1-8)}$Orn$_2$,

Arg$_4$Lys$_1$His$_{(1-8)}$Orn$_2$, Arg$_3$Lys$_3$His$_{(1-8)}$Orn$_1$,

Arg$_3$Lys$_1$His$_{(1-8)}$Orn$_3$, Arg$_1$Lys$_3$His$_{(1-8)}$Orn$_3$,

Arg$_5$Lys$_1$His$_1$Orn$_{(1-8)}$, Arg$_1$Lys$_5$His$_1$Orn$_{(1-8)}$,

Arg$_1$Lys$_1$His$_5$Orn$_{(1-8)}$, Arg$_4$Lys$_2$His$_1$Orn$_{(1-8)}$,

Arg$_2$Lys$_4$His$_1$Orn$_{(1-8)}$, Arg$_2$Lys$_1$His$_4$Orn$_{(1-8)}$,

Arg$_1$Lys$_2$His$_4$Orn$_{(1-8)}$, Arg$_1$Lys$_4$His$_2$Orn$_{(1-8)}$,

Arg$_4$Lys$_1$His$_2$Orn$_{(1-8)}$, Arg$_3$Lys$_3$His$_1$Orn$_{(1-8)}$,

Arg$_3$Lys$_1$His$_3$Orn$_{(1-8)}$, Arg$_1$Lys$_3$His$_3$Orn$_{(1-8)}$;

According to another preferred aspect, the oligopeptide of formula (V) as shown above is selected from the subgroup comprising a sequence according to:

His$_3$Arg$_9$
(SEQ ID NO: 191)
His-His-His-Arg-Arg-Arg-Arg-Arg-Arg-Arg-Arg-Arg

Arg$_9$His$_3$:
(SEQ ID NO: 192)
Arg-Arg-Arg-Arg-Arg-Arg-Arg-Arg-Arg-His-His-His

His$_3$Arg$_4$His$_3$:
(SEQ ID NO: 193)
His-His-His-Arg-Arg-Arg-Arg-His-His-His

His$_3$Arg$_9$His$_3$:
(SEQ ID NO: 194)
His-His-His-Arg-Arg-Arg-Arg-Arg-Arg-Arg-Arg-His-His-His

His$_6$Arg$_4$His$_6$:
(SEQ ID NO: 195)
His-His-His-His-His-His-Arg-Arg-Arg-Arg-His-His-His-His-His-His

His$_6$Arg$_9$His$_6$:
(SEQ ID NO: 196)
His-His-His-His-His-His-Arg-Arg-Arg-Arg-Arg-Arg-Arg-Arg-Arg-His-His-His-His-His-His

-continued

TyrSer$_2$Arg$_9$Ser$_2$Tyr:
(SEQ ID NO: 197)
Tyr-Ser-Ser-Arg-Arg-Arg-Arg-Arg-Arg-Arg-Arg-Ser-Ser-Tyr

His$_3$Arg$_9$SerSerTyr:
(SEQ ID NO: 198)
His-His-His-Arg-Arg-Arg-Arg-Arg-Arg-Arg-Arg-Ser-Ser-Tyr (ArgLysHis)$_4$:
(SEQ ID NO: 199)
Arg-Lys-His-Arg-Lys-His-Arg-Lys-His-Arg-Lys-His

Tyr(ArgLysHis)$_2$Arg:
(SEQ ID NO: 200)
Tyr-Arg-Lys-His-Arg-Lys-His-Arg

Further preferred cationic or polycationic compounds, which can be used for complexing the at least one immunostimulatory nucleic acid sequence of the adjuvant component as defined above may comprise disulfide-crosslinked cationic compounds, i.e. cationic compounds, which have been formed by crosslinking at least two (same or different) disulfide-crosslinkable cationic components. In this context such disulfide-crosslinkable cationic components are typically selected from any cationic or polycationic peptide, protein or polymer suitable for this purpose, preferably as defined above, wherein each such cationic or polycationic protein, peptide or polymer suitable as a disulfide-crosslinkable cationic component preferably contains at least one —SH moiety. Most preferably each such cationic or polycationic protein, peptide or polymer suitable as a disulfide-crosslinkable cationic component contains at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

Each disulfide-crosslinked cationic compound is preferably formed by linking a disulfide-crosslinkable component as defined herein to a neighbouring disulfide-crosslinkable component as defined herein or other components via disulfide-crosslinking. Preferably, the disulfide-crosslinking is a (reversible) disulfide bond (—S—S—) between at least one cationic or polycationic protein, peptide or polymer, used as a disulfide-crosslinkable cationic component, and at least one further cationic or polycationic protein, peptide or polymer, likewise used as a disulfide-crosslinkable cationic component or any other component. The disulfide-crosslinking is typically formed by condensation of —SH-moieties of the disulfide-crosslinkable cationic components. Such an —SH-moiety may be part of the structure of the cationic or polycationic protein, peptide or polymer used as a disulfide-crosslinkable cationic component or may be added prior to disulfide-crosslinking by a modification as defined below. In this context, the sulphurs adjacent to one component of the disulfide-crosslinkable cationic component, necessary for providing a disulfide bond, may be provided by the disulfide-crosslinkable cationic component itself, e.g. by a —SH moiety as defined herein or may be provided by modifying the disulfide-crosslinkable cationic component accordingly to exhibit a —SH moiety. These —SH-moieties are typically provided by each of the disulfide-crosslinkable cationic component, e.g. via a cysteine or any further (modified) amino acid or compound of the component, which carries a —SH moiety. In the case that the disulfide-crosslinkable cationic component is a peptide or protein it is preferred that the —SH moiety is provided by at least one cysteine residue. Alternatively, the cationic or polycationic component used as a disulfide-crosslinkable cationic component may be modified accordingly with an —SH moiety, preferably via a chemical reaction with a compound carrying a —SH moiety, such that each of the components carries at least one such —SH moiety. Such a compound carrying a —SH moiety may be e.g. an (additional) cysteine or any further (modified) amino acid or compound, which carries a —SH moiety. Such a compound may also be any non-amino acid compound or moiety, which contains or allows to introduce a —SH moiety into the disulfide-crosslinkable cationic component as defined herein. Such non-amino acid compounds may be attached to the component of the polymeric carrier according to the present invention via chemical reactions or binding of compounds, e.g. by binding of a 3-thio propionic acid or 2-iminothiolane (Traut's reagent), by amide formation (e.g. carboxylic acids, sulphonic acids, amines, etc), by Michael addition (e.g maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylannins, amines), complexation reactions (avidin, biotin, protein G) or components which allow S$_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. In some cases the —SH moiety may be masked by protecting groups during chemical attachment to the component. Such protecting groups are known in the art and may be removed after chemical coupling. In each case, the —SH moiety, e.g. of a cysteine or of any further (modified) amino acid or compound, may be present at (one or both of) the terminal ends or internally at any position of the disulfide-crosslinkable cationic component. As defined herein, each of the disulfide-crosslinkable cationic components typically exhibits at least one —SH-moiety, but may also contain two, three, four, five, or even more —SH-moieties. Additionally to binding of other disulfide-crosslinkable cationic components a —SH moiety may be used to attach further components to the disulfide-crosslinkable cationic component as defined herein, particularly an amino acid component, e.g. antigen epitopes, antigens, antibodies, cell penetrating peptides (e.g. TAT), ligands, etc.

According to one first alternative, at least one disulfide-crosslinkable cationic component may be selected from cationic or polycationic peptides or proteins as defined herein. Such cationic or polycationic peptides or proteins typically exhibit a length of about 3 to 200, preferably 3 to 100 amino acids, more preferably a length of about 3 to 50 amino acids, even more preferably a length of about 3 to 25 amino acids, e.g. a length of about 3 to 10, 5 to 15, 10 to 20 or 15 to 25 amino acids. Alternatively or additionally, such cationic or polycationic peptides or proteins may exhibit a molecular weight of about 0.3 kDa to about 20 kDa, preferably 0.3 kDa to about 10 kDa, including a molecular weight of about 0.4 kDa to about 10 kDa, 0.5 kDa to about 10 kDa, preferably of about 0.5 kDa to about 7.5 kDa, 0.5 kDa to about 5 kDa, 0.5 kDa to about 4 kDa, 0.5 kDa to about 3 kDa, or even 0.67 kDa to about 2.7 kDa.

In the specific case that the disulfide-crosslinkable cationic component comprises a cationic or polycationic peptide or protein, the cationic properties of a disulfide-crosslinkable cationic component (or of the disulfide-crosslinked cationic compound formed by the disulfide-crosslinkable cationic component), may be determined upon its content of cationic amino acids. Preferably, the content of cationic amino acids in such a cationic or polycationic peptide or protein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in such a disulfide-crosslinked cationic compound is 100%.

Preferably, such disulfide-crosslinkable cationic components, which comprise or are additionally modified to comprise at least one —SH moiety, are selected from, without being restricted thereto, cationic peptides or proteins such as protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such disulfide-crosslinkable cationic components, which comprise or are additionally modified to comprise at least one —SH moiety, are selected from, without being restricted thereto, oligopeptides having the sum formula (V) as defined above.

According to a further particular preferred aspect, disulfide-crosslinkable cationic components, preferably oligopeptides having the sum formula (V) as shown above, and which comprise or are additionally modified to comprise at least one —SH moiety, may be, without being restricted thereto, selected from an oligopeptide of subformula (Va):

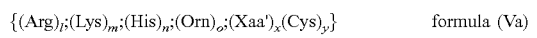

{(Arg)$_l$;(Lys)$_m$;(His)$_n$;(Orn)$_o$;(Xaa')$_x$(Cys)$_y$}  formula (Va)

wherein (Arg)$_l$;(Lys)$_m$;(His)$_n$;(Orn)$_o$; and x is preferably are as defined above for formula (V), Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This aspect may apply to situations, wherein the disulfide-crosslinkable cationic component, e.g. when defined according to empirical formula (Arg)$_l$;(Lys)$_m$;(His)$_n$;(Orn)$_o$;(Xaa)$_x$ (formula (V)) as shown above, comprises or has been modified with at least one cysteine as —SH moiety in the above meaning such that the disulfide-crosslinkable cationic component as cationic or polycationic component carries at least one cysteine, which is capable to form a disulfide bond with other cationic or polycationic components.

According to another particular preferred aspect, the disulfide-crosslinkable cationic component may be, without being restricted thereto, selected from subformula (Vb):

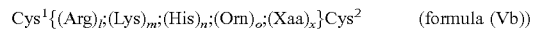

Cys$^1${(Arg)$_l$;(Lys)$_m$;(His)$_n$;(Orn)$_o$;(Xaa)$_x$}Cys$^2$  (formula (Vb))

wherein component {(Arg)$_l$;(Lys)$_m$;(His)$_n$;(Orn)$_o$;(Xaa)$_x$} (formula (V)) within formula (Vb) is as defined herein and forms a core of subformula (Vb), and wherein Cys$^1$ and Cys$^2$ are Cysteines proximal to, or terminal to (Arg)$_l$;(Lys)$_m$;(His)$_n$;(Orn)$_o$;(Xaa)$_x$. Exemplary examples may comprise any of the above sequences flanked by two Cys and following sequences:

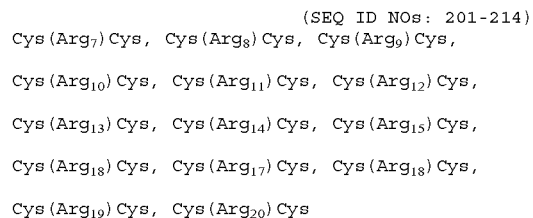

```
                                    (SEQ ID NOs: 201-214)
Cys(Arg7)Cys,   Cys(Arg8)Cys,   Cys(Arg9)Cys,

Cys(Arg10)Cys,  Cys(Arg11)Cys,  Cys(Arg12)Cys,

Cys(Arg13)Cys,  Cys(Arg14)Cys,  Cys(Arg15)Cys,

Cys(Arg16)Cys,  Cys(Arg17)Cys,  Cys(Arg18)Cys,

Cys(Arg19)Cys,  Cys(Arg20)Cys
```

Further examples may comprise any of the following sequences:

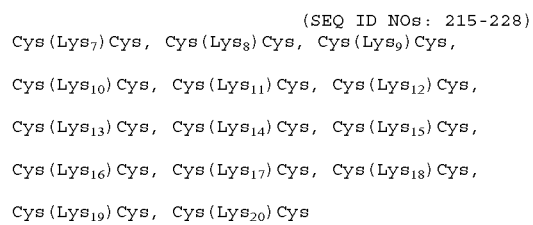

```
                                    (SEQ ID NOs: 215-228)
Cys(Lys7)Cys,   Cys(Lys8)Cys,   Cys(Lys9)Cys,

Cys(Lys10)Cys,  Cys(Lys11)Cys,  Cys(Lys12)Cys,

Cys(Lys13)Cys,  Cys(Lys14)Cys,  Cys(Lys15)Cys,

Cys(Lys16)Cys,  Cys(Lys17)Cys,  Cys(Lys18)Cys,

Cys(Lys19)Cys,  Cys(Lys20)Cys
```

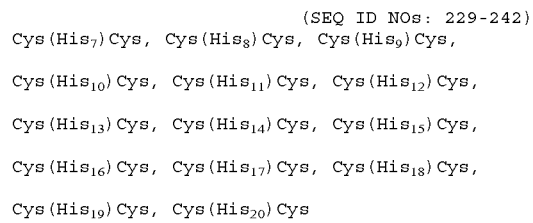

```
                                    (SEQ ID NOs: 229-242)
Cys(His7)Cys,   Cys(His8)Cys,   Cys(His9)Cys,

Cys(His10)Cys,  Cys(His11)Cys,  Cys(His12)Cys,

Cys(His13)Cys,  Cys(His14)Cys,  Cys(His15)Cys,

Cys(His16)Cys,  Cys(His17)Cys,  Cys(His18)Cys,

Cys(His19)Cys,  Cys(His20)Cys
```

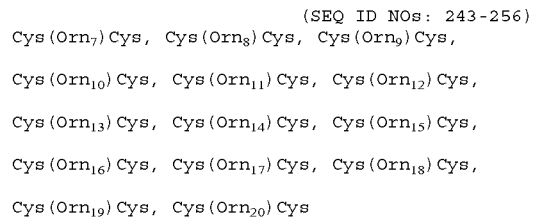

```
                                    (SEQ ID NOs: 243-256)
Cys(Orn7)Cys,   Cys(Orn8)Cys,   Cys(Orn9)Cys,

Cys(Orn10)Cys,  Cys(Orn11)Cys,  Cys(Orn12)Cys,

Cys(Orn13)Cys,  Cys(Orn14)Cys,  Cys(Orn15)Cys,

Cys(Orn16)Cys,  Cys(Orn17)Cys,  Cys(Orn18)Cys,

Cys(Orn19)Cys,  Cys(Orn20)Cys
``` or following exemplary sequences:

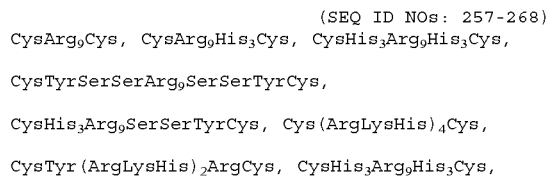

```
                                    (SEQ ID NOs: 257-268)
CysArg9Cys,   CysArg9His3Cys,   CysHis3Arg9His3Cys,

CysTyrSerSerArg9SerSerTyrCys,

CysHis3Arg9SerSerTyrCys,   Cys(ArgLysHis)4Cys,

CysTyr(ArgLysHis)2ArgCys,  CysHis3Arg9His3Cys,
```

CysHis$_6$Arg$_9$His$_6$Cys, CysHis$_3$Arg$_4$His$_3$Cys,

CysHis$_6$Arg$_4$His$_6$Cys, CysArg$_{12}$Cys;.

This aspect may apply to situations, wherein the disulfide-crosslinkable cationic components, e.g. when defined according to empirical formula (Arg)$_l$;(Lys)$_m$;(His)$_n$;(Orn)$_o$; (Xaa)$_x$ (formula (V)) as shown above, has been modified with at least two cysteines as —SH moieties in the above meaning such that the disulfide-crosslinkable cationic component carries at least two (terminal) cysteines, which are capable to form a disulfide bond with other components.

According to a second alternative, at least one cationic (or polycationic) component, used as a disulfide-crosslinkable cationic (or polycationic) component to form a disulfide-crosslinked cationic compound to complex the immunostimulatory nucleic acid sequence of the adjuvant component, may comprise e.g. any (non-peptidic) cationic or polycationic polymer suitable in this context, provided that this (non-peptidic) cationic or polycationic polymer exhibits or is modified to exhibit at least one —SH-moiety, which provides for a disulfide bond linking with a further cationic or polycationic polymer or with another component as defined herein, e.g. a further disulfide-crosslinkable cationic (or polycationic) component. Likewise as defined herein, the cationic (or polycationic) component, used as a disulfide-crosslinkable cationic (or polycationic) component to form a disulfide-crosslinked cationic compound to complex the immunostimulatory nucleic acid sequence of the adjuvant component, may comprise the same or different cationic or polycationic polymers, exhibiting or being modified to exhibit at least one —SH-moiety.

In the specific case that the cationic (or polycationic) component, used as a disulfide-crosslinkable cationic (or polycationic) component to form a disulfide-crosslinked cationic compound to complex the immunostimulatory nucleic acid sequence of the adjuvant component as described herein, comprises a (non-peptidic) cationic or polycationic polymer, the cationic properties of this (non-peptidic) cationic or polycationic component (and eventually of the entire disulfide-crosslinked cationic compound, if entirely formed by such (non-peptidic) cationic or polycationic components as defined herein) may be determined upon its content of cationic charges when compared to the overall charges of the cationic (or polycationic) component, preferably the disulfide-crosslinkable cationic (or polycationic) component, or the disulfide-crosslinked cationic compound. Preferably, the content of cationic charges in the cationic (or polycationic) component (or in the disulfide-crosslinked cationic compound) at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore Mentioned values, provided, that the content of all charges, e.g. positive and negative charges at a (physiological) pH as defined herein, in the entire disulfide-crosslinkable cationic (or polycationic) component or in the entire disulfide-crosslinked cationic compound is 100%.

Preferably, the (non-peptidic) cationic or polycationic component, used as a disulfide-crosslinkable cationic (or polycationic) component to form a disulfide-crosslinked cationic compound to complex the immunostimulatory nucleic acid sequence of the adjuvant component, may be formed by a cationic or polycationic polymer, typically exhibiting a molecular weight of about 0.1 kDa to about 20 kDa, usually a molecular weight of about 0.5 kDa to about 11.5 kDa, preferably of about 1 kDa to about 10 kDa, more preferably of about 0.1 kDa to about 8 kDa, even more preferably of about 0.1 kDa to about 6 kDa, or a molecular weight of about 0.1 kDa to about 5 kDa, even more preferably of about 0.5 kDa to about 5 kDa, likewise preferably a molecular weight of about 0.3 kDa to about 20 kDa, preferably 0.3 kDa to about 10 kDa, including a molecular weight of about 0.4 kDa to about 10 kDa, 0.5 kDa to about 10 kDa, preferably of about 0.5 kDa to about 7.5 kDa, 0.5 kDa to about 5 kDa, 0.5 kDa to about 4 kDa, 0.5 kDa to about 3 kDa, or even 0.67 kDa to about 2.7 kDa.

Additionally, the (non-peptidic) cationic or polycationic polymer typically exhibits at least one (preferably two) —SH-moiety, which is capable to form a disulfide linkage upon condensation with (—SH moieties of) other cationic or polycationic components as defined herein.

In the above context, the (non-peptidic) cationic or polycationic component, which may be used to form a disulfide-crosslinked cationic compound to complex the immunostimulatory nucleic acid sequence of the adjuvant component, may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

In the context of disulfide-crosslinked cationic compounds, used as a complexing agent to complex the immunostimulatory nucleic acid sequence of the adjuvant component, the single disulfide-crosslinkable cationic components thereof forming the disulfide-crosslinked cationic compound may be the same or different from each other. It is also particularly preferred that the disulfide-crosslinked cationic compound comprises mixtures of disulfide-crosslinkable cationic components, preferably peptides, proteins or polymers and optionally further components as defined herein, which are crosslinked by disulfide bonds as described herein, preferably mixtures of any of the disulfide-crosslinkable cationic components as defined herein.

In this context, the disulfide-crosslinked cationic compounds, used as a complexing agent to complex the immunostimulatory nucleic acid sequence of the adjuvant component, advantageously allow to combine desired properties of different (short) cationic or polycationic peptides, proteins or polymers or other components.

In particular, the disulfide-crosslinked cationic compound, used as a complexing agent to complex the immunostimulatory nucleic acid sequence of the adjuvant component, allow considerably to vary its peptide or polymeric content and thus to modulate its biophysical/biochemical properties, particularly its cationic properties, quite easily and fast, e.g. by incorporating as (cationic) components the same or different (cationic) peptide(s) or polymer(s) and optionally adding other components. Even though consisting of quite small non-toxic repeat units the disulfide-cross-linked cationic compound, used as a complexing agent to complex the immunostimulatory nucleic acid sequence of the adjuvant component form a long cationic binding sequence providing a strong condensation of the nucleic acid sequence cargo and complex stability. Under the reducing conditions of the cytosol (e.g. cytosolic GSH), the complex formed with the disulfide-crosslinked cationic compound and the immunostimulatory nucleic acid sequence (adjuvant component) is rapidly degraded into its (cationic) components, which are further degraded (e.g. oligopeptides). This supports deliberation of the nucleic acid sequence cargo in the cytosol. Due to degradation into small oligopeptides or polymers in the cytosol, no toxicity is observed as known for high-molecular oligopeptides or polymers, e.g. from high-molecular polyarginine.

Accordingly, the disulfide-crosslinked cationic compound, used as a complexing agent to complex the immunostimulatory nucleic acid sequence of the adjuvant component, may comprise different (short) disulfide-crosslinkable cationic or polycationic components, preferably peptides, proteins or polymers selected from cationic or polycationic peptides, proteins or (non-peptidic) polymers as defined above, optionally together with further components as defined herein.

Additionally, the disulfide-crosslinked cationic compound, used as a complexing agent to complex the immunostimulatory nucleic acid sequence of the adjuvant component, more preferably at least one of the different (short) disulfide-crosslinkable cationic or polycationic peptides or (non-peptidic) polymers forming basis for the polymeric carrier via disulfide-crosslinking, may be, preferably prior to the disulfide-crosslinking, be modified with at least one further component. Alternatively, the disulfide-crosslinked cationic compound as such may be modified with at least one further component. It may also optionally comprise at least one further component, which typically forms the disulfide-crosslinked cationic compound together with the other the (short) cationic or polycationic peptides as defined above via disulfide crosslinking.

To allow modification of the disulfide-crosslinked cationic compound, used as a complexing agent to complex the immunostimulatory nucleic acid sequence of the adjuvant component, as defined above, each of the disulfide-crosslinkable cationic or polycationic components of the disulfide-crosslinked cationic compound may (preferably already prior to disulfide-crosslinking) also contain at least one further functional moiety, which allows attaching such further components as defined herein. Such functional moieties may be selected from, e.g. functionalities as defined herein, obtained e.g. by amide formation (e.g. carboxylic acids, sulphonic acids, amines, etc), by Michael addition (e.g maleinimide moieties, $\alpha,\beta$ unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

According to another aspect, the disulfide-crosslinked cationic compound or single disulfide-crosslinkable cationic or polycationic components thereof, e.g. of the above mentioned (disulfide-crosslinkable) cationic or polycationic peptides, proteins or polymers or further components, may be further modified with a ligand, preferably a carbohydrate, more preferably a sugar, even more preferably mannose. Preferably this ligand is bound to the disulfide-crosslinked cationic compound or to a (disulfide-crosslinkable) cationic or polycationic component of the disulfide-crosslinked cationic compound via a (reversible) disulfide bond or via Michael addition. In the case that the ligand is bound by a disulfide bond the ligand additionally comprises at least one —SH-moiety. These ligands may be used to direct the adjuvant component or the inventive composition or vaccine composition to specific target cells (e.g. hepatocytes or antigen-presenting cells). In this context mannose is particular preferred as ligand in the case that dendritic cells are the target especially for vaccination or adjuvant purposes.

According to one specific aspect, the entire adjuvant component may be formed by a polymerization condensation (of at least one) of the above mentioned (disulfide-crosslinkable) cationic or polycationic components, preferably peptides, proteins or polymers or further components as defined above, via their —SH-moieties in a first step to form the disulfide-crosslinked cationic compound and complexing the immunostimulatory nucleic acid sequence to such a disulfide-crosslinked cationic compound in a second step. The disulfide-crosslinked cationic compound may thus contain a number of at least one or even more of the same or different of the above defined cationic or polycationic peptides, proteins or polymers or further components, the number preferably determined by the above range.

According to one alternative specific aspect, the entire adjuvant component may be formed by carrying out the polymerization condensation of at least one of the above mentioned (disulfide-crosslinkable) cationic components, preferably cationic or polycationic peptides, proteins or polymers or further components, via their —SH-moieties simultaneously to complexing the immunostimulatory nucleic acid sequence to the (in situ prepared) disulfide-crosslinked cationic compound. Likewise, the disulfide-crosslinked cationic compound may thus also here contain a number of at least one or even more of the same or different of the above defined (disulfide-crosslinkable) cationic or polycationic components, preferably peptides, proteins or polymers or further components, the number preferably determined by the above range.

According to the first embodiment, the inventive composition or vaccine composition furthermore comprises an antigen, preferably a protein or peptide antigen and/or a nucleic acid sequence encoding said antigen. According to the present invention, the term "antigen" refers to a substance which is recognized by the immune system and is capable of triggering an antigen-specific immune response, e.g. by formation of antibodies or antigen-specific T-cells as part of an adaptive immune response. In this context, the first step of an adaptive immune response is the activation of nave antigen-specific T cells by antigen-presenting cells. This occurs in the lymphoid tissues and organs through which nave T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. $CD4^+$ T cells bind to a MHC class II molecule and $CD8^+$ T cells to a MHC class I molecule. MHC class I and MHC class II molecules have distinct distributions among cells that reflect the different effector functions of the T cells that recognize them. MHC class I molecules present peptides from pathogens, commonly viruses to $CD8^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. Thereby MHC class I molecules on the surface of cells infected with viruses or other cytosolic pathogens display peptides from these pathogens. The $CD8^+$ T cells that recognize MHC class I:peptide complexes are specialized to kill any cells displaying foreign peptides and so rid the body of cells infected with viruses and other cytosolic pathogens. The main function of $CC4^+$ T cells ($CD4^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating nave B cells to secrete IgM, and induce the production of weakly opsonising antibodies such as IgG1 and IgG3 (mouse) and IgG2 and IgG4 (human) as well as IgA and IgE (mouse and human).

In the context of the present invention, antigens as contained in the inventive composition or vaccine composition any antigen, antigenic epitope or antigenic peptide, falling under the above definition, more preferably protein and peptide antigens or their encoding nucleic acid sequences, e.g. tumour antigens, allergenic antigens, auto-immune self-antigens, pathogenic antigens, etc. In particular antigens as contained in the inventive composition or vaccine composition, either as a protein or peptide or encoded by a nucleic acid sequence may selected from antigens generated outside the cell, more typically from antigens not derived from the host organism (e.g. a human) itself (i.e. non-self antigens) but rather derived from host cells outside the host organism, e.g. viral antigens, bacterial antigens, fungal antigens, protozoological antigens, animal antigens, allergenic antigens, etc. Allergenic antigens (allergy antigens) are typically antigens, which cause an allergy in a human and may be derived from either a human or other sources. Additionally, antigens as contained in the inventive composition or vaccine composition may be furthermore antigens generated inside the cell, the tissue or the body. Such antigens include antigens derived from the host organism (e.g. a human) itself, e.g. tumour antigens, self-antigens or auto-antigens, such as auto-immune self-antigens, etc., but also (non-self) antigens as defined herein, which have been originally been derived from host cells outside the host organism, but which are fragmented or degraded inside the body, tissue or cell, e.g. by (protease) degradation, metabolism, etc.

One class of antigens as contained in the inventive composition or vaccine composition may comprise tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are (were) associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however, they may not be antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies. Particular preferred tumour antigens are selected from the group consisting of 5T4, 707-AP, 9D7, AFP, AlbZIP HPG1, alpha-5-beta-1-integrin, alpha-5- beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R171, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class l/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, 5-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR-2/FLK-1, and WT1. Such tumour antigens preferably may be selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), surviving (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFRI (epidermal growth factor receptor 1) (e.g. EGFRI (epidermal growth factor receptor 1) according to accession number AF288738), MUC1, mucin-1 (e.g. mucin-1 according to accession number NM_002456), SEC61G (e.g. SEC61G according to accession number NM_014302), hTERT (e.g. hTERT accession number NM_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

According to another alternative, one further class of antigens as contained in the inventive composition or vaccine composition may comprise allergenic antigens. Such allergenic antigens may be selected from antigens derived from different sources, e.g. from animals, plants, fungi, bacteria, etc. Allergens in this context include e.g. grasses, pollens, molds, drugs, or numerous environmental triggers, etc. Allergenic antigens typically belong to different classes of compounds, such as nucleic acid sequences and their fragments, or proteins or peptides and their fragments, carbohydrates, polysaccharides, sugars, lipids, phospholipids, etc.

Antigens as contained in the inventive composition or vaccine composition may occur as a protein or peptide antigen, or a fragment, variant or epitope thereof and/or may occur as a nucleic acid sequence encoding said protein or peptide antigen or a fragment, variant or epitope thereof.

According to one alternative, the antigen of the inventive composition or vaccine composition may occur as a protein or peptide antigen, or as a fragment, variant or epitope thereof. In this context, fragments and/or variants may have a sequence identity to one of the aforementioned protein or peptide antigens of at least 5%, 10%, 20%, 30%, 40%, 50%, 60%, 70%, 80% or 85%, preferably at least 90%, more preferably at least 95% and most preferably at least 99% over the whole length of these protein or peptide antigens. In the context of the present invention a fragment of such a protein or peptide antigen is to be understood as a truncated protein or peptide thereof, i.e. an amino acid sequence, which is N-terminally, C-terminally and/or intrasequentially truncated compared to the amino acid sequence of the original (native) protein or peptide antigen. Especially, fragments including an antigenic epitope are preferred. In this context, fragments and epitopes are preferably as specifically defined herein for antigens.

"Fragments" of protein or peptide antigens in the context of the present invention may comprise a sequence of a protein or peptide antigen as defined herein, which is, with regard to its amino acid sequence (or its encoded nucleic acid sequence), N-terminally, C-terminally and/or intrasequentially truncated compared to the amino acid sequence of the original (native) protein or peptide antigen (or its encoded nucleic acid sequence). Such truncation may thus occur either on the amino acid level or correspondingly on the nucleic acid sequence level. A sequence identity with respect to such a fragment as defined herein may therefore preferably refer to the entire protein or peptide antigen as defined herein or to the entire (coding) nucleic acid sequence of such a protein or peptide antigen. The same applies accordingly to nucleic acid sequences.

Such fragments of protein or peptide antigens in the context of the present invention may furthermore comprise a sequence of a protein or peptide antigen as defined herein, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form.

The fragments of protein or peptide antigens as defined herein may also comprise epitopes of those protein or peptide antigens. Epitopes (also called "antigen determinants") in the context of the present invention are typically fragments located on the outer surface of (native) proteins or peptides as defined herein, preferably having 5 to 15 amino acids, more preferably having 5 to 12 amino acids, even more preferably having 6 to 9 amino acids, which may be recognized by antibodies or B-cell receptors, i.e. in their native form. Such epitopes of protein or peptide antigens may furthermore be selected from any of the herein mentioned variants of such protein or peptide antigens. In this context antigenic determinants can be conformational or discontinous epitopes which are composed of segments of the protein or peptide antigens as defined herein that are discontinuous in the amino acid sequence of the protein or peptide antigens as defined herein but are brought together in the three-dimensional structure or continuous or linear epitopes which are composed of a single polypeptide chain.

"Variants" of protein or peptide antigens as defined herein may be encoded by a nucleic acid sequence as defined herein, wherein nucleotides of the nucleic acid sequence, encoding the protein or peptide antigen as defined herein, are exchanged. Thereby, a protein or peptide antigen may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein or peptide antigen, e.g. its specific antigenic property.

Protein or peptide antigens, or a fragment, variant or epitope thereof as defined herein, which have (a) conservative substitution(s) compared to the physiological, i.e. native and non-modified, sequence in particular fall under the term "variants". Substitutions in which encoded amino acids which originate from the same class are exchanged for one another are called conservative substitutions. In particular, these are encoded amino acids, encoded aliphatic side chains, positively or negatively charged side chains, aromatic groups in the side chains or encoded amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification of the three-dimensional structure or do not affect the binding region or the catalytic domain. Modifications of the three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed), Elsevier, Amsterdam).

According to one further alternative, the antigen of the inventive composition or vaccine composition may occur as a nucleic acid sequence encoding said protein or peptide antigen or a fragment, variant or epitope thereof as defined above. In the context of the present invention, such a nucleic acid sequence may be any suitable nucleic acid sequence, selected e.g. from any (single-stranded or double-stranded) DNA, preferably, without being limited thereto, e.g. genomic DNA, single-stranded DNA molecules, double-stranded DNA molecules, coding DNA, DNA primers, DNA probes, a (short) DNA oligonucleotide ((short) oligodesoxyribonucleotides), or may be selected e.g. from any PNA (peptide nucleic acid sequence) or may be selected e.g. from any (single-stranded or double-stranded) RNA, preferably, without being limited thereto, a (short) RNA oligonucleotide ((short) oligoribonucleotide), a coding RNA, a messenger RNA (mRNA), etc. Preferably, the nucleic acid sequence encoding said protein or peptide antigen or a fragment, variant or epitope thereof is an RNA, more preferably a (linear) single-stranded RNA, even more preferably an mRNA. In the context of the present invention, an mRNA is typically an RNA, which is composed of several structural elements, e.g. an optional 5'-CAP structure, an optional 5'-UTR region, an upstream positioned ribosomal binding site followed by a coding region, an optional 3'-UTR region, which may be followed by a poly-A tail (and/or a poly-C-tail). An mRNA may occur as a mono-, di-, or even multicistronic RNA, i.e. a RNA which carries the coding sequences of one, two or more proteins or peptides, e.g. one, two or more protein or peptide antigens or fragments, variants or epitopes thereof. Such coding sequences in di-, or even multicistronic mRNA may be separated by at least one IRES (internal ribosomal entry site) sequence, e.g. as defined herein. Examples of IRES sequences which may be used include those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

Furthermore, the nucleic acid sequence encoding said protein or peptide antigen or a fragment, variant or epitope thereof as defined above, may be a single- or a double-stranded nucleic acid sequence (molecule) (which may also be regarded as a nucleic acid sequence (molecule) due to non-covalent association of two single-stranded nucleic acid sequence(s) (molecules)) or a partially double-stranded or partially single stranded nucleic acid sequence, which are at least partially self complementary (both of these partially double-stranded or partially single stranded nucleic acid sequences are typically formed by a longer and a shorter single-stranded nucleic acid sequence or by two single stranded nucleic acid sequences, which are about equal in length, wherein one single-stranded nucleic acid sequence is in part complementary to the other single-stranded nucleic acid sequence and both thus form a double-stranded nucleic acid sequence in this region, i.e. a partially double-stranded or partially single stranded nucleic acid sequence (molecule). Preferably, the nucleic acid sequence (molecule) may be a single-stranded nucleic acid sequence. Furthermore, the nucleic acid sequence (molecule) may be a circular or linear nucleic acid sequence, preferably a linear nucleic acid sequence.

In order to determine the percentage to which two sequences are identical, particularly the sequences of protein or peptide antigens, or a fragment, variant or epitope thereof as defined herein or the sequences of nucleic acid sequences encoding said protein or peptide antigens or a fragment, variant or epitope thereof, as defined herein, or sequences of any further protein or nucleic acid sequence as defined herein, the sequences can be aligned in order to be subsequently compared to one another. Therefore, as an example, e.g. gaps can be inserted into the sequence of the first sequence (e.g. (m)RNA or mRNA) and the component at the corresponding position of the second sequence (e.g. (m)RNA or mRNA) can be compared. If a position in the first sequence (e.g. (m)RNA or mRNA) sequence is occupied by the same component as is the case at a position in the second sequence (e.g. (m)RNA or mRNA), the two sequences are identical at this position. The percentage to which two (m)RNA (or mRNA) sequences are identical is a function of the number of identical positions divided by the total number of positions. The same, of course also applies accordingly to DNA sequences or the encoded amino acid sequences. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic acid sequences Res, 25:3389-3402. Such an algorithm is integrated e.g. in the BLAST or NBLAST program.

In a further preferred aspect, a nucleic acid sequence as herein defined may also occur in the form of a modified nucleic acid sequence.

According to a first specific aspect, a nucleic acid sequence as herein defined may be provided as a "stabilized nucleic acid sequence", preferably as a stabilized RNA or DNA, more preferably as a RNA that is essentially resistant to in vivo degradation (e.g. by an exo- or endonuclease).

In this context, a nucleic acid sequence as herein defined may contain backbone modifications, sugar modifications or base modifications. A backbone modification in connection with the present invention is a modification in which phosphates of the backbone of the nucleotides contained in the nucleic acid sequence are chemically modified. A sugar modification in connection with the present invention is a chemical modification of the sugar of the nucleotides of a nucleic acid sequence as defined herein. Furthermore, a base modification in connection with the present invention is a chemical modification of the base moiety of the nucleotides of a nucleic acid sequence as defined herein.

According to a further aspect, a nucleic acid sequence as defined herein can contain a lipid modification. Such a lipid-modified nucleic acid sequence typically further comprises at least one linker covalently linked with that nucleic acid sequence, and at least one lipid covalently linked with the respective linker. Alternatively, the lipid-modified nucleic acid sequence comprises at least one nucleic acid sequence as defined herein and at least one (bifunctional) lipid covalently linked (without a linker) with that nucleic acid sequence. According to a third alternative, the lipid-modified nucleic acid sequence comprises a nucleic acid sequence as defined herein, at least one linker covalently linked with that nucleic acid sequence, and at least one lipid covalently linked with the respective linker, and also at least one (bifunctional) lipid covalently linked (without a linker) with that nucleic acid sequence.

The nucleic acid sequence as defined herein may likewise be stabilized in order to prevent degradation of the nucleic acid sequence by various approaches, particularly, when RNA or mRNA is used as a nucleic acid sequence for the inventive purpose. It is known in the art that instability and (fast) degradation of RNA in general may represent a serious problem in the application of RNA based compositions. This instability of RNA is typically due to RNA-degrading enzymes, "RNAases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance particularly for an mRNA. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

According to another aspect, a nucleic acid sequence as defined herein may be modified, and thus stabilized, especially if the nucleic acid sequence is in the form of a coding nucleic acid sequence e.g. an mRNA, by modifying the G/C content of the nucleic acid sequence, particularly an mRNA, preferably of the coding region thereof.

In a particularly preferred aspect of the present invention, the G/C content of the coding region of a nucleic acid sequence as defined herein, especially if the nucleic acid sequence is in the form of an mRNA, is modified, particularly increased, compared to the G/C content of the coding region of its particular wild type coding sequence, i.e. the unmodified mRNA. The encoded amino acid sequence of the nucleic acid sequence is preferably not modified compared to the coded amino acid sequence of the particular wild type mRNA.

The modification of the G/C-content of a nucleic acid sequence as defined herein, especially if the nucleic acid sequence is in the form of an mRNA or codes for an mRNA, is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. According to the invention, the codons of the coding sequence or mRNA are therefore varied compared to its wild type coding sequence or mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Preferably, the G/C content of the coding region of a nucleic acid sequence as defined herein, especially if the nucleic acid sequence is in the form of an mRNA or codes for an mRNA, is increased by at least 7%, more preferably by at least 15%, particularly preferably by at least 20%, compared to the G/C content of the coded region of the wild type mRNA. According to a specific aspect at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence.

In this context, it is particularly preferable to increase the G/C content of a nucleic acid sequence as defined herein, especially if the nucleic acid sequence is in the form of an mRNA or codes for an mRNA, to the maximum (i.e. 100% of the substitutable codons), in particular in the region coding for a protein, compared to the wild type sequence.

According to the invention, a further preferred modification of a nucleic acid sequence as defined herein, especially if the nucleic acid sequence is in the form of an mRNA or codes for an mRNA, is based on the finding that the translation efficiency is also determined by a different frequency in the occurrence of tRNAs in cells. Thus, if so-called "rare codons" are present in the nucleic acid sequence, especially if the nucleic acid sequence is in the form of an mRNA or codes for an mRNA, to an increased extent, the corresponding modified nucleic acid sequence is translated to a significantly poorer degree than in the case where codons coding for relatively "frequent" tRNAs are present.

Especially if the modified nucleic acid sequence of a nucleic acid sequence as defined is in the form of an mRNA or codes for an mRNA, the coding region of the modified nucleic acid sequence is preferably modified compared to the corresponding region of the wild type mRNA or coding sequence such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the nucleic acid sequence, especially if the nucleic acid sequence is in the form of an mRNA or codes for an mRNA, is modified such that codons for which frequently occurring tRNAs are available are inserted. In other words, according to the invention, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified nucleic acid sequence as herein defined, especially if the nucleic acid sequence is in the form of an mRNA or codes for an mRNA, with the "frequent" codons without modifying the amino acid sequence of a protein encoded by the coding region of such a nucleic acid sequence. This preferred aspect allows provision of a particularly efficiently translated and stabilized (modified) nucleic acid sequence, especially if the nucleic acid sequence is in the form of an mRNA or codes for an mRNA.

According to a further preferred aspect of the invention, a nucleic acid sequence as defined herein, especially if the nucleic acid sequence is in the form of a coding nucleic acid sequence, preferably has at least one 5' and/or 3' stabilizing sequence. These stabilizing sequences in the 5' and/or 3' untranslated regions have the effect of increasing the half-life of the nucleic acid sequence in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from Homo sapiens or Xenopus laevis may be mentioned as an example of stabilizing sequences which can be used in the present invention for a stabilized nucleic acid sequence. Another example of a stabilizing sequence has the general formula (C/U)CCAN$_x$CCC(U/A)Py$_x$UC(C/U)CC (SEQ ID NO: 543), which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art.

Nevertheless, substitutions, additions or eliminations of bases are preferably carried out with a nucleic acid sequence as defined herein, especially if the nucleic acid sequence is in the form of an mRNA, using a DNA matrix for preparation of the nucleic acid sequence by techniques of the well known site directed mutagenesis or with an oligonucleotide ligation strategy (see e.g. Maniatis et al, Molecular Cloning: A Laboratory Manual, Cold Spring Harbor Laboratory Press, 3rd ed., Cold Spring Harbor, N.Y., 2001). In such a process, for preparation of the nucleic acid sequence, especially if the nucleic acid sequence is in the form of an mRNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the nucleic acid sequence, e.g. mRNA, to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed), PCR Technology:

Nucleic acid sequences as defined and used herein may be prepared using any method known in the art, including synthetic methods such as e.g. solid phase synthesis, as well as in vitro methods, such as in vitro transcription reactions.

According to the first embodiment, the inventive composition or vaccine composition furthermore comprises a carrier molecule for combined packaging the adjuvant component and the antigen as defined herein. In this context, a carrier molecule is preferably a polymeric carrier molecule, more preferably a polymeric carrier molecule according to generic formula (VI):

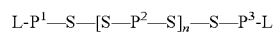

wherein,

P$^1$ and P$^3$ are different or identical to each other and represent a linear or branched hydrophilic polymer chain, each P$^1$ and P$^3$ exhibiting at least one —SH-moiety, capable to form a disulfide linkage upon condensation with component P$^2$, or alternatively with (AA), (AA)$_x$, or [(AA)$_x$]$_z$ if such components are used as a linker between P$^1$ and P$^2$ or P$^3$ and P$^2$) and/or with further components (e.g. (AA), (AA)$_x$, [(AA)$_x$]$_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy) ethylphosphorylcholine), hydroxyethylstarch or poly (hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationic peptide or protein, e.g. as defined herein, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20;

is a cationic or polycationic polymer, e.g. as defined herein, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_x$, or $[(AA)_x]_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_x$, $[(AA)_x]_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galctose or synthetic ligands), small molecule agonists, inhibitors or antagonists of receptors (e.g. RGD peptidomimetic analogues) etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

The inventive polymeric carrier molecule according to generic formula (VI) is preferably prepared by a new synthesis strategy and advantageously allows to define the length of the polymer chain and to combine desired properties of different (short) polymers in one polymer, e.g. to efficiently compact cargos for the purpose of efficient transfection of said (nucleic acid) cargo. Such a (nucleic acid) cargo may be e.g. the adjuvant component of the inventive composition or vaccine composition comprising or consisting of at least one immunostimulatory nucleic acid, complexed with a complexing agent; and/or the antigen of the inventive composition or vaccine composition, preferably a protein or peptide antigen and/or a nucleic acid encoding said antigen, or a mixture of both, etc. The (nucleic acid) cargo, and preferably the entire inventive composition or vaccine composition is preferably efficiently transfected into different cell lines in vitro but also in vivo due to the properties of the inventive polymeric carrier molecule without loss of activity. The inventive polymeric carrier molecule used for this purpose is furthermore not toxic to cells and provides for efficient release of its (nucleic acid) cargo, i.e. the adjuvant component of the inventive composition or vaccine composition comprising or consisting of at least one immunostimulatory nucleic acid, complexed with a complexing agent; and/or the antigen of the inventive composition or vaccine composition, preferably a protein or peptide antigen and/or a nucleic acid encoding said antigen. Finally, the inventive polymeric carrier molecule and thus the inventive composition or vaccine composition shows improved resistance to agglomeration due to the reversible addition of hydrophilic polymer chains (e.g. PEG-monomers) particularly to the terminal ends of the inventive polymeric carrier molecule according to generic formula (VI). The inventive polymeric carrier molecule additionally confers enhanced stability to the (nucleic acid) cargo with respect to serum containing media.

Even more advantageously, the inventive polymeric carrier molecule according to generic formula (VI) allows to considerably vary its peptide or polymeric content and thus to modulate its biophysical/biochemical properties, particularly the cationic properties of component $[S—P^2-5]$, quite easily and fast, e.g. by incorporating as components $P^2$ the same or different cationic peptide(s), protein(s) or polymer(s) and optionally adding other components, e.g. amino acid component(s) (AA) or $(AA)_x$, into the repetitive component $[S—P^2—S]$ to form a modified repetitive component such as $\{[S—P^2—S]_a/[S-(AA)_x-S]_b\}$ as a core motif of the inventive polymeric carrier (wherein a+b=n, see below). Even though consisting of quite small non-toxic repeat units the inventive polymeric carrier molecule allows effectively packaging the components of the inventive composition or vaccine composition. Additionally, under the reducing conditions of the cytosol (e.g. cytosolic GSH), the inventive polymeric carrier molecule of the entire complex of the inventive composition or vaccine composition is rapidly degraded into its monomers, which are further degraded (e.g. oligopeptides) or secreted (e.g. PEG). This supports deliberation of the components of the inventive composition or vaccine composition in the cytosol. Due to degradation into small oligopeptides in the cytosol, no toxicity is observed as known for high-molecular oligopeptides, e.g. from high-molecular oligoarginine. The PEG-"coating" also allows to somehow "coat" the polymeric carrier and thus the entire "cargo" (the adjuvant component and/or the antigen of the inventive composition or vaccine composition) with a hydrophilic coating at its terminal ends, which prevents salt-mediated agglomeration and undesired interactions with serum contents. In the cytosole, this "coating" is easily removed under the reducing conditions of the cell. Also, this effect promotes deliberation of the cargo in the cytosol.

As defined above, ligands (L), may be optionally used in the inventive polymeric carrier molecule according to generic formula (VI), e.g. for direction of the inventive carrier polymer and its entire "cargo" (the adjuvant component and/or the antigen of the inventive composition or vaccine composition) into specific cells. They may be selected independent from the other from RGD, Transferrin, Folate, a signal peptide or signal sequence, a localization signal or sequence, a nuclear localization signal or sequence (NLS), an antibody, a cell penetrating peptide (CPP), (e.g. TAT, KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues) or any such molecule as further defined below. etc. Particularly preferred are cell penetrating peptides (CPPs), which induce a pH-mediated conformational change in the endosome and lead to an improved release of the inventive polymeric carrier (in complex with a nucleic acid) from the endosome by insertion into the lipid layer of the liposome. Such called CPPs or cationic peptides for transportation, may include, without being limited thereto protamine, nucleoline, spermine or spermidine, poly-L-lysine (PLL), basic polypeptides, polyarginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from Drosophila antennapedia), pAntp, pIsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, Loligomers, Arginine-rich peptides, Calcitonin-peptides, FGF, Lactoferrin poly-L-Lysine, poly-Arginine, histones, VP22 derived or analog peptides, HSV, VP22 (Herpes simplex), MAP, KALA or protein transduction domains (PTDs, PpT620, prol in-rich peptides, arginine-rich peptides, lysine-rich peptides, Pep-1, L-oligomers, Calcitonin peptide(s), etc. Particularly preferred in this context is mannose as ligand to target antigen presenting cells which carries on their cell membrane mannose receptors. In a further preferred aspect of the first embodiment of the present invention galactose as optional ligand can be used to target hepatocytes. Such ligands may be attached to component $P^1$ and/or $P^3$ by reversible disulfide bonds as defined below or by any other possible chemical attachment, e.g. by amide formation (e.g. carboxylic acids, sulphonic acids, amines, etc), by Michael addition (e.g. maleinimide moieties, $\alpha,\beta$ unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

In the context of formula (VI) of the present invention components $P^1$ and $P^3$ represent a linear or branched hydrophilic polymer chain, containing at least one —SH-moiety, each $P^1$ and $P^3$ independently selected from each other, e.g. from polyethylene glycol (PEG), poly-N-(2-hydroxypropyl) methacrylamide, poly-2-(methacryloyloxy)ethyl phosphorylcholines, poly(hydroxyalkyl L-asparagine) or poly(hydroxyalkyl L-glutamine). $P^1$ and $P^3$ may be identical or different to each other. Preferably, each of hydrophilic polymers $P^1$ and $P^3$ exhibits a molecular weight of about 1 kDa to about 100 kDa, preferably of about 1 kDa to about 75 kDa, more preferably of about 5 kDa to about 50 kDa, even more preferably of about 5 kDa to about 25 kDa. Additionally, each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (VI) above (the brackets are omitted for better readability), wherein any of S, $P^1$ and $P^3$ are as defined herein, typically represent a situation, wherein one —SH-moiety of hydrophilic polymers $P^1$ and $P^3$ was condensed with one —SH-moiety of component $P^2$ of generic formula (VI) above, wherein both sulphurs of these —SH-moieties form a disulfide bond —S—S— as defined herein in formula (VI). These —SH-moieties are typically provided by each of the hydrophilic polymers $P^1$ and $P^3$, e.g. via an internal cysteine or any further (modified) amino acid or compound which carries a SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the SH-moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, a43 unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the —SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

According to one preferred alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the inventive polymeric carrier (in complex with a nucleic acid) from the endosome by insertion into the lipid layer of the liposome. Such called cell penetrating peptides (CPPs) or cationic peptides for transportation, may include, without being limited thereto protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, Loligomers, Arginine-rich peptides, Calcitonin-peptides, FGF, Lactoferrin poly-L-Lysine, poly-Arginine, histones, VP22 derived or analog peptides, HSV, VP22 (Herpes simplex), MAP, KALA or protein transduction domains (PTDs), PpT620, prol in-rich peptides, arginine-rich peptides, lysine-rich peptides, Pep-1, L-oligomers, Calcitonin peptide(s), etc.

According to a further preferred aspect of the first embodiment of the present invention, each of hydrophilic polymers $P^1$ and $P^3$ of formula (VI) of the polymeric carrier used according to the present invention may also contain at least one further functional moiety, which allows attaching further components as defined herein, e.g. a ligand, an amino acid component (AA) or $(AA)_x$, etc. Such functional moieties may be selected from functionalities which allow the attachment of further components, e.g. functionalities as defined herein, e.g. by amide formation (e.g. carboxylic acids, sulphonic acids, amines, etc), by Michael addition (e.g maleinimide moieties, $\alpha,\beta$ unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

Component $P^2$ of formula (VI) of the polymeric carrier used according to the first embodiment of the present invention preferably represents a cationic or polycationic peptide or protein or alternatively a cationic or polycationic polymer. Each component $P^2$ typically exhibits at least two —SH-moieties, capable to form a disulfide linkage upon condensation with further components $P^2$, component(s) $P^1$ and/or $P^3$ or alternatively with further components, e.g. amino acid components $(AA)_x$. Component $P^2$ typically occurs within the repetitive component [—S—$P^2$—S-] of formula (VI) of the present invention. The term "cationic or polycationic" typically refers to a charged molecule, which is positively charged (cation) at a pH value of about 1 to 9, preferably 4 to 9, 5 to 8 or even 6 to 8, more preferably of a pH value of or below 9, of or below 8, of or below 7, most preferably at physiological pH values, e.g. about 7.3 to 7.4. Accordingly, a cationic or polycationic peptide or protein as component $P^2$ or alternatively a cationic or polycationic polymer as component $P^2$ of formula (VI) of the polymeric carrier according to the present invention is positively charged under physiological conditions, particularly under physiological salt conditions of the cell in vivo.

In the specific case that component $P^2$ of formula (VI) of the present invention is a cationic or polycationic peptide or protein the cationic properties of component [S—$P^2$—S]$_n$ or {[S—$P^2$—S]$_a$/[S-(AA)$_x$-S]$_b$}, (as defined below) may be determined upon its content of cationic amino acids in the entire component [S—$P^2$—S]$_n$ or {[S—$P^2$—S]$_a$/[S-(AA)$_x$-S]$_b$}. Preferably, the content of cationic amino acids in component [S—$P^2$—S]$_n$ or {[S—$P^2$—S]$_a$/[S-(AA)$_x$-S]$_b$} is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the entire component [S—$P^2$—S]$_n$ or {[S—$P^2$—S]$_a$/[S-(AA)$_x$-S]$_b$} is 100%.

In the specific case that component $P^2$ of formula (VI) of the polymeric carrier of the present invention is a cationic or polycationic polymer the cationic properties of component [S—$P^2$—S]$_n$ or {[S—$P^2$—S]$_a$/[S-(AA)$_x$-S]$_b$} may be determined upon its content of cationic charges in the entire component [S—$P^2$—S]$_n$ or {[S—$P^2$—S]$_a$/[S-(AA)$_x$-S]$_b$} when compared to the overall charges of component [S—$P^2$—S]$_n$ or {[S—$P^2$—S]$_a$/[S-(AA)$_x$-S]$_b$}. Preferably, the content of cationic charges in component [S—$P^2$—S]$_n$ or {[S—$P^2$—S]$_a$/[S-(AA)$_x$-S]$_b$} at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even preferably in the range of about 20% to 50%, e.g. 20, 30, 40 or 50%, or in a range formed by any two of the afore mentioned values, provided, that the content of all charges, e.g. positive and negative charges at a (physiological) pH as defined herein, in the entire component [S—$P^2$—S]$_n$ or {[S—$P^2$—S]$_a$/[S-(AA)$_x$-S]$_b$} is 100%.

In the specific context of a complex formed by the adjuvant component, the antigen and the inventive polymeric carrier molecule according to generic formula (VI) L-$P^1$—S—[S—$P^2$—S]$_n$—S—$P^3$-L as defined herein (or according to any of its subformulae herein), forming the inventive composition, preferably the inventive vaccine, it is particularly preferred that at least 10% of all charges in the whole repetitive component [S—$P^2$—S]$_n$ or {[S—$P^2$—S]$_a$/[S-(AA)$_x$-S]$_b$} are cationic to allow complexation of the negatively charged "cargo".

The cationic or polycationic peptide or protein as component $P^2$ of formula (VI) of the inventive polymeric carrier, or the cationic or polycationic polymer as component $P^2$, is preferably a linear molecule, however, branched cationic or polycationic peptides or proteins as component $P^2$ or branched cationic or polycationic polymers as component $P^2$ may also be used.

Typically, component $P^2$ of formula (VI) of the inventive polymeric carrier, e.g. the cationic or polycationic peptide or protein or the cationic or polycationic polymer as defined herein, is linked to its neighbouring components, e.g. components $P^1$ and $P^3$, and/or as a part of repetitive component $[S—P^2—S]_n$ to further components $P^2$, via disulfide bonds (—S—S—) or to $(AA)_x$ components as part of $\{[S—P^2—S]_a/[S-(AA)_x-S]_b\}$. In this context, the sulphurs adjacent to component $P^2$ in the repetitive component $[S—P^2—S]_n$ and as defined in generic formula (VI) L-$P^1$—S—$[S—P^2—S]_n$—S—$P^3$-L of the inventive polymeric carrier, necessary for providing a disulfide bond, may be provided by component $P^2$ itself by a —SH moiety as defined herein or may be provided by modifying component $P^2$ accordingly to exhibit a —SH moiety within the above definition of repetitive component $[S—P^2—S]_n$. The —SH moieties for component $P^2$ are preferably as defined herein for components $P^1$ and $P^3$. If such —SH-moieties, necessary to form a disulfide bond (—S—S—) within the above meaning, are provided by component $P^2$ itself this may occur e.g. by at least two cysteines or any further (modified) amino acids or chemical compounds, which carry a —SH moiety, already occurring within the amino acid sequence of component $P^2$ at whatever position of the amino acid sequence of component $P^2$. Alternatively, component $P^2$ may be modified accordingly with a chemical compound, e.g. a cysteine or any further (modified) amino acid or chemical compound, which carries a (free) —SH moiety. Thereby, component $P^2$ preferably carries at least two —SH-moieties, which sulphurs atoms are capable to form a disulfide bond upon condensation with a —SH-moiety of components $P^1$ or $P^3$ as defined herein, or between a first component $P^2$ and a further component $P^2$, etc. Such —SH-moieties are preferably as defined herein. Preferably the at least two —SH-moieties are located at the terminal ends or near to the terminal ends of component $P^2$ According to one specific aspect component $P^2$ of formula (VI) of the inventive polymeric carrier may comprise within repetitive component $[S—P^2—S]_n$ a cysteine as a —SH moiety, e.g. one or both of S as defined above may be a Cysteine. In this context, repetitive component $[S—P^2—S]_n$ may thus be written as follows:

[Cys-$P^2$-Cys]$_n$ wherein n and $P^2$ are as defined herein and each Cys provides for the —SH-moiety for the disulfide bond. Cys is the amino acid cysteine in its three letter code. (For illustrative purposes, in the present description the disulfide bond —S—S— generally may also be written as -(Cys-S)—(S-Cys)-, wherein Cys-S represents a Cysteine with an naturally occurring —SH moiety, wherein this —SH moiety forms a disulfide bond with a —SH moiety of a second cysteine. Accordingly, repetitive component [Cys-$P^2$-Cys]$_n$ may also be written as [(S-Cys)-$P^2$-(Cys-S)]$_n$, which indicates that the —SH-moiety is provided by a cysteine and the Cysteine itself provides for the sulphur of the disulfide bond).

In the context of the entire formula (VI) of the inventive polymeric carrier may thus be defined as follows:

L-$P^1$—S-[Cys-$P^2$-Cys]$_n$-S—$P^3$-L wherein L, $P^1$, $P^2$, $P^3$ and n are as defined herein, S is sulphur and each Cys provides for one —SH-moiety for the disulfide bond.

In each case, the SH-moiety, e.g. of a cysteine or any further (modified) amino acid or further compound used for modification of component $P^2$, may be present in the cationic or polycationic peptide or protein or cationic or polycationic polymer as component $P^2$, internally or at one or both of its terminal ends, e.g. if a cationic or polycationic peptide or protein is used as component $P^2$ at the N-terminal end or at the C-terminal end, at both these terminal ends, and/or internally at any position of the cationic or polycationic peptide or protein as component $P^2$. Preferably, the —SH moiety may be present in component $P^2$ at least at one terminal end, more preferably at both terminal ends, e.g. at the N-terminal end and/or at the C-terminal end, more preferably at both the N-terminal and the C-terminal end of a cationic or polycationic peptide or protein as component $P^2$.

Due to its repetitive character component $[S—P^2—S]_n$ within formula (VI) of the inventive polymeric carrier may represent a situation, wherein one of the at least two —SH-moieties of component $P^2$ was condensed with a —SH-moiety of a further component $P^2$ of generic formula (VI) above, wherein both sulphurs of these —SH-moieties form a disulfide bond (—S—S—) between a first component $P^2$ and at least one further component $P^2$.

In this context, the number of repetitions of component $P^2$ in formula (VI) according to the present invention is defined by integer n. n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. If, for example, in repetitive component $[S—P^2—S]_n$ integer n is 5, repetitive component $[S—P^2—S]_n$ preferably reads as follows:

[S—$P^2$—S—S—$P^2$—S—S—$P^2$—S—S—$P^2$—S—S—$P^2$—S]

In the above example component $P^2$ occurs 5 times (preferably in a linear order), wherein each component $P^2$ is linked to its neighbor component by a disulfide bond within the above definition of repetitive component $[S—P^2—S]_n$. Any of components $P^2$ may be the same or different from each other.

According to one particular aspect, component $P^2$ of formula (VI) of the inventive polymeric carrier represents a cationic or polycationic peptide or protein having a length of about 3 to about 100 amino acids, more preferably having a length of about 3 to about 50 amino acids, even more preferably having a length of about 3 to about 25 amino acids, e.g. having a length of about 3 to 10, 5 to 15, 10 to 20 or 15 to 25 amino acids, more preferably a length of about 5 to about 20 and even more preferably a length of about 10 to about 20.

The cationic or polycationic peptide or protein as component $P^2$ of formula (VI) of the inventive polymeric carrier may be any protein or peptide suitable for this purpose and exhibiting at least two —SH-moieties, particular any cationic or polycationic peptide or protein capable to complex a nucleic acid as defined according to the present invention, and thereby preferably condensing the nucleic acid.

Likewise preferred, cationic or polycationic peptides or proteins as component $P^2$ of formula (VI) of the inventive polymeric carrier exhibiting at least two —SH-moieties may be selected from protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, Loligomere, Arginine-rich peptides, Calcitonin-peptides, FGF, Lactoferrin, histones, VP22 derived or analog peptides, HSV, VP22 (Herpes simplex), MAP, KALA or protein transduction domains (PTDs, PpT620, prolin-rich peptides, lysine-rich peptides, Pep-1, L-oligomers, Calcitonin peptide(s), etc.

According to one further particular aspect of the first embodiment of the present invention, cationic or polycationic peptides or proteins as component $P^2$ of formula (VI) of the inventive polymeric carrier are selected from following cationic peptides having the following total sum formula (V) or of any of subformulae (Va) or (Vb) or specific sequences thereof as defined above, preferably under the proviso that these sequences additionally exhibit at least one or two —SH-moieties (as defined above):

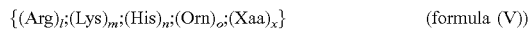  (formula (V))

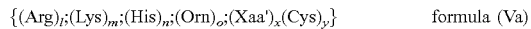  formula (Va)

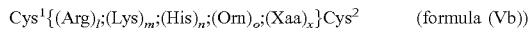  (formula (Vb))

Preferably, component $P^2$ of formula (VI) of the inventive polymeric carrier represents a cationic or polycationic polymer, typically exhibiting a molecular weight of about 0.5 kDa about 5 kDa to about 30 kDa, or a molecular weight of about 10 kDa to about 50 kDa, or of about 10 kDa to about 30 kDa, preferably of about 0.5 kDa to about 30 kDa, more preferably of about 1 kDa to about 20 kDa, and even more preferably of about 1.5 kDa to about 10 kDa, likewise preferably a molecular weight of about 0.3 kDa to about 20 kDa, preferably 0.3 kDa to about 10 kDa, including a molecular weight of about 0.4 kDa to about 10 kDa, 0.5 kDa to about 10 kDa, preferably of about 0.5 kDa to about 7.5 kDa, 0.5 kDa to about 5 kDa, 0.5 kDa to about 4 kDa, 0.5 kDa to about 3 kDa, or even 0.67 kDa to about 2.7 kDa.

Additionally, the cationic or polycationic polymer as component $P^2$ typically exhibits at least two —SH moieties, which are capable to form a disulfide linkage upon condensation with either components $P^1$ or $P^3$ or with other components $P^2$ or amino acid components (AA) or (AA)$_x$, as defined herein.

When component $P^2$ of formula (VI) of the inventive polymeric carrier represents a cationic or polycationic polymer, such a polymer may likewise be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these cationic or polycationic polymers typically exhibits at least two —SH-moieties, wherein these at least two —SH-moieties may be introduced into the cationic or polycationic polymer by chemical modifications, e.g. using imonothiolan, 3-thio propionic acid or introduction of —SH-moieties containing amino acids, such as cystein, methionine or any further (modified) amino acid. Such —SH-moieties are preferably as already defined above for components $P^1$, $P^2$ or $P^3$.

Component $P^2$ of formula (VI) of the inventive polymeric carrier preferably occurs as repetitive component [—S—$P^2$—S-]$_n$. Such a repetitive component [S—$P^2$—S]$_n$ may be prepared using at least one or even more of the same or different of the above defined components $P^2$ and polymerizing same in a polymerization condensation reaction via their —SH-moieties.

According to one specific aspect, such a repetitive component [S—$P^2$—S]$_n$ within formula (VI) of the inventive polymeric carrier may be prepared using at least one or even more of the same or different of the above defined cationic or polycationic peptides or proteins, and polymerizing same in a polymerization condensation reaction via their —SH-moieties. Accordingly, such a repetitive component [S—$P^2$—S]$_n$ within formula (VI) of the inventive polymeric carrier contains a number of at least one or even more of the same or different of the above defined cationic or polycationic proteins or peptides determined by integer n.

According to another specific aspect, such a repetitive component [S—$P^2$—S]$_n$ within formula (VI) of the inventive polymeric carrier may be prepared using at least one or even more of the same or different of the above defined cationic or polycationic polymers, and polymerizing same in a polymerization condensation reaction via their —SH-moieties. Accordingly, such a repetitive component [S—$P^2$—S]$_n$ contains a number of at least one or even more of the same or different of the above defined cationic or polycationic polymers determined by integer n.

According to a further specific aspect, such a repetitive component [S—$P^2$—S]$_n$ within formula (VI) of the inventive polymeric carrier may be prepared using at least one or even more of the same or different of the above defined cationic or polycationic polymers and at least one or even more of the same or different of the above defined cationic or polycationic proteins or peptides, and polymerizing same in a polymerization condensation reaction via their —SH-moieties. Accordingly, such a repetitive component [S—$P^2$—S]$_n$ within formula (VI) of the inventive polymeric carrier contains a number of at least one or even more of the same or different of the above defined cationic or polycationic polymers and at least one or even more of the same or different of the above defined cationic or polycationic proteins or peptides, both together determined by integer n.

According to a particular aspect, the inventive polymeric carrier according to formula (VI) as defined above, may comprise at least one amino acid component (AA), wherein AA is preferably an amino acid as defined in the following or a combination of amino acids as defined in the following, e.g. selected from an aromatic, a hydrophilic, a lipophilic, or a weak basic amino acid or peptide as defined in the following. Amino acid component (AA) preferably allows to (substantially) modify the biophysical/biochemical properties of the inventive polymeric carrier according to formula (VI) as defined herein. Preferably, the amino acid component may occur as amino acid component (AA)$_x$, wherein the number of amino acids in such an amino acid component (AA)$_x$ (repetitions) is defined by x. In the above context, x is preferably an integer and may be selected from a range of about 1 to 100, preferably from a range of about 1 to 50, more preferably 1 to 30, and even more preferably selected from a number comprising 1, 2, 3, 4, 5, 6, 7, 8, 9, 10, 11, 12, 13, 14 or 15-30, e.g. from a range of about 1 to 30, from a range of about 1 to 15, or from a number comprising 1, 2, 3, 4, 5, 6, 7, 8, 9, 10, 11, 12, 13, 14 or 15, or may be selected from a range formed by any two of the afore mentioned values. Most preferably, x is 1.

Such an amino acid component (AA) or $(AA)_x$ may be contained in every part of the inventive polymeric carrier according to formula (VI) above and therefore may be attached to all components of the inventive polymeric carrier according to formula (VI). It is particularly preferred that amino acid component (AA) or $(AA)_x$ is present as a ligand or part of the repetitive component $[S-P^2-S]_n$ within formula (VI) of the inventive polymeric carrier.

In this context it is particularly preferred that the amino acid component (AA) or $(AA)_x$ contains or is flanked (e.g. terminally) by at least one —SH containing moiety, which allows introducing this component (AA) or $(AA)_x$ via a disulfide bond into the polymeric carrier according to formula (VI) as defined herein. In this context, the amino acid component (AA) or $(AA)_x$ may also be read as a component —S-$(AA)_x$- or —S-$(AA)_x$-S—, wherein S represents a —SH containing moiety (or, of course, one sulphur of a disulfide bond), e.g. a cysteine residue. In the specific case that the —SH containing moiety represents a cysteine, the amino acid component $(AA)_x$ may also be read as -Cys-(AA)- or -Cys-(AA)-Cys- wherein Cys represents Cysteine and provides for the necessary —SH-moiety for a disulfide bond. (Accordingly, -Cys-$(AA)_x$-Cys- may also be written as —(S-Cys)-$(AA)_x$-(Cys-S)— and -Cys-$(AA)_x$- may also be written as —(S-Cys)-$(AA)_x$-)) The —SH containing moiety may be also introduced into the amino acid component $(AA)_x$ using any of modifications or reactions as shown above for components $P^1$, $P^2$ or $P^3$. In the specific case that the amino acid component $(AA)_x$ is linked to two components of the inventive polymeric carrier according to formula (VI) it is preferred that (AA) or $(AA)_x$ contains at least two —SH-moieties, e.g. at least two Cysteines, preferably at its terminal ends. This is particularly preferred if (AA) or $(AA)_x$ is part of the repetitive component $[S-P^2-S]_n$.

In an alternative the amino acid component (AA) or $(AA)_x$ is introduced into the inventive polymeric carrier according to formula (VI) as defined herein via any chemical possible addition reaction. Therefore the amino acid component (AA) or $(AA)_x$ contains at least one further functional moiety, which allows attaching same to a further component as defined herein, e.g. component $P^1$ or $P^3$, $P^2$, L, or a further amino acid component (AA) or $(AA)_x$, etc. Such functional moieties may be selected from functionalities which allow the attachment of further components, e.g. functionalities as defined herein, e.g. by amide formation (e.g. carboxylic acids, sulphonic acids, amines, etc), by Michael addition (e.g maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

The amino acid component (AA) or $(AA)_x$ may also occur as a mixed repetitive amino acid component $[(AA)_x]_z$, wherein the number of amino acid components (AA) or $(AA)_x$ is further defined by integer z. In this context, z may be selected from a range of about 1 to 30, preferably from a range of about 1 to 15, more preferably 1 to 10 or 1 to 5 and even more preferably selected from a number selected from 1, 2, 3, 4, 5, 6, 7, 8, 9, 10, 11, 12, 13, 14 or 15, or may be selected from a range formed by any two of the afore mentioned values. Such a mixed repetitive amino acid component $[(AA)_x]_z$ may be used to integrate several of the same or different amino acid components $(AA)_x$ as defined herein in the inventive polymeric carrier. Preferably, in the mixed repetitive amino acid component $[(AA)_x]_z$ the amino acid component $(AA)_x$ may contain or may be flanked (e.g. terminally) by at least one SH containing moiety, preferably at least two —SH containing moieties as already defined above, which allows coupling the different amino acid components $(AA)_x$ using a disulfide bond via a condensation polymerization. Likewise as above, the mixed repetitive amino acid component $[(AA)_x]_z$ may also be read as [S-$(AA)_x$-S]$_z$, wherein S represents a —SH containing moiety, e.g. a cysteine residue. In the specific case that the —SH containing moiety represents a cysteine, the mixed repetitive amino acid component $[(AA)_x]_z$ may also be read as [Cys-$(AA)_x$-Cys]$_z$, wherein Cys represents Cysteine and provides for the necessary —SH-moiety for a disulfide bond. The —SH containing moiety may be also introduced into the amino acid component (AA) or $(AA)_x$ using any of modifications or reactions as shown above for components $P^1$, $P^2$ or $P^3$.

The amino acid component (AA) or $(AA)_x$ or the mixed repetitive amino acid component $[(AA)_x]_z$ may be provided with at least one —SH-moiety, e.g. in a form represented by formula $(AA)_x$-SH. Then, the component (AA) or $(AA)_x$ according to formula $(AA)_x$-SH or the mixed repetitive amino acid component $[(AA)_x]_z$ according to formula $[(AA)_x]_z$-SH, may be bound to any of components L, $P^1$, $P^2$ and/or $P^3$ or another component (AA) or $(AA)_x$ via a disulfide bond. If bound to component $P^1$ and/or component $P^3$, components $P^1$ and/or $P^3$ preferably exhibit at least two —SH-moieties to allow further binding of components $P^1$ and/or $P^3$ to a component $P^2$ via a —SH-moiety forming a disulfide bond (see above). The amino acid component (AA) or $(AA)_x$ in a form represented by formula $(AA)_x$-SH or the mixed repetitive amino acid component $[(AA)_x]_z$ according to formula $[(AA)_x]_z$-SH may be also used to terminate a condensation reaction due to its single —SH moiety. In this case, the amino acid component (AA) or $(AA)_x$ in a form represented by formula $(AA)_x$-SH is preferably coupled terminally to components $P^1$ and/or $P^3$. The amino acid component (AA) or $(AA)_x$ in a form represented by formula $(AA)_x$-SH or the mixed repetitive amino acid component $[(AA)_x]_z$ according to formula $[(AA)_x]_z$-SH may be also used to bind internally to any of components L, $P^1$, $P^2$ and/or $P^3$ or a further component (AA) or $(AA)_x$ via a further internal —SH-moiety of any of components L, $P^1$, $P^2$ and/or $P^3$ or $(AA)_x$.

Furthermore, the amino acid component (AA) or $(AA)_x$ may be provided with two —SH-moieties (or even more), e.g. in a form represented by formula HS-$(AA)_x$-SH. Additionally, the mixed repetitive amino acid component $[(AA)_x]_z$ may be provided with two —SH-moieties (or even more), e.g. in a form represented by formula HS-$[(AA)_x]_z$-SH, to allow binding to two functionalities via disulfide bonds, e.g. if the amino acid component $(AA)_x$ or the mixed repetitive amino acid component $[(AA)_x]_z$ is used as a linker between two further components (e.g. as a linker between components L and $P^1$, between components $P^1$ and $P^2$, in or as a part of repetitive component $[S-P^2-S]_n$, between components $P^2$ and $P^3$ and/or between components $P^3$ and L). In this case, one —SH moiety is preferably protected in a first step using a protecting group as known in the art, leading to an amino acid component $(AA)_x$ of formula HS-$(AA)_x$-S-protecting group or to a mixed repetitive amino acid component $[(AA)_x]_z$ of formula HS-$[(AA)_x]_z$-S-protecting group. Then, the amino acid component $(AA)_x$ or the mixed repetitive amino acid component [(AA)$_x$]$_z$ may be bound to a component L, P$^1$, P$^2$ and/or P$^3$, to form a first disulfide bond via the non-protected —SH moiety. The protected —SH-moiety is then typically deprotected and bound to a further free —SH-moiety of a further component L, P$^1$, P$^2$ and/or P$^3$ to form a second disulfide bond. In the case that the amino acid component (AA)$_x$ or the mixed repetitive amino acid component [(AA)$_x$]$_z$ is part of the repetitive component [S—P$^2$—S]$_n$ it is preferred that the formation of the disulfide bonds between (AA) or (AA)$_x$ and P$^2$ concurrently occurs with the polycondensation reaction of the repetitive component [S—P$^2$—S]$_n$ and therefore no protection of the at least two terminal —SH-moieties is not necessary.

Alternatively, the amino acid component (AA) or (AA)$_x$ or the mixed repetitive amino acid component [(AA)$_x$]$_z$ may be provided with other functionalities as already described above for components P$^1$ and P$^2$ and/or P$^3$, which allow binding of the amino acid component (AA)$_x$ or binding of the mixed repetitive amino acid component [(AA)$_x$]$_z$ to any of components P$^1$, P$^2$ and/or P$^3$ or (AA) or (AA)$_x$ and optionally to component L.

Thus, according to the present invention, the amino acid component (AA) or (AA)$_x$ and/or the mixed repetitive amino acid component [(AA)$_x$]$_z$ may be bound to P$^1$, P$^2$, P$^3$, (AA) or (AA)$_x$ and/or L with or without using a disulfide linkage. Binding without using a disulfide linkage may be accomplished by any of the reactions described above, preferably by binding the amino acid component (AA) or (AA)$_x$ or the mixed repetitive amino acid component [(AA)$_x$]$_z$ to P$^1$, P$^2$, P$^3$, (AA)$_x$ and/or L using an amid-chemistry as defined herein. If desired or necessary, the other terminus of the amino acid component (AA) or (AA)$_x$ or the mixed repetitive amino acid component [(AA)$_x$]$_z$, e.g. the N- or C-terminus, may be used to couple another component, e.g. a ligand L. For this purpose, the other terminus of the amino acid component (AA) or (AA)$_x$ or the mixed repetitive amino acid component [(AA)$_x$]$_z$ preferably comprises or is modified to comprise a further functionality, e.g. an alkyn-species (see above), which may be used to add the other component via e.g. click-chemistry. Such a construct, e.g. L-(AA)$_x$-P$^1$—S— or L-[(AA)$_x$]$_z$-P$^1$—S—, may be used to terminate the polymerization condensation reaction of repetitive component [S—P$^2$—S]$_n$. If the ligand is bound via an acid-labile bond, the bond may be cleaved off in the endosome and the inventive polymeric carrier presents amino acid component (AA) or (AA)$_x$ or the mixed repetitive amino acid component [(AA)$_x$]$_z$ at its surface.

The amino acid component (AA) or (AA)$_x$ or the mixed repetitive amino acid component [(AA)$_x$]$_z$ may occur as a further component of generic formula (VI) above, e.g. as a linker between components P$^1$ or P$^3$ and P$^2$, as a linker between components L and P$^1$ or P$^2$ or as an additional component of the repetitive component [S—P$^2$—S]$_n$.

According to a first alternative, such an amino acid component (AA) or (AA)$_x$ or the mixed repetitive amino acid component [(AA)$_x$]$_z$ may be present as a linker between components P$^1$ or P$^3$ and component P$^2$. This is preferably represented in the context of the entire inventive polymeric carrier according to formula (VI) by following formulae:

L-P$^1$—S—S-(AA)$_x$-S—[S—P$^2$—S]$_n$—S-(AA)$_x$-S—S—P$^3$-L, or

L-P$^1$—S—[S-(AA)$_x$-S]$_z$—[S—P$^2$—S]$_n$—[S-(AA)$_x$-S]$_z$—S—P$^3$-L, wherein n, x, z, S, L, AA, P$^1$, P$^2$ and P$^3$ are preferably as defined herein. In the above formulae, the term "—S—S—" represents a disulfide bond, wherein this at least one sulphur of the disulfide bond may also be provided by a cysteine. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their SH-moieties to form a disulfide bond. Accordingly, the term "-Cys-Cys-" may also be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S".

According to a second alternative, such an amino acid component (AA) or (AA)$_x$ or the mixed repetitive amino acid component [(AA)$_x$]$_z$ may be present as a linker between components P$^1$ or P$^3$ and component L. This is preferably represented in the context of the entire inventive polymeric carrier according to formula (VI) by following formulae:

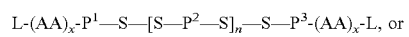

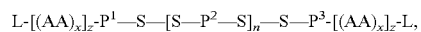

or alternatively

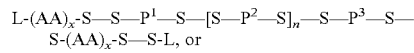

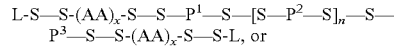

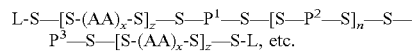

wherein n, x, z, S, L, AA, P$^1$, P$^2$ and P$^3$ are preferably as defined herein. In the above formulae, the term "—S—S—" represents a disulfide bond, as already defined above.

According to a third alternative, such an amino acid component (AA) or (AA)$_x$ or the mixed repetitive amino acid component [(AA)$_x$]$_z$ may be present as a part of components P$^1$ and/or P$^3$, wherein the amino acid component (AA)$_x$ may be directly bound to (e.g. the terminus of) component P$^1$ and/or P$^3$ without a further ligand L. In this case the (AA) or (AA)$_x$ component may be in the form of a ligand as defined above. This is preferably represented in the context of the entire inventive polymeric carrier according to formula (VI) by following formulae:

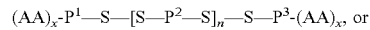

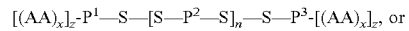

or alternatively

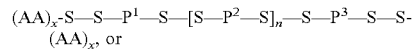

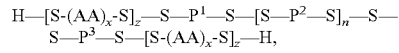

wherein n, x, z, S, AA, P$^1$, P$^2$ and P$^3$ are preferably as defined herein. In the above formulae, the term "—S—S—" represents a disulfide bond, as already defined above. The free —SH moiety at the terminal ends in the last formula may also be terminated using a monothiol compound as defined herein.

According to a fourth and particularly preferred alternative, the amino acid component (AA) or (AA)$_x$, preferably written as S-(AA)$_x$-S or [S-(AA)$_x$-S] may be used to modify component P$^2$, particularly the content of component S—P$^2$—S in repetitive component [S—P$^2$—S]$_n$ of formula (VI) above. This may be represented in the context of the entire polymeric carrier according to formula (VI) e.g. by following formula (VIa):

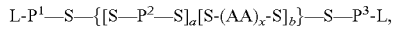

wherein x, S, L, AA, $P^1$, $P^2$ and $P^3$ are preferably as defined herein. In formula (VIa) above, any of the single components [S—$P^2$—S] and [S-(AA)$_x$-S] may occur in any order in the subformula $\{[S-P^2-S]_a[S-(AA)_x-S]_b\}$. The numbers of single components [S—$P^2$—S] and [S-(AA)$_x$-S] in the subformula $\{[S-P^2-S]_a[S-(AA)_x-S]_b\}$ are determined by integers a and b, wherein a+b=n. n is an integer and is defined as above for formula (VI).

a is an integer, typically selected independent from integer b from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, a is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

b is an integer, typically selected independent from integer a from a range of about 0 to 50 or 1 to 50, preferably from a range of about 0, 1, 2 or 3 to 30, more preferably from a range of about 0, 1, 2, 3, 4, or 5 to 25, or a range of about 0, 1, 2, 3, 4, or 5 to 20, or a range of about 0, 1, 2, 3, 4, or 5 to 15, or a range of about 0, 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 toll or 7 to 10. Most preferably, b is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In the above formula, the term "—S—S—" (the brackets are omitted for better readability) represents a disulfide bond as already defined above.

The modification of component $P^2$, particularly of component S—$P^2$—S of repetitive component [S—$P^2$—S]$_n$, by "diluting" same with amino acid components (AA) or (AA)$_x$ may be also realized in the context of any of the aforementioned alternatives of the entire polymeric carrier according to formula (VI), L-$P^1$—S—S-(AA)$_x$-S—{[S—$P^2$—S]$_a$[S-(AA)$_x$-S]$_b$}—S-(AA)$_x$-S—S—$P^3$-L, or L-$P^1$—S—[S-(AA)$_x$-S]$_z$—{[S—$P^2$—S]$_a$[S-(AA)$_x$-S]$_b$}—[S-(AA)$_x$-S]$_z$—S—$P^3$-L, or L-(AA)$_x$-$P^1$—S—{[S—$P^2$—S]$_a$[S-(AA)$_x$-S]$_b$}—S—$P^3$-(AA)$_x$-L, or L-[(AA)$_x$]$_z$-$P^1$—S—{[S—$P^2$—S]$_a$[S-(AA)$_x$-S]$_b$}—S—$P^3$-[(AA)$_x$]$_z$-L, or L-(AA)$_x$-S—S—$P^1$—S—{[S—$P^2$—S]$_a$[S-(AA)$_x$-S]$_b$}—S—$P^3$—S—S-(AA)$_x$-S—S-L, or L-S—S-(AA)$_x$-S—S—$P^1$—S—{[S—$P^2$—S]$_a$[S-(AA)$_x$-S]$_b$}—S—$P^3$—S—S-(AA)$_x$-S—S-L, or L-S—[S-(AA)$_x$-S]$_z$—S—$P^1$—S—{[S—$P^2$—S]$_a$[S-(AA)$_x$-S]$_b$}—S—$P^3$—S—[S-(AA)$_x$-S]$_z$—S-L, or (AA)$_x$-$P^1$—S—{[S—$P^2$—S]$_a$[S-(AA)$_x$-S]$_b$}—S—$P^3$-(AA)$_x$, or

[(AA)$_x$]$_z$-$P^1$—S—{[S—$P^2$—S]$_a$[S-(AA)$_x$-S]$_b$}—S—$P^3$-[(AA)$_x$]$_z$, or (AA)$_x$-S—S—$P^1$—S—{[S—$P^2$—S]$_a$[S-(AA)$_x$-S]$_b$}—S—$P^3$—S—S-(AA)$_x$, or

H—[S-(AA)$_x$-S]$_z$—S—$P^1$—S—{[S—$P^2$—S]$_a$[S-(AA)$_x$-S]$_b$}—S—$P^3$—S—[S-(AA)$_x$-S]$_z$—H, wherein n, x, z, a, b, S, L, AA, $P^1$, $P^2$ and $P^3$ are preferably as defined herein. Likewise, the term "—S—S—" represents a disulfide bond and is preferably as defined herein.

In the above alternatives, wherein the component [S—$P^2$—S] is preferably "diluted" with amino acid components [S-(AA)$_x$-S], the ratio is determined by integers a and b, wherein a+b=n. Preferably, integers a and b are selected such that the cationic binding properties of component [S—$P^2$—S] are not lost but remain to a minimum extent in subformula/component $\{[S-P^2-S]_a[S-(AA)_x-S]_b\}$. This allows to weaken ("dilute") the cationic binding strength of component [S—$P^2$—S] in repetitive component [S—$P^2$—S]$_n$ of inventive polymeric carrier of formula (VI) to a desired extent.

In this specific context the (desired) cationic binding strength of subformula/component $\{[S-P^2-S]_a[S-(AA)_x-S]_b\}$ may be determined using different methods.

According to a first alternative, component $P^2$ of formula (VI) of the present invention is particularly preferable a cationic or polycationic peptide as defined herein. Furthermore, the amino acid component (AA) or (AA)$_x$, preferably written as [S-(AA)$_x$-S], typically resembles a peptide sequence. In this specific case, the cationic properties of subformula/component $\{[S-P^2-S]_a[S-(AA)_x-S]_b\}$ may be determined upon their content of cationic amino acids in the entire subformula/component. Preferably, the content of cationic amino acids in subformula/component $\{[S-P^2-S]_a[S-(AA)_x-S]_b\}$ is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the entire subformula/component $\{[S-P^2-S]_a[S-(AA)_x-S]_b\}$ is 100%.

According to a second alternative, component $P^2$ of formula (VI) of the present invention is particularly preferable a cationic or polycationic polymer as defined herein. The amino acid component (AA) or (AA)$_x$, preferably written as [S-(AA)$_x$-S], typically resembles a peptide sequence. In this specific case, the cationic properties of subformula/component $\{[S-P^2-S]_a[S-(AA)_x-S]_b\}$ may be determined upon their content of cationic charges in the entire subformula/component. Preferably, the content of cationic charges in subformula/component $\{[S-P^2-S]_a[S-(AA)_x-S]_b\}$ at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even preferably in the range of about 20% to 50%, e.g. 20, 30, 40 or 50%, or in a range formed by any two of the afore mentioned values, provided, that the content of all charges, e.g. positive and negative charges at a (physiological) pH as defined herein, in the entire subformula/component $\{[S\text{—}P^2\text{—}S]_a[S\text{-}(AA)_x\text{-}S]_b\}$ is 100%.

According to the present invention, the amino acid component (AA) preferably comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the afore mentioned values. In this context the amino acids of amino acid component (AA) can be chosen independently from each other. For example if in the polymeric carrier according to formula (VI) above (or according to any of its subformulae herein) two or more (AA) components are present they can be the same or can be different from each other.

The amino acid component (AA) may contain or may be flanked (e.g. terminally) by an —SH containing moiety, which allows introducing this amino acid component (AA) via a disulfide bond into the polymeric carrier according to formula (VI) above (or according to any of its subformulae herein) as defined herein. In the specific case that the —SH containing moiety represents a cysteine, the amino acid component (AA) may also be read as -Cys-(AA)-Cys- or -Cys-(AA), wherein Cys represents Cysteine and provides for the necessary —SH-moiety for a disulfide bond. The —SH containing moiety may be also introduced into amino acid component (AA) itself using any of modifications or reactions as shown above for the polymeric carrier according to formula (VI) above (or according to any of its subformulae herein).

Furthermore, the amino acid component (AA) may be provided with two —SH-moieties (or even more), e.g. in a form represented by formula HS-(AA)-SH to allow binding to two functionalities via disulfide bonds, e.g. if the amino acid component (AA) is used as a linker between two further components (e.g. as a linker between two disulfide-cross-linked cationic compounds, e.g. of the polymeric carrier according to formula (VI) above (or according to any of its subformulae herein)). In this case, one —SH moiety is preferably protected in a first step using a protecting group as known in the art, leading to an amino acid component (AA) of formula HS-(AA)-S-protecting group. Then, the amino acid component (AA) may be bound to a further component of the polymeric carrier according to formula (VI) above (or according to any of its subformulae herein), to form a first disulfide bond via the non-protected —SH moiety. The protected-SH-moiety is then typically deprotected and bound to a further free —SH-moiety of a further component of the polymeric carrier to form a second disulfide bond.

Alternatively, the amino acid component (AA) may be provided with other functionalities as already described above for the other components of the polymeric carrier according to formula (VI) above (or according to any of its subformulae herein), which allow binding of the amino acid component (AA) to any of components of the polymeric carrier.

Thus, according to the present invention, the amino acid component (AA) as defined above may likewise be bound to further components of the polymeric carrier according to formula (VI) above (or according to any of its subformulae herein) with or without using a disulfide linkage. Binding without using a disulfide linkage may be accomplished by any of the reactions described above, preferably by binding the amino acid component (AA) to the other component of the polymeric carrier according to formula (VI) above (or according to any of its subformulae herein) using an amid-chemistry as defined herein. If desired or necessary, the other terminus of the amino acid component (AA), e.g. the N- or C-terminus, may be used to couple another component. For this purpose, the other terminus of the amino acid component (AA) preferably comprises or is modified to comprise a further functionality, e.g. an alkyn-species (see above), which may be used to add the other component via e.g. click-chemistry. If the other component is bound via an acid-labile bond, the bond is preferably cleaved off in the endosome and the polymeric carrier according to formula (VI) above (or according to any of its subformulae herein) presents an amino acid component (AA) at its surface.

The amino acid component (AA) may also occur as a further component of the polymeric carrier according to formula (VI) above (or according to any of its subformulae herein) as defined above, e.g. as a linker between cationic components, e.g. as a linker between one cationic peptide and a further cationic peptide, as a linker between one cationic polymer and a further cationic polymer, as a linker between one cationic peptide and a cationic polymer, all preferably as defined herein, or as an additional component of the polymeric carrier according to formula (VI) above (or according to any of its subformulae herein), e.g. by binding the amino acid component (AA) to the polymeric carrier or a component thereof, e.g. via side chains, SH-moieties or via further moieties as defined herein, wherein the amino acid component (AA) is preferably accordingly modified.

According to a particularly preferred alternative, the amino acid component (AA), may be used to modify the polymeric carrier according to formula (VI) above (or according to any of its subformulae herein), particularly the content of cationic components in the polymeric carrier as defined above.

In this context it is preferable, that the content of cationic components in the polymeric carrier according to formula (VI) above (or according to any of its subformulae herein) is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 30% to 100%, more preferably in the range of about 50% to 100%, even preferably in the range of about 70% to 100%, e.g. 70, 80, 90 or 100%, or in a range formed by any two of the afore mentioned values, provided, that the content of all components in the polymeric carrier according to formula (VI) above (or according to any of its subformulae herein) is 100%.

In the context of the present invention, the amino acid component(s) (AA) (likewise in the context of (AA) or $[(AA)_x]_y$ as defined above) may be independently selected from the following alternatives.

According to a first alternative, the amino acid component (AA) may be an aromatic amino acid component (AA). The incorporation of aromatic amino acids or sequences as amino aromatic acid component (AA) into the polymeric carrier molecule according to formula (VI) above (or according to any of its subformulae herein) of the present invention enables a different (second) binding of the polymeric carrier to the nucleic acid sequence due to interactions of the aromatic amino acids with the bases of the "cargo" of the polymeric carrier (e.g. the adjuvant component and/or the antigen as defined herein) in contrast to the binding thereof via cationic charged sequences of the polymeric carrier molecule to e.g. the phosphate backbone of a nucleic acid of the "cargo". This interaction may occur e.g. by intercalations or by minor or major groove binding. This kind of interaction is not prone to decompaction by anionic complexing partners (e.g. Heparin, hyaluronic acid, etc) which are found mainly in the extracellular matrix in vivo and is also less susceptible to salt effects.

For this purpose, the amino acids in the aromatic amino acid component (AA) may be selected from either the same or different aromatic amino acids e.g. selected from Trp, Tyr, or Phe. Alternatively, the amino acids (or the entire aromatic amino acid component (AA)) may be selected from following peptide combinations Trp-Tyr, Tyr-Trp, Trp-Trp, Tyr-Tyr, Trp-Tyr-Trp, Tyr-Trp-Tyr, Trp-Trp-Trp, Tyr-Tyr-Tyr, Trp-Tyr-Trp-Tyr, Tyr-Trp-Tyr-Trp, Trp-Trp-Trp-Trp, Phe-Tyr, Tyr-Phe, Phe-Phe, Phe-Tyr-Phe, Tyr-Phe-Tyr, Phe-Phe-Phe, Phe-Tyr-Phe-Tyr, Tyr-Phe-Tyr-Phe, Phe-Phe-Phe-Phe, Phe-Trp, Trp-Phe, Phe-Phe, Phe-Trp-Phe, Trp-Phe-Trp, Phe-Trp-Phe-Trp, Trp-Phe-Trp-Phe, or Tyr-Tyr-Tyr-Tyr, etc. (SEQ ID NOs: 269-296). Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the aromatic amino acid component (AA) may contain or may be flanked by a —SH containing moiety, which allows introducing this component via a disulfide bond as a (further) part of the polymeric carrier according to formula (VI) above (or according to any of its subformulae herein) as defined above, e.g. as a component of the polymeric carrier or as a linker. Such a —SH containing moiety may be any moiety as defined herein suitable to couple one component as defined herein to a further component as defined herein. As an example, such a —SH containing moiety may be a cysteine. Then, e.g. the aromatic amino acid component (AA) may be selected from e.g. peptide combinations Cys-Tyr-Cys, Cys-Trp-Cys, Cys-Trp-Tyr-Cys, Cys-Tyr-Trp-Cys, Cys-Trp-Trp-Cys, Cys-Tyr-Tyr-Cys, Cys-Trp-Tyr-Trp-Cys, Cys-Tyr-Trp-Tyr-Cys, Cys-Trp-Trp-Trp-Cys, Cys-Tyr-Tyr-Tyr-Cys, Cys-Trp-Tyr-Trp-Tyr-Cys, Cys-Tyr-Trp-Tyr-Trp-Cys, Cys-Trp-Trp-Trp-Trp-Cys, Cys-Tyr-Tyr-Tyr-Tyr-Cys, Cys-Phe-Cys, Cys-Phe-Tyr-Cys, Cys-Tyr-Phe-Cys, Cys-Phe-Phe-Cys, Cys-Tyr-Tyr-Cys, Cys-Phe-Tyr-Phe-Cys, Cys-Tyr-Phe-Tyr-Cys, Cys-Phe-Phe-Phe-Cys, Cys-Tyr-Tyr-Tyr-Cys, Cys-Phe-Tyr-Phe-Tyr-Cys, Cys-Tyr-Phe-Tyr-Phe-Cys, or Cys-Phe-Phe-Phe-Phe-Cys, Cys-Phe-Trp-Cys, Cys-Trp-Phe-Cys, Cys-Phe-Phe-Cys, Cys-Phe-Trp-Phe-Cys, Cys-Trp-Phe-Trp-Cys, Cys-Phe-Trp-Phe-Trp-Cys, Cys-Trp-Phe-Trp-Phe-Cys, etc. (SEQ ID NOs: 297-329). Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the aromatic amino acid component (AA) may contain or represent at least one proline, which may serve as a structure breaker of longer sequences of Trp, Tyr and Phe in the aromatic amino acid component (AA), preferably two, three or more prolines.

According to a second alternative, the amino acid component (AA) may be a hydrophilic (and preferably non charged polar) amino acid component (AA). The incorporation of hydrophilic (and preferably non charged polar) amino acids or sequences as amino hydrophilic (and preferably non charged polar) acid component (AA) into the polymeric carrier according to formula (VI) above (or according to any of its subformulae herein) of the present invention enables a more flexible binding of the polymeric carrier to the "cargo" of the polymeric carrier, e.g. the adjuvant component and/or the antigen as defined above. This preferably leads to a more effective compaction of the components of the cargo and hence to a better protection against nucleases and unwanted decompaction. It also allows provision of a (long) polymeric carrier according to formula (VI) above (or according to any of its subformulae herein) which exhibits a reduced cationic, preferably a neutral or even a negative charge over the entire polymeric carrier and in this context to better adjusted binding properties, if desired or necessary.

For this purpose, the amino acids in the hydrophilic (and preferably non charged polar) amino acid component (AA) may be selected from either the same or different hydrophilic (and preferably non charged polar) amino acids e.g. selected from Thr, Ser, Asn or Gln. Alternatively, the amino acids (or the entire hydrophilic (and preferably non charged polar) amino acid component (AA) may be selected from following peptide combinations Ser-Thr, Thr-Ser, Ser-Ser, Thr-Thr, Ser-Thr-Ser, Thr-Ser-Thr, Ser-Ser-Ser, Thr-Thr-Thr, Ser-Thr-Ser-Thr, Thr-Ser-Thr-Ser, Ser-Ser-Ser-Ser, Thr-Thr-Thr-Thr, Gln-Asn, Asn-Gln, Gln-Gln, Asn-Asn, Gln-Asn-Gln, Asn-Gln-Asn, Gln-Gln-Gln, Asn-Asn-Asn, Gln-Asn-Gln-Asn, Asn-Gln-Asn-Gln, Gln-Gln-Gln-Gln, Asn-Asn-Asn-Asn, Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn, Asn-Ser-Asn-Ser, Ser-Ser-Ser-Ser, or Asn-Asn-Asn-Asn, etc. (SEQ ID NOs: 330-365). Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the hydrophilic (and preferably non-charged polar) amino acid component (AA) may contain or may be flanked by a —SH containing moiety, which allows introducing this component via a disulfide bond as a further part of generic formula (V) above, e.g. as a linker. Such a —SH containing moiety may be any moiety as defined herein suitable to couple one component as defined herein to a further component as defined herein. As an example, such a —SH containing moiety may be a cysteine. Then, e.g. the hydrophilic (and preferably non-charged polar) amino acid component (AA) may be selected from e.g. peptide combinations Cys-Thr-Cys, Cys-Ser-Cys, Cys-Ser-Thr-Cys, Cys-Thr-Ser-Cys, Cys-Ser-Ser-Cys, Cys-Thr-Thr-Cys, Cys-Ser-Thr-Ser-Cys, Cys-Thr-Ser-Thr-Cys, Cys-Ser-Ser-Ser-Cys, Cys-Thr-Thr-Thr-Cys, Cys-Ser-Thr-Ser-Thr-Cys, Cys-Thr-Ser-Thr-Ser-Cys, Cys-Ser-Ser-Ser-Ser-Cys, Cys-Thr-Thr-Thr-Thr-Cys, Cys-Asn-Cys, Cys-Gln-Cys, Cys-Gln-Asn-Cys, Cys-Asn-Gln-Cys, Cys-Gln-Gln-Cys, Cys-Asn-Asn-Cys, Cys-Gln-Asn-Gln-Cys, Cys-Asn-Gln-Asn-Cys, Cys-Gln-Gln-Gl n-Cys, Cys-Asn-Asn-Asn-Cys, Cys-Gln-Asn-Gl n-Asn-Cys, Cys-Asn-Gln-Asn-Gln-Cys, Cys-Gln-Gln-Gln-Gln-Cys, Cys-Asn-Asn-Asn-Asn-Cys, Cys-Asn-Cys, Cys-Ser-Cys, Cys-Ser-Asn-Cys, Cys-Asn-Ser-Cys, Cys-Ser-Ser-Cys, Cys-Asn-Asn-Cys, Cys-Ser-Asn-Ser-Cys, Cys-Asn-Ser-Asn-Cys, Cys-Ser-Ser-Ser-Cys, Cys-Asn-Asn-Asn-Cys, Cys-Ser-Asn-Ser-Asn-Cys, Cys-Asn-Ser-Asn-Ser-Cys, Cys-Ser-Ser-Ser-Ser-Cys, or Cys-Asn-Asn-Asn-Asn-Cys, etc. (SEQ ID NOs: 366-407). Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the hydrophilic (and preferably non-charged polar) amino acid component (AA) may contain at least one proline, which may serve as a structure breaker of longer sequences of Ser, Thr and Asn in the hydrophilic (and preferably non charged polar) amino acid component (AA), preferably two, three or more prolines.

According to a third alternative, the amino acid component (AA) may be a lipophilic amino acid component (AA). The incorporation of lipophilic amino acids or sequences as lipophilic amino acid component (AA) into the polymeric carrier according to formula (VI) above (or according to any of its subformulae herein) of the present invention enables a stronger compaction of the "cargo" (e.g. the adjuvant component and/or the antigen as defined above) when forming a complex. This is particularly due to interactions of one or more components of the polymeric carrier, particularly of lipophilic sections of lipophilic amino acid component (AA) and the components of the cargo, e.g. a nucleic acid sequence encoding the antigen. This interaction will preferably add an additional stability to the complex between the polymeric carrier as a sort of outer shell and the complexed adjuvant component together with the antigen as defined herein. This stabilization may somehow be compared to a sort of non covalent crosslinking between different polymer strands. Especially in aqueous environment this interaction is typically strong and provides a significant effect.

For this purpose, the amino acids in the lipophilic amino acid component (AA) may be selected from either the same or different lipophilic amino acids, e.g., selected from Leu, Val, Ile, Ala, Met. Alternatively, the amino acid AA (or the entire lipophilic amino acid component (AA)) may be selected from following peptide combinations Leu-Val, Val-Leu, Leu-Leu, Val-Val, Leu-Val-Leu, Val-Leu-Val, Leu-Leu-Leu, Val-Val-Val, Leu-Val-Leu-Val, Val-Leu-Val-Leu, Leu-Leu-Leu-Leu, Val-Val-Val-Val, Ile-Ala, Ala-Iie, Ile-Ile, Ala-Ala, Ile-Ala-Ile, Ala-Iie-Ala, Ile-Ile-Ile, Ala-Ala-Ala, Ile-Ala-Ile-Ala, Ala-Iie-Ala-Ile, Ile-Ile-Ile-Ile, Ala-Ala-Ala-Ala, Met-Ala, Ala-Met, Met-Met, Ala-Ala, Met-Ala-Met, Ala-Met-Ala, Met-Met-Met, Ala-Ala-Ala, Met-Ala-Met-Ala, Ala-Met-Ala-Met, or Met-Met-Met-Met etc. (SEQ ID NOs: 408-442) Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the lipophilic amino acid component (AA) may contain or may be flanked by a —SH containing moiety, which allows introducing this component via a disulfide bond as a further part of the polymeric carrier according to formula (VI) above (or according to any of its subformulae herein) as defined above, e.g. as a linker. Such a —SH containing moiety may be any moiety as defined herein suitable to couple one component as defined herein to a further component as defined herein. As an example, such a —SH containing moiety may be a cysteine. Then, e.g. the lipophilic amino acid component (AA) may be selected from e.g. peptide combinations Cys-Val-Cys, Cys-Leu-Cys, Cys-Leu-Val-Cys, Cys-Val-Leu-Cys, Cys-Leu-Leu-Cys, Cys-Val-Val-Cys, Cys-Leu-Val-Leu-Cys, Cys-Val-Leu-Val-Cys, Cys-Leu-Leu-Leu-Cys, Cys-Val-Val-Val-Cys, Cys-Leu-Val-Leu-Val-Cys, Cys-Val-Leu-Val-Leu-Cys, Cys-Leu-Leu-Leu-Leu-Cys, Cys-Val-Val-Val-Val-Cys, Cys-Ala-Cys, Cys-Ile-Cys, Cys-Ile-Ala-Cys, Cys-Ala-ile-Cys, Cys-Ile-Ile-Cys, Cys-Ala-Ala-Cys, Cys-Ile-Ala-Ile-Cys, Cys-Ala-Ile-Ala-Cys, Cys-Ile-Ile-Ile-Cys, Cys-Ala-Ala-Ala-Cys, Cys-Ile-Ala-Ile-Ala-Cys, Cys-Ala-Ile-Ala-Ile-Cys, Cys-Ile-Ile-Ile-Ile-Cys, or Cys-Ala-Ala-Ala-Ala-Cys, Cys-Met-Cys, Cys-Met-Ala-Cys, Cys-Ala-Met-Cys, Cys-Met-Met-Cys, Cys-Ala-Ala-Cys, Cys-Met-Ala-Met-Cys, Cys-Ala-Met-Ala-Cys, Cys-Met-Met-Met-Cys, Cys-Ala-Ala-Ala-Cys, Cys-Met-Ala-Met-Ala-Cys, Cys-Ala-Met-Ala-Met-Cys, Cys-Met-Met-Met-Met-Cys, or Cys-Ala-Ala-Ala-Ala-Cys, etc. Each Cys above may also be replaced by any modified peptide or chemical compound carrying a free —SH-moiety as defined herein. (SEQ ID NOs: 443-483) Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the lipophilic amino acid component (AA) may contain at least one proline, which may serve as a structure breaker of longer sequences of Leu, Val, Ile, Ala and Met in the lipophilic amino acid component (AA), preferably two, three or more prolines.

Finally, according to a fourth alternative, the amino acid component (AA) may be a weak basic amino acid component (AA). The incorporation of weak basic amino acids or sequences as weak basic amino acid component (AA) into the polymeric carrier according to formula (VI) above (or according to any of its subformulae herein) may serve as a proton sponge and facilitates endosomal escape (also called endosomal release) (proton sponge effect). Incorporation of such a weak basic amino acid component (AA) preferably enhances transfection efficiency.

For this purpose, the amino acids in the weak basic amino acid component (AA) may be selected from either the same or different weak amino acids e.g. selected from histidine or aspartate (aspartic acid). Alternatively, the weak basic amino acids (or the entire weak basic amino acid component (AA)) may be selected from following peptide combinations Asp-His, His-Asp, Asp-Asp, His-His, Asp-His-Asp, His-Asp-His, Asp-Asp-Asp, His-His-His, Asp-His-Asp-His, His-Asp-His-Asp, Asp-Asp-Asp-Asp, or His-His-His-His, etc. (SEQ ID NOs: 484-495) Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the weak basic amino acid component (AA) may contain or may be flanked by a —SH containing moiety, which allows introducing this component via a disulfide bond as a further part of generic formula (V) above, e.g. as a linker. Such a —SH containing moiety may be any moiety as defined herein suitable to couple one component as defined herein to a further component as defined herein as used in the polymeric carrier according to formula (VI) above (or according to any of its subformulae herein). As an example, such a —SH containing moiety may be a cysteine. Then, e.g. the weak basic amino acid component (AA) may be selected from e.g. peptide combinations Cys-His-Cys, Cys-Asp-Cys, Cys-Asp-His-Cys, Cys-His-Asp-Cys, Cys-Asp-Asp-Cys, Cys-His-His-Cys, Cys-Asp-His-Asp-Cys, Cys-His-Asp-His-Cys, Cys-Asp-Asp-Asp-Cys, Cys-His-His-His-Cys, Cys-Asp-His-Asp-His-Cys, Cys-His-Asp-His-Asp-Cys, Cys-Asp-Asp-Asp-Asp-Cys, or Cys-His-His-His-His-Cys, etc. Each Cys above may also be replaced by any modified peptide or chemical compound carrying a free —SH-moiety as defined herein. (SEQ ID NOs: 496-509) Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the weak basic amino acid component (AA) may contain at least one proline, which may serve as a structure breaker of longer sequences of histidine or aspartate (aspartic acid) in the weak basic amino acid component (AA), preferably two, three or more prolines.

The polymeric carrier according to formula (VI) above (or according to any of its subformulae herein) may also comprise as an additional component, preferably as a ligand L or as an amino acid component (AA) or $(AA)_x$ a signal peptide or signal sequence, a localization signal or sequence, a nuclear localization signal or sequence (NLS), an antibody, a cell penetrating peptide (CPP), (e.g. TAT), etc. Likewise preferably such an additional component may occur as component L as defined herein. Alternatively, such an additional component may also be bound e.g. to a component L, $P^1$, $P^2$, $P^3$, (AA) or $(AA)_x$ as defined herein, e.g. to a side chain of any of components L, $P^1$, $P^2$, $P^3$, (AA) or $(AA)_x$, preferably via a side chain of component $P^2$, or optionally as a linker between components L and $P^1$ or $P^3$ and L. The binding to any of components L, $P^1$, $P^2$, or $P^3$ may also be accomplished using an acid-labile bond, preferably via a side chain of any of components L, $P^1$, $P^2$, $P^3$, which allows to detach or release the additional component at lower pH-values, e.g. at physiological pH-values as defined herein. Preferably such an additional component is bound to the polymeric carrier according to formula (VI) above (or according to any of its subformulae herein) or to another component of the polymeric carrier via a (reversible) disulfide bond. In the above context the signal peptide or signal sequence, a localization signal or sequence, a nuclear localization signal or sequence (NLS), an antibody, a cell penetrating peptide, (e.g. TAT), etc., additionally comprises at least one —SH-moiety. Preferably, a signal peptide, a localization signal or sequence or a nuclear localization signal or sequence (NLS), may be used to direct the complex formed by the polymeric carrier and its "cargo" (preferably the adjuvant component and/or the antigen as defined herein) to specific target cells (e.g. hepatocytes or antigen-presenting cells) and preferably allows a translocalization of the polymeric carrier or such a complex to a specific target, e.g. into the cell, into the nucleus, into the endosomal compartment, sequences for the mitochondrial matrix, localisation sequences for the plasma membrane, localisation sequences for the Golgi apparatus, the nucleus, the cytoplasm and the cytosceleton, etc. Such signal peptide, a localization signal or sequence or a nuclear localization signal may be used for the transport of any of the herein defined components of the complex, e.g. the polymeric carrier, its "cargo" (preferably the adjuvant component and/or the antigen as defined herein), preferably nucleic acid sequences, preferably an RNA or a DNA as defined and/or used herein, e.g. into the nucleus. Without being limited thereto, particular localization signals or sequences or a nuclear localization signals may include e.g. KDEL (SEQ ID NO: 510), DDEL (SEQ ID NO: 511), DEEL (SEQ ID NO: 512), QEDL (SEQ ID NO: 513), RDEL (SEQ ID NO: 514), and GQNLSTSN (SEQ ID NO: 515), nuclear localisation sequences, including PKKKRKV (SEQ ID NO: 516), PQKKIKS (SEQ ID NO: 517), QPKKP (SEQ ID NO: 518), RKKR (SEQ ID NO: 519), RKKRRQRRRAHQ (SEQ ID NO: 520), RQARRNRRRRWRERQR (SEQ ID NO: 521), MPLTRRRPAASQALAPPTP (SEQ ID NO: 522), GAALTILV (SEQ ID NO: 523), and GAALTLLG (SEQ ID NO: 524), localisation sequences for the endosomal compartment, including MDDQRDLISNNEQLP (SEQ ID NO: 525), localisation sequences for the mitochondrial matrix, including MLFNLRXXLNNAAFRHGHNFMVRNFRCGQPLX (SEQ ID NO: 526), localisation sequences for the plasma membrane: GCVCSSNP (SEQ ID NO: 527), GQTVTTPL (SEQ ID NO: 528), GQELSQHE (SEQ ID NO: 529), GNSPSYNP (SEQ ID NO: 530), GVSGSKGQ (SEQ ID NO: 531), GQTITTPL (SEQ ID NO: 532), GQTLTTPL (SEQ ID NO: 533), GQIFSRSA (SEQ ID NO: 534), GQIHGLSP (SEQ ID NO: 535), GARASVLS (SEQ ID NO: 536), and GCTLSAEE (SEQ ID NO: 537), localisation sequences for the endoplasmic reticulum and the nucleus, including GAQVSSQK (SEQ ID NO: 538), and GAQLSRNT (SEQ ID NO: 539), localisation sequences for the Golgi apparatus, the nucleus, the cytoplasm and the cytosceleton, including GNAAAAKK (SEQ ID NO: 540), localisation sequences for the cytoplasm and cytosceleton, including GNEASYPL (SEQ ID NO: 541), localisation sequences for the plasma membrane and cytosceleton, including GSSKSKPK (SEQ ID NO: 542), etc. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulins as defined herein, signal sequences of the invariant chain of immunoglobulins or antibodies as defined herein, signal sequences of Lamp1, Tapasin, Erp57, Calreticulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention. Such an additional component may be bound e.g. to a cationic polymer or to any other component of the polymeric carrier as defined herein or may be added to the polymeric carrier when forming the complex with its "cargo" as defined above. Preferably this signal peptide, localization signal or sequence or nuclear localization signal or sequence (NLS), is bound to the polymeric carrier or to another component of the polymeric carrier via a (reversible) disulfide bond. For this purpose the (AA) component additionally comprises at least one —SH moiety as defined herein. The binding to any of components of the polymeric carrier may also be accomplished using an acid-labile bond, preferably via a side chain of any of components of the polymeric carrier, which allows to detach or release the additional component at lower pH-values, e.g. at physiological pH-values as defined herein.

Additionally, the inventive polymeric carrier according to formula (VI) above (or according to any of its subformulae herein), may comprise further functional peptides or proteins preferably as ligand or amino acid component (AA) or $(AA)_x$, which may modulate the functionality of the inventive polymeric carrier accordingly, preferably so called cell penetrating peptides (CPPs) or cationic peptides for transportation as defined herein. Likewise, such an additional component may occur as component L or (AA) or $(AA)_x$ as defined herein. Alternatively, such an additional component may also be bound to a component L, $P^1$, $P^2$, $P^3$, (AA) or $(AA)_x$ as defined herein, e.g. to a side chain of any of components L, $P^1$, $P^2$, $P^3$, (AA) or $(AA)_x$ preferably via a side chain of component $P^2$, or optionally as a linker between components L and $P^1$ or $P^3$ and L. The binding to any of components L, $P^1$, $P^2$, $P^3$, (AA) or $(AA)_x$ may also be accomplished using an acid-labile bond, preferably via a side chain of any of components L, $P^1$, $P^2$, $P^3$, (AA) or $(AA)_x$ which allows to detach or release the additional component at lower pH-values, e.g. at physiological pH-values as defined herein. In this context it is particularly preferred that this additional component occurs as ligand L or as amino acid component (AA) or $(AA)_x$ of the repetitive component $[S—P^2—S]_n$ of formula (VI). Such functional peptides or proteins preferably comprise any peptides or proteins as defined herein, e.g. so called cell penetrating peptides (CPPs) or cationic peptides for transportation. Particularly preferred are CPPs, which induce a pH-mediated conformational change in the endosome and lead to an improved release of the complex formed by the polymeric carrier according to formula (VI) above (or according to any of its subformulae herein) or its components from the endosome by insertion into the lipid layer of the liposome. These cell penetrating peptides (CPPs) or cationic peptides for transportation, may include, without being limited thereto protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc. Such functional peptides or proteins may also comprise any peptide or protein which can execute any favourable function in the cell. Particularly preferred are peptides or proteins selected from therapeutically active proteins or peptides, from antigens as defined herein, e.g. tumour antigens, pathogenic antigens (animal antigens, viral antigens, protozoan antigens, bacterial antigens, allergic antigens), autoimmune antigens, or further antigens, from allergens, from antibodies, from immunostimulatory proteins or peptides, from antigen-specific T-cell receptors, or from any other protein or peptide suitable for a specific (therapeutic) application. Particularly preferred are peptide epitopes from antigens as defined herein. Such functional peptides or proteins may also be added to the polymeric carrier when forming the complex with its "cargo" as defined above.

The polymeric carrier according to formula (VI) above (or according to any of its subformulae herein) may comprise at least one of the above mentioned cationic or polycationic peptides, proteins or polymers or further components, wherein any of the above defined alternatives and components may be combined with each other, and may be formed by polymerizing same in a polymerization condensation reaction via their —SH-moieties.

The inventive polymeric carrier according to formula (VI) may comprise at least one of the above mentioned cationic or polycationic peptides, proteins or polymers or further components, e.g. (AA) or $(AA)_x$, wherein any of the above alternatives may be combined with each other, and may be formed by polymerizing same in a polymerization condensation reaction via their —SH-moieties.

The inventive polymeric carrier according to formula (VI), which may be used for combined packaging the adjuvant component and the antigen of the inventive composition or vaccine composition as defined above, may be prepared according to the following method. In this context, the present invention also provides and utilizes a polymeric carrier according to formula (VI) (as a product by process) obtained or obtainable by such method steps. The method may be furthermore be extended to obtain the inventive composition or vaccine composition. The method preferably comprises following steps:

a) providing at least one cationic or polycationic protein or peptide as component $P^2$ as defined herein and/or at least one cationic or polycationic polymer as component $P^2$ as defined herein, and optionally at least one further component (e.g. (AA), $(AA)_x$, $[(AA)_x]_z$, etc.), preferably in the ratios indicated herein, mixing these components, preferably in a basic milieu as defined herein, preferably in the presence of oxygen or a further starter as defined herein which leads to mild oxidation conditions, preferably at a pH, at a temperature and at time as defined herein, and thereby condensing and thus polymerizing these components with each other via disulfide bonds (in a polymerization condensation or polycondensation) to obtain a repetitive component $H-[S-P^2-S]_n-H$ or $H\{[S-P^2-S]_a[S-(AA)_x-S]_b\}H$, etc.;

b) providing a hydrophilic polymer $P^1$ and/or $P^3$ as defined herein, optionally modified with a ligand L and/or an amino acid component (AA) or $(AA)_x$ as defined herein;

c) mixing the hydrophilic polymer $P^1$ and/or $P^3$ provided according to step b) with the repetitive component $H-[S-P^2-S]_n-H$ or $H\{[S-P^2-S]_a[S-(AA)_x-S]_b\}H$, etc. obtained according to step a), typically in a ratio of about 2:1, (and thereby typically terminating the polymerization condensation or polycondensation reaction) and obtaining the inventive polymeric carrier, preferably according to formula (VI) as defined herein or according to any subformula thereof as defined herein;

d) optionally purifying the inventive polymeric carrier obtained or obtainable according to step c), preferably using a method as defined herein;

e) optionally adding the inventive polymeric carrier obtained or obtainable according to step c) or d) to a mixture of an adjuvant component and an antigen as defined herein for the inventive composition or vaccine composition, preferably in the herein mentioned ratios, and thereby packaging the (complex of the) adjuvant component and the antigen, optionally in the presence of further components as defined herein, e.g. enhancer peptides, CPPs, etc. as defined herein, with the inventive polymeric carrier to obtain the inventive composition or vaccine composition as defined herein.

The inventive method of preparing the inventive polymeric carrier according to formula (I) as defined herein represents a multi-step condensation polymerization or polycondensation reaction via —SH moieties of the educts, e.g. component(s) $P^2$ as defined herein, further components $P^1$ and/or $P^3$ and optionally further components (AA) or $(AA)_x$. The condensation polymerization or polycondensation reaction preferably leads to the inventive polymeric carrier as a condensation polymer, wherein the single components are linked by disulfide bonds. This condensation polymerization leads to the inventive polymeric carrier according to formula (VI) preparing in a first step a) of the condensation reaction the inventive repetitive component $H-[S-P^2-S]_n-H$ or a variant thereof as a sort of a "core" or "central motif" of the inventive polymeric carrier. In a second step b) components $P^1$ and/or $P^3$ are provided, which allow to terminate or to somehow "coat" the inventive repetitive component $H-[S-P^2-S]_n-H$ or a variant thereof in a third step c) by adding components $P^1$ and/or $P^3$ as defined herein (optionally modified with a ligand L and/or an amino acid component (AA) or $(AA)_x$ as defined herein) to the condensation product obtained according to step a). In subsequent step d), this product may be purified and further in a further step e) the product of step c) or d) may be added to a mixture of an adjuvant component and an antigen as defined herein for the inventive composition or vaccine composition, preferably in the herein mentioned ratios, to allow packaging the adjuvant component and the antigen together with the polymeric carrier to obtain the inventive composition or vaccine composition as defined herein It is important to understand that the inventive method is based on an equilibrity reaction under mild oxidation conditions in steps a), b) and c), which, upon balancing the equilibrity state, allows to obtain the inventive polymeric carrier according to formula (VI) above or according to any of its subformulae comprising the selected components in the desired molar ratios. For this purpose, long reaction times are envisaged to achieve an equilibrity state in steps a), b) and c). If for example a condensation polymerization is to be carried out using a molar ratio of 5 components $P^2$ in step a), the equilibrium is surprisingly settled at a polymer length of about 5 after sufficient time, preferably e.g. >12 hours. However, due to the equilibrium the polymer length (as defined by n) is not fixed at a specific value, e.g. 5, but may vary accordingly within the equilibrium reaction. Accordingly, about 5 may mean about 4 to 6, or even about 3 to 7. Preferably, the polymer length and thus the integer n (and thus a, band a+b) varies within a limit of about ±1, or ±2.

As defined herein in a step a) of the inventive method of preparing the inventive polymeric carrier according to formula (VI) at least one cationic or polycationic protein or peptide as component $P^2$ as defined herein and/or at least one cationic or polycationic polymer as component $P^2$ as defined herein are provided, preferably in the ratios indicated above by formula (VI). These components are mixed, preferably in a basic milieu as defined herein, preferably in the presence of oxygen or a further starter as defined herein which leads to mild oxidation conditions, preferably at a pH, and at a temperature and at a time as defined herein, and thereby condensing and thus polymerizing these components with each other via disulfide bonds (in a polymerization condensation or polycondensation) to obtain a repetitive component H—[S—$P^2$—S]$_n$—H.

According to an alternative, in step a) of the inventive method of preparing the inventive polymeric carrier at least one cationic or polycationic protein or peptide and/or at least one cationic or polycationic polymer are provided and used as component(s) $P^2$ as defined herein, and additionally at least one amino acid component (AA) or (AA)$_x$, is provided as defined herein, and components $P^2$ and (AA) or (AA)$_x$ are used for a polymerization condensation or polycondensation according to step a). Preferably, the components are all provided in the ratios indicated above by formula (VIa), mixed, preferably in a basic milieu as defined herein, preferably in the presence of oxygen or a further starter as defined herein which leads to mild oxidation conditions, preferably at a pH, at a temperature and at time as defined herein. Upon mixing and starting the reaction, the components are condensed and thus polymerized with each other via disulfide bonds (in a polymerization condensation or polycondensation) to obtain a repetitive component H—{[S—$P^2$—S]$_a$[S-(AA)$_x$-S]$_b$}—H.

In both of the above alternatives, different component(s) $P^2$, particularly different peptides and/or different polymers as component $P^2$, may be selected in the condensation polymerization as indicated above. In this context, the selection of different component(s) $P^2$ is typically dependent upon the desired properties of the final inventive polymeric carrier and the desired cationic strength of the final inventive polymeric carrier or its central core motif. Accordingly, the repetitive component [S—$P^2$—S]$_n$, may furthermore be "diluted" or modified in the above alternative of step a) e.g. by introducing an amino acid component (AA)$_x$ as defined herein, preferably in the above defined ratios. Thereby, a modified central core motif {[S—$P^2$—S]$_a$[S-(AA)$_x$-S]$_b$} may be obtained, wherein the cationic character of (unmodified) repetitive component [S—$P^2$—S]$_n$ typically remains in the limitations as defined herein. The properties of the final inventive polymeric carrier may thus be adjusted as desired with properties of components (AA)$_x$ by inserting amino acid component (AA)$_x$ as defined herein in steps a), b) and/or c).

In all cases, step a) is based on an equilibrity reaction under mild oxidation conditions which, upon balancing the equilibrity state, allows to obtain either inventive repetitive component H—[S—$P^2$—S]$_n$—H or inventive repetitive component H—{[S—$P^2$—S]$_a$[S-(AA)$_x$-S]$_b$}—H in the desired molar ratios. In the equilibrity state, n is preferably 1, 2, 3, 4, or 5 to 10, more preferably 4 to 9, and a+b=n is as defined above, preferably a+b=1, 2, 3, 4, or 5 to 10, more preferably 4 to 9. For this purpose, long reaction times are envisaged to achieve an equilibrity state in step a), most preferably e.g. >12 hours. Accordingly, step a) of the inventive method of preparing a polymeric carrier typically requires at least about 5 hours, even more preferably at least about 7.5 hours or even 10 hours, most preferably at least about 12 hours, e.g. a reaction time of about 12 to 60 hours, a reaction time of about 12 to 48 hours, a reaction time of about 12 to 36 hours, or a reaction time of about 12 to 24 hours, etc, wherein the lower border of 12 hours of the latter ranges may also be adjusted to 10, 7.5, or even 5 hours. Advantageously, the equilibrity state can be balanced using the inventive method.

In step a), the at least one cationic or polycationic protein or peptide as component $P^2$ as defined herein and/or at least one cationic or polycationic polymer as component $P^2$ as defined herein, and optionally at least one amino acid component (AA) or (AA)$_x$ as defined herein, are preferably contained in a basic milieu in the step a) of the inventive method of preparing the inventive polymeric carrier according to formula (VI) (or any of its subformulae, e.g. (VIa)). Such a basic milieu typically exhibits a pH range of about 6 to about 12, preferably a pH range of about 7 to about 10, more preferably a pH range of about 8 to about 10, e.g. about 8, 8.5, 9, 9.5, or 10 or any range selected from any two of these or the aforementioned values.

Furthermore, the temperature of the solution in step a) is preferably in a range of about 5° C. to about 60° C., more preferably in a range of about 15° C. to about 40° C., even more preferably in a range of about 20° C. to about 30° C., and most preferably in a range of about 20° C. to about 25° C., e.g. about 25° C.

In step a) of the inventive method of preparing the inventive polymeric carrier according to formula (VI) (or any of its subformulae, e.g. (VIa)) as defined herein buffers may be used as suitable. Preferred buffers may comprise, but are not limited to carbonate buffers, borate buffers, Bicine buffer, CHES buffer, CAPS buffer, Ethanolamine containing buffers, HEPES, MOPS buffer, Phosphate buffer, PIPES buffer, Tris buffer, Tricine buffer, TAPS buffer, and/or TES buffer as buffering agents. Particularly preferred is a carbonate buffer.

Upon mixing the components, preferably in the presence of oxygen, preferably in the presence of a basic milieu as defined herein, the condensation polymerization or polycondensation reaction is started. For this purpose, the mixture in step a) is preferably exposed to oxygen or may be started using a further starter, e.g. a catalytic amount of an oxidizing agent, e.g. DMSO, etc. To determine the desired polymer chain length the condensation reaction has to be carried out under mild oxidation conditions, preferably in the presence of less than 30% DMSO, more preferably in the presence of less than 20% DMSO and most preferably in the presence of less than 10% DMSO. Upon start of the condensation polymerization or polycondensation reaction the at least one cationic or polycationic protein or peptide and/or at least one cationic or polycationic polymer as component $P^2$ and optionally at least one amino acid component (AA) or $(AA)_x$ as defined herein, are condensed and thus polymerized with each other via disulfide bonds (polymerization condensation or polycondensation). In this reaction step a) preferably linear polymers are created using monomers with at least two reactive —SH moieties, i.e. at least one cationic or polycationic protein or peptide and/or at least one cationic or polycationic polymer as component $P^2$ as defined herein, each component $P^2$ exhibiting at least two free SH-moieties as defined herein, e.g. at their terminal ends. However, components $P^2$ with more than two free —SH-moieties may be used, which may lead to branched polymers.

According to one other specific aspect, the condensation product obtained according to step a) may be modified (e.g. in a step a1)) by adding an amino acid component (AA) or $(AA)_x$ or a mixed repetitive amino acid component $[(AA)_x]_z$ as defined herein e.g. to the terminal ends of the condensation product of step a). This may occur via any functionality as defined herein, e.g. a —SH moiety or any further functionality described herein, preferably a —SH moiety. For this purpose, amino acid component (AA) or $(AA)_x$ or a mixed repetitive amino acid component $[(AA)_x]_z$ may be provided with two (or even more) —SH-moieties, e.g. in a form represented by formulae "$H(S-AA-S)_xH$" or "$H[S-(AA)_x-S]_zH$". Then, a polycondensation reaction may be carried out with the products of step a), i.e. inventive repetitive component $H—[S—P^2—S]_n—H$ or inventive repetitive component $H—\{[S—P^2—S]_a[S-(AA)_x-S]_b\}—H$, leading to intermediate components

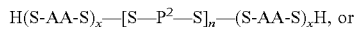

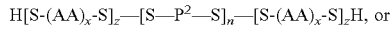

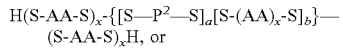

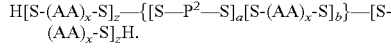

Any single or all of these intermediate components or the inventive repetitive component

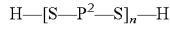

or the inventive repetitive component

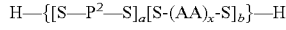

obtained according to step a), may be used to be coupled to the polymers provided in step b) of the inventive method.

According to a second step b) of the inventive method of preparing the inventive polymeric carrier according to formula (VI) as defined herein (or according to any of its subformulae), a hydrophilic polymer $P^1$ and/or $P^3$ as defined herein is added to the condensation product obtained according to step a). In this context, the hydrophilic polymers $P^1$ and/or $P^3$ as defined herein, preferably exhibit at least one —SH-moiety, more preferably only one —SH-moiety per hydrophilic polymers $P^1$ and/or $P^3$ as defined herein, thereby terminally stopping the polymerization condensation or polycondensation according to step a) in step c). Hydrophilic polymers $P^1$ and/or $P^3$ as defined herein may be the same or different, wherein these polymers may be selected according to the desired properties. Typically, hydrophilic polymers $P^1$ and/or $P^3$ as a whole may be added to the condensation product obtained according to step a) in a ratio of about 2:1 hydrophilic polymer $P^1$ and/or $P^3$: condensation product obtained according to step a).

According to one alternative, the hydrophilic polymer(s) $P^1$ and/or $P^3$ additionally may be modified with either a component L (ligand) as defined herein or a component (AA) or $(AA)_x$ or $[(AA)_x]_z$ as defined herein or both a component L (ligand) as defined herein and a component (AA) or $(AA)_x$ or $[(AA)_x]_z$ as defined herein.

According to a first example, a ligand is attached to component(s) $P^1$ and/or $P^3$ as component L prior to providing component(s) $P^1$ and/or $P^3$ in step b) via any functionality as defined herein, e.g. a —SH moiety. This ligand is preferably attached to the hydrophilic polymer(s) $P^1$ and/or $P^3$ at one terminus of these polymers. If the attachment is carried out via —SH bonds, the hydrophilic polymer(s) $P^1$ and/or $P^3$ are preferably provided with two (or even more) —SH-moieties., e.g. in a form represented by formulae $HS—P^1—SH$ or $HS—P^3—SH$. Ligand L preferably carries only one —SH moiety. In this case, one —SH moiety of hydrophilic polymer(s) $P^1$ and/or $P^3$ is preferably protected in a first step using a protecting group as known in the art. Then, the hydrophilic polymer(s) $P^1$ and/or $P^3$ may be bound to a component L to form a first disulfide bond via the non-protected —SH moiety. The protected —SH-moiety of hydrophilic polymer(s) $P^1$ and/or $P^3$ is then typically deprotected for further reactions. This preferably leads to following intermediate components

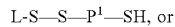

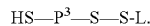

Alternatively, the above intermediate components may be provided similarly without the necessity of blocking the free —SH-moieties. These intermediate components may be used in step c) to be coupled with the condensation products obtained according to step a) above, e.g. to form a second disulfide bond with inventive repetitive component $H—[S—P^2—S]_n—H$ or inventive mixed repetitive component $H—\{[S—P^2—S]_a[S-(AA)_x-S]_b\}—H$ obtained according to step a) or any of its modifications, e.g. according to step a1). If the attachment is carried out via other moieties, any of the reactions as defined herein may be used accordingly.

According to a further example, an amino acid component (AA) or $(AA)_x$ or a mixed repetitive amino acid component $[(AA)_x]_z$ as defined herein may be attached to component(s) $P^1$ and/or $P^3$ prior to providing component(s) $P^1$ and/or $P^3$ via any functionality as defined herein, e.g. a —SH moiety. The amino acid component (AA) or $(AA)_x$ or a mixed repetitive amino acid component $[(AA)_x]_z$ may be attached to the hydrophilic polymer(s) $P^1$ and/or $P^3$ at any position within these polymers or at one or both termini of these polymers. In one specific case, the amino acid component $(AA)_x$ or a mixed repetitive amino acid component $[(AA)_x]_z$ may be provided as a linker between component(s) $P^1$ and/or $P^3$ and the condensation product obtained according to step a) above or as a linker between component(s) $P^1$ and/or $P^3$ and a further component, e.g. a linker L, or according to another alternative, as a terminating component at one terminus of component(s) $P^1$ and/or $P^3$. In any of these cases, the attachment preferably may carried out via —SH bonds, wherein the hydrophilic polymer(s) $P^1$ and/or $P^3$ are preferably provided with two (or even more) —SH-moieties., e.g. in a form represented by formula "HS—$P^1$—SH" or "HS—$P^3$—SH", wherein preferably one of these to —SH moieties is protected, e.g. in a form represented by formula "HS—$P^1$—S-protecting group" or "protecting group-S—$P^3$—SH". Furthermore, amino acid component (AA) or $(AA)_x$ or a mixed repetitive amino acid component $[(AA)_x]_z$ are also preferably provided with two (or even more) —SH-moieties, e.g. in a form represented by formulae "H(S-AA-S)$_x$—H" or "H[S-(AA)$_x$-S]$_z$H", wherein preferably one of these to —SH moieties is protected, e.g. in a form represented by formulae "protecting group-(S-AA-S)$_x$—SH" or "H[S-(AA)$_x$-S]$_z$-protecting group". Then, a polycondensation reaction may be carried out with polymers "HS—$P^1$—S-protecting group" or "protecting group-S—$P^3$—SH" leading to intermediate components "protecting group-S—$P^1$—S—(S-AA-S)$_x$—S-protecting group", "protecting group-(S-AA-S)$_x$—S—S—$P^3$—S-protecting group", "protecting group-S—$P^1$—S—[S-(AA)$_x$-S]$_z$-protecting group", or "protecting group-[S-(AA)$_x$-S]$_z$—S—$P^3$—S-protecting group".

Any single or all of these intermediate components may then be used in step c) of the inventive method to be coupled to the condensation product according to step a).

For this purpose, at least one or both protecting groups (selected upon the desired direction of the component in the final polymeric carrier) of each intermediate compound may be deprotected prior to providing them in step b), preferably leading to following intermediate components "HS—$P^1$—S—(S-AA-S)$_x$—SH", "H(S-AA-S)$_x$—S—S—$P^3$—SH", "HS—$P^1$—S—[S-(AA)$_x$-S]$_z$H", or "H[S-(AA)$_x$-S]$_z$—S—$P^3$—SH", Alternatively, the above intermediate components may be provided similarly without the necessity of blocking the free —SH-moieties. Any single or all of these intermediate components may then be provided in step b) of the inventive method to be coupled to the condensation product according to step a).

If any of the afore mentioned intermediate components is provided in step b), this condensation reaction may be terminated in a step c) by adding a linker component as defined herein with one —SH-moiety (e.g. L-SH) or any further component with a single —SH moiety, e.g. as defined herein. In one further specific case, the amino acid component (AA) or $(AA)_x$ or a mixed repetitive amino acid component $[(AA)_x]_z$ may be used as a terminal component at one terminus of component(s) $P^1$ and/or $P^3$ without adding a further component to the amino acid component (AA) or $(AA)_x$ or a mixed repetitive amino acid component $[(AA)_x]_z$.

According to a further example, an amino acid component (AA) or $(AA)_x$ or a mixed repetitive amino acid component $[(AA)_x]_z$ as defined herein may be attached to component(s) $P^1$ and/or $P^3$ prior to step c), wherein component(s) $P^1$ and/or $P^3$ have been already modified with a linker. For this purpose, component(s) $P^1$ and/or $P^3$ preferably carry (at least) two —SH moieties as defined herein, wherein a polycondensation is carried out with a linker, carrying e.g. one —SH moiety. This reaction may be carried out by using protecting groups as defined herein, or, preferably, without protecting groups. Alternatively, any further functionality as defined herein except —SH moieties may be used for coupling. Then, the second —SH moiety of component(s) $P^1$ and/or $P^3$ may be used to couple an amino acid component (AA) or $(AA)_x$ or a mixed repetitive amino acid component $[(AA)_x]_z$ as defined herein via —SH-moieties, e.g. in a form represented by formulae "H(S-AA-S)$_x$—H" or "H[S-(AA)$_x$-S]$_z$H". The reaction preferably leads to following intermediate compounds "L-S—S—$P^1$—S—(S-AA-S)$_x$—SH", "L-S—S—$P^1$—S—[S-(AA)$_x$-S]$_z$H", or "HS—(S-AA-S)$_x$—S—S—$P^3$—S-S-L", or "HS—[S-(AA)$_x$-S]$_z$—S—$P^3$—S-S-L";

or, if component L has been linked without a disulfide bond to following intermediate products "L-$P^1$—S—(S-AA-S)$_x$—SH", "L-$P^1$—S—[S-(AA)$_x$-S]$_z$H", or "HS—(S-AA-S)$_x$—S—S—$P^3$-L", or "HS—[S-(AA)$_x$-S]$_z$—S—$P^3$-L";

In step c) the hydrophilic polymers $P^1$ and/or $P^3$ (or any of the intermediate components provided according to step b)) as defined herein, are provided and mixed with the repetitive component H—[S—$P^2$—S]$_n$—H, with the mixed repetitive component H—{[S—$P^2$—S]$_a$[S-(AA)$_x$-S]$_b$}—H, or any of the intermediate components obtained according to step a), typically in a ratio of about 2:1. The reaction is typically started and carried out under conditions already described above for step a) (pH, temperature, reaction time, buffers, etc). Step c) allows to terminate the polymerization condensation or polycondensation reaction and to obtain the inventive polymeric carrier according to formula (VI) or (VIa) or according to any of subformulae thereof as defined herein, preferably the inventive polymeric carrier according to formula (VI)

L-$P^1$—S—[S—$P^2$—S]$_n$—S—$P^3$-L or according to formula (VIa)

L-$P^1$—S—{[S—$P^2$—S]$_a$[S-(AA)$_x$-S]$_b$}—S—$P^3$-L.

According to a further step d) of the inventive method of preparing the inventive polymeric carrier according to formula (VI) or (VIa) as defined herein, or according to any of subformulae thereof as defined herein, the inventive polymeric carrier obtained according to step c) is optionally purified. Purification may occur by using chromatographic methods, such as HPLC, FPLC, GPS, dialysis, etc.

According to optional step e) of the inventive method of preparing the inventive polymeric carrier according to formula (VI) or (VIa) as defined herein, or according to any of subformulae thereof as defined herein, the inventive polymeric carrier, preferably as obtained according to step c) or d) of the inventive method, may be added to a mixture of an adjuvant component and an antigen as defined herein for the inventive composition or vaccine composition. The mixture of an adjuvant component and an antigen as defined herein are preferably present in the herein mentioned ratios Furthermore, such a mixture of an adjuvant component and an antigen as defined herein for the inventive composition may also comprise further functional peptides or proteins as defined herein, e.g. so called cell penetrating peptides (CPPs) or cationic peptides for transportation. Such further functional peptides or proteins as defined herein, however, are preferably added to the mixture of an adjuvant component and an antigen as defined herein for the inventive composition as a last component. Addition of such components, preferably observes the N/P ratio as defined herein for the entire inventive composition or vaccine composition.

In the above context, such further functional peptides or proteins as defined herein comprise e.g. so called cell penetrating peptides (CPPs) or cationic peptides for transportation. particularly CPPs, which induce a pH-mediated conformational change in the endosome and lead to an improved release of the inventive polymeric carrier (in complex with a nucleic acid) from the endosome by insertion into the lipid layer of the liposome. Such called cell penetrating peptides (CPPs) or cationic peptides for transportation, may include, without being limited thereto protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from Drosophila antennapedia), pAntp, pIsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, Loligomers, Arginine-rich peptides, Calcitonin-peptides, FGF, Lactoferrin poly-L-Lysine, poly-Arginine, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Adding the inventive polymeric carrier, preferably as obtained according to step c) or d) of the inventive method, to a mixture of an adjuvant component and an antigen as defined herein for the inventive composition or vaccine composition, optionally in the presence of further components as defined herein, e.g. enhancer peptides, CPPs, etc. as defined herein, as defined above, allows packaging the adjuvant component and the antigen with the polymeric carrier and preferably yields the inventive composition or vaccine composition as defined herein.

The ratio of the components of the entire inventive composition or vaccine composition, i.e. a) an adjuvant component comprising or consisting of at least one immunostimulatory nucleic acid sequence, complexed with a complexing agent; b) an antigen, preferably a protein or peptide antigen and/or a nucleic acid sequence encoding said antigen; and c) a carrier molecule for combined packaging the adjuvant component and the antigen, preferably if the complexing agent is present in a protein or peptide form, preferably if component $P^2$ of the carrier molecule is present in a protein or peptide form and/or if the antigen is encoded by a nucleic acid, and optionally in the presence of further components as defined above, may also be calculated on the basis of the nitrogen/phosphate ratio (NIP-ratio) of all these components. In the context of the present invention, an N/P-ratio is preferably in the range of about 0.01-2, 0.1-2 or 0.1-1.5 regarding the ratio of nucleic acids: cationic or polycationic peptide in the complex, and most preferably in the range of about 0.1-1. Such an N/P ratio is preferably designed to provide good transfection properties in vivo and transport into and through cell membranes.

In this context, the components of such an inventive composition may be contained in a molar ratio of e.g. the (preferably entire) nucleic acid as defined herein, preferably isRNA and/or mRNA as defined herein typically in a relative amount of about 1 mol, the complexing agent typically in a relative amount of about 0 or 1 mol to about 250 mol, preferably about 1 to 250 mol, more preferably about 1 to about 100 mol, most preferably about 10 to about 40 mol, e.g. about 25 mol, the carrier molecule as defined herein typically in a relative amount of about 5 mol to about 500 mol, preferably about 5 mol to about 250 mol, more preferably about 5 mol to about 100 mol, even more preferably about 20 mol to about 80 mol, and optionally any further component as defined herein, preferably an enhancer peptide or a CPP as defined herein, e.g. KALA, in a relative amount of about 0 or 1 mol to about 50 mol, preferably about 0 or 1 mol to about 25 mol, more preferably about 0 or 1 mol to about 10 mol, e.g. about 5 mol. Further components may also be contained, if necessary.

Particularly Preferred is Following Ratio

| Component | mRNA | Carrier | Complexation reagent | Enhancer Peptide (e.g. KALA) |
|---|---|---|---|---|
| Ratio (mol) | 1 | about 5-500, preferably about 50 | about 0-250, preferably about 25 | about 0-50, preferably about 5 |

The inventive method of preparing the inventive polymeric carrier according to formula (VI) or (VIa) or according to any of subformulae thereof as defined herein and further the entire inventive composition or vaccine composition is particularly suitable to adapt the chemical properties of the desired inventive polymeric carrier and of the entire inventive composition or vaccine composition due to specific selection of its components $P^2$, L, (AA), $(AA)_x$, or $[(AA)_x]_z$ thereby avoiding agglomeration and toxicity in vivo.

Furthermore, a skilled person would not have expected to obtain such an inventive polymeric carrier according to formula (VI) or (VIa) or according to any of subformulae thereof as defined herein and thus would not have suggested preparing the inventive composition or vaccine composition using the above inventive method. A skilled person would always have expected that the inventive polymeric carrier according to formula (VI) or (VIa) or according to any of subformulae thereof, e.g. as obtained according to the inventive method, due to general rules of equilibrity reactions leads to a monomeric content formed by disulfide bonds. In contrast, the present inventors were surprisingly able to show that when using a specific ratio of polymers and method steps as defined herein, particularly mild oxidation conditions during the polymerization reaction, the polymerization condensation can be directed to specifically obtain a desired distribution of polymers and a desired average length and the desired inventive polymeric carrier according to generic formula (VI) or (VIa) or according to any of subformulae thereof as defined herein without the necessity of blocking the free —SH-moieties. This was not expected by a skilled person.

In a further preferred aspect of the present invention the inventive composition or vaccine composition may be formulated with or comprises a pharmaceutically acceptable carrier and/or vehicle. In the context of the present invention, a pharmaceutically acceptable carrier typically includes the liquid or non-liquid basis of the inventive composition or vaccine composition. If such a composition is provided in liquid form, the carrier typically will be pyrogen-free water, isotonic saline or buffered (aqueous) solutions, e.g. phosphate, citrate, etc. or further buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis if the at least one antigen comprised in the vaccine or the inhibitor of the inventive composition or vaccine composition is provided as nucleic acid sequence.

However, one or more compatible solid or liquid fillers or diluents or encapsulating compounds, which are suitable for administration to a patient to be treated, may be used as well for the inventive composition or vaccine composition. The term "compatible" as used here means that these constituents of the inventive composition or vaccine composition are capable of being mixed in such a manner that no interaction occurs which would substantially reduce the effectiveness of the inventive composition or vaccine composition under typical use conditions.

According to a specific aspect, the inventive composition or vaccine composition may comprise an adjuvant (additional to the adjuvant component of the inventive composition or vaccine composition). In this context, an adjuvant may be understood as any compound, which is suitable to initiate or increase an immune response of the innate immune system, i.e. a non-specific immune response. With other words, when administered, the vaccine preferably also elicits an innate immune response due to the adjuvant, optionally contained therein. Preferably, such an adjuvant may be selected from an adjuvant known to a skilled person and suitable for the present case, i.e. supporting the induction of an innate immune response in a mammal.

Preferably, the adjuvant may be selected from the group consisting of, without being limited thereto, cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer $P^{1205}$); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes UN-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo [4,5-c]quinoline-1-ethanol); SAF-1™ ("Syntex adjuvant formulation"); Sendai proteoliposomes and Sendaicontaining lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearylytyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

The inventive composition or vaccine composition can additionally contain one or more auxiliary substances in order to increase its immunogenicity or immunostimulatory capacity, if desired. A synergistic action of the components of the inventive composition or vaccine composition as defined herein and of an auxiliary substance, which may be optionally contained in the inventive composition or vaccine composition or may be formulated therewith, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

The inventive composition or vaccine composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

In this context especially preferred as immunostimulating compounds are immunostimulatory nucleic acids which are known to bind to TLR receptors. Such an immunostimulatory nucleic acid can be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated.

In this context, the adjuvant may be an immunostimulatory nucleic acid as defined herein, preferably an immunostimulatory RNA (isRNA) as defined herein, which preferably elicits an innate immune response. Such an immunostimulatory nucleic acid may furthermore comprise or be complexed with a cationic or polycationic compound as described for the adjuvant component as defined herein. Alternatively, the adjuvant component as defined herein may be used an adjuvant.

According to a particularly preferred aspect, such immunostimulatory nucleic acid sequences, preferably an isRNA, consists of or comprises a nucleic acid of formula (I), (II), (III) or (IV) as defined above.

Further additives which may be included in the inventive composition or vaccine composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

Additionally, the inventive composition or vaccine composition may comprise further functional peptides or proteins as already defined herein, e.g. so called cell penetrating peptides (CPPs) or cationic peptides for transportation.

The inventive composition or vaccine composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive composition or vaccine composition may be administered intradermally to reach APCs in the dermis.

The inventive composition or vaccine composition may also be administered orally in any orally acceptable dosage form including, but not limited to, capsules, tablets, aqueous suspensions or solutions.

The inventive composition or vaccine composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive composition or vaccine composition may be formulated in a suitable ointment, containing the components of the inventive composition or vaccine composition and optionally further compounds as defined herein suspended or dissolved in one or more carriers.

The inventive composition or vaccine composition typically comprises a "safe and effective amount" of the components of the inventive composition or vaccine composition as defined herein. As used herein, a "safe and effective amount" preferably means an amount of these components, preferably the immunostimulatory nucleic acid, the adjuvant component and/or the antigen as defined herein, that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

The inventive composition or vaccine composition as defined herein may be used for human and also for veterinary medical purposes, preferably for human medical purposes. More preferably, the inventive composition or vaccine composition may be used for treating a mammal for diseases as mentioned herein. In the context of the present invention, a mammal may be selected from any mammal, preferably from a mammal, selected from the group comprising, without being limited thereto, e.g. goat, cattle, swine, dog, cat, donkey, monkey, ape, a rodent such as a mouse, hamster, rabbit, and, in particular, human. Administration modes may be as defined herein.

According to one further specific embodiment, the present invention is directed to the first medical use of the inventive composition or vaccine composition as defined herein as a medicament.

According to another embodiment, the present invention is directed to the second medical use of the inventive composition or vaccine composition as defined herein, optionally in form of a kit, for the treatment of diseases as defined herein. Alternatively or additionally, the present invention is directed to the second medical use of the compounds of the inventive composition or vaccine composition as defined herein, i.e. a) an adjuvant component comprising or consisting of at least one immunostimulatory nucleic acid sequence, complexed with a complexing agent; b) an antigen, preferably a protein or peptide antigen and/or a nucleic acid sequence encoding said antigen; and c) a carrier molecule for combined packaging the adjuvant component and the antigen, all as defined herein, for the preparation of a composition or vaccine composition, preferably as defined herein, for the treatment of diseases as defined herein.

Preferably, diseases as mentioned herein are selected from cancer or tumour diseases, infectious diseases, preferably (viral, bacterial or protozoological) infectious diseases, autoimmune diseases, allergies or allergic diseases, cardiovascular diseases, or neuronal diseases.

Such diseases include cancer or tumour diseases, preferably selected from melanomas, malignant melanomas, colon carcinomas, lymphomas, sarcomas, blastomas, renal carcinomas, gastrointestinal tumours, gliomas, prostate tumours, bladder cancer, rectal tumours, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, various virus-induced tumours such as, for example, papilloma virus-induced carcinomas (e.g. cervical carcinoma=cervical cancer), adenocarcinomas, herpes virus-induced tumours (e.g. Burkitt's lymphoma, EBV-induced B-cell lymphoma), heptatitis B-induced tumours (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumours, retinoblastoma, basalioma, brain metastases, medulloblastomas, vaginal cancer, pancreatic cancer, testicular cancer, Hodgkin's syndrome, meningiomas, Schneeberger disease, hypophysis tumour, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumours, oligodendroglioma, vulval cancer, intestinal cancer, colon carcinoma, oesophageal carcinoma (=oesophageal cancer), wart involvement, tumours of the small intestine, craniopharyngeomas, ovarian carcinoma, genital tumours, ovarian cancer (=ovarian carcinoma), pancreatic carcinoma (=pancreatic cancer), endometrial carcinoma, liver metastases, penile cancer, tongue cancer, gall bladder cancer, leukaemia, plasmocytoma, lid tumour, prostate cancer (=prostate tumours), etc.

According to one further specific aspect, diseases as defined herein comprise infectious diseases, preferably (viral, bacterial or protozoological) infectious diseases. Such infectious diseases, preferably viral, bacterial or protozoological infectious diseases, are typically selected from viral infectious diseases such as influenza, preferably influenza-A, influenza-B, influenza-C or thogotovirus, more preferably influenza-A comprising e.g. haemagglutinin subtypes H1, H2, H3, H4, H5, H6, H7, H8, H9, H10, H11, H12, H13, H14 or H15, and/or neuroamidase subtypes N1, N2, N3, N4, N5, N6, N7, N8 or N9, or preferably influenza-A subtypes H1N1, H1N2, H2N2, H2N3, H3N1, H3N2, H3N3, H5N1, H5N2, H7N7 or H9N2, etc., or any further combination malaria, severe acute respiratory syndrome (SARS), yellow fever, AIDS, Lyme borreliosis, Leishmaniasis, anthrax, meningitis, Condyloma acuminata, hollow warts, Dengue fever, three-day fever, Ebola virus, cold, early summer meningoencephalitis (FSME), shingles, hepatitis, herpes simplex type I, herpes simplex type II, Herpes zoster, Japanese encephalitis, Arenavirus-associated diseases (Lassa fever infection), Marburg virus, measles, foot-and-mouth disease, mononucleosis infectiosa (Pfeiffer's glandular fever), mumps, Norwalk virus infection, smallpox, polio (childhood lameness), pseudo-croup, Erythema infectiosum (fifth disease), rabies, warts, West Nile fever, chickenpox, cytomegalic virus (CMV), bacterial infectious diseases such as miscarriage (prostate inflammation), anthrax, appendicitis, borreliosis, botulism, Camphylobacter, *Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, *paratyphus*, plague, Reiter's syndrome, Rocky Mountain spotted fever, *Salmonella paratyphus, Salmonella* typhus, scarlet fever, syphilis, tetanus, tripper, tsutsugamushi disease, tuberculosis, typhus, vaginitis (colpitis), soft chancre, and infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

According to another specific aspect, diseases as defined herein comprise autoimmune diseases as defined in the following. Autoimmune diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjögren's syndrome, Scleroderma, Rheumatoid Arthritis and polymyositis or local syndromes which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus Type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T cell bypass. A normal immune system requires the activation of B-cells by T cells before the former can produce antibodies in large quantities. This requirement of a T cell can be by-passed in rare instances, such as infection by organisms producing superantigens, which are capable of initiating polyclonal activation of B-cells, or even of T cells, by directly binding to the β-subunit of T cell receptors in a non-specific fashion. Another explanation deduces autoimmune diseases from a "Molecular Mimicry": an exogenous antigen may share structural similarities with certain host antigens; thus, any antibody produced against this antigen (which mimics the self-antigens) can also, in theory, bind to the host antigens and amplify the immune response. Autoimmune diseases based on molecular mimicry are known to a skilled person for various viral and bacterial antigens. The most striking form of molecular mimicry is observed in Group A beta-haemolytic streptococci, which shares antigens with human myocardium, and is responsible for the cardiac manifestations of rheumatic fever.

Additionally, according to one further specific aspect, diseases as defined herein comprise allergies or allergic diseases, i.e. diseases related to allergies. Allergy is a condition that typically involves an abnormal, acquired immunological hypersensitivity to certain foreign antigens or allergens, such as the allergy antigens as defined herein. Such allergy antigens or allergens may be selected from allergy antigens as defined herein antigens derived from different sources, e.g. from animals, plants, fungi, bacteria, etc. Allergens in this context include e.g. danders, grasses, pollens, molds, drugs, or numerous environmental triggers, etc. Allergies normally result in a local or systemic inflammatory response to these antigens or allergens and lead to immunity in the body against these allergens. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, asthma, allergic asthma (leading to swelling of the nasal mucosa), allergic conjunctivitis (leading to redness and itching of the conjunctiva), allergic rhinitis ("hay fever"), anaphylaxis, angiodema, atopy, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc.; etc. Treatment of such allergic disorders or diseases may occur preferably by desensitizing the immune reaction which triggers a specific immune response. Such a desensitizing may be carried out by administering an effective amount of the allergen or allergic antigen encoded by the nucleic acid as defined herein, preferably, when formulated as a pharmaceutical composition, to induce a slight immune reaction. The amount of the allergen or allergic antigen may then be raised step by step in subsequent administrations until the immune system of the patient to be treated tolerates a specific amount of allergen or allergic antigen.

Diseases in the context of the present invention may also include type II hypersensitivity reactions (cytotoxic, antibody-dependent), including e.g. autoimmune hemolytic anemia, thrombocytopenia, erythroblastosis fetalis, Goodpasture's syndrome, Graves' disease, Myasthenia Gravis, etc.; type III hypersensitivity reactions (immune complex disease) including e.g. serum sickness, Arthus reaction, Systemic lupus erythematosus (SLE), etc.; type IV hypersensitivity reactions (delayed-type hypersensitivity (DTH), cell-mediated immune memory response, antibody-independent), including e.g. contact dermatitis, Mantoux test, chronic transplant rejection, multiple sclerosis, etc.; and type V hypersensitivity reactions (receptor mediated autoimmune disease), including e.g. Graves' disease, Myasthenia Gravis, etc.;

Likewise, diseases in the context of the present invention may include cardiovascular diseases chosen from, without being limited thereto, coronary heart disease, arteriosclerosis, apoplexy and hypertension, etc.

Finally, diseases in the context of the present invention may be chosen from neuronal diseases including e.g. Alzheimer's disease, amyotrophic lateral sclerosis, dystonia, epilepsy, multiple sclerosis and Parkinson's disease etc.

According to a final embodiment, the present invention also provides a kit, which may comprise the inventive composition or vaccine composition as defined herein and optional technical instructions with information on the administration and dosage of the inventive composition or vaccine composition as defined herein or of any of its components. The present application may also provide a kit of parts, which may comprise in one part of the kit the inventive composition or vaccine composition as defined herein, and optionally in at least one further part of the kit additional components of the inventive composition or vaccine composition as defined herein, and optionally in one further part technical instructions with information on the administration and dosage of the inventive composition or vaccine composition as defined herein or of any of its components. Preferably, such an inventive kit of parts may comprise one inventive composition or vaccine composition as defined herein, wherein the inventive composition or vaccine composition preferably comprises or encodes at least one antigen as defined herein, e.g. one or more (preferably different) antigens as defined herein, preferably a cocktail of antigens as defined herein. The inventive composition or vaccine composition may be contained in one part of the kit. Further parts of the kit may preferably contain additional components, additives, etc., preferably together in one part or each of the additional components, additives, etc., in a separate part of the kit. The kit may also comprise in a further part of the kit technical instructions with information on the administration and dosage of the inventive composition or vaccine composition as defined herein or of any of its components. The inventive kit may also comprise different inventive compositions or vaccine compositions as defined herein, each inventive composition or vaccine composition preferably comprising or encoding a different antigen as defined herein. Such a kit may also comprise in a further part of the kit technical instructions with information on the administration and dosage of the inventive composition or vaccine composition as defined herein or of any of its components.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

FIGURES

The following Figures are intended to illustrate the invention further. They are not intended to limit the subject matter of the invention thereto.

FIG. 1: shows the particle size measurement of inventive complexes. The single measurements are displayed by Records 4 to 6, wherein Record 4 shows the inventive vaccine R1435/PB83, wherein
the adjuvant component is mRNA R1435 coding for *Gallus gallus* ovalbumine complexed with protamine (2:1; (w/w);
the antigen is free mRNA R1435 (ratio 1:1; complexed RNA:free RNA); and
the carrier is PB83: HO-PEG$_{5000}$-S—(S—CHHHH-HHRRRRHHHHHHC—S—)$_7$-S-PEG$_{5000}$-OH;

Record 5 shows the inventive vaccine R1435/PB83/KALA, wherein
the adjuvant component is mRNA R1435 coding for *Gallus gallus* ovalbumine complexed with protamine (2:1; (w/w));
the antigen is free mRNA R1435 (ratio 1:1; complexed RNA:free RNA); and
the carrier is PB83: HO-PEG$_{5000}$-S—(S—CHHHH-HHRRRRHHHHHHC—S—)$_7$-S-PEG$_{5000}$-OH, with enhancer peptide KALA;

Record 6 shows as a control the "parent" formulation R1435, wherein
the adjuvant component consists of mRNA coding for *Gallus gallus* ovalbumine complexed with protamine (2:1; (w/w));
the antigen is free mRNA coding for *Gallus gallus* ovalbumine (ratio 1:1; complexed RNA:free RNA).

As can be seen, the parent formulation R1435 shows two components, the adjuvant component consisting of complexed RNA with an average particle size of 200 nm and the antigen component consisting of free mRNA with an average particle size of 40 nm. The complexation of the parent formulation R1435 with the carrier PB83 leads to generation of a uniform component with an average particle size of 300 nm. As can be seen, the addition of KALA to such a complex does not change the particle properties.

Figure 2:
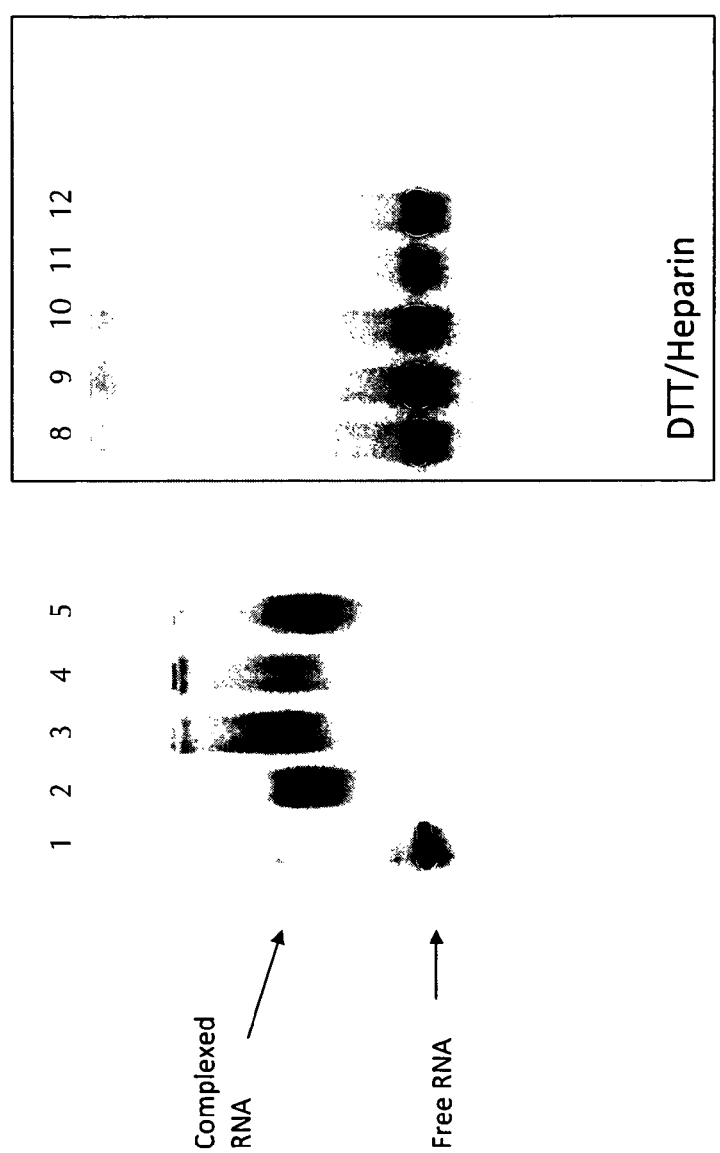

FIG. 2: shows an agarose gel shift assay, wherein the left part of FIG. 2 shows the agarose gel shift of the "parent" formulation R1435 or different amounts of the inventive vaccine formulations with the carrier PB83 (R1425/PB83). As can be seen, the parent formulation consists of two components, the complexed RNA (upper band) and free mRNA (lower band). By contrast the inventive vaccine formulation only shows one band and no band of free mRNA. The right part of FIG. 2 shows the agarose gel shift of the formulations after 30 minutes treatment with heparin/DTT at 37° C. As can be easily seen the RNA is electrostatically replaced by heparin and therefore leads to the same gel shift as the free RNA. Consequently, complexation of the RNA as carried out in the inventive vaccine formulation is reversible under reducible conditions as present in the endosome.

Figure 3A:
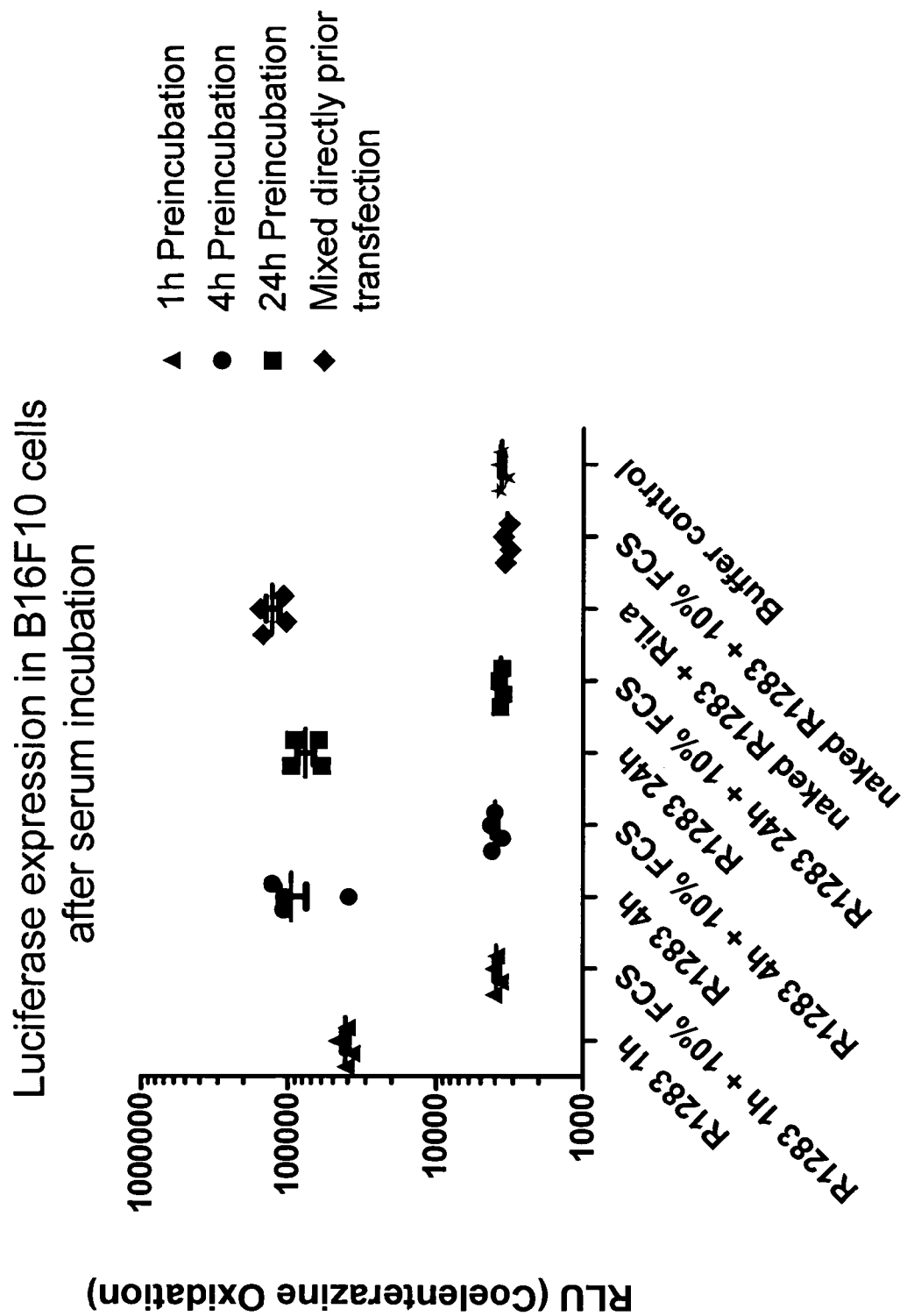

FIG. 3a: shows results from serum stability experiments of "parent" formulations of R1283 consisting of naked mRNA and protamine complexed RNA. As can be seen serum incubation leads to loss of luciferase activity in all parent formulations (R1283). Naked RNA (naked R1283) is even degraded after several seconds of incubation with serum. Thus, RNA comprised in the parent formulation is not protected against nucleases.

Figure 3B:
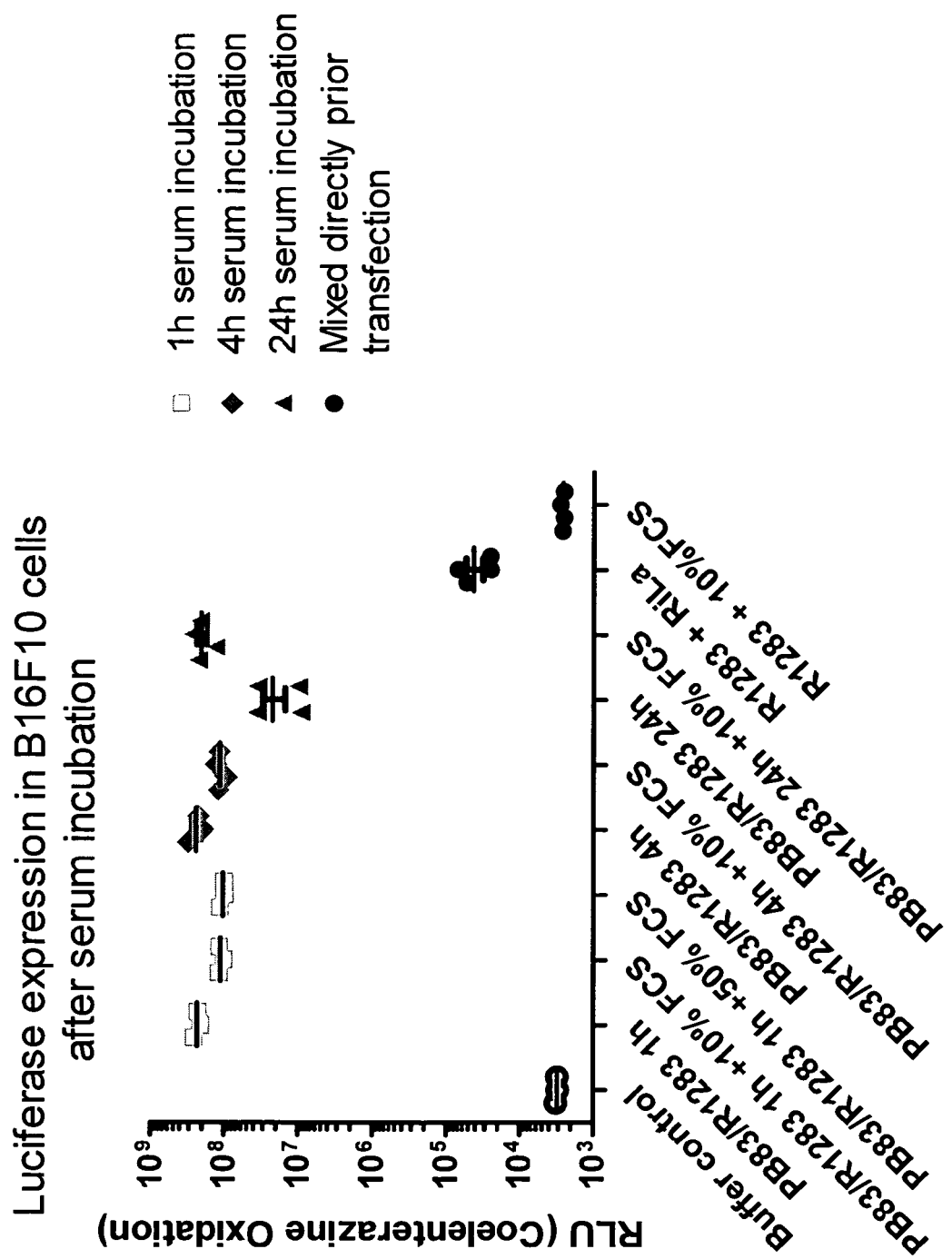

FIG. 3b: shows results from serum stability experiments of inventive vaccine formulations based on a R1283 parent formulation, which has been further formulated with the carrier PB83. As can be seen, the carrier PB83 (R1283/PB83) confers protection on the RNA against RNAses compared to the (unprotected) parent formulation (R1283).

Figure 4A:
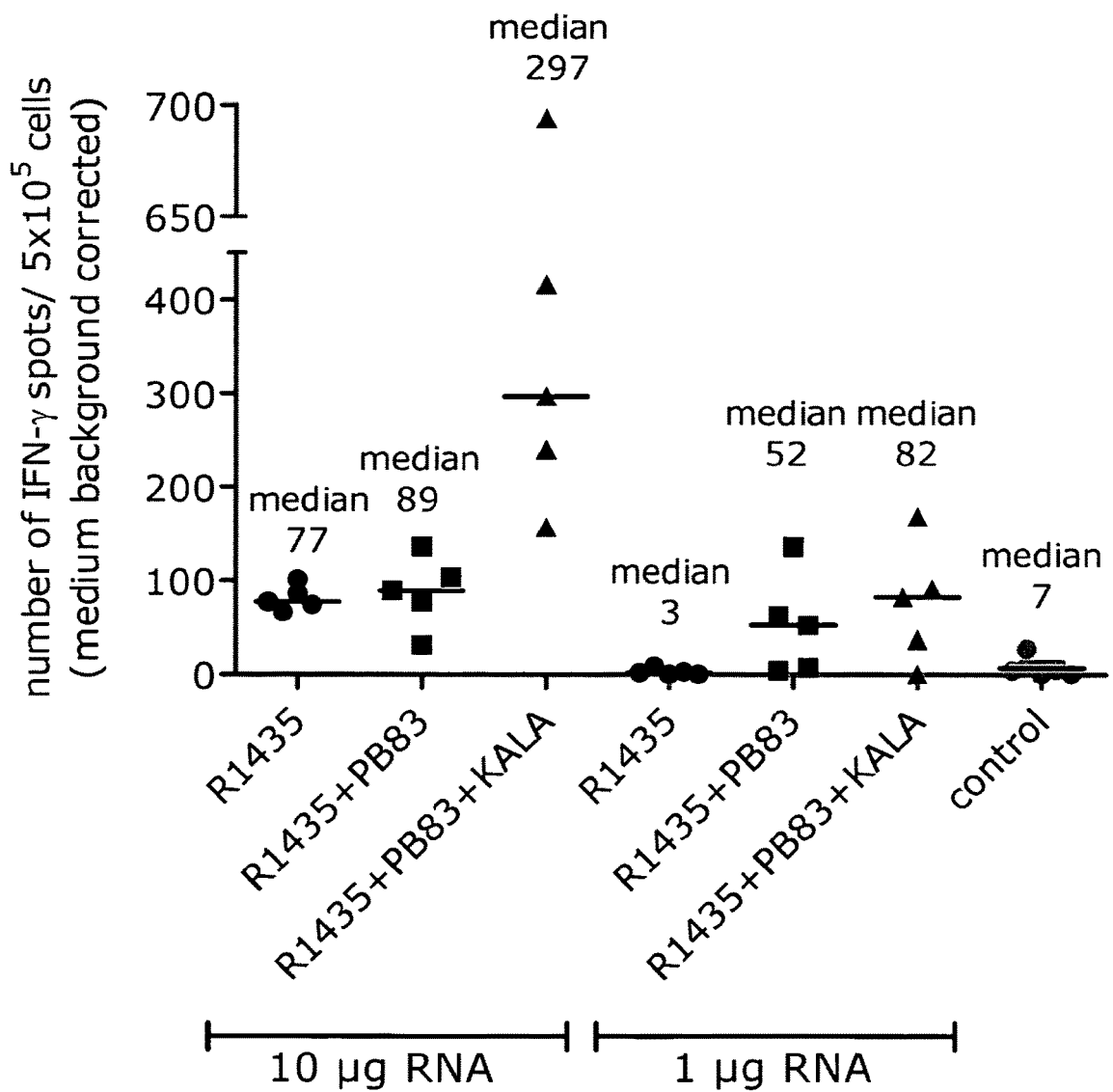

FIG. 4A: shows the results from an IFN-γ ELISPOT assay. As can be seen, the inventive vaccine formulations (R1435/PB83) show significantly higher induction of ovalbumine specific cytotoxic T cells (CTLs) at low doses (1 μg) compared to the parent formulations (R1435) which is inactive at this dose level. Thus, the inventive vaccine formulation improves the CTL specific immune response against the antigen ovalbumine compared to the parent formulation. Advantageously, addition of the enhancer peptide KALA further improves the antigen-specific immune response.

Figure 4B:
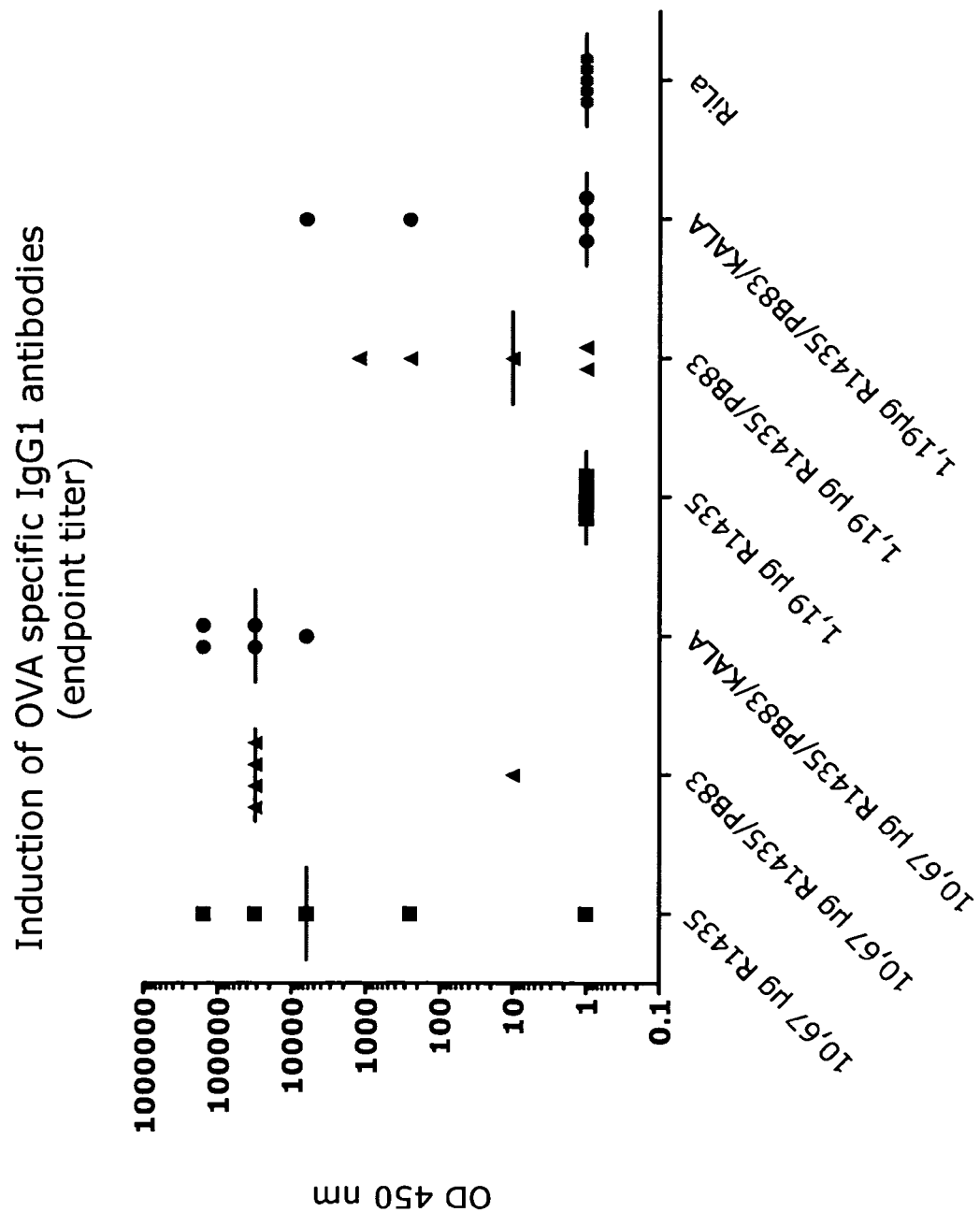

FIG. 4B: shows the results from vaccination of mice with different formulations of R1435. Shown is the induction of OVA specific IgG1 antibodies (endpoint titer). As can be seen, complexation of the parent formulation with carrier PB83 improves the antibody response against the antigen ovalbumine. It can be seen that at the dose of 1.19 μg mRNA there is no response in the parent formulation group (R1435). In contrast, complexation with the carrier leads to an at least partially immune response (R1435/PB83).

Figure 4C:
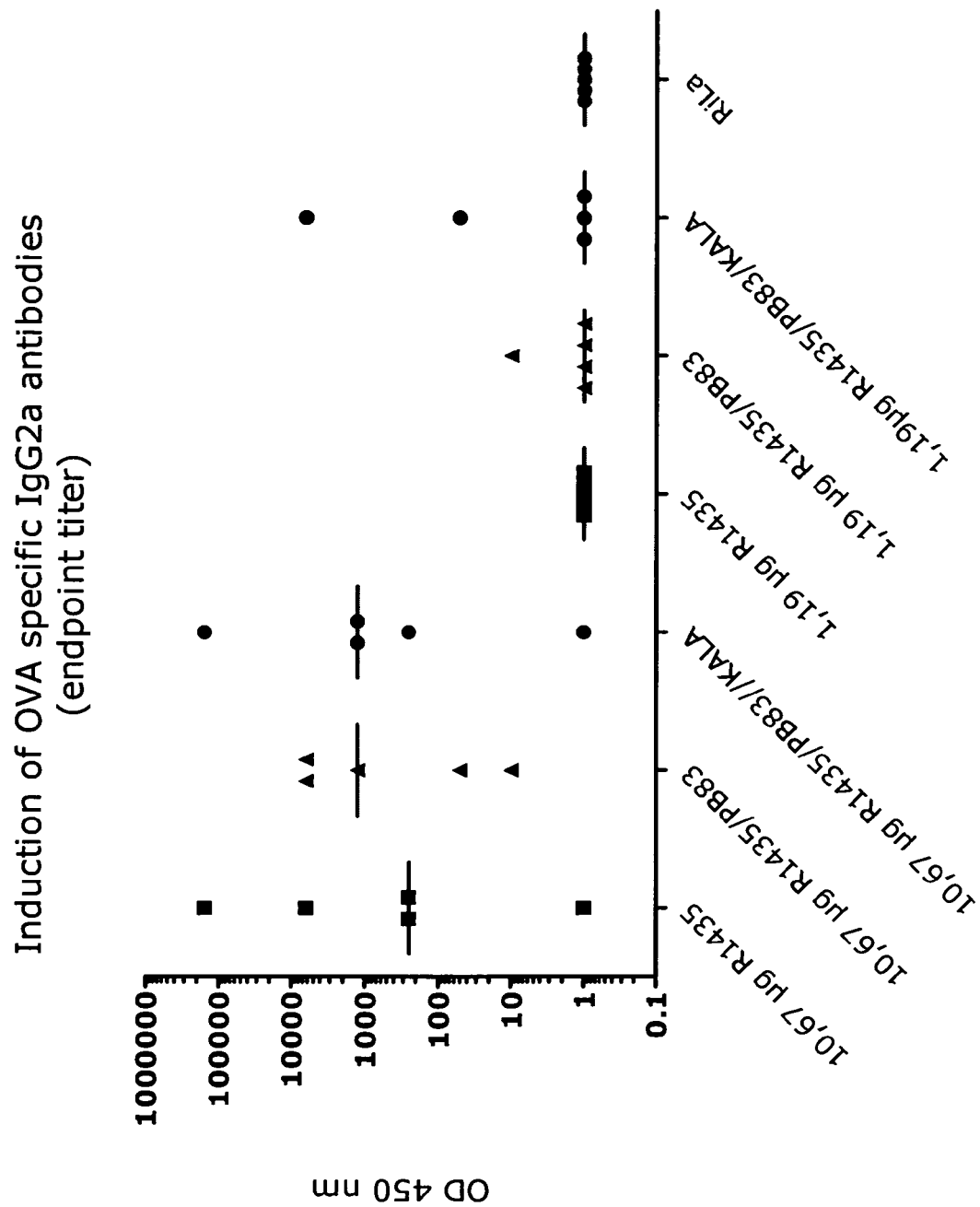

FIG. 4C: shows the results from vaccination of mice with different formulations of R1435. Shown is the induction of OVA specific IgG2 antibodies (endpoint titer). As can be seen, complexation of the parent formulation with carrier PB83 improves the antibody response against the antigen ovalbumine. It can be seen that at the dose of 1.19 μg mRNA there is no response in the parent formulation group (R1435). In contrast, complexation with the carrier leads to an at least partially immune response (R1435/PB83).

Figure 5:
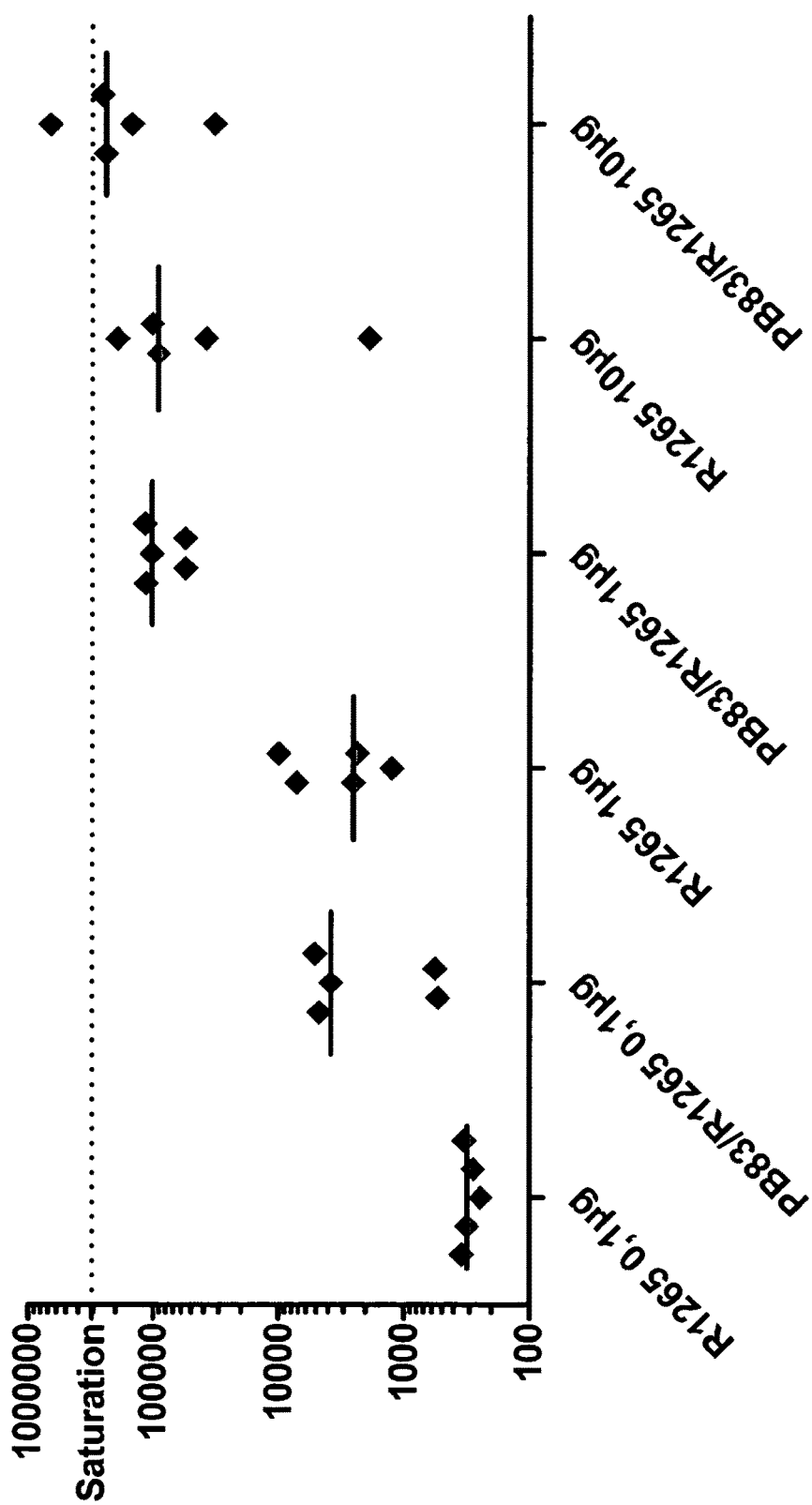

FIG. 5: shows the effect of the complexation of a "parent" formulation (R1265) with a carrier on the efficiency of reporter mRNA expression after ID injection into BALB/c mice. As can be seen complexation of the "parent" formulation (R1265) with a carrier (R1265/PB83) significantly increases the expression of the encoded reporter protein luciferase. The achieved levels are even higher than levels achieved with naked mRNA (R1265 naked).

Figure 6:
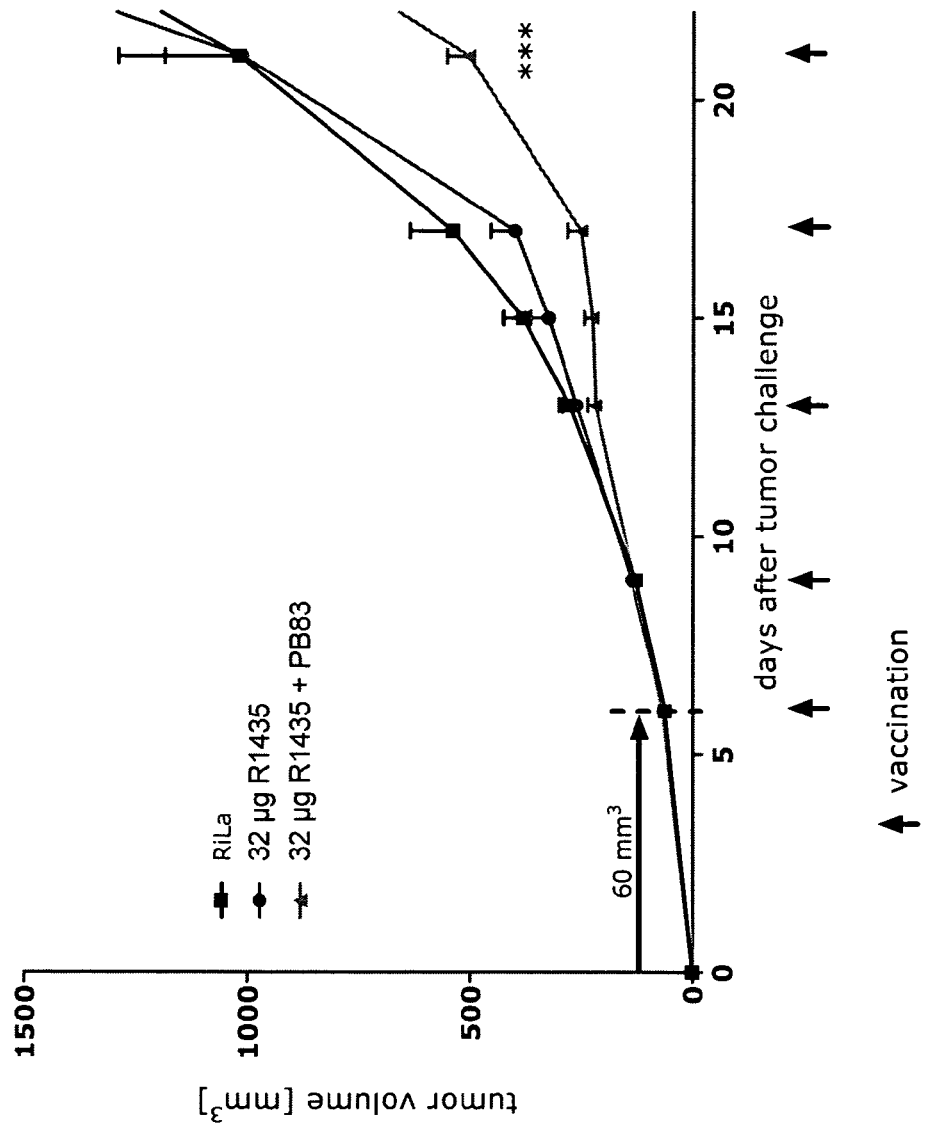

FIG. 6: shows the effect of the inventive vaccine formulation of 32 μg mRNA coding for the antigen ovalbumine on tumour growth. As can be seen, vaccination of mice in a therapeutic setting using the inventive vaccine formulation decelerates tumour growth significantly. This was absolutely surprising as the vaccination schedule used herein usually does not lead to an influence on E.G7-OVA tumour growth.

Figure 7:
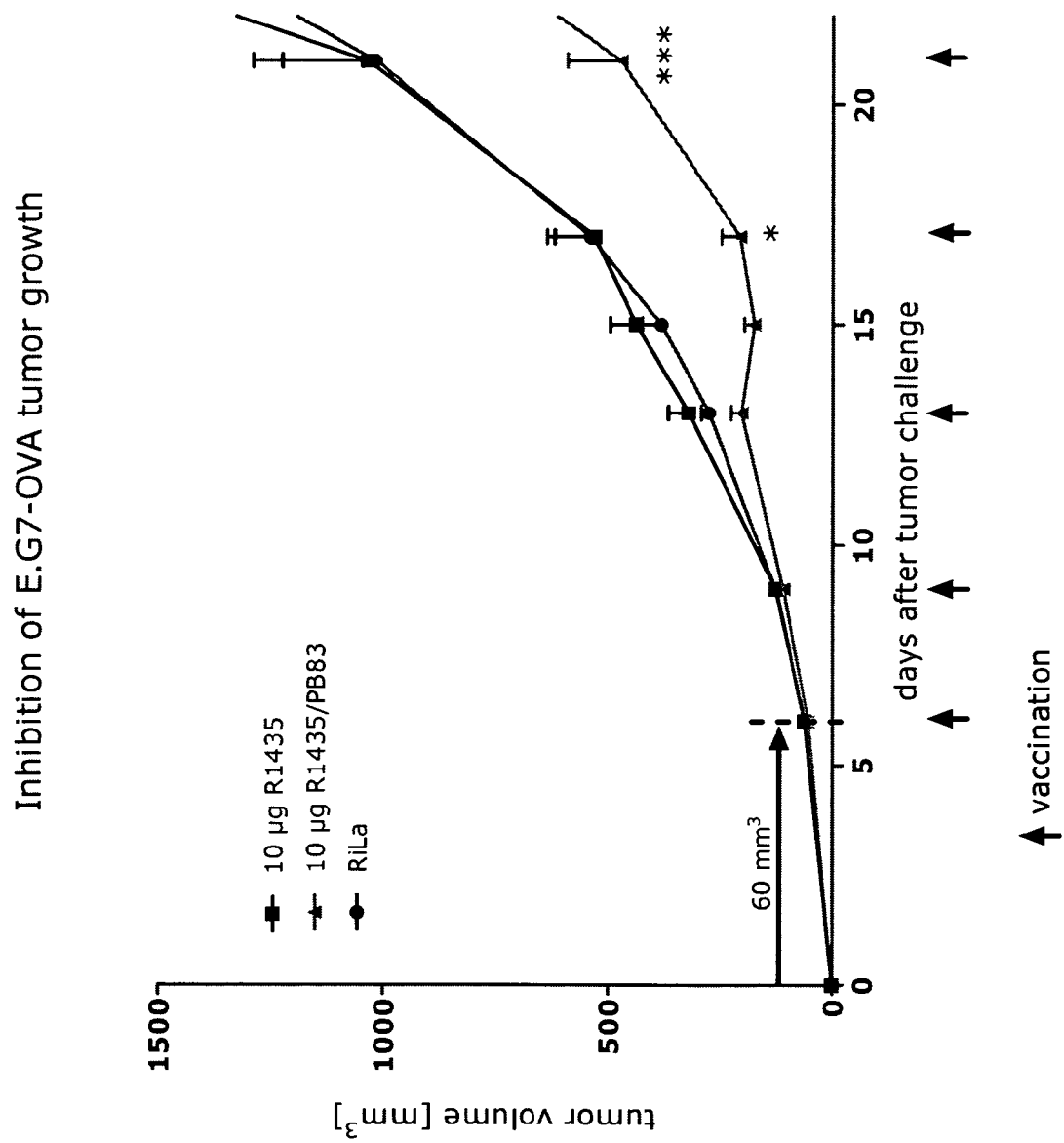

FIG. 7: shows the effect of the inventive vaccine formulation of 10 μg mRNA coding for the antigen ovalbumine on tumour growth. As can be seen, vaccination of mice in a therapeutic setting using the inventive vaccine formulation decelerates the tumour growth significantly. This was absolutely surprising as the vaccination schedule used herein normally does not lead to an influence on E.G7-OVA tumour growth. Furthermore it was absolutely surprising that already 10 RNA are sufficient to significantly decelerate tumour growth.

FIG. 8: The sequence of Pp Luc R1265 (SEQ ID NO: 544).

FIG. 9: The sequence of Gp Luc R1283 (SEQ ID NO: 545).

FIG. 10: The sequence of Ova R1435 (SEQ ID NO: 546).

EXAMPLES

The following examples are intended to further illustrate the invention. They are not intended to limit the subject matter of the invention thereto.

1. Preparation of DNA and mRNA Constructs

For the present examples DNA sequences, encoding *Photinus pyralis* luciferase (R1265), *Gaussia princeps* luciferase (R1283), or *Gallus gallus* ovalbumin (R1435), were prepared and used for subsequent in vitro transcription reactions.

According to a first preparation, the DNA sequences coding for the mRNA R1265, R1283 or R1435 were prepared. The constructs were prepared by modifying the wild type *Photinus pyralis* luciferase, *Gaussia princeps* luciferase or *Gallus gallus* ovalbumine encoding DNA sequences by introducing a GC-optimized sequence for a better codon usage and stabilization, stabilizing sequences derived from alpha-globin-3'-UTR (muag (mutated alpha-globin-3'-UTR)), a stretch of 70× adenosine at the 3'-terminal end (poly-A-tail), a stretch of 30× cytosine at the 3'-terminal end (poly-C-tail), and a histone stem-loop sequence leading to SEQ ID NO: 544 (see FIG. 8) for mRNA R1265, to SEQ ID NO: 545 (see FIG. 9) for mRNA R1283, and to SEQ ID NO: 546 (see FIG. 10) for mRNA R1435. In SEQ ID NOs: 544-546 (see FIGS. 8, 9 and 10) the sequence of the corresponding mRNAs are shown.

2. In Vitro Transcription:

The respective DNA plasmid prepared according to Example 1 was transcribed in vitro using T7 polymerase. Subsequently the mRNA was purified using PureMessenger® (CureVac, Tubingen, Germany).

3. Reagents:

Complexation Reagent:
Protamine
Carrier:
PB83: HO-PEG$_{5000}$-S—(S—CHHHHHHRRRRHHHH-HHC—S—)$_7$—S— PEG$_{5000}$-OH PB83 (SEQ ID NO: 547) represents an exemplary carrier as described in the present invention.

4. Preparation of the Adjuvant Component and Addition of the Antigen:

The mRNA to be used as immunostimulatory nucleic acid sequence in the experiments below was complexed with protamine by addition of protamine to the mRNA in the indicated ratios (1:2) (w/w). After incubation for 10 min, the free mRNA to be used as antigen was added.

These combinations of an adjuvant component and an antigen mRNA without a further carrier were termed "parent" formulations: Following "parent" formulations were prepared:

R1265: adjuvant component consisting of mRNA coding for *Photinus pyralis* Luciferase according to SEQ ID NO: 544 complexed with protamine in a ratio of 2:1 (w/w) and free mRNA coding for *Photinus pyrialis* Luciferase (antigen mRNA) according to SEQ ID NO 544 (ratio 1:1; complexed RNA:free RNA).

R1283: adjuvant component consisting of mRNA coding for *Gaussia princeps* luciferase according to SEQ ID NO: 545 complexed with protamine in a ratio of 2:1 (w/w) and free mRNA coding for Luciferase (antigen mRNA) according to SEQ ID NO 545 (ratio 1:1; complexed RNA:free RNA).

R1435: adjuvant component consisting of mRNA coding for *Gallus gallus* ovalbumine according to SEQ ID NO: 546 complexed with protamine in a ratio of 2:1 (w/w) and free mRNA coding for *Gallus gallus* ovalbumine (antigen mRNA) according to SEQ ID NO 546 (ratio 1:1; complexed RNA:free RNA).

5. Synthesis of the Carrier:

The condensation reaction was performed with the calculated amount of peptide (component P$^2$) which was dissolved in a mixture of a buffered aqueous solution at pH 8.5 with an optional additive of 5% (v/v) Dimethylsulfoxide (DMSO) (which represent mild oxidation conditions and therefore allow the establishment of an equilibrium) and stirred for 18 h at ambient temperature. Afterwards the calculated amount of a thiol group containing PEG derivative (alpha-Methoxy-omega-mercapto poly(ethylene glycol)) (component P$^1$) (dissolved in water) was added and the resulting solution was stirred for another 18 h. Subsequent lyophilisation and purification yield the desired polymer. The ratio between PEG component P$^1$ to peptide component P$^2$ typically defines the chain length of the P$^2$ polymer.

The condensation reaction in this reaction environment is reversible, therefore the chain length of the polymer was determined by the amount of the monothiol compound which terminates the polymerisation reaction. In summary the length of the polymer chain was determined by the ratio of oligo-peptide and monothiol component. This reaction was supported by the chosen mild oxidation conditions. With more stringent oxidation conditions (30% DMSO) the generation of high molecular (long chain) polymers was induced.

1$^{st}$ Step: Exemplary Polymerization Reaction:

2$^{nd}$ Step: Exemplary Stop Reaction:

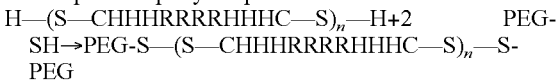

Exemplary Synthesis Reaction:

1$^{st}$ step:

2$^{nd}$ step:

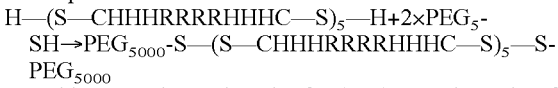

To achieve a polymer length of 5 (n=5), a molar ratio of peptide:PEG of 5:2 was used.

6. Packaging of Adjuvant Component and Antigen:

The adjuvant components in combination with the antigen ("parent" formulation prepared according to Example 4), were complexed for the purposes of the present invention with a carrier, preferably the carrier as defined in Example 5. In some cases an enhancer peptide (KALA) was added before complexation with the carrier. Afterwards the resulting solution was adjusted with water to a final volume of 50 µl and incubated for 30 minutes at room temperature.

| Component | mRNA | Carrier | Complexation reagent | Enhancer Peptide (e.g. KALA) |
|---|---|---|---|---|
| Ratio (mol) | 1 | 5-500 (50) | 0-250 (25) | 0-50 (5) |

The inventive vaccines are termed:
R1265/PB83
R1283/PB83
R1435/PB83

7. Size Measurement:

The hydrodynamic diameters of polyplexes as prepared above were measured by dynamic light scattering using a Zetasizer Nano (Malvern Instruments, Malvern, UK)

according to the SOPs (standard operation procedure) distributed by Malvern. The measurements were performed at 25° C. in Ringer Lactate solution and analyzed by a cumulant method to obtain the hydrodynamic diameters and polydispersity indices of the polyplexes.

8. Gel Shift Assay

Furthermore, different amounts of inventive vaccine complexes (R1435/PB83) were prepared as indicated in Example 6 above and aliquots were incubated with heparin (100 µg) and dithiothreitol (DTT) for 30 minutes at 37° C. In one group the enhancer peptide KALA was added to the inventive vaccine complexes (R1435/PB83/KALA). Subsequently electrophoresis was done on agarose gel and the nucleic acid sequences were visualized by ethidium bromide staining. For comparison the inventive vaccine formulation without packaging with the carrier (parent formulation) was used (R1435).

9. Transfection of B16110 Cells:

The inventive vaccine complexes were prepared according to Example 6. After serum incubation for the indicated time (1, 4, 24 h) the complexes containing 5 µg RNA were transfected in B16F10 cells. Then, B16F10 cells ($150 \times 10^3$/well) were seeded 1 day prior to transfection on 24-well microtiter plates leading to a 70% confluence when transfection was carried out. For transfection 50 µl of the vaccine complex solution were mixed with 250 µl serum free or FCS containing DEMEM and added to the cells (final RNA concentration: 13 µg/ml). Prior to addition of the serum free transfection solution the HeLa-cells were washed gently and carefully 2 times with 1 ml Optimen (Invitrogen) per well. Then, the transfection solution (300 µl per well) was added to the cells and the cells were incubated for 4 h at 37° C. Subsequently 300 µl RPMI-medium (Camprex) containing 10% FCS was added per well and the cells were incubated for additional 20 h at 37° C. The transfection solution was sucked off 24 h after transfection and the cells were lysed in 300 µl lysis buffer (25 mM Tris-$PO_4$, 2 mM EDTA, 10% glycerol, 1% Triton-X 100, 2 mM DTT). The supernatants were then mixed with luciferin buffer (25 mM Glycylglycin, 15 mM $MgSO_4$, 5 mM ATP, 62.5 µM luciferin) and luminescence was detected using a luminometer (Lumat LB 9507 (Berthold Technologies, Bad Wildbad, Germany)).

The results of experiments with "parent" formulations of R1283 consisting of naked mRNA and protamine complexed RNA and of experiments with inventive vaccine formulations based on a R1283 parent formulation, which have been further formulated with the carrier PB83 are shown in FIGS. 3a and 3b. As can be seen in FIG. 3a serum incubation leads to loss of luciferase activity in all parent formulations (R1283). Naked RNA (naked R1283) is even degraded after several seconds of incubation with serum. Thus, RNA comprised in the parent formulation is not protected against nucleases. In contrast thereto, as can be seen in FIG. 3b, the carrier PB83 (R1283/PB83) confers protection on the RNA against RNAses compared to the (unprotected) parent formulation (R1283).

10. Expression of Luciferase In Viva

"Parent" formulations or inventive vaccine complexes were prepared according to Example 4 or 6 above. For determining luciferase expression in vivo, the indicated amount of mRNA containing complexes were injected intradermally (ear pinna or back) to 7 week old BALB/c mice (see FIG. 5: 0.1 µg, 1 µg, 10 µg). After 24 h the mice were sacrificed and the samples (ear, skin from the back or muscle) were collected, frozen at −78° C. and lysed for 3 Minutes at full speed in a tissue lyser (Qiagen, Hilden, Germany). Afterwards 600 µl of lysis buffer were added and the resulting solutions were subjected another 6 minutes at full speed in the tissue lyser. After 10 minutes centrifugation at 13,500 rpm at 4° C. the supernatants were mixed with luciferin buffer (25 mM Glycylglycin, 15 mM $MgSO_4$, 5 mM ATP, 62.5 µM luciferin) and luminescence was detected using a luminometer (Lumat LB 9507 (Berthold Technologies, Bad Wildbad, Germany)).

The results can be seen in FIG. 5. FIG. 5 shows the effect of the complexation of a "parent" formulation (R1265) with a carrier on the efficiency of reporter mRNA expression after ID injection into BALB/c mice. As can be seen complexation of the "parent" formulation (R1265) with a carrier (R1265/PB83) significantly increases the expression of the encoded reporter protein luciferase. The achieved levels are even higher than levels achieved with naked mRNA (R1265 naked).

11. Immunization Experiments:

For immunization the inventive vaccine complexes R1435/PB83, wherein the mRNA codes for *Gallus gallus* ovalbumin, were prepared according to Example 6 and transfected into C57 BL/6 mice. For comparison one group was transfected with a "parent" formulation consisting of the adjuvant component and antigen without complexation with the carrier (R1435). 4 mice per group were immunized intradermally 2 times with the indicated amount of mRNA containing complexes.

The results from an IFN-γ ELISPOT assay are shown in FIG. 4a. As can be seen, the inventive vaccine formulations (R1435/PB83) show significantly higher induction of ovalbumine specific cytotoxic T cells (CTLs) at low doses (1 µg) compared to the parent formulations (R1435) which is inactive at this dose level. Thus, the inventive vaccine formulation improves the CTL specific immune response against the antigen ovalbumine compared to the parent formulation. Advantageously, addition of the enhancer peptide KALA further improves the antigen-specific immune response.

12. Detection of an Antigen-Specific Immune Response (B-Cell Immune Response):

Detection of an antigen specific immune response (B-cell immune response) was carried out by detecting antigen specific antibodies. Therefore, blood samples were taken from vaccinated mice one week after the last vaccination and sera were prepared. MaxiSorb plates (Nalgene Nunc International) were coated with *Gallus gallus* ovalbumine protein. After blocking with 1×PBS containing 0.05% Tween-20 and 1% BSA the plates were incubated with diluted mouse serum (1:30, 1.90, 1:270, 1:810). Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis (3-ethyl-benzthiazoline-6-sulfonic acid) was measured.

The results from vaccination of mice with different formulations of R1435 are shown in FIGS. 4b and 4c. FIG. 4b shows the induction of OVA specific IgG1 antibodies (endpoint titer). As can be seen, complexation of the parent formulation with carrier PB83 improves the antibody response against the antigen ovalbumine. It can be seen that at the dose of 1.19 µg mRNA there is no response in the parent formulation group (R1435). In contrast, complexation with the carrier leads to an at least partially immune response (R1435/PB83). FIG. 4c shows the induction of OVA specific IgG2 antibodies (endpoint titer). As can be seen, complexation of the parent formulation with carrier PB83 improves the antibody response against the antigen ovalbumine. It can be seen that at the dose of 1.19 µg mRNA there is no response in the parent formulation group (R1435). In contrast, complexation with the carrier leads to an at least partially immune response (R1435/PB83).

13. Detection of an Antigen Specific Cellular Immune Response by ELISPOT:

One week after the last vaccination mice were sacrificed, the spleens were removed and the splenocytes were isolated. For detection of INFgamma a coat multiscreen plate (Millipore) was incubated overnight with coating buffer 0.1 M Carbonat-Bicarbonat Buffer pH 9.6, 10.59 g/l $Na_2CO_3$, 8.4 g/l $NaHCO_3$) comprising antibody against INFγ (BD Pharmingen, Heidelberg, Germany). The next day $2 \times 10^5$ cells/well were added and re-stimulated with 0.25 µg/well of relevant (SIINFEKL of ovalbumine); irrelevant peptide (Cennexin) or buffer without peptide. Afterwards the cells are incubated for 24 h at 37° C. The next day the plates were washed twice with PBS, once with water and once with PBS/0.05% Tween-20 and afterwards incubated with a biotin-coupled secondary antibody for 11-24 h at 4° C. Then the plates were washed with PBS/0.05% Tween-20 and incubated for 2 h with alkaline phosphatase coupled to streptavidin in blocking buffer. After washing with PBS/0.05% Tween-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction.

14. Tumour Challenge:

The samples used in this experiment were:

R1435: Vaccine consisting of protamine complexed mRNA and free mRNA coding for *Gallus gallus* ovalbumine prepared according to example 4.

R1435/PB83: Inventive vaccine prepared according to example 6 containing protamine complexed mRNA and free mRNA coding for *Gallus gallus* ovalbumine complexed with the carrier PB83.

RiLa control: 80% Ringer lactate was used as control

At day 0 $1 \times 10^6$ E.G7-OVA cells (tumour cells which stably express ovalbumine) were implanted subcutaneously in 7 week old C57BL/6 mice. Beginning with a tumour volume of 60 $mm^3$ mice were vaccinated intradermally with 5 cycles of 80 µl formulations containing 10 or 32 µg mRNA coding for *Gallus gallus* ovalbumine. As a negative control 80 µl 80% Ringer lactate without any RNA were injected. Tumour growth was monitored by measuring the tumour size in 3 dimensions using a calliper.

The effect of the inventive vaccine formulation of 32 µg mRNA coding for the antigen ovalbumine on tumour growth is shown in FIGS. 6 and 7. As can be seen in FIG. 6, vaccination of mice in a therapeutic setting using the inventive vaccine formulation decelerates tumour growth significantly. This was absolutely surprising as the vaccination schedule used herein usually does not lead to an influence on E.G7-OVA tumour growth. In FIG. 7 the effect of the inventive vaccine formulation of 10 µg mRNA coding for the antigen ovalbumine on tumour growth is shown. As can be seen, vaccination of mice in a therapeutic setting using the inventive vaccine formulation decelerates the tumour growth significantly. This was absolutely surprising as the vaccination schedule used herein normally does not lead to an influence on E.G7-OVA tumour growth. Furthermore it was absolutely surprising that already 10 µg RNA are sufficient to significantly decelerate tumour growth.

---

The invention claimed is:

1. An immune stimulating composition, comprising:
   a) an adjuvant component comprising at least one immunostimulatory RNA (isRNA), complexed with a complexing agent, wherein the immunostimulatory RNA is an antigen-encoding mRNA;
   b) a mRNA encoding an antigen; and
   c) a carrier molecule for combined packaging of the adjuvant component and the nucleic acid encoding the antigen, the carrier molecule having a formula (I):

L-P1-S[S—P2-S]$_n$-S—P3-L wherein P1 and P3 are different or identical to each other and represent a linear or branched hydrophilic polyethylene glycol (PEG) polymer chain, wherein the hydrophilic PEG polymer chain exhibits a molecular weight of 1 kDa to 100 kDa;
   P2 is a cationic or polycationic polypeptide, having a length of 3 to 100 amino acids, and comprising at least 2 cysteine residues;
   —S—S— is a (reversible) disulfide bond, wherein one of the sulfur positions of each of the disulfide bonds is provided by the at least 2 cysteine residues of the polypeptide of P2; and
   L is an optional ligand and may be selected independent from the other from RGD, Transferrin, Folate, a signal peptide or signal sequence, a localization signal or sequence, a nuclear localization signal or sequence (NLS), an antibody, a cell penetrating peptide, a human immunodeficiency virus TAT peptide, a ligand of a receptor, cytokines, hormones, growth factors, small molecules, carbohydrates, mannose, galactose, synthetic ligands, small molecule agonists, inhibitors or antagonists of receptors, or Arg-Gly-Asp (RGD) peptidomimetic analogues,
   wherein n is an integer between 1 and 50.

2. The composition according to claim 1, wherein the complexing agent of the adjuvant component is a cationic or polycationic compound selected from cationic or polycationic proteins or peptides or cationic or polycationic polymers.

3. The composition according to claim 2, wherein the complexing agent of the adjuvant component is selected from
   an oligopeptide having following sum formula (V):

$\{(Arg)_l;(Lys)_m;(His)_n;(Orn)_o;(Xaa)_x\};$    (formula (V))

wherein 1+m+n+o+x=3-100, and 1, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide of formula (V); and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide of formula (V),
   or from a disulfide-crosslinked cationic compound comprising as a repeat unit an oligopeptide having following subformula (Va):

$\{(Arg)_l;(Lys)_m;(His)_n;(Orn)_o;(Xaa')_x(Cys)_y\};$    formula (Va)

wherein $(Arg)_l;(Lys)_m;(His)_n;(Orn)_o$; and x is preferably are as defined above for formula (V), Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide,
   or from a disulfide-crosslinked cationic compound comprising as a repeat unit an oligopeptide having following subformula (Vb):

$Cys^1\{(Arg)_l;(Lys)_m;(His)_n;(Orn)_o;(Xaa)_x\}Cys^2;$    (formula (Vb))

wherein component $\{(Arg)_i;(Lys)_m;(His)_n;(Orn)_o;(Xaa)_x\}$ (formula (V)) within formula (Vb) is as defined herein and forms a core of subformula (Vb), and wherein $Cys^1$ and $Cys^2$ are Cysteines proximal to, or terminal to $(Arg)_i;(Lys)_m;(His)_n;(Orn)_o;(Xaa)_x$.

4. The composition according to claim 1, wherein the at least one immunostimulatory RNA to the complexing agent has a nitrogen/phosphate ratio (N/P) of about 0.01-4.

5. The composition according to claim 1, wherein the antigen is selected from tumour antigens, pathogenic antigens, animal antigens, viral antigens, protozoan antigens, bacterial antigens, allergic antigens, autoimmune antigens, and allergens.

6. The composition according to claim 1, wherein all components of the composition have a nitrogen/phosphate ratio (N/P) of about 0.01-2.

7. The composition according to claim 1, wherein the complexing agent of the adjuvant component is protamine.

8. The composition according to claim 5, wherein the antigen is a tumour antigen.

9. The composition according to claim 5, wherein the antigen is a viral antigen.

10. The composition according to claim 5, wherein the antigen is a bacterial antigen.

11. The composition according to claim 1, wherein the mRNA encoding an antigen and the immunostimulatory RNA of the adjuvant component have the same nucleic acid sequence.

12. A kit, comprising a composition according to claim 1 in one or more parts of the kit, and optionally comprising instructions for use of the kit.

* * * * *

SEQUENCE LISTING

<160> NUMBER OF SEQ ID NOS: 547

<210> SEQ ID NO 1
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 1
gguuuuuuuu uuuuuuuggg                                              20

<210> SEQ ID NO 2
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 2
gggggguuuu uuuuuggggg                                              20

<210> SEQ ID NO 3
<211> LENGTH: 40

```
<212> TYPE: RNA
<213> ORGANISM: Artificial
<220> FEATURE:
<223> OTHER INFORMATION: nucleic acid sequence according to formula (I)

<400> SEQUENCE: 3
gggggUuuuu uuuuuuuuuu uuuuuuuuuu uuuuugggg                              40

<210> SEQ ID NO 4
<211> LENGTH: 39
<212> TYPE: RNA
<213> ORGANISM: Artificial
<220> FEATURE:
<223> OTHER INFORMATION: nucleic acid sequence according to formula (I)

<400> SEQUENCE: 4
gugugugugu guuuuuuuuu uuuuuugug ugugugugu                               39

<210> SEQ ID NO 5
<211> LENGTH: 39
<212> TYPE: RNA
<213> ORGANISM: Artificial
<220> FEATURE:
<223> OTHER INFORMATION: nucleic acid sequence according to formula (I)

<400> SEQUENCE: 5
gguugguugg uuuuuuuuuu uuuuuuuggu ugguugguu                              39

<210> SEQ ID NO 6
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 6 ggggggggggu uugggggggg                                                  20

<210> SEQ ID NO 7
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 7 ggggggggguu uugggggggg                                                  20

<210> SEQ ID NO 8
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 8
ggggggguuu uuugggggggg                                                  20

<210> SEQ ID NO 9
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 9
```

```
ggggggguuu uuuuggggggg                                              20

<210> SEQ ID NO 10
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 10
gggggguuuu uuuugggggg                                               20

<210> SEQ ID NO 11
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 11
gggggguuuu uuuuuggggg                                               20

<210> SEQ ID NO 12
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 12 gggggguuuuu uuuuuugggg                                              20

<210> SEQ ID NO 13
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 13
gggggunuuu uuuuugggg                                                20

<210> SEQ ID NO 14
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 14 gggggunuu uuuuuugggg                                                20

<210> SEQ ID NO 15
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 15
ggggunuuuu uuuuuuuggg                                               20

<210> SEQ ID NO 16
<211> LENGTH: 20
<212> TYPE: RNA
<213> ORGANISM: Artificial
```

```
<220> FEATURE:
<223> OTHER INFORMATION: nucleic acid sequence according to formula (I)

<400> SEQUENCE: 16
ggggguuuuu uuuuuuuugg                                              20

<210> SEQ ID NO 17
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 17
gguuuuuuuu uuuuuuuugg                                              20

<210> SEQ ID NO 18
<211> LENGTH: 20
<212> TYPE: RNA
<213> ORGANISM: Artificial
<220> FEATURE:
<223> OTHER INFORMATION: nucleic acid sequence according to formula (I)

<400> SEQUENCE: 18
guuuuuuuuu uuuuuuuuug                                              20

<210> SEQ ID NO 19
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 19
gggggggggg uuuggggggg gg                                           22

<210> SEQ ID NO 20
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 20 ggggggggggu uuuggggggg gg                                          22

<210> SEQ ID NO 21
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 21 ggggggggguu uuuggggggg gg                                          22

<210> SEQ ID NO 22
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 22 ggggggggu uuuuggggg gg                                             22
```

<210> SEQ ID NO 23
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 23 gggggggduuu uuuuuggggg gg                                              22

<210> SEQ ID NO 24
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 24 gggggggduuu uuuuugggg gg                                               22

<210> SEQ ID NO 25
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 25 gggggggduuu uuuuuuggg gg                                               22

<210> SEQ ID NO 26
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 26
gggggguuuu uuuuuuuggg gg                                               22

<210> SEQ ID NO 27
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 27
gggggguuuu uuuuuuugg gg                                                22

<210> SEQ ID NO 28
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 28
gggggduuuu uuuuuuuugg gg                                               22

<210> SEQ ID NO 29
<211> LENGTH: 22
<212> TYPE: RNA
<213> ORGANISM: Artificial
<220> FEATURE:
<223> OTHER INFORMATION: nucleic acid sequence according to formula (I)

```
<400> SEQUENCE: 29 gggggguuuuu uuuuuuuug gg                                          22

<210> SEQ ID NO 30
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 30
ggguuuuuuu uuuuuuuug gg                                           22

<210> SEQ ID NO 31
<211> LENGTH: 22
<212> TYPE: RNA
<213> ORGANISM: Artificial
<220> FEATURE:
<223> OTHER INFORMATION: nucleic acid sequence according to formula (I)

<400> SEQUENCE: 31
gguuuuuuuu uuuuuuuuuu gg                                          22

<210> SEQ ID NO 32
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 32
gggggggggg guuuggggg gggg                                         24

<210> SEQ ID NO 33
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 33
gggggggggg uuuuggggg gggg                                         24

<210> SEQ ID NO 34
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 34 ggggggggggu uuuuggggg gggg                                        24

<210> SEQ ID NO 35
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 35
gggggggggu uuuuugggg gggg                                         24

<210> SEQ ID NO 36
```

```
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 36 ggggggggguu uuuuuugggg gggg                                          24

<210> SEQ ID NO 37
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 37 ggggggggguu uuuuuuuggg gggg                                          24

<210> SEQ ID NO 38
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 38 ggggggggguu uuuuuuuugg gggg                                          24

<210> SEQ ID NO 39
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 39 ggggggggguuu uuuuuuuugg gggg                                         24

<210> SEQ ID NO 40
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 40
ggggggguuu uuuuuuuug gggg                                            24

<210> SEQ ID NO 41
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 41
gggggguuuu uuuuuuuug gggg                                            24

<210> SEQ ID NO 42
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 42
```

```
gggggguuuu uuuuuuuuu gggg                                          24

<210> SEQ ID NO 43
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 43
gggguuuuuu uuuuuuuuu gggg                                          24

<210> SEQ ID NO 44
<211> LENGTH: 24
<212> TYPE: RNA
<213> ORGANISM: Artificial
<220> FEATURE:
<223> OTHER INFORMATION: nucleic acid sequence according to formula (I)

<400> SEQUENCE: 44
ggguuuuuuu uuuuuuuuu uggg                                          24

<210> SEQ ID NO 45
<211> LENGTH: 32
<212> TYPE: RNA
<213> ORGANISM: Artificial
<220> FEATURE:
<223> OTHER INFORMATION: nucleic acid sequence according to formula (I)

<400> SEQUENCE: 45
guuuuuuuuu uuuuuuuuuu uuuuuuuuuu ug                                32

<210> SEQ ID NO 46
<211> LENGTH: 34
<212> TYPE: RNA
<213> ORGANISM: Artificial
<220> FEATURE:
<223> OTHER INFORMATION: nucleic acid sequence according to formula (I)

<400> SEQUENCE: 46
gguuuuuuuu uuuuuuuuuu uuuuuuuuuu uugg                              34

<210> SEQ ID NO 47
<211> LENGTH: 36
<212> TYPE: RNA
<213> ORGANISM: Artificial
<220> FEATURE:
<223> OTHER INFORMATION: nucleic acid sequence according to formula (I)

<400> SEQUENCE: 47
ggguuuuuuu uuuuuuuuuu uuuuuuuuuu uuuggg                            36

<210> SEQ ID NO 48
<211> LENGTH: 37
<212> TYPE: RNA
<213> ORGANISM: Artificial
<220> FEATURE:
<223> OTHER INFORMATION: nucleic acid sequence according to formula (I)

<400> SEQUENCE: 48
gggguuuuuu uuuuuuuuuu uuuuuuuuuu uuuggg                            37

<210> SEQ ID NO 49
<211> LENGTH: 39
<212> TYPE: RNA
```

<213> ORGANISM: Artificial
<220> FEATURE:
<223> OTHER INFORMATION: nucleic acid sequence according to formula (I)

<400> SEQUENCE: 49
ggggguuuuu uuuuuuuuuu uuuuuuuuuu uuuugggg                    39

<210> SEQ ID NO 50
<211> LENGTH: 41
<212> TYPE: RNA
<213> ORGANISM: Artificial
<220> FEATURE:
<223> OTHER INFORMATION: nucleic acid sequence according to formula (I)

<400> SEQUENCE: 50
gggggguuuu uuuuuuuuuu uuuuuuuuuu uuuuugggg g                 41

<210> SEQ ID NO 51
<211> LENGTH: 43
<212> TYPE: RNA
<213> ORGANISM: Artificial
<220> FEATURE:
<223> OTHER INFORMATION: nucleic acid sequence according to formula (I)

<400> SEQUENCE: 51
ggggggguuu uuuuuuuuuu uuuuuuuuuu uuuuuuggg ggg               43

<210> SEQ ID NO 52
<211> LENGTH: 45
<212> TYPE: RNA
<213> ORGANISM: Artificial
<220> FEATURE:
<223> OTHER INFORMATION: nucleic acid sequence according to formula (I)

<400> SEQUENCE: 52
gggggggguu uuuuuuuuuu uuuuuuuuuu uuuuuuugg ggggg             45

<210> SEQ ID NO 53
<211> LENGTH: 47
<212> TYPE: RNA
<213> ORGANISM: Artificial
<220> FEATURE:
<223> OTHER INFORMATION: nucleic acid sequence according to formula (I)

<400> SEQUENCE: 53 ggggggggggu uuuuuuuuu uuuuuuuuuu uuuuuuuug ggggggg           47

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

-continued

```
<211> LENGTH: 10
<212> TYPE: RNA
<213> ORGANISM: Artificial
<220> FEATURE:
<223> OTHER INFORMATION: nucleic acid sequence according to formula (I)

<400> SEQUENCE: 57
gguuuuuugg                                                              10

<210> SEQ ID NO 58
<211> LENGTH: 11
<212> TYPE: RNA
<213> ORGANISM: Artificial
<220> FEATURE:
<223> OTHER INFORMATION: nucleic acid sequence according to formula (I)

<400> SEQUENCE: 58
gguuuuuuug g                                                            11

<210> SEQ ID NO 59
<211> LENGTH: 12
<212> TYPE: RNA
<213> ORGANISM: Artificial
<220> FEATURE:
<223> OTHER INFORMATION: nucleic acid sequence according to formula (I)

<400> SEQUENCE: 59
gguuuuuuuu gg                                                           12

<210> SEQ ID NO 60
<211> LENGTH: 13
<212> TYPE: RNA
<213> ORGANISM: Artificial
<220> FEATURE:
<223> OTHER INFORMATION: nucleic acid sequence according to formula (I)

<400> SEQUENCE: 60
gguuuuuuuu ugg                                                          13

<210> SEQ ID NO 61
<211> LENGTH: 14
<212> TYPE: RNA
<213> ORGANISM: Artificial
<220> FEATURE:
<223> OTHER INFORMATION: nucleic acid sequence according to formula (I)

<400> SEQUENCE: 61
gguuuuuuuu uugg                                                         14

<210> SEQ ID NO 62
<211> LENGTH: 15
<212> TYPE: RNA
<213> ORGANISM: Artificial
<220> FEATURE:
<223> OTHER INFORMATION: nucleic acid sequence according to formula (I)

<400> SEQUENCE: 62
gguuuuuuuu uuugg                                                        15

<210> SEQ ID NO 63
<211> LENGTH: 16
<212> TYPE: RNA
<213> ORGANISM: Artificial
<220> FEATURE:
<223> OTHER INFORMATION: nucleic acid sequence according to formula (I)

<400> SEQUENCE: 63
```

-continued gguuuuuuuu uuuugg                                              16

<210> SEQ ID NO 64
<211> LENGTH: 17
<212> TYPE: RNA
<213> ORGANISM: Artificial
<220> FEATURE:
<223> OTHER INFORMATION: nucleic acid sequence according to formula (I)

<400> SEQUENCE: 64
gguuuuuuuu uuuuugg                                             17

<210> SEQ ID NO 65
<211> LENGTH: 18
<212> TYPE: RNA
<213> ORGANISM: Artificial
<220> FEATURE:
<223> OTHER INFORMATION: nucleic acid sequence according to formula (I)

<400> SEQUENCE: 65
gguuuuuuuu uuuuuugg                                            18

<210> SEQ ID NO 66
<211> LENGTH: 19
<212> TYPE: RNA
<213> ORGANISM: Artificial
<220> FEATURE:
<223> OTHER INFORMATION: nucleic acid sequence according to formula (I)

<400> SEQUENCE: 66
gguuuuuuuu uuuuuuugg                                           19

<210> SEQ ID NO 67

<400> SEQUENCE: 67

000

<210> SEQ ID NO 68
<211> LENGTH: 10
<212> TYPE: RNA
<213> ORGANISM: Artificial
<220> FEATURE:
<223> OTHER INFORMATION: nucleic acid sequence according to formula (I)

<400> SEQUENCE: 68
ggguuuuggg                                                     10

<210> SEQ ID NO 69
<211> LENGTH: 11
<212> TYPE: RNA
<213> ORGANISM: Artificial
<220> FEATURE:
<223> OTHER INFORMATION: nucleic acid sequence according to formula (I)

<400> SEQUENCE: 69
ggguuuuugg g                                                   11

<210> SEQ ID NO 70
<211> LENGTH: 12
<212> TYPE: RNA
<213> ORGANISM: Artificial
<220> FEATURE:
<223> OTHER INFORMATION: nucleic acid sequence according to formula (I)

<400> SEQUENCE: 70
ggguuuuuug gg                                                        12

<210> SEQ ID NO 71
<211> LENGTH: 13
<212> TYPE: RNA
<213> ORGANISM: Artificial
<220> FEATURE:
<223> OTHER INFORMATION: nucleic acid sequence according to formula (I)

<400> SEQUENCE: 71
ggguuuuuuu ggg                                                       13

<210> SEQ ID NO 72
<211> LENGTH: 14
<212> TYPE: RNA
<213> ORGANISM: Artificial
<220> FEATURE:
<223> OTHER INFORMATION: nucleic acid sequence according to formula (I)

<400> SEQUENCE: 72
ggguuuuuuu uggg                                                      14

<210> SEQ ID NO 73
<211> LENGTH: 15
<212> TYPE: RNA
<213> ORGANISM: Artificial
<220> FEATURE:
<223> OTHER INFORMATION: nucleic acid sequence according to formula (I)

<400> SEQUENCE: 73
ggguuuuuuu uuggg                                                     15

<210> SEQ ID NO 74
<211> LENGTH: 16
<212> TYPE: RNA
<213> ORGANISM: Artificial
<220> FEATURE:
<223> OTHER INFORMATION: nucleic acid sequence according to formula (I)

<400> SEQUENCE: 74
ggguuuuuuu uuuggg                                                    16

<210> SEQ ID NO 75
<211> LENGTH: 17
<212> TYPE: RNA
<213> ORGANISM: Artificial
<220> FEATURE:
<223> OTHER INFORMATION: nucleic acid sequence according to formula (I)

<400> SEQUENCE: 75
ggguuuuuuu uuuuggg                                                   17

<210> SEQ ID NO 76
<211> LENGTH: 18
<212> TYPE: RNA
<213> ORGANISM: Artificial
<220> FEATURE:
<223> OTHER INFORMATION: nucleic acid sequence according to formula (I)

<400> SEQUENCE: 76
ggguuuuuuu uuuuuggg                                                  18

<210> SEQ ID NO 77
<211> LENGTH: 19
<212> TYPE: RNA

```
<213> ORGANISM: Artificial
<220> FEATURE:
<223> OTHER INFORMATION: nucleic acid sequence according to formula (I)

<400> SEQUENCE: 77
ggguuuuuuu uuuuuuggg                                              19

<210> SEQ ID NO 78
<211> LENGTH: 57
<212> TYPE: RNA
<213> ORGANISM: Artificial
<220> FEATURE:
<223> OTHER INFORMATION: nucleic acid sequence according to formula (I)

<400> SEQUENCE: 78
ggguuuuuuu uuuuuugggu guuuuuuuuu uuuuugggu uuuuuuuuuu uuuggg      57

<210> SEQ ID NO 79
<211> LENGTH: 42
<212> TYPE: RNA
<213> ORGANISM: Artificial
<220> FEATURE:
<223> OTHER INFORMATION: nucleic acid sequence according to formula (I)

<400> SEQUENCE: 79
ggguuuuuuu uuuuuuugg gggguuuuuu uuuuuuuug gg                      42

<210> SEQ ID NO 80
<211> LENGTH: 51
<212> TYPE: RNA
<213> ORGANISM: Artificial
<220> FEATURE:
<223> OTHER INFORMATION: nucleic acid sequence according to formula (I)

<400> SEQUENCE: 80
ggguuugggu uugggguugg guuugggutuu ggguugggu uugggguugg g          51

<210> SEQ ID NO 81
<211> LENGTH: 20
<212> TYPE: RNA
<213> ORGANISM: Artificial Sequence
<220> FEATURE:
<223> OTHER INFORMATION: nucleic acid sequence according to formula (I)

<400> SEQUENCE: 81
gguuuuuuuu uuuuuuuggg                                             20

<210> SEQ ID NO 82
<211> LENGTH: 57
<212> TYPE: RNA
<213> ORGANISM: Artificial
<220> FEATURE:
<223> OTHER INFORMATION: nucleic acid sequence according to formula (II)

<400> SEQUENCE: 82
cccuuuuuuu uuuuuuucc cuuuuuuuuu uuuuuccccu uuuuuuuuuu uuuccc      57

<210> SEQ ID NO 83
<211> LENGTH: 51
<212> TYPE: RNA
<213> ORGANISM: Artificial
<220> FEATURE:
<223> OTHER INFORMATION: nucleic acid sequence according to formula (II)

<400> SEQUENCE: 83 cccuucccu uucccuuucc cuuucccuuu cccuucccu uucccuuucc c            51
```

<210> SEQ ID NO 84
<211> LENGTH: 42
<212> TYPE: RNA
<213> ORGANISM: Artificial
<220> FEATURE:
<223> OTHER INFORMATION: nucleic acid sequence according to formula (II)

<400> SEQUENCE: 84
cccuuuuuuu uuuuuuucc cccuuuuuu uuuuuuuuc cc          42

<210> SEQ ID NO 85
<211> LENGTH: 60
<212> TYPE: RNA
<213> ORGANISM: Artificial Sequence
<220> FEATURE:
<223> OTHER INFORMATION: nucleic acid sequence according to formula
      (III)

<400> SEQUENCE: 85
uagcgaagcu cuuggaccua gguuuuuuuu uuuuuuggg ugcguuccua gaaguacacg          60

<210> SEQ ID NO 86
<211> LENGTH: 120
<212> TYPE: RNA
<213> ORGANISM: Artificial Sequence
<220> FEATURE:
<223> OTHER INFORMATION: nucleic acid sequence according to formula
      (III)

<400> SEQUENCE: 86
uagcgaagcu cuuggaccua gguuuuuuuu uuuuuuggg ugcguuccua gaaguacacg          60
aucgcuucga gaaccuggau ccaaaaaaaa aaaaaaaccc acgcaaggau cuucaugugc         120

<210> SEQ ID NO 87
<211> LENGTH: 229
<212> TYPE: RNA
<213> ORGANISM: Artificial Sequence
<220> FEATURE:
<223> OTHER INFORMATION: nucleic acid sequence according to formula
      (III)

<400> SEQUENCE: 87
gggagaaagc ucaagcuugg agcaaugccc gcacauugag gaaaccgagu ugcauaucuc          60
agaguauugg cccccgugua gguuauucuu gacagacagu ggagcuuauu cacucccagg         120
auccgagucg cauacuacgg uacggugac agaccuaggu cgucaguuga ccaguccgcc         180
acuagacgug aguccgucaa agcaguuaga uguuacacuc uauuagauc                     229

<210> SEQ ID NO 88
<211> LENGTH: 547
<212> TYPE: RNA
<213> ORGANISM: Artificial Sequence
<220> FEATURE:
<223> OTHER INFORMATION: nucleic acid sequence according to formula
      (III)

<400> SEQUENCE: 88
gggagaaagc ucaagcuugg agcaaugccc gcacauugag gaaaccgagu ugcauaucuc          60
agaguauugg cccccgugua gguuauucuu gacagacagu ggagcuuauu cacucccagg         120
auccgagucg cauacuacgg uacggugac agaccuaggu cgucaguuga ccaguccgcc         180
acuagacgug aguccgucaa agcaguuaga uguuacacuc uauuagaucu cggauuacag        240

```
cuggaaggag caggaguagu guucuugcuc uaaguaccga gugugcccaa uacccgauca    300
gcuuauuaac gaacggcucc uccucuuaga cugcagcgua agugcggaau cuggggauca    360
aauuacugac ugccuggauu acccucggac auauaaccuu guagcacgcu guugcuguau    420
aggugaccaa cgcccacucg aguagaccag cucucuuagu ccggacaaug auaggaggcg    480
cggucaaucu acuucuggcu aguuaagaau aggcugcacc gaccucuaua aguagcgugu    540
ccucuag                                                              547

<210> SEQ ID NO 89
<211> LENGTH: 1083
<212> TYPE: RNA
<213> ORGANISM: Artificial Sequence
<220> FEATURE:
<223> OTHER INFORMATION: nucleic acid sequence according to formula
      (III)

<400> SEQUENCE: 89
gggagaaagc ucaagcuugg agcaaugccc gcacauugag gaaaccgagu ugcauaucuc     60
agaguauugg cccccgugua gguuauucuu gacagacagu ggagcuuauu cacucccagg    120
auccgagucg cauacuacgg uacggugac agaccaggu cgucaguuga ccaguccgcc      180
acuagacgug aguccgucaa agcaguuaga uguuacacuc uauuagaucu cggauuacag    240
cuggaaggag caggaguagu guucuugcuc uaaguaccga gugugcccaa uacccgauca    300
gcuuauuaac gaacggcucc uccucuuaga cugcagcgua agugcggaau cuggggauca    360
aauuacugac ugccuggauu acccucggac auauaaccuu guagcacgcu guugcuguau    420
aggugaccaa cgcccacucg aguagaccag cucucuuagu ccggacaaug auaggaggcg    480
cggucaaucu acuucuggcu aguuaagaau aggcugcacc gaccucuaua aguagcgugu    540
ccucuagagc uacgcagguu cgcaauaaaa gcguugauua gugugcauag aacagaccuc    600
uuauucggug aaacgccaga augcuaaauu ccaauaacuc uucccaaaac gcguacggcc    660
gaagacgcgc gcuuaucuug uguacguucu cgcacaugga agaaucagcg ggcaugguugg   720 uagggcaaua ggggagcugg guagcagcga aaaagggccc cugcgcacgu agcuucgcug    780
uucgucugaa acaacccggc auccguugua gcgaucccgu uaucaguguu auucuugugc    840
gcacuaagau ucauggugua gucgacaaua acagcgucuu ggcagauucu ggucacgugc    900
ccuaugcccg ggcuugugcc ucucaggugc acagcgauac uuaaagccuu caagguacuc    960
gacgugggua ccgauucgug acacuuccua agauuauucc acuguguuag ccccgcaccg   1020
ccgaccuaaa cugguccaau guauacgcau ucgcugagcg gaucgauaau aaaagcuuga   1080
auu                                                                 1083

<210> SEQ ID NO 90
<211> LENGTH: 229
<212> TYPE: RNA
<213> ORGANISM: Artificial Sequence
<220> FEATURE:
<223> OTHER INFORMATION: nucleic acid sequence according to formula
      (III)

<400> SEQUENCE: 90
gggagaaagc ucaagcuuau ccaaguaggc uggucaccug uacaacguag ccgguauuuu     60 uuuuuuuuu uuuuuuuuga ccgucucaag guccaaguua gucugccuau aaaggugcgg    120
auccacagcu gaugaaagac uugugcggua cgguuaaucu ccccuuuuuu uuuuuuuuu    180 uuuuuaguaa augcgucuac ugaauccagc gaugaugcug gcccagauc               229
```

<210> SEQ ID NO 91
<211> LENGTH: 546
<212> TYPE: RNA
<213> ORGANISM: Artificial Sequence
<220> FEATURE:
<223> OTHER INFORMATION: nucleic acid sequence according to formula (III)

<400> SEQUENCE: 91

```
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu cccuuuuuu uuuuuuuuu      180
uuuuuaguaa augcgucuac ugaauccagc gaugaugcug gcccagaucu ucgaccacaa     240
gugcauauag uagucaucga ggucgccuu uuuuuuuuu uuuuuuuuu uggcccaguu       300
cugagacuuc gcuagagacu acaguuacag cugcaguagu aaccacgcg gcuauugcag     360
gaaaucccgu ucagguuuuu uuuuuuuuuu uuuuuccgc ucacuaugau uaagaaccag     420
guggaguguc acugcucucg aggucucacg agagcgcucg auacaguccu uggaagaauc    480
uuuuuuuuuu uuuuuuuuuu ugugcgacg aucacagaga acuucuauuc augcaggucu    540
gcucua                                                             546
```

<210> SEQ ID NO 92
<211> LENGTH: 1083
<212> TYPE: RNA
<213> ORGANISM: Artificial Sequence
<220> FEATURE:
<223> OTHER INFORMATION: nucleic acid sequence according to formula (III)

<400> SEQUENCE: 92

```
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu cccuuuuuu uuuuuuuuu      180
uuuuuaguaa augcgucuac ugaauccagc gaugaugcug gcccagaucu ucgaccacaa     240
gugcauauag uagucaucga ggucgccuu uuuuuuuuu uuuuuuuuu uggcccaguu       300
cugagacuuc gcuagagacu acaguuacag cugcaguagu aaccacgcg gcuauugcag     360
gaaaucccgu ucagguuuuu uuuuuuuuuu uuuuuccgc ucacuaugau uaagaaccag     420
guggaguguc acugcucucg aggucucacg agagcgcucg auacaguccu uggaagaauc    480
uuuuuuuuuu uuuuuuuuuu ugugcgacg aucacagaga acuucuauuc augcaggucu    540
gcucuagaac gaacugaccu gacgccugaa cuuaugagcg ugcguauuu uuuuuuuuu     600
uuuuuuuuc cucccaacaa augucgauca auagcugggc uguggagac gcucagcaa      660
augccguggc uccauaggac guguagacuu cuauuuuuu uuuuuuuuu uuucccggg      720
accacaaaua auauucuugc uugguugggc gcaagggccc cguaucaggu cauaaacggg    780
uacauguugc acaggcuccu uuuuuuuuu uuuuuuuuu uucgcugagu auuccgguc     840
ucaaaagacg gcagacguca gucgacaaca cggucuaaag cagugcuaca aucugccgug    900
uucguguuuu uuuuuuuuu uuuuuguga accuacacgg cgugcacugu agucgcaau      960
ucauagggua ccggcucaga guuaugccuu gguugaaaac ugcccagcau acuuuuuuu   1020
uuuuuuuuuu uucauauucc caugcuaagc aagggaugcc gcgagucaug uuaagcuuga   1080
```

```
auu                                                                 1083

<210> SEQ ID NO 93
<211> LENGTH: 59
<212> TYPE: RNA
<213> ORGANISM: Artificial Sequence
<220> FEATURE:
<223> OTHER INFORMATION: nucleic acid sequence according to formula (IV)

<400> SEQUENCE: 93
uagcgaagcu cuuggaccua ccuuuuuuuu uuuuuucccu gcguuccuag aaguacacg    59

<210> SEQ ID NO 94
<211> LENGTH: 120
<212> TYPE: RNA
<213> ORGANISM: Artificial Sequence
<220> FEATURE:
<223> OTHER INFORMATION: nucleic acid sequence according to formula (IV)

<400> SEQUENCE: 94
uagcgaagcu cuuggaccua ccuuuuuuuu uuuuuuccc ugcguuccua gaaguacacg    60
aucgcuucga gaaccuggau ggaaaaaaaa aaaaaagggg acgcaaggau cuucaugugc  120

<210> SEQ ID NO 95
<211> LENGTH: 7
<212> TYPE: PRT
<213> ORGANISM: Artificial Sequence
<220> FEATURE:
<223> OTHER INFORMATION: Oligopeptide of formula (V)

<400> SEQUENCE: 95

Arg Arg Arg Arg Arg Arg Arg
1               5

<210> SEQ ID NO 96
<211> LENGTH: 8
<212> TYPE: PRT
<213> ORGANISM: Artificial Sequence
<220> FEATURE:
<223> OTHER INFORMATION: Oligopeptide of formula (V)

<400> SEQUENCE: 96

Arg Arg Arg Arg Arg Arg Arg Arg
1               5

<210> SEQ ID NO 97
<211> LENGTH: 9
<212> TYPE: PRT
<213> ORGANISM: Artificial Sequence
<220> FEATURE:
<223> OTHER INFORMATION: Oligopeptide of formula (V)

<400> SEQUENCE: 97

Arg Arg Arg Arg Arg Arg Arg Arg Arg
1               5

<210> SEQ ID NO 98
<211> LENGTH: 10
<212> TYPE: PRT
<213> ORGANISM: Artificial Sequence
<220> FEATURE:
<223> OTHER INFORMATION: Oligopeptide of formula (V)

<400> SEQUENCE: 98

Arg Arg Arg Arg Arg Arg Arg Arg Arg Arg
1               5                   10
```

<210> SEQ ID NO 99
<211> LENGTH: 11
<212> TYPE: PRT
<213> ORGANISM: Artificial Sequence
<220> FEATURE:
<223> OTHER INFORMATION: Oligopeptide of formula (V)

<400> SEQUENCE: 99

Arg Arg Arg Arg Arg Arg Arg Arg Arg Arg Arg
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Oligopeptide of formula (V)

<400> SEQUENCE: 100

Arg Arg Arg Arg Arg Arg Arg Arg Arg Arg Arg Arg
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Oligopeptide of formula (V)

<400> SEQUENCE: 101

Arg Arg Arg Arg Arg Arg Arg Arg Arg Arg Arg Arg Arg
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Oligopeptide of formula (V)

<400> SEQUENCE: 102

Arg Arg Arg Arg Arg Arg Arg Arg Arg Arg Arg Arg Arg Arg
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Oligopeptide of formula (V)

<400> SEQUENCE: 103

Arg Arg Arg Arg Arg Arg Arg Arg Arg Arg Arg Arg Arg Arg Arg
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Oligopeptide of formula (V)

<400> SEQUENCE: 104

Arg Arg Arg Arg Arg Arg Arg Arg Arg Arg Arg Arg Arg Arg Arg Arg
1               5                   10                  15

<210> SEQ ID NO 105
<211> LENGTH: 17
<212> TYPE: PRT
<213> ORGANISM: Artificial Sequence
<220> FEATURE:
<223> OTHER INFORMATION: Oligopeptide of formula (V)

<400> SEQUENCE: 105

Arg Arg Arg Arg Arg Arg Arg Arg Arg Arg Arg Arg Arg Arg Arg
1               5                   10                  15

Arg

<210> SEQ ID NO 106
<211> LENGTH: 18
<212> TYPE: PRT
<213> ORGANISM: Artificial Sequence
<220> FEATURE:
<223> OTHER INFORMATION: Oligopeptide of formula (V)

<400> SEQUENCE: 106

Arg Arg Arg Arg Arg Arg Arg Arg Arg Arg Arg Arg Arg Arg Arg
1               5                   10                  15

Arg Arg

<210> SEQ ID NO 107
<211> LENGTH: 19
<212> TYPE: PRT
<213> ORGANISM: Artificial Sequence
<220> FEATURE:
<223> OTHER INFORMATION: Oligopeptide of formula (V)

<400> SEQUENCE: 107

Arg Arg Arg Arg Arg Arg Arg Arg Arg Arg Arg Arg Arg Arg Arg
1               5                   10                  15

Arg Arg Arg

<210> SEQ ID NO 108
<211> LENGTH: 20
<212> TYPE: PRT
<213> ORGANISM: Artificial Sequence
<220> FEATURE:
<223> OTHER INFORMATION: Oligopeptide of formula (V)

<400> SEQUENCE: 108

Arg Arg Arg Arg Arg Arg Arg Arg Arg Arg Arg Arg Arg Arg Arg
1               5                   10                  15

Arg Arg Arg Arg
            20

<210> SEQ ID NO 109
<211> LENGTH: 21
<212> TYPE: PRT
<213> ORGANISM: Artificial Sequence
<220> FEATURE:
<223> OTHER INFORMATION: Oligopeptide of formula (V)

<400> SEQUENCE: 109

Arg Arg Arg Arg Arg Arg Arg Arg Arg Arg Arg Arg Arg Arg Arg
1               5                   10                  15

Arg Arg Arg Arg Arg
            20

<210> SEQ ID NO 110

<211> LENGTH: 22
<212> TYPE: PRT
<213> ORGANISM: Artificial Sequence
<220> FEATURE:
<223> OTHER INFORMATION: Oligopeptide of formula (V)

<400> SEQUENCE: 110

Arg Arg Arg Arg Arg Arg Arg Arg Arg Arg Arg Arg Arg Arg Arg Arg
1               5                   10                  15

Arg Arg Arg Arg Arg Arg
            20

<210> SEQ ID NO 111
<211> LENGTH: 23
<212> TYPE: PRT
<213> ORGANISM: Artificial Sequence
<220> FEATURE:
<223> OTHER INFORMATION: Oligopeptide of formula (V)

<400> SEQUENCE: 111

Arg Arg Arg Arg Arg Arg Arg Arg Arg Arg Arg Arg Arg Arg Arg Arg
1               5                   10                  15

Arg Arg Arg Arg Arg Arg Arg
            20

<210> SEQ ID NO 112
<211> LENGTH: 24
<212> TYPE: PRT
<213> ORGANISM: Artificial Sequence
<220> FEATURE:
<223> OTHER INFORMATION: Oligopeptide of formula (V)

<400> SEQUENCE: 112

Arg Arg Arg Arg Arg Arg Arg Arg Arg Arg Arg Arg Arg Arg Arg Arg
1               5                   10                  15

Arg Arg Arg Arg Arg Arg Arg Arg
            20

<210> SEQ ID NO 113
<211> LENGTH: 25
<212> TYPE: PRT
<213> ORGANISM: Artificial Sequence
<220> FEATURE:
<223> OTHER INFORMATION: Oligopeptide of formula (V)

<400> SEQUENCE: 113

Arg Arg Arg Arg Arg Arg Arg Arg Arg Arg Arg Arg Arg Arg Arg Arg
1               5                   10                  15

Arg Arg Arg Arg Arg Arg Arg Arg Arg
            20                  25

<210> SEQ ID NO 114
<211> LENGTH: 26
<212> TYPE: PRT
<213> ORGANISM: Artificial Sequence
<220> FEATURE:
<223> OTHER INFORMATION: Oligopeptide of formula (V)

<400> SEQUENCE: 114

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg
            20                  25

```
<210> SEQ ID NO 115
<211> LENGTH: 27
<212> TYPE: PRT
<213> ORGANISM: Artificial Sequence
<220> FEATURE:
<223> OTHER INFORMATION: Oligopeptide of formula (V)

<400> SEQUENCE: 115

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg
            20                  25

<210> SEQ ID NO 116
<211> LENGTH: 28
<212> TYPE: PRT
<213> ORGANISM: Artificial Sequence
<220> FEATURE:
<223> OTHER INFORMATION: Oligopeptide of formula (V)

<400> SEQUENCE: 116

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg
            20                  25

<210> SEQ ID NO 117
<211> LENGTH: 29
<212> TYPE: PRT
<213> ORGANISM: Artificial Sequence
<220> FEATURE:
<223> OTHER INFORMATION: Oligopeptide of formula (V)

<400> SEQUENCE: 117

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg
            20                  25

<210> SEQ ID NO 118
<211> LENGTH: 30
<212> TYPE: PRT
<213> ORGANISM: Artificial Sequence
<220> FEATURE:
<223> OTHER INFORMATION: Oligopeptide of formula (V)

<400> SEQUENCE: 118

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg
            20                  25                  30

<210> SEQ ID NO 119
<211> LENGTH: 7
<212> TYPE: PRT
<213> ORGANISM: Artificial Sequence
<220> FEATURE:
<223> OTHER INFORMATION: Oligopeptide of formula (V)

<400> SEQUENCE: 119

Lys Lys Lys Lys Lys Lys Lys
1               5

<210> SEQ ID NO 120
<211> LENGTH: 8
```

<212> TYPE: PRT
<213> ORGANISM: Artificial Sequence
<220> FEATURE:
<223> OTHER INFORMATION: Oligopeptide of formula (V)

<400> SEQUENCE: 120

Lys Lys Lys Lys Lys Lys Lys Lys
1               5

<210> SEQ ID NO 121
<211> LENGTH: 9
<212> TYPE: PRT
<213> ORGANISM: Artificial Sequence
<220> FEATURE:
<223> OTHER INFORMATION: Oligopeptide of formula (V)

<400> SEQUENCE: 121

Lys Lys Lys Lys Lys Lys Lys Lys Lys
1               5

<210> SEQ ID NO 122
<211> LENGTH: 10
<212> TYPE: PRT
<213> ORGANISM: Artificial Sequence
<220> FEATURE:
<223> OTHER INFORMATION: Oligopeptide of formula (V)

<400> SEQUENCE: 122

Lys Lys Lys Lys Lys Lys Lys Lys Lys Lys
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Oligopeptide of formula (V)

<400> SEQUENCE: 123

Lys Lys Lys Lys Lys Lys Lys Lys Lys Lys Lys
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Oligopeptide of formula (V)

<400> SEQUENCE: 124

Lys Lys Lys Lys Lys Lys Lys Lys Lys Lys Lys Lys
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Oligopeptide of formula (V)

<400> SEQUENCE: 125

Lys Lys Lys Lys Lys Lys Lys Lys Lys Lys Lys Lys Lys
1               5                   10

<210> SEQ ID NO 126
<211> LENGTH: 14
<212> TYPE: PRT

```
<213> ORGANISM: Artificial Sequence
<220> FEATURE:
<223> OTHER INFORMATION: Oligopeptide of formula (V)

<400> SEQUENCE: 126

Lys Lys Lys Lys Lys Lys Lys Lys Lys Lys Lys Lys
1               5                   10

<210> SEQ ID NO 127
<211> LENGTH: 15
<212> TYPE: PRT
<213> ORGANISM: Artificial Sequence
<220> FEATURE:
<223> OTHER INFORMATION: Oligopeptide of formula (V)

<400> SEQUENCE: 127

Lys Lys Lys Lys Lys Lys Lys Lys Lys Lys Lys Lys Lys Lys Lys
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Oligopeptide of formula (V)

<400> SEQUENCE: 128

Lys Lys Lys Lys Lys Lys Lys Lys Lys Lys Lys Lys Lys Lys Lys Lys
1               5                   10                  15

<210> SEQ ID NO 129
<211> LENGTH: 17
<212> TYPE: PRT
<213> ORGANISM: Artificial Sequence
<220> FEATURE:
<223> OTHER INFORMATION: Oligopeptide of formula (V)

<400> SEQUENCE: 129

Lys Lys Lys Lys Lys Lys Lys Lys Lys Lys Lys Lys Lys Lys Lys Lys
1               5                   10                  15

Lys

<210> SEQ ID NO 130
<211> LENGTH: 18
<212> TYPE: PRT
<213> ORGANISM: Artificial Sequence
<220> FEATURE:
<223> OTHER INFORMATION: Oligopeptide of formula (V)

<400> SEQUENCE: 130

Lys Lys Lys Lys Lys Lys Lys Lys Lys Lys Lys Lys Lys Lys Lys Lys
1               5                   10                  15

Lys Lys

<210> SEQ ID NO 131
<211> LENGTH: 19
<212> TYPE: PRT
<213> ORGANISM: Artificial Sequence
<220> FEATURE:
<223> OTHER INFORMATION: Oligopeptide of formula (V)

<400> SEQUENCE: 131

Lys Lys Lys Lys Lys Lys Lys Lys Lys Lys Lys Lys Lys Lys Lys Lys
1               5                   10                  15

Lys Lys Lys
```

```
<210> SEQ ID NO 132
<211> LENGTH: 20
<212> TYPE: PRT
<213> ORGANISM: Artificial Sequence
<220> FEATURE:
<223> OTHER INFORMATION: Oligopeptide of formula (V)

<400> SEQUENCE: 132

Lys Lys Lys Lys Lys Lys Lys Lys Lys Lys Lys Lys Lys Lys Lys Lys
1               5                   10                  15

Lys Lys Lys Lys
            20

<210> SEQ ID NO 133
<211> LENGTH: 21
<212> TYPE: PRT
<213> ORGANISM: Artificial Sequence
<220> FEATURE:
<223> OTHER INFORMATION: Oligopeptide of formula (V)

<400> SEQUENCE: 133

Lys Lys Lys Lys Lys Lys Lys Lys Lys Lys Lys Lys Lys Lys Lys Lys
1               5                   10                  15

Lys Lys Lys Lys Lys
            20

<210> SEQ ID NO 134
<211> LENGTH: 22
<212> TYPE: PRT
<213> ORGANISM: Artificial Sequence
<220> FEATURE:
<223> OTHER INFORMATION: Oligopeptide of formula (V)

<400> SEQUENCE: 134

Lys Lys Lys Lys Lys Lys Lys Lys Lys Lys Lys Lys Lys Lys Lys Lys
1               5                   10                  15

Lys Lys Lys Lys Lys Lys
            20

<210> SEQ ID NO 135
<211> LENGTH: 23
<212> TYPE: PRT
<213> ORGANISM: Artificial Sequence
<220> FEATURE:
<223> OTHER INFORMATION: Oligopeptide of formula (V)

<400> SEQUENCE: 135

Lys Lys Lys Lys Lys Lys Lys Lys Lys Lys Lys Lys Lys Lys Lys Lys
1               5                   10                  15

Lys Lys Lys Lys Lys Lys Lys
            20

<210> SEQ ID NO 136
<211> LENGTH: 24
<212> TYPE: PRT
<213> ORGANISM: Artificial Sequence
<220> FEATURE:
<223> OTHER INFORMATION: Oligopeptide of formula (V)

<400> SEQUENCE: 136

Lys Lys Lys Lys Lys Lys Lys Lys Lys Lys Lys Lys Lys Lys Lys Lys
1               5                   10                  15

Lys Lys Lys Lys Lys Lys Lys Lys
```

20

<210> SEQ ID NO 137
<211> LENGTH: 25
<212> TYPE: PRT
<213> ORGANISM: Artificial Sequence
<220> FEATURE:
<223> OTHER INFORMATION: Oligopeptide of formula (V)

<400> SEQUENCE: 137

Lys Lys Lys Lys Lys Lys Lys Lys Lys Lys Lys Lys Lys Lys Lys
1               5                   10                  15

Lys Lys Lys Lys Lys Lys Lys Lys Lys
            20                  25

<210> SEQ ID NO 138
<211> LENGTH: 26
<212> TYPE: PRT
<213> ORGANISM: Artificial Sequence
<220> FEATURE:
<223> OTHER INFORMATION: Oligopeptide of formula (V)

<400> SEQUENCE: 138

Lys Lys Lys Lys Lys Lys Lys Lys Lys Lys Lys Lys Lys Lys Lys
1               5                   10                  15

Lys Lys Lys Lys Lys Lys Lys Lys Lys Lys
            20                  25

<210> SEQ ID NO 139
<211> LENGTH: 27
<212> TYPE: PRT
<213> ORGANISM: Artificial Sequence
<220> FEATURE:
<223> OTHER INFORMATION: Oligopeptide of formula (V)

<400> SEQUENCE: 139

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys
            20                  25

<210> SEQ ID NO 140
<211> LENGTH: 28
<212> TYPE: PRT
<213> ORGANISM: Artificial Sequence
<220> FEATURE:
<223> OTHER INFORMATION: Oligopeptide of formula (V)

<400> SEQUENCE: 140

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys
            20                  25

<210> SEQ ID NO 141
<211> LENGTH: 29
<212> TYPE: PRT
<213> ORGANISM: Artificial Sequence
<220> FEATURE:
<223> OTHER INFORMATION: Oligopeptide of formula (V)

<400> SEQUENCE: 141

Lys Lys Lys Lys Lys Lys Lys Lys Lys Lys Lys Lys Lys Lys Lys
1               5                   10                  15

```
Lys Lys Lys Lys Lys Lys Lys Lys Lys Lys
        20                  25
```

<210> SEQ ID NO 142
<211> LENGTH: 30
<212> TYPE: PRT
<213> ORGANISM: Artificial Sequence
<220> FEATURE:
<223> OTHER INFORMATION: Oligopeptide of formula (V)

<400> SEQUENCE: 142

```
Lys Lys Lys Lys Lys Lys Lys Lys Lys Lys Lys Lys Lys Lys Lys
1               5                   10                  15
Lys Lys Lys Lys Lys Lys Lys Lys Lys Lys Lys Lys Lys Lys Lys
        20                  25                  30
```

<210> SEQ ID NO 143
<211> LENGTH: 7
<212> TYPE: PRT
<213> ORGANISM: Artificial Sequence
<220> FEATURE:
<223> OTHER INFORMATION: Oligopeptide of formula (V)

<400> SEQUENCE: 143

```
His His His His His His His
1               5
```

<210> SEQ ID NO 144
<211> LENGTH: 8
<212> TYPE: PRT
<213> ORGANISM: Artificial Sequence
<220> FEATURE:
<223> OTHER INFORMATION: Oligopeptide of formula (V)

<400> SEQUENCE: 144

```
His His His His His His His His
1               5
```

<210> SEQ ID NO 145
<211> LENGTH: 9
<212> TYPE: PRT
<213> ORGANISM: Artificial Sequence
<220> FEATURE:
<223> OTHER INFORMATION: Oligopeptide of formula (V)

<400> SEQUENCE: 145

```
His His His His His His His His His
1               5
```

<210> SEQ ID NO 146
<211> LENGTH: 10
<212> TYPE: PRT
<213> ORGANISM: Artificial Sequence
<220> FEATURE:
<223> OTHER INFORMATION: Oligopeptide of formula (V)

<400> SEQUENCE: 146

```
His His His His His His His His His His
1               5                   10
```

<210> SEQ ID NO 147
<211> LENGTH: 11
<212> TYPE: PRT
<213> ORGANISM: Artificial Sequence
<220> FEATURE:
<223> OTHER INFORMATION: Oligopeptide of formula (V)

<400> SEQUENCE: 147

His His His His His His His His His His His
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Oligopeptide of formula (V)

<400> SEQUENCE: 148

His His His His His His His His His His His His
1               5                   10

<210> SEQ ID NO 149
<211> LENGTH: 13
<212> TYPE: PRT
<213> ORGANISM: Artificial Sequence
<220> FEATURE:
<223> OTHER INFORMATION: Oligopeptide of formula (V)

<400> SEQUENCE: 149

His His His His His His His His His His His His His
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Oligopeptide of formula (V)

<400> SEQUENCE: 150

His His His His His His His His His His His His His His
1               5                   10

<210> SEQ ID NO 151
<211> LENGTH: 15
<212> TYPE: PRT
<213> ORGANISM: Artificial Sequence
<220> FEATURE:
<223> OTHER INFORMATION: Oligopeptide of formula (V)

<400> SEQUENCE: 151

His His His His His His His His His His His His His His His
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Oligopeptide of formula (V)

<400> SEQUENCE: 152

His His His His His His His His His His His His His His His His
1               5                   10                  15

<210> SEQ ID NO 153
<211> LENGTH: 17
<212> TYPE: PRT
<213> ORGANISM: Artificial Sequence
<220> FEATURE:
<223> OTHER INFORMATION: Oligopeptide of formula (V)

<400> SEQUENCE: 153

His His His His His His His His His His His His His His His
1               5                   10                  15

His

<210> SEQ ID NO 154
<211> LENGTH: 18
<212> TYPE: PRT
<213> ORGANISM: Artificial Sequence
<220> FEATURE:
<223> OTHER INFORMATION: Oligopeptide of formula (V)

<400> SEQUENCE: 154

His His His His His His His His His His His His His His His
1               5                   10                  15

His His

<210> SEQ ID NO 155
<211> LENGTH: 19
<212> TYPE: PRT
<213> ORGANISM: Artificial Sequence
<220> FEATURE:
<223> OTHER INFORMATION: Oligopeptide of formula (V)

<400> SEQUENCE: 155

His His His His His His His His His His His His His His His
1               5                   10                  15

His His His

<210> SEQ ID NO 156
<211> LENGTH: 20
<212> TYPE: PRT
<213> ORGANISM: Artificial Sequence
<220> FEATURE:
<223> OTHER INFORMATION: Oligopeptide of formula (V)

<400> SEQUENCE: 156

His His His His His His His His His His His His His His His
1               5                   10                  15

His His His His
            20

<210> SEQ ID NO 157
<211> LENGTH: 21
<212> TYPE: PRT
<213> ORGANISM: Artificial Sequence
<220> FEATURE:
<223> OTHER INFORMATION: Oligopeptide of formula (V)

<400> SEQUENCE: 157

His His His His His His His His His His His His His His His
1               5                   10                  15

His His His His His
            20

<210> SEQ ID NO 158
<211> LENGTH: 22
<212> TYPE: PRT
<213> ORGANISM: Artificial Sequence
<220> FEATURE:
<223> OTHER INFORMATION: Oligopeptide of formula (V)

<400> SEQUENCE: 158

His His His His His His His His His His His His His His His

-continued

```
                1               5                  10                  15
His His His His His His
            20

<210> SEQ ID NO 159
<211> LENGTH: 23
<212> TYPE: PRT
<213> ORGANISM: Artificial Sequence
<220> FEATURE:
<223> OTHER INFORMATION: Oligopeptide of formula (V)

<400> SEQUENCE: 159

His His His His His His His His His His His His His His His His
1               5                  10                  15

His His His His His His His
            20

<210> SEQ ID NO 160
<211> LENGTH: 24
<212> TYPE: PRT
<213> ORGANISM: Artificial Sequence
<220> FEATURE:
<223> OTHER INFORMATION: Oligopeptide of formula (V)

<400> SEQUENCE: 160

His His His His His His His His His His His His His His His His
1               5                  10                  15

His His His His His His His His
            20

<210> SEQ ID NO 161
<211> LENGTH: 25
<212> TYPE: PRT
<213> ORGANISM: Artificial Sequence
<220> FEATURE:
<223> OTHER INFORMATION: Oligopeptide of formula (V)

<400> SEQUENCE: 161

His His His His His His His His His His His His His His His His
1               5                  10                  15

His His His His His His His His His
            20                  25

<210> SEQ ID NO 162
<211> LENGTH: 26
<212> TYPE: PRT
<213> ORGANISM: Artificial Sequence
<220> FEATURE:
<223> OTHER INFORMATION: Oligopeptide of formula (V)

<400> SEQUENCE: 162

His His His His His His His His His His His His His His His His
1               5                  10                  15

His His His His His His His His His His
            20                  25

<210> SEQ ID NO 163
<211> LENGTH: 27
<212> TYPE: PRT
<213> ORGANISM: Artificial Sequence
<220> FEATURE:
<223> OTHER INFORMATION: Oligopeptide of formula (V)

<400> SEQUENCE: 163
```

His His His His His His His His His His His His His His His
1               5                   10                  15

His His His His His His His His His His His
            20                  25

<210> SEQ ID NO 164
<211> LENGTH: 28
<212> TYPE: PRT
<213> ORGANISM: Artificial Sequence
<220> FEATURE:
<223> OTHER INFORMATION: Oligopeptide of formula (V)

<400> SEQUENCE: 164

His His His His His His His His His His His His His His His
1               5                   10                  15

His His His His His His His His His His His His His
            20                  25

<210> SEQ ID NO 165
<211> LENGTH: 29
<212> TYPE: PRT
<213> ORGANISM: Artificial Sequence
<220> FEATURE:
<223> OTHER INFORMATION: Oligopeptide of formula (V)

<400> SEQUENCE: 165

His His His His His His His His His His His His His His His
1               5                   10                  15

His His His His His His His His His His His His His His
            20                  25

<210> SEQ ID NO 166
<211> LENGTH: 30
<212> TYPE: PRT
<213> ORGANISM: Artificial Sequence
<220> FEATURE:
<223> OTHER INFORMATION: Oligopeptide of formula (V)

<400> SEQUENCE: 166

His His His His His His His His His His His His His His His
1               5                   10                  15

His His His His His His His His His His His His His His His
            20                  25                  30

<210> SEQ ID NO 167
<211> LENGTH: 7
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(7)
<223> OTHER INFORMATION: /replace="Orn"

<400> SEQUENCE: 167

Xaa Xaa Xaa Xaa Xaa Xaa Xaa
1               5

<210> SEQ ID NO 168
<211> LENGTH: 8
<212> TYPE: PRT
<213> ORGANISM: Artificial Sequence
<220> FEATURE:
<223> OTHER INFORMATION: Oligopeptide of formula (V)
<220> FEATURE:

-continued

```
<221> NAME/KEY: MOD_RES
<222> LOCATION: (1)..(8)
<223> OTHER INFORMATION: /replace="Orn"

<400> SEQUENCE: 168

Xaa Xaa Xaa Xaa Xaa Xaa Xaa Xaa
1               5

<210> SEQ ID NO 169
<211> LENGTH: 9
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(9)
<223> OTHER INFORMATION: /replace="Orn"

<400> SEQUENCE: 169

Xaa Xaa Xaa Xaa Xaa Xaa Xaa Xaa Xaa
1               5

<210> SEQ ID NO 170
<211> LENGTH: 10
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(10)
<223> OTHER INFORMATION: /replace="Orn"

<400> SEQUENCE: 170

Xaa Xaa Xaa Xaa Xaa Xaa Xaa Xaa Xaa Xaa
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(11)
<223> OTHER INFORMATION: /replace="Orn"

<400> SEQUENCE: 171

Xaa Xaa Xaa Xaa Xaa Xaa Xaa Xaa Xaa Xaa Xaa
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(12)
<223> OTHER INFORMATION: /replace="Orn"

<400> SEQUENCE: 172

Xaa Xaa Xaa Xaa Xaa Xaa Xaa Xaa Xaa Xaa Xaa Xaa
1               5                   10

<210> SEQ ID NO 173
```

```
<211> LENGTH: 13
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(13)
<223> OTHER INFORMATION: /replace="Orn"

<400> SEQUENCE: 173

Xaa Xaa Xaa Xaa Xaa Xaa Xaa Xaa Xaa Xaa Xaa Xaa Xaa
 1               5                  10

<210> SEQ ID NO 174
<211> LENGTH: 14
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(14)
<223> OTHER INFORMATION: /replace="Orn"

<400> SEQUENCE: 174

Xaa Xaa Xaa Xaa Xaa Xaa Xaa Xaa Xaa Xaa Xaa Xaa Xaa Xaa
 1               5                  10

<210> SEQ ID NO 175
<211> LENGTH: 15
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(15)
<223> OTHER INFORMATION: /replace="Orn"

<400> SEQUENCE: 175

Xaa Xaa Xaa Xaa Xaa Xaa Xaa Xaa Xaa Xaa Xaa Xaa Xaa Xaa Xaa
 1               5                  10                  15

<210> SEQ ID NO 176
<211> LENGTH: 16
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(16)
<223> OTHER INFORMATION: /replace="Orn"

<400> SEQUENCE: 176

Xaa Xaa Xaa Xaa Xaa Xaa Xaa Xaa Xaa Xaa Xaa Xaa Xaa Xaa Xaa Xaa
 1               5                  10                  15

<210> SEQ ID NO 177
<211> LENGTH: 17
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(17)
<223> OTHER INFORMATION: /replace="Orn"

<400> SEQUENCE: 177
```

Xaa Xaa Xaa Xaa Xaa Xaa Xaa Xaa Xaa Xaa Xaa Xaa Xaa Xaa Xaa
1               5                   10                  15

Xaa

<210> SEQ ID NO 178
<211> LENGTH: 18
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(18)
<223> OTHER INFORMATION: /replace="Orn"

<400> SEQUENCE: 178

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 179
<211> LENGTH: 19
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(19)
<223> OTHER INFORMATION: /replace="Orn"

<400> SEQUENCE: 179

Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 180
<211> LENGTH: 20
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(20)
<223> OTHER INFORMATION: /replace="Orn"

<400> SEQUENCE: 180

Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 181
<211> LENGTH: 21
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(21)
<223> OTHER INFORMATION: /replace="Orn"

<400> SEQUENCE: 181

Xaa Xaa Xaa Xaa Xaa Xaa Xaa Xaa Xaa Xaa Xaa Xaa Xaa Xaa Xaa

-continued

```
                1               5                  10                 15
Xaa Xaa Xaa Xaa Xaa
            20

<210> SEQ ID NO 182
<211> LENGTH: 22
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(22)
<223> OTHER INFORMATION: /replace="Orn"

<400> SEQUENCE: 182

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 183
<211> LENGTH: 23
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(23)
<223> OTHER INFORMATION: /replace="Orn"

<400> SEQUENCE: 183

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 184
<211> LENGTH: 24
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(24)
<223> OTHER INFORMATION: /replace="Orn"

<400> SEQUENCE: 184

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 185
<211> LENGTH: 25
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(25)
<223> OTHER INFORMATION: /replace="Orn"

<400> SEQUENCE: 185
```

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 186
<211> LENGTH: 26
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(26)
<223> OTHER INFORMATION: /replace="Orn"

<400> SEQUENCE: 186

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 187
<211> LENGTH: 27
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(27)
<223> OTHER INFORMATION: /replace="Orn"

<400> SEQUENCE: 187

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 188
<211> LENGTH: 28
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(28)
<223> OTHER INFORMATION: /replace="Orn"

<400> SEQUENCE: 188

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 189
<211> LENGTH: 29
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(29)
<223> OTHER INFORMATION: /replace="Orn"

<400> SEQUENCE: 189

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 190
<211> LENGTH: 30
<212> TYPE: PRT
<213> ORGANISM: Artificial Sequence
<220> FEATURE:
<223> OTHER INFORMATION: Oligopeptide of formula (V)
<220> FEATURE:
<221> NAME/KEY: MOD_RES
<222> LOCATION: (1)..(30)
<223> OTHER INFORMATION: /replace="Orn"

<400> SEQUENCE: 190

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 191
<211> LENGTH: 12
<212> TYPE: PRT
<213> ORGANISM: Artificial Sequence
<220> FEATURE:
<223> OTHER INFORMATION: Oligopeptide of formula (V)

<400> SEQUENCE: 191

His His His Arg Arg Arg Arg Arg Arg Arg Arg Arg
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Oligopeptide of formula (V)

<400> SEQUENCE: 192

Arg Arg Arg Arg Arg Arg Arg Arg Arg His His His
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Oligopeptide of formula (V)

<400> SEQUENCE: 193

His His His Arg Arg Arg Arg His His His
1               5                   10

<210> SEQ ID NO 194
<211> LENGTH: 15
<212> TYPE: PRT
<213> ORGANISM: Artificial Sequence
<220> FEATURE:
<223> OTHER INFORMATION: Oligopeptide of formula (V)

<400> SEQUENCE: 194

His His His Arg Arg Arg Arg Arg Arg Arg Arg Arg His His His
1               5                   10                  15
```

<210> SEQ ID NO 195
<211> LENGTH: 16
<212> TYPE: PRT
<213> ORGANISM: Artificial Sequence
<220> FEATURE:
<223> OTHER INFORMATION: Oligopeptide of formula (V)

<400> SEQUENCE: 195

His His His His His His Arg Arg Arg Arg His His His His His His
1               5                   10                  15

<210> SEQ ID NO 196
<211> LENGTH: 21
<212> TYPE: PRT
<213> ORGANISM: Artificial Sequence
<220> FEATURE:
<223> OTHER INFORMATION: Oligopeptide of formula (V)

<400> SEQUENCE: 196

His His His His His His Arg Arg Arg Arg Arg Arg Arg Arg Arg His
1               5                   10                  15

His His His His His
            20

<210> SEQ ID NO 197
<211> LENGTH: 15
<212> TYPE: PRT
<213> ORGANISM: Artificial Sequence
<220> FEATURE:
<223> OTHER INFORMATION: Oligopeptide of formula (V)

<400> SEQUENCE: 197

Tyr Ser Ser Arg Arg Arg Arg Arg Arg Arg Arg Arg Ser Ser Tyr
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Oligopeptide of formula (V)

<400> SEQUENCE: 198

His His His Arg Arg Arg Arg Arg Arg Arg Arg Arg Ser Ser Tyr
1               5                   10                  15

<210> SEQ ID NO 199
<211> LENGTH: 12
<212> TYPE: PRT
<213> ORGANISM: Artificial Sequence
<220> FEATURE:
<223> OTHER INFORMATION: Oligopeptide of formula (V)

<400> SEQUENCE: 199

Arg Lys His Arg Lys His Arg Lys His Arg Lys His
1               5                   10

<210> SEQ ID NO 200
<211> LENGTH: 8
<212> TYPE: PRT
<213> ORGANISM: Artificial Sequence
<220> FEATURE:
<223> OTHER INFORMATION: Oligopeptide of formula (V)

<400> SEQUENCE: 200

Tyr Arg Lys His Arg Lys His Arg
1               5

```
1               5
```

<210> SEQ ID NO 201
<211> LENGTH: 9
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 201

```
Cys Arg Arg Arg Arg Arg Arg Arg Cys
1               5
```

<210> SEQ ID NO 202
<211> LENGTH: 10
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 202

```
Cys Arg Arg Arg Arg Arg Arg Arg Arg Cys
1               5                   10
```

<210> SEQ ID NO 203
<211> LENGTH: 11
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 203

```
Cys Arg Arg Arg Arg Arg Arg Arg Arg Arg Cys
1               5                   10
```

<210> SEQ ID NO 204
<211> LENGTH: 12
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 204

```
Cys Arg Arg Arg Arg Arg Arg Arg Arg Arg Arg Cys
1               5                   10
```

<210> SEQ ID NO 205
<211> LENGTH: 13
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 205

```
Cys Arg Arg Arg Arg Arg Arg Arg Arg Arg Arg Arg Cys
1               5                   10
```

<210> SEQ ID NO 206
<211> LENGTH: 14
<212> TYPE: PRT
<213> ORGANISM: Artificial Sequence
<220> FEATURE:
<223> OTHER INFORMATION: Disulfide-crosslinkable cationic compound according to subformula (Vb)

<400> SEQUENCE: 206

Cys Arg Arg Arg Arg Arg Arg Arg Arg Arg Arg Cys
1               5                   10

<210> SEQ ID NO 207
<211> LENGTH: 15
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 207

Cys Arg Arg Arg Arg Arg Arg Arg Arg Arg Arg Arg Arg Cys
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 208

Cys Arg Arg Arg Arg Arg Arg Arg Arg Arg Arg Arg Arg Arg Cys
1               5                   10                  15

<210> SEQ ID NO 209
<211> LENGTH: 17
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 209

Cys Arg Arg Arg Arg Arg Arg Arg Arg Arg Arg Arg Arg Arg Arg
1               5                   10                  15

Cys

<210> SEQ ID NO 210
<211> LENGTH: 18
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 210

Cys Arg Arg Arg Arg Arg Arg Arg Arg Arg Arg Arg Arg Arg Arg
1               5                   10                  15

Arg Cys

<210> SEQ ID NO 211
<211> LENGTH: 19
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 211

Cys Arg Arg Arg Arg Arg Arg Arg Arg Arg Arg Arg Arg Arg Arg Arg

<210> SEQ ID NO 212
<211> LENGTH: 20
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 212

Cys Arg Arg Arg Arg Arg Arg Arg Arg Arg Arg Arg Arg Arg Arg
1               5                   10                  15

Arg Arg Arg Cys
            20

<210> SEQ ID NO 213
<211> LENGTH: 21
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 213

Cys Arg Arg Arg Arg Arg Arg Arg Arg Arg Arg Arg Arg Arg Arg
1               5                   10                  15

Arg Arg Arg Arg Cys
            20

<210> SEQ ID NO 214
<211> LENGTH: 22
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 214

Cys Arg Arg Arg Arg Arg Arg Arg Arg Arg Arg Arg Arg Arg Arg
1               5                   10                  15

Arg Arg Arg Arg Arg Cys
            20

<210> SEQ ID NO 215
<211> LENGTH: 9
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 215

Cys Lys Lys Lys Lys Lys Lys Lys Cys
1               5

<210> SEQ ID NO 216
<211> LENGTH: 10
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 216

Cys Lys Lys Lys Lys Lys Lys Lys Cys
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 217

Cys Lys Lys Lys Lys Lys Lys Lys Lys Cys
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 218

Cys Lys Lys Lys Lys Lys Lys Lys Lys Lys Cys
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 219

Cys Lys Lys Lys Lys Lys Lys Lys Lys Lys Lys Cys
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 220

Cys Lys Lys Lys Lys Lys Lys Lys Lys Lys Lys Lys Cys
1               5                   10

<210> SEQ ID NO 221
<211> LENGTH: 15
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 221

Cys Lys Lys Lys Lys Lys Lys Lys Lys Lys Lys Lys Lys Cys
1               5                   10                  15

<210> SEQ ID NO 222
<211> LENGTH: 16
<212> TYPE: PRT
<213> ORGANISM: Artificial Sequence

```
<220> FEATURE:
<223> OTHER INFORMATION: Disulfide-crosslinkable cationic compound
      according to subformula (Vb)

<400> SEQUENCE: 222

Cys Lys Lys Lys Lys Lys Lys Lys Lys Lys Lys Lys Lys Lys Cys
1               5                   10                  15

<210> SEQ ID NO 223
<211> LENGTH: 17
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 223

Cys Lys Lys Lys Lys Lys Lys Lys Lys Lys Lys Lys Lys Lys Lys
1               5                   10                  15

Cys

<210> SEQ ID NO 224
<211> LENGTH: 18
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 224

Cys Lys Lys Lys Lys Lys Lys Lys Lys Lys Lys Lys Lys Lys Lys
1               5                   10                  15

Lys Cys

<210> SEQ ID NO 225
<211> LENGTH: 19
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 225

Cys Lys Lys Lys Lys Lys Lys Lys Lys Lys Lys Lys Lys Lys Lys
1               5                   10                  15

Lys Lys Cys

<210> SEQ ID NO 226
<211> LENGTH: 20
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 226

Cys Lys Lys Lys Lys Lys Lys Lys Lys Lys Lys Lys Lys Lys Lys
1               5                   10                  15

Lys Lys Lys Cys
            20

<210> SEQ ID NO 227
<211> LENGTH: 21
<212> TYPE: PRT
<213> ORGANISM: Artificial Sequence
```

```
<220> FEATURE:
<223> OTHER INFORMATION: Disulfide-crosslinkable cationic compound
      according to subformula (Vb)

<400> SEQUENCE: 227

Cys Lys Lys Lys Lys Lys Lys Lys Lys Lys Lys Lys Lys Lys Lys
1               5                   10                  15

Lys Lys Lys Lys Cys
            20

<210> SEQ ID NO 228
<211> LENGTH: 22
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 228

Cys Lys Lys Lys Lys Lys Lys Lys Lys Lys Lys Lys Lys Lys Lys
1               5                   10                  15

Lys Lys Lys Lys Lys Cys
            20

<210> SEQ ID NO 229
<211> LENGTH: 9
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 229

Cys His His His His His His His Cys
1               5

<210> SEQ ID NO 230
<211> LENGTH: 10
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 230

Cys His His His His His His His His Cys
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 231

Cys His His His His His His His His His Cys
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Disulfide-crosslinkable cationic compound
      according to subformula (Vb)
```

```
<400> SEQUENCE: 232

Cys His His His His His His His His His Cys
1               5                   10

<210> SEQ ID NO 233
<211> LENGTH: 13
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 233

Cys His His His His His His His His His His Cys
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 234

Cys His His His His His His His His His His His Cys
1               5                   10

<210> SEQ ID NO 235
<211> LENGTH: 15
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 235

Cys His His His His His His His His His His His His Cys
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 236

Cys His His His His His His His His His His His His His Cys
1               5                   10                  15

<210> SEQ ID NO 237
<211> LENGTH: 17
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 237

Cys His His His His His His His His His His His His His His
1               5                   10                  15

Cys
```

```
<210> SEQ ID NO 238
<211> LENGTH: 18
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 238

Cys His His His His His His His His His His His His His His
1               5                   10                  15

His Cys

<210> SEQ ID NO 239
<211> LENGTH: 19
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 239

Cys His His His His His His His His His His His His His His
1               5                   10                  15

His His Cys

<210> SEQ ID NO 240
<211> LENGTH: 20
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 240

Cys His His His His His His His His His His His His His His
1               5                   10                  15

His His His Cys
            20

<210> SEQ ID NO 241
<211> LENGTH: 21
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 241

Cys His His His His His His His His His His His His His His
1               5                   10                  15

His His His His Cys
            20

<210> SEQ ID NO 242
<211> LENGTH: 22
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 242

Cys His His His His His His His His His His His His His His
1               5                   10                  15
```

```
His His His His His Cys
            20
```

```
<210> SEQ ID NO 243
<211> LENGTH: 9
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(9)
<223> OTHER INFORMATION: /replace="orn"

<400> SEQUENCE: 243

Cys Xaa Xaa Xaa Xaa Xaa Xaa Xaa Cys
1               5
```

```
<210> SEQ ID NO 244
<211> LENGTH: 10
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: misc_feature
<222> LOCATION: (1)..(10)
<223> OTHER INFORMATION: /replace="orn"

<400> SEQUENCE: 244

Cys Xaa Xaa Xaa Xaa Xaa Xaa Xaa Xaa Cys
1               5                   10
```

```
<210> SEQ ID NO 245
<211> LENGTH: 11
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: misc_feature
<222> LOCATION: (1)..(11)
<223> OTHER INFORMATION: /replace="orn"

<400> SEQUENCE: 245

Cys Xaa Xaa Xaa Xaa Xaa Xaa Xaa Xaa Xaa Cys
1               5                   10
```

```
<210> SEQ ID NO 246
<211> LENGTH: 12
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: misc_feature
<222> LOCATION: (1)..(12)
<223> OTHER INFORMATION: /replace="orn"
<220> FEATURE:
<221> NAME/KEY: MOD_RES
<222> LOCATION: (1)..(12)
<223> OTHER INFORMATION: /replace="orn"

<400> SEQUENCE: 246

Cys Xaa Xaa Xaa Xaa Xaa Xaa Xaa Xaa Xaa Xaa Cys
1               5                   10
```

<210> SEQ ID NO 247
<211> LENGTH: 13
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(13)
<223> OTHER INFORMATION: /replace="orn"

<400> SEQUENCE: 247

Cys Xaa Xaa Xaa Xaa Xaa Xaa Xaa Xaa Xaa Xaa Xaa Cys
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(14)
<223> OTHER INFORMATION: /replace="orn"

<400> SEQUENCE: 248

Cys Xaa Xaa Xaa Xaa Xaa Xaa Xaa Xaa Xaa Xaa Xaa Xaa Cys
1               5                   10

<210> SEQ ID NO 249
<211> LENGTH: 15
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(15)
<223> OTHER INFORMATION: /replace="orn"

<400> SEQUENCE: 249

Cys Xaa Xaa Xaa Xaa Xaa Xaa Xaa Xaa Xaa Xaa Xaa Xaa Xaa Cys
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(16)
<223> OTHER INFORMATION: /replace="orn"

<400> SEQUENCE: 250

Cys Xaa Xaa Xaa Xaa Xaa Xaa Xaa Xaa Xaa Xaa Xaa Xaa Xaa Xaa Cys
1               5                   10                  15

<210> SEQ ID NO 251
<211> LENGTH: 17
<212> TYPE: PRT
<213> ORGANISM: Artificial Sequence
<220> FEATURE:
<223> OTHER INFORMATION: Disulfide-crosslinkable cationic compound according to subformula (Vb)
<220> FEATURE:
<221> NAME/KEY: MOD_RES
<222> LOCATION: (1)..(17)
<223> OTHER INFORMATION: /replace="orn"

<400> SEQUENCE: 251

Cys Xaa Xaa Xaa Xaa Xaa Xaa Xaa Xaa Xaa Xaa Xaa Xaa Xaa Xaa Xaa
1               5                   10                  15

Cys

<210> SEQ ID NO 252
<211> LENGTH: 18
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(18)
<223> OTHER INFORMATION: /replace="orn"

<400> SEQUENCE: 252

Cys Xaa Xaa Xaa Xaa Xaa Xaa Xaa Xaa Xaa Xaa Xaa Xaa Xaa Xaa Xaa
1               5                   10                  15

Xaa Cys

<210> SEQ ID NO 253
<211> LENGTH: 19
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(19)
<223> OTHER INFORMATION: /replace="orn"

<400> SEQUENCE: 253

Cys Xaa Xaa Xaa Xaa Xaa Xaa Xaa Xaa Xaa Xaa Xaa Xaa Xaa Xaa Xaa
1               5                   10                  15

Xaa Xaa Cys

<210> SEQ ID NO 254
<211> LENGTH: 20
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(20)
<223> OTHER INFORMATION: /replace="orn"

<400> SEQUENCE: 254

Cys Xaa Xaa Xaa Xaa Xaa Xaa Xaa Xaa Xaa Xaa Xaa Xaa Xaa Xaa Xaa
1               5                   10                  15

Xaa Xaa Xaa Cys
            20

<210> SEQ ID NO 255
<211> LENGTH: 21
<212> TYPE: PRT
<213> ORGANISM: Artificial Sequence

```
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(21)
<223> OTHER INFORMATION: /replace="orn"

<400> SEQUENCE: 255

Cys Xaa Xaa Xaa Xaa Xaa Xaa Xaa Xaa Xaa Xaa Xaa Xaa Xaa Xaa
1               5                   10                  15

Xaa Xaa Xaa Xaa Cys
            20

<210> SEQ ID NO 256
<211> LENGTH: 22
<212> TYPE: PRT
<213> ORGANISM: Artificial Sequence
<220> FEATURE:
<223> OTHER INFORMATION: Disulfide-crosslinkable cationic compound
      according to subformula (Vb)
<220> FEATURE:
<221> NAME/KEY: MOD_RES
<222> LOCATION: (1)..(22)
<223> OTHER INFORMATION: /replace="orn"

<400> SEQUENCE: 256

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Cys
            20

<210> SEQ ID NO 257
<211> LENGTH: 11
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 257

Cys Arg Arg Arg Arg Arg Arg Arg Arg Arg Cys
1               5                   10

<210> SEQ ID NO 258
<211> LENGTH: 14
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 258

Cys Arg Arg Arg Arg Arg Arg Arg Arg Arg His His His Cys
1               5                   10

<210> SEQ ID NO 259
<211> LENGTH: 17
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 259

Cys His His His Arg Arg Arg Arg Arg Arg Arg Arg His His His
1               5                   10                  15
```

Cys

```
<210> SEQ ID NO 260
<211> LENGTH: 17
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 260

Cys Tyr Ser Ser Arg Arg Arg Arg Arg Arg Arg Arg Ser Ser Tyr
1               5                   10                  15

Cys

<210> SEQ ID NO 261
<211> LENGTH: 17
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 261

Cys His His His Arg Arg Arg Arg Arg Arg Arg Arg Ser Ser Tyr
1               5                   10                  15

Cys

<210> SEQ ID NO 262
<211> LENGTH: 14
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 262

Cys Ala Lys His Ala Lys His Ala Lys His Ala Lys His Cys
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 263

Cys Tyr Ala Lys His Ala Lys His Arg Cys
1               5                   10

<210> SEQ ID NO 264
<211> LENGTH: 17
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 264

Cys His His His Arg Arg Arg Arg Arg Arg Arg Arg His His His
1               5                   10                  15

Cys
```

```
<210> SEQ ID NO 265
<211> LENGTH: 23
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 265

Cys His His His His His His Arg Arg Arg Arg Arg Arg Arg Arg
1               5                   10                  15

His His His His His His Cys
            20

<210> SEQ ID NO 266
<211> LENGTH: 12
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 266

Cys His His His Arg Arg Arg Arg His His His Cys
1               5                   10

<210> SEQ ID NO 267
<211> LENGTH: 18
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 267

Cys His His His His His His Arg Arg Arg Arg His His His His His
1               5                   10                  15

His Cys

<210> SEQ ID NO 268
<211> LENGTH: 14
<212> TYPE: PRT
<213> ORGANISM: Artificial Sequence
<220> FEATURE:
<223> OTHER INFORMATION: Disulfide-crosslinkable cationic compound
      according to subformula (Vb)

<400> SEQUENCE: 268

Cys Arg Arg Arg Arg Arg Arg Arg Arg Arg Arg Arg Arg Cys
1               5                   10

<210> SEQ ID NO 269

<400> SEQUENCE: 269

000

<210> SEQ ID NO 270

<400> SEQUENCE: 270

000

<210> SEQ ID NO 271

<400> SEQUENCE: 271
```

```
000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 277

Trp Tyr Trp Tyr
1

<210> SEQ ID NO 278
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 278

Tyr Trp Tyr Trp
1

<210> SEQ ID NO 279
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 279

Trp Trp Trp Trp
1

<210> SEQ ID NO 280
```

```
<400> SEQUENCE: 280

000

<210> SEQ ID NO 281
<400> SEQUENCE: 281

000

<210> SEQ ID NO 282
<400> SEQUENCE: 282

000

<210> SEQ ID NO 283
<400> SEQUENCE: 283

000

<210> SEQ ID NO 284
<400> SEQUENCE: 284

000

<210> SEQ ID NO 285
<400> SEQUENCE: 285

000

<210> SEQ ID NO 286
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 286

Phe Tyr Phe Tyr
1

<210> SEQ ID NO 287
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 287

Tyr Phe Tyr Phe
1

<210> SEQ ID NO 288
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 288

Phe Phe Phe Phe
1
```

```
<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 294

Phe Trp Phe Trp
1

<210> SEQ ID NO 295
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 295

Trp Phe Trp Phe
1

<210> SEQ ID NO 296
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 296

Tyr Tyr Tyr Tyr
1

<210> SEQ ID NO 297

<400> SEQUENCE: 297

000
```

<210> SEQ ID NO 298

<400> SEQUENCE: 298

000

<210> SEQ ID NO 299
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 299

Cys Trp Tyr Cys
1

<210> SEQ ID NO 300
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 300

Cys Tyr Trp Cys
1

<210> SEQ ID NO 301
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 301

Cys Trp Trp Cys
1

<210> SEQ ID NO 302
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 302

Cys Tyr Tyr Cys
1

<210> SEQ ID NO 303
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 303

Cys Trp Tyr Trp Cys
1               5

<210> SEQ ID NO 304
<211> LENGTH: 5
<212> TYPE: PRT
<213> ORGANISM: Artificial Sequence
<220> FEATURE:

```
<223> OTHER INFORMATION: Exemplary aromatic amino acid component (AA)

<400> SEQUENCE: 304

Cys Tyr Trp Tyr Cys
1               5

<210> SEQ ID NO 305
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 305

Cys Trp Trp Trp Cys
1               5

<210> SEQ ID NO 306
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 306

Cys Tyr Tyr Tyr Cys
1               5

<210> SEQ ID NO 307
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 307

Cys Trp Tyr Trp Tyr Cys
1               5

<210> SEQ ID NO 308
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 308

Cys Tyr Trp Tyr Trp Cys
1               5

<210> SEQ ID NO 309
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 309

Cys Trp Trp Trp Trp Cys
1               5

<210> SEQ ID NO 310
<211> LENGTH: 6
<212> TYPE: PRT
<213> ORGANISM: Artificial Sequence
<220> FEATURE:
<223> OTHER INFORMATION: Exemplary aromatic amino acid component (AA)
```

```
<400> SEQUENCE: 310

Cys Tyr Tyr Tyr Tyr Cys
1               5

<210> SEQ ID NO 311

<400> SEQUENCE: 311

000

<210> SEQ ID NO 312
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 312

Cys Phe Tyr Cys
1

<210> SEQ ID NO 313
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 313

Cys Tyr Phe Cys
1

<210> SEQ ID NO 314
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 314

Cys Phe Phe Cys
1

<210> SEQ ID NO 315
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 315

Cys Tyr Tyr Cys
1

<210> SEQ ID NO 316
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 316

Cys Phe Tyr Phe Cys
1               5
```

```
<210> SEQ ID NO 317
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 317

Cys Tyr Phe Tyr Cys
1               5

<210> SEQ ID NO 318
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 318

Cys Phe Phe Phe Cys
1               5

<210> SEQ ID NO 319
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 319

Cys Tyr Tyr Tyr Cys
1               5

<210> SEQ ID NO 320
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 320

Cys Phe Tyr Phe Tyr Cys
1               5

<210> SEQ ID NO 321
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 321

Cys Tyr Phe Tyr Phe
1               5

<210> SEQ ID NO 322
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 322

Cys Phe Phe Phe Phe Cys
1               5

<210> SEQ ID NO 323
```

```
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 323

Cys Phe Trp Cys
1

<210> SEQ ID NO 324
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 324

Cys Trp Phe Cys
1

<210> SEQ ID NO 325
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 325

Cys Phe Phe Cys
1

<210> SEQ ID NO 326
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 326

Cys Phe Trp Phe Cys
1               5

<210> SEQ ID NO 327
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 327

Cys Trp Phe Trp Cys
1               5

<210> SEQ ID NO 328
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 328

Cys Phe Trp Phe Trp Cys
1               5

<210> SEQ ID NO 329
<211> LENGTH: 6
```

```
<212> TYPE: PRT
<213> ORGANISM: Artificial Sequence
<220> FEATURE:
<223> OTHER INFORMATION: Exemplary aromatic amino acid component (AA)

<400> SEQUENCE: 329

Cys Trp Phe Trp Phe Cys
1               5

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 338

Ser Thr Ser Thr
1
```

```
<210> SEQ ID NO 339
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 339

Thr Ser Thr Ser
1

<210> SEQ ID NO 340
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 340

Ser Ser Ser Ser
1

<210> SEQ ID NO 341
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 341

Thr Thr Thr Thr
1

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000
```

```
<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 350

Gln Asn Gln Asn
1

<210> SEQ ID NO 351
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 351

Asn Gln Asn Gln
1

<210> SEQ ID NO 352
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 352

Gln Gln Gln Gln
1

<210> SEQ ID NO 353
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 353

Asn Asn Asn Asn
1

<210> SEQ ID NO 354
```

```
<400> SEQUENCE: 354

000

<210> SEQ ID NO 355
<400> SEQUENCE: 355

000

<210> SEQ ID NO 356
<400> SEQUENCE: 356

000

<210> SEQ ID NO 357
<400> SEQUENCE: 357

000

<210> SEQ ID NO 358
<400> SEQUENCE: 358

000

<210> SEQ ID NO 359
<400> SEQUENCE: 359

000

<210> SEQ ID NO 360
<400> SEQUENCE: 360

000

<210> SEQ ID NO 361
<400> SEQUENCE: 361

000

<210> SEQ ID NO 362
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 362

Ser Asn Ser Asn
1

<210> SEQ ID NO 363
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 363

Asn Ser Asn Ser
```

```
<210> SEQ ID NO 364
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 364

Ser Ser Ser Ser
1

<210> SEQ ID NO 365
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 365

Asn Asn Asn Asn
1

<210> SEQ ID NO 366

<400> SEQUENCE: 366

000

<210> SEQ ID NO 367

<400> SEQUENCE: 367

000

<210> SEQ ID NO 368
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 368

Cys Ser Thr Cys
1

<210> SEQ ID NO 369
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 369

Cys Thr Ser Cys
1

<210> SEQ ID NO 370
<211> LENGTH: 4
<212> TYPE: PRT
<213> ORGANISM: Artificial Sequence
<220> FEATURE:
<223> OTHER INFORMATION: Exemplary hydrophilic (and preferably non
``` charged polar) amino acid component (AA)

<400> SEQUENCE: 370

Cys Ser Ser Cys
1

<210> SEQ ID NO 371
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 371

Cys Thr Thr Cys
1

<210> SEQ ID NO 372
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 372

Cys Ser Thr Ser Cys
1               5

<210> SEQ ID NO 373
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 373

Cys Thr Ser Thr Cys
1               5

<210> SEQ ID NO 374
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 374

Cys Ser Ser Ser Cys
1               5

<210> SEQ ID NO 375
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 375

Cys Thr Thr Thr Cys
1               5

<210> SEQ ID NO 376

```
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 376

Cys Ser Thr Ser Thr Cys
1               5

<210> SEQ ID NO 377
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 377

Cys Thr Ser Thr Ser Cys
1               5

<210> SEQ ID NO 378
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 378

Cys Ser Ser Ser Ser Cys
1               5

<210> SEQ ID NO 379
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 379

Cys Thr Thr Thr Thr Cys
1               5

<210> SEQ ID NO 380

<400> SEQUENCE: 380

000

<210> SEQ ID NO 381

<400> SEQUENCE: 381

000

<210> SEQ ID NO 382
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 382
```

```
Cys Gln Asn Cys
1

<210> SEQ ID NO 383
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 383

Cys Asn Gln Cys
1

<210> SEQ ID NO 384
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 384

Cys Gln Gln Cys
1

<210> SEQ ID NO 385
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 385

Cys Asn Asn Cys
1

<210> SEQ ID NO 386
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 386

Cys Gln Asn Gln Cys
1               5

<210> SEQ ID NO 387
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 387

Cys Asn Gln Asn Cys
1               5

<210> SEQ ID NO 388
<211> LENGTH: 5
<212> TYPE: PRT
<213> ORGANISM: Artificial Sequence
<220> FEATURE:
```

-continued

<223> OTHER INFORMATION: Exemplary hydrophilic (and preferably non
      charged polar) amino acid component (AA)

<400> SEQUENCE: 388

Cys Gln Gln Gln Cys
1               5

<210> SEQ ID NO 389
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 389

Cys Asn Asn Asn Cys
1               5

<210> SEQ ID NO 390
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 390

Cys Gln Asn Gln Asn Cys
1               5

<210> SEQ ID NO 391
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 391

Cys Asn Gln Asn Gln Cys
1               5

<210> SEQ ID NO 392
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 392

Cys Gln Gln Gln Gln Cys
1               5

<210> SEQ ID NO 393
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 393

Cys Asn Asn Asn Asn Cys
1               5

```
<210> SEQ ID NO 394

<400> SEQUENCE: 394

000

<210> SEQ ID NO 395

<400> SEQUENCE: 395

000

<210> SEQ ID NO 396
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 396

Cys Ser Asn Cys
1

<210> SEQ ID NO 397
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 397

Cys Asn Ser Cys
1

<210> SEQ ID NO 398
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 398

Cys Ser Ser Cys
1

<210> SEQ ID NO 399
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 399

Cys Asn Asn Cys
1

<210> SEQ ID NO 400
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 400
```

Cys Ser Asn Ser Cys
1               5

<210> SEQ ID NO 401
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 401

Cys Asn Ser Asn Cys
1               5

<210> SEQ ID NO 402
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 402

Cys Ser Ser Ser Cys
1               5

<210> SEQ ID NO 403
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 403

Cys Asn Asn Asn Cys
1               5

<210> SEQ ID NO 404
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 404

Cys Ser Asn Ser Asn Cys
1               5

<210> SEQ ID NO 405
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 405

Cys Asn Ser Asn Ser Cys
1               5

<210> SEQ ID NO 406
<211> LENGTH: 6
<212> TYPE: PRT
<213> ORGANISM: Artificial Sequence

```
<220> FEATURE:
<223> OTHER INFORMATION: Exemplary hydrophilic (and preferably non
      charged polar) amino acid component (AA)

<400> SEQUENCE: 406

Cys Ser Ser Ser Ser Cys
1               5

<210> SEQ ID NO 407
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 407

Cys Asn Asn Asn Asn Cys
1               5

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000
```

<210> SEQ ID NO 416
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 416

Leu Val Leu Val
1

<210> SEQ ID NO 417
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 417

Val Leu Val Leu
1

<210> SEQ ID NO 418
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 418

Leu Leu Leu Leu
1

<210> SEQ ID NO 419
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 419

Val Val Val Val
1

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 428

Ile Ala Ile Ala
1

<210> SEQ ID NO 429
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 429

Ala Ile Ala Ile
1

<210> SEQ ID NO 430
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 430

Ile Ile Ile Ile
1

<210> SEQ ID NO 431
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 431

Ala Ala Ala Ala

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 440

Met Ala Met Ala
1

<210> SEQ ID NO 441
<211> LENGTH: 4
<212> TYPE: PRT
<213> ORGANISM: Artificial Sequence
<220> FEATURE:
<223> OTHER INFORMATION: Exemplary lipophilic amino acid component (AA)

```
<400> SEQUENCE: 441

Ala Met Ala Met
1

<210> SEQ ID NO 442
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 442

Met Met Met Met
1

<210> SEQ ID NO 443

<400> SEQUENCE: 443

000

<210> SEQ ID NO 444

<400> SEQUENCE: 444

000

<210> SEQ ID NO 445
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 445

Cys Leu Val Cys
1

<210> SEQ ID NO 446
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 446

Cys Val Leu Cys
1

<210> SEQ ID NO 447
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 447

Cys Leu Leu Cys
1

<210> SEQ ID NO 448
<211> LENGTH: 4
<212> TYPE: PRT
<213> ORGANISM: Artificial Sequence
<220> FEATURE:
<223> OTHER INFORMATION: Exemplary lipophilic amino acid component (AA)
```

```
<400> SEQUENCE: 448

Cys Val Val Cys
1

<210> SEQ ID NO 449
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 449

Cys Leu Val Leu Cys
1               5

<210> SEQ ID NO 450
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 450

Cys Val Leu Val Cys
1               5

<210> SEQ ID NO 451
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 451

Cys Leu Leu Leu Cys
1               5

<210> SEQ ID NO 452
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 452

Cys Val Val Val Cys
1               5

<210> SEQ ID NO 453
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 453

Cys Leu Val Leu Val Cys
1               5

<210> SEQ ID NO 454
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 454
```

```
Cys Val Leu Val Leu Cys
1               5

<210> SEQ ID NO 455
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 455

Cys Leu Leu Leu Leu Cys
1               5

<210> SEQ ID NO 456
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 456

Cys Val Val Val Val Cys
1               5

<210> SEQ ID NO 457

<400> SEQUENCE: 457

000

<210> SEQ ID NO 458

<400> SEQUENCE: 458

000

<210> SEQ ID NO 459
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 459

Cys Ile Ala Cys
1

<210> SEQ ID NO 460
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 460

Cys Ala Ile Cys
1

<210> SEQ ID NO 461
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 461
```

Cys Ile Ile Cys
1

<210> SEQ ID NO 462
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 462

Cys Ala Ala Cys
1

<210> SEQ ID NO 463
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 463

Cys Ile Ala Ile Cys
1               5

<210> SEQ ID NO 464
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 464

Cys Ala Ile Ala Cys
1               5

<210> SEQ ID NO 465
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 465

Cys Ile Ile Ile Cys
1               5

<210> SEQ ID NO 466
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 466

Cys Ala Ala Ala Cys
1               5

<210> SEQ ID NO 467
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 467

Cys Ile Ala Ile Ala Cys
1               5

<210> SEQ ID NO 468
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 468

Cys Ala Ile Ala Ile Cys
1               5

<210> SEQ ID NO 469
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 469

Cys Ile Ile Ile Ile Cys
1               5

<210> SEQ ID NO 470
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 470

Cys Ala Ala Ala Ala Cys
1               5

<210> SEQ ID NO 471

<400> SEQUENCE: 471

000

<210> SEQ ID NO 472
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 472

Cys Met Ala Cys
1

<210> SEQ ID NO 473
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 473

Cys Ala Met Cys
1

<210> SEQ ID NO 474
<211> LENGTH: 4
<212> TYPE: PRT

```
<213> ORGANISM: Artificial Sequence
<220> FEATURE:
<223> OTHER INFORMATION: Exemplary lipophilic amino acid component (AA)

<400> SEQUENCE: 474

Cys Met Met Cys
1

<210> SEQ ID NO 475
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 475

Cys Ala Ala Cys
1

<210> SEQ ID NO 476
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 476

Cys Met Ala Met Cys
1               5

<210> SEQ ID NO 477
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 477

Cys Ala Met Ala Cys
1               5

<210> SEQ ID NO 478
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 478

Cys Met Met Met Cys
1               5

<210> SEQ ID NO 479
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 479

Cys Ala Ala Ala Cys
1               5

<210> SEQ ID NO 480
<211> LENGTH: 6
<212> TYPE: PRT
<213> ORGANISM: Artificial Sequence
```

```
<220> FEATURE:
<223> OTHER INFORMATION: Exemplary lipophilic amino acid component (AA)

<400> SEQUENCE: 480

Cys Met Ala Met Ala Cys
1               5

<210> SEQ ID NO 481
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 481

Cys Ala Met Ala Met Cys
1               5

<210> SEQ ID NO 482
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 482

Cys Met Met Met Met Cys
1               5

<210> SEQ ID NO 483
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 483

Cys Ala Ala Ala Ala Cys
1               5

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488
```

```
000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 492

Asp His Asp His
1

<210> SEQ ID NO 493
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 493

His Asp His Asp
1

<210> SEQ ID NO 494
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 494

Asp Asp Asp Asp
1

<210> SEQ ID NO 495
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 495

His His His His
1

<210> SEQ ID NO 496
```

```
<400> SEQUENCE: 496

000

<210> SEQ ID NO 497

<400> SEQUENCE: 497

000

<210> SEQ ID NO 498
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 498

Cys Asp His Cys
1

<210> SEQ ID NO 499
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 499

Cys His Asp Cys
1

<210> SEQ ID NO 500
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 500

Cys Asp Asp Cys
1

<210> SEQ ID NO 501
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 501

Cys His His Cys
1

<210> SEQ ID NO 502
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 502

Cys Asp His Asp Cys
1               5

<210> SEQ ID NO 503
<211> LENGTH: 5
```

```
<212> TYPE: PRT
<213> ORGANISM: Artificial Sequence
<220> FEATURE:
<223> OTHER INFORMATION: Exemplary weak basic amino acid component (AA)

<400> SEQUENCE: 503

Cys His Asp His Cys
1               5

<210> SEQ ID NO 504
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 504

Cys Asp Asp Asp Cys
1               5

<210> SEQ ID NO 505
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 505

Cys His His His Cys
1               5

<210> SEQ ID NO 506
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 506

Cys Asp His Asp His Cys
1               5

<210> SEQ ID NO 507
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 507

Cys His Asp His Asp Cys
1               5

<210> SEQ ID NO 508
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 508

Cys Asp Asp Asp Asp Cys
1               5

<210> SEQ ID NO 509
<211> LENGTH: 6
<212> TYPE: PRT
```

```
<213> ORGANISM: Artificial Sequence
<220> FEATURE:
<223> OTHER INFORMATION: Exemplary weak basic amino acid component (AA)

<400> SEQUENCE: 509

Cys His His His His Cys
1               5

<210> SEQ ID NO 510
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 510

Lys Asp Glu Leu
1

<210> SEQ ID NO 511
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 511

Asp Asp Glu Leu
1

<210> SEQ ID NO 512
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 512

Asp Glu Glu Leu
1

<210> SEQ ID NO 513
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 513

Gln Glu Asp Leu
1

<210> SEQ ID NO 514
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 514

Arg Asp Glu Leu
1
```

<210> SEQ ID NO 515
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 515

Gly Gln Asn Leu Ser Thr Ser Asn
1               5

<210> SEQ ID NO 516
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 516

Pro Lys Lys Lys Arg Lys Val
1               5

<210> SEQ ID NO 517
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 517

Pro Gln Lys Lys Ile Lys Ser
1               5

<210> SEQ ID NO 518
<211> LENGTH: 5
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 518

Gln Pro Lys Lys Pro
1               5

<210> SEQ ID NO 519
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 519

Arg Lys Lys Arg
1

<210> SEQ ID NO 520
<211> LENGTH: 12
<212> TYPE: PRT
<213> ORGANISM: Artificial Sequence
<220> FEATURE:
<223> OTHER INFORMATION: Description of sequence: signal peptide,
      localization signal or sequence or nuclear localization signal

```
<400> SEQUENCE: 520

Arg Lys Lys Arg Arg Gln Arg Arg Ala His Gln
1               5                   10

<210> SEQ ID NO 521
<211> LENGTH: 16
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 521

Arg Gln Ala Arg Arg Asn Arg Arg Arg Trp Arg Glu Arg Gln Arg
1               5                   10                  15

<210> SEQ ID NO 522
<211> LENGTH: 19
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 522

Met Pro Leu Thr Arg Arg Arg Pro Ala Ala Ser Gln Ala Leu Ala Pro
1               5                   10                  15

Pro Thr Pro

<210> SEQ ID NO 523
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 523

Gly Ala Ala Leu Thr Ile Leu Val
1               5

<210> SEQ ID NO 524
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 524

Gly Ala Ala Leu Thr Leu Leu Gly
1               5

<210> SEQ ID NO 525
<211> LENGTH: 15
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 525

Met Asp Asp Gln Arg Asp Leu Ile Ser Asn Asn Glu Gln Leu Pro
1               5                   10                  15

<210> SEQ ID NO 526
```

```
<211> LENGTH: 32
<212> TYPE: PRT
<213> ORGANISM: Artificial Sequence
<220> FEATURE:
<223> OTHER INFORMATION: Description of sequence: signal peptide,
      localization signal or sequence or nuclear localization signal
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 526

Met Leu Phe Asn Leu Arg Xaa Xaa Leu Asn Asn Ala Ala Phe Arg His
1               5                   10                  15

Gly His Asn Phe Met Val Arg Asn Phe Arg Cys Gly Gln Pro Leu Xaa
            20                  25                  30

<210> SEQ ID NO 527
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 527

Gly Cys Val Cys Ser Ser Asn Pro
1               5

<210> SEQ ID NO 528
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 528

Gly Gln Thr Val Thr Thr Pro Leu
1               5

<210> SEQ ID NO 529
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 529

Gly Gln Glu Leu Ser Gln His Glu
1               5

<210> SEQ ID NO 530
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 530

Gly Asn Ser Pro Ser Tyr Asn Pro
1               5
```

<210> SEQ ID NO 531
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 531

Gly Val Ser Gly Ser Lys Gly Gln
1               5

<210> SEQ ID NO 532
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 532

Gly Gln Thr Ile Thr Thr Pro Leu
1               5

<210> SEQ ID NO 533
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 533

Gly Gln Thr Leu Thr Thr Pro Leu
1               5

<210> SEQ ID NO 534
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 534

Gly Gln Ile Phe Ser Arg Ser Ala
1               5

<210> SEQ ID NO 535
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 535

Gly Gln Ile His Gly Leu Ser Pro
1               5

<210> SEQ ID NO 536
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

```
<400> SEQUENCE: 536

Gly Ala Arg Ala Ser Val Leu Ser
1               5

<210> SEQ ID NO 537
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 537

Gly Cys Thr Leu Ser Ala Glu Glu
1               5

<210> SEQ ID NO 538
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 538

Gly Ala Gln Val Ser Ser Gln Lys
1               5

<210> SEQ ID NO 539
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 539

Gly Ala Gln Leu Ser Arg Asn Thr
1               5

<210> SEQ ID NO 540
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 540

Gly Asn Ala Ala Ala Ala Lys Lys
1               5

<210> SEQ ID NO 541
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 541

Gly Asn Glu Ala Ser Tyr Pro Leu
1               5

<210> SEQ ID NO 542
<211> LENGTH: 8
<212> TYPE: PRT
```

```
<213> ORGANISM: Artificial Sequence
<220> FEATURE:
<223> OTHER INFORMATION: Description of sequence: signal peptide,
      localization signal or sequence or nuclear localization signal

<400> SEQUENCE: 542

Gly Ser Ser Lys Ser Lys Pro Lys
1               5

<210> SEQ ID NO 543
<211> LENGTH: 15
<212> TYPE: RNA
<213> ORGANISM: Artificial
<220> FEATURE:
<223> OTHER INFORMATION: Description of sequence: generic stabilizing
      sequence of the formula (C/U)CCANxCCC(U/A)PyxUC(C/U)CC
<220> FEATURE:
<221> NAME/KEY: variation
<222> LOCATION: (1)..(1)
<223> OTHER INFORMATION: /replace="cytosine" /replace="uracile"
<220> FEATURE:
<221> NAME/KEY: misc_feature
<222> LOCATION: (1)..(1)
<223> OTHER INFORMATION: nucleic acid = cytosine or uracil
<220> FEATURE:
<221> NAME/KEY: misc_feature
<222> LOCATION: (5)..(5)
<223> OTHER INFORMATION: Nx = a, g, c or u or any other nucleic acid
<220> FEATURE:
<221> NAME/KEY: variation
<222> LOCATION: (5)..(5)
<223> OTHER INFORMATION: /replace="cytosine" /replace="uracile"
      /replace="guanosine" /replace="adenosine", or any other nucleic
      acid
<220> FEATURE:
<221> NAME/KEY: repeat_unit
<222> LOCATION: (5)..(5)
<223> OTHER INFORMATION: x = any number
<220> FEATURE:
<221> NAME/KEY: misc_feature
<222> LOCATION: (9)..(9)
<223> OTHER INFORMATION: nucleic acid = uracil or adenosine
<220> FEATURE:
<221> NAME/KEY: variation
<222> LOCATION: (9)..(9)
<223> OTHER INFORMATION: /replace="uracile" /replace="adonosine"
<220> FEATURE:
<221> NAME/KEY: misc_feature
<222> LOCATION: (10)..(10)
<223> OTHER INFORMATION: Py = pyrimidine
<220> FEATURE:
<221> NAME/KEY: repeat_unit
<222> LOCATION: (10)..(10)
<223> OTHER INFORMATION: x = any number
<220> FEATURE:
<221> NAME/KEY: variation
<222> LOCATION: (10)..(10)
<223> OTHER INFORMATION: /replace="pyrimidine"
<220> FEATURE:
<221> NAME/KEY: misc_feature
<222> LOCATION: (13)..(13)
<223> OTHER INFORMATION: nucleic acid = cytosine or uracil
<220> FEATURE:
<221> NAME/KEY: variation
<222> LOCATION: (13)..(13)
<223> OTHER INFORMATION: /replace="cytosine" /replace="uracile"

<400> SEQUENCE: 543
nccancccnn ucncc                                                  15

<210> SEQ ID NO 544
<211> LENGTH: 1870
<212> TYPE: RNA
<213> ORGANISM: Artificial Sequence
<220> FEATURE:
```

<223> OTHER INFORMATION: Pp Luc R1265

<400> SEQUENCE: 544

```
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacgccc ugaacaccaa     240
ccaccggauc guggugugcu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu ggaguucgug agcaagaagg ccugcagaa      420
gauccugaac gugcagaaga gcugcccau cauccagaag aucaucauca uggacagcaa     480
gaccgacuac cagggcuucc agucgaugua cacguucgug accagccacc ucccgccggg     540
cuucaacgag uacgacuucg ucccggagag cuucgaccgg gacaagacca ucgcccugau     600
caugaacagc agcggcagca ccggccugcc gaagggggug gcccugccgc accgaccgc      660
cugcgugcgc uucucgcacg cccgggaccc caucuucggc aaccagauca ucccggacac     720
cgccauccug agcgugguc cguuccacca cggcuucggc auguucacga cccugggcua     780
ccucaucugc ggcuuccggg uguccugau guaccgguuc gaggaggagc uguccgcgcg     840
gagccugcag gacuacaaga uccagagcgc gcugcucgug ccgacccgu ucagcuucu      900
cgccaagagc acccugaucg acaaguacga ccugucgaac cugcacgaga ucgccagcgg     960
gggcgcccg cugagcaagg aggugggcga ggccgguggcc aagcgguucc accucccggg    1020
cauccgccag ggcuacggcc ugaccgagac cacgagcgcg auccugauca ccccgaggg    1080
ggacgacaag ccgggcgccg uggcaaggu gguccgcguc uucgaggca aggguguga    1140
ccuggacacc ggcaagaccc ugggcgugaa ccagcggggc gagcugugcg ugcggggcc    1200
gauguacaug agcggcuacg ugaacaaccc ggaggccacc aacgcccuca ucgacaagga    1260
cggcuggcug cacagcggcg acaucgccua cugggacgag gacgagcacu ucuucaucgu    1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcggcgguu ggugcuggag cacggcaaga ccaugacgga    1500
gaaggagauc gucgacuacg uggccagcca ggugaccacc gccaagaagc ugcggggcgg    1560
cguggguuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccuugc accgagauua    1740
auaaaaaaaa aaaaaaaaa aaaaaaaaa aaaaaaaaa aaaaaaaaaa aaaaaaaaaa    1800
aaaaaaugca uccccccccc ccccccccc ccccccccc ccaaaggcuc uuucagagc      1860
caccagaauu                                                           1870
```

<210> SEQ ID NO 545
<211> LENGTH: 774
<212> TYPE: DNA
<213> ORGANISM: Artificial Sequence
<220> FEATURE:
<223> OTHER INFORMATION: Gp Luc R1283

<400> SEQUENCE: 545

```
gggagaaagc gatccagcca ccatgggagt caaagttctg tttgccctga tctgcatcgc      60
```

```
tgtggccgag gccaagccca ccgagaacaa cgaagacttc aacatcgtgg ccgtggccag      120
caacttcgcg accacggatc tcgatgctga ccgcgggaag ttgcccggca agaagctgcc      180
gctggaggtg ctcaaagaga tggaagccaa tgcccggaaa gctggctgca ccaggggctg      240
tctgatctgc ctgtcccaca tcaagtgcac gcccaagatg aagaagttca tcccaggacg      300
ctgccacacc tacgaaggcg acaaagagtc cgcacagggc ggcataggcg aggcgatcgt      360
cgacattcct gagattcctg ggttcaagga cttggagccc atggagcagt tcatcgcaca      420
ggtcgatctg tgtgtggact gcacaactgg ctgcctcaaa gggcttgcca acgtgcagtg      480
ttctgacctg ctcaagaagt ggctgccgca acgctgtgcg acctttgcca gcaagatcca      540
gggccaggtg acaagatca aggggccgg tggtgactaa gcggccgctc gagcatgcat      600
ctagttataa gactgactag cccgatgggc ctcccaacgg gccctcctcc cctccttgca      660
ccgagattaa taaaaaaaaa aaaaaaaaaa aaaaaaaaaa aaaaaaaaaa aaaaaaaaaa      720
aaaaaaaaaa aaaatattc cccccccccc cccccccccc ccccccccct ctag            774
```

<210> SEQ ID NO 546
<211> LENGTH: 1353
<212> TYPE: RNA
<213> ORGANISM: Artificial Sequence
<220> FEATURE:
<223> OTHER INFORMATION: Ova R1435

<400> SEQUENCE: 546

```
gggagaaagc uuaccauggg cagcaucggg gccgcgucga uggaguucug cuucgacgug       60
uucaaggagc ugaaggucca ccacgccaac gagaacaucu cuacugcccc gaucgccauc      120
augagcgcgc ucgccauggu guaccugggc gccaaggaca gcacccggac gcagaucaac      180 aaggugguccc gcuucgacaa gcugcccggc uucggggacu cgaucgaggc gcagugcggc      240
accagcguga acgugcacag cucgcuccgg gacauccuga accagaucac caagccgaac      300
gacgucuaca gcuucagccu ggccucgcgg cucuacgccg aggagcgcua cccgauccug      360
cccgaguacc ugcagugcgu gaaggagcuc uacaggggcg ggcuggagcc gaucaacuuc      420
cagacggcgg ccgaccaggc ccgggagcug aucaacagcu ggguggagag ccagaccaac      480
ggcaucaucc gcaacgucu ccagccgucg agcguggaca gccagaccgc gauggugcug      540
gucaacgcca ucguguucaa gggccugugg gagaagacgu ucaaggacga ggacacccag      600
gccaugcccu uccggguga cgagcaggag ucgaagccgg uccagaugau guaccagauc      660
gggcucuucc ggguggcgag cauggccagc gagaagauga agauccugga gcugccguuc      720
gccucgggca cgaugagcau gcucgugcug cugcccgacg aggucagcgg ccucgagcag      780
cuggagucga ucaucaacuu cgagaagcug accgaguga ccagcagcaa cgugauggag      840
gagcgcaaga ucaaggugua ccucccgcgg augaagaugg aggagaagua caaccugacg      900
ucgguccuga ugcgcaugggg gaucaccgac guguucagca gcucggccaa ccucagcggc      960
aucagcucgg ccgagagccu gaagaucagc caggcggugc acgccgccca cgcggagauc     1020
aacgaggccg gccgggaggu cguggggucg gccgaggcgg gcguggacgc cgccagcgu      1080 agcgaggagu ccgcgcgga ccacccguuc cuguucgca ucaagcacau cgccaccaac     1140
gccgugcucu ucuucggccg gugcguguc cccugaccac uaguuauaag acugacuagc     1200
ccgaugggcc ucccaacggg cccuccuccc cuccuugcac cgagauuaau aaaaaaaaaa     1260
aaaaaaaaaa aaaaaaaaaa aaaaaaaaaa aaaaaaaaaa aaaaaaaaaa aaaauauucc     1320
```

```
ccccccccc ccccccccc ccccccccuc uag                           1353

<210> SEQ ID NO 547
<211> LENGTH: 18
<212> TYPE: PRT
<213> ORGANISM: Artificial Sequence
<220> FEATURE:
<223> OTHER INFORMATION: Exemplary carrier PB83 (HO-
      PEG5000-S-(S-CHHHHHHRRRRHHHHHHC-S-)7-S- PEG5000-OH)
<220> FEATURE:
<221> NAME/KEY: MOD_RES
<222> LOCATION: (1)..(1)
<223> OTHER INFORMATION: PEG covalently coupled via disulfide bond
<220> FEATURE:
<221> NAME/KEY: MOD_RES
<222> LOCATION: (18)..(18)
<223> OTHER INFORMATION: PEG covalently coupled via disulfide bond

<400> SEQUENCE: 547

Cys His His His His His His Arg Arg Arg Arg His His His His
1               5                  10                  15

His Cys
```